US008278074B2

(12) United States Patent
Nakamura et al.

(10) Patent No.: US 8,278,074 B2
(45) Date of Patent: Oct. 2, 2012

(54) L-GLUTAMIC ACID-PRODUCING MICROORGANISM AND A METHOD FOR PRODUCING L-GLUTAMIC ACID

(75) Inventors: Jun Nakamura, Kawasaki (JP); Seiko Hirano, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/047,260

(22) Filed: Mar. 14, 2011

(65) Prior Publication Data
US 2011/0171679 A1 Jul. 14, 2011

Related U.S. Application Data

(62) Division of application No. 12/550,929, filed on Aug. 31, 2009, now Pat. No. 7,927,844, which is a division of application No. 11/275,346, filed on Dec. 28, 2005, now Pat. No. 7,794,989.

(60) Provisional application No. 60/641,079, filed on Jan. 4, 2005, provisional application No. 60/641,080, filed on Jan. 4, 2005, provisional application No. 60/715,131, filed on Sep. 9, 2005.

(30) Foreign Application Priority Data

Dec. 28, 2004 (JP) ................. 2004-378604
Dec. 28, 2004 (JP) ................. 2004-378615
Sep. 9, 2005 (JP) ................. 2005-262087

(51) Int. Cl.
C12P 13/14 (2006.01)
C12N 1/20 (2006.01)
(52) U.S. Cl. .................. 435/110; 435/252.33
(58) Field of Classification Search .............. None
See application file for complete search history.

(56) References Cited

U.S. PATENT DOCUMENTS

| | | | |
|---|---|---|---|
| 3,002,889 A | 10/1961 | Kinoshita et al. |
| 5,272,067 A | 12/1993 | Tsuchida et al. |
| 5,492,818 A | 2/1996 | Nakazawa et al. |
| 5,977,331 A | 11/1999 | Asakura et al. |
| 7,097,999 B2 | 8/2006 | Tsujimoto et al. |
| 7,205,132 B2 | 4/2007 | Hirano et al. |
| 7,211,416 B2 | 5/2007 | Asahara et al. |
| 7,300,776 B2 | 11/2007 | Ito et al. |
| 7,335,496 B2 | 2/2008 | Yamamoto et al. |
| 7,344,874 B2 | 3/2008 | Hara et al. |
| 7,482,140 B2 | 1/2009 | Takai et al. |
| 7,547,531 B2 | 6/2009 | Kataoka et al. |
| 7,785,845 B2 | 8/2010 | Hara et al. |
| 2002/0160461 A1 | 10/2002 | Nakai et al. |
| 2004/0121428 A1 | 6/2004 | Sugimoto et al. |
| 2004/0152175 A1 | 8/2004 | Nakamura et al. |
| 2004/0229311 A1 | 11/2004 | Hirano et al. |
| 2005/0014236 A1 | 1/2005 | Matsuzaki et al. |
| 2006/0003424 A1 | 1/2006 | Asakura et al. |
| 2006/0141588 A1 | 6/2006 | Nakamura et al. |
| 2006/0205043 A1 | 9/2006 | Tsujimoto et al. |
| 2006/0216796 A1 | 9/2006 | Hashiguchi et al. |
| 2007/0172932 A1 | 7/2007 | Hirano et al. |
| 2007/0254345 A1 | 11/2007 | Fukui et al. |
| 2009/0104683 A1 | 4/2009 | Takai et al. |
| 2009/0258402 A1 | 10/2009 | Hirano et al. |
| 2009/0286290 A1 | 11/2009 | Hara et al. |
| 2010/0099152 A1 | 4/2010 | Chinen et al. |
| 2010/0190216 A1 | 7/2010 | Gunji et al. |
| 2010/0279363 A1 | 11/2010 | Hirano et al. |

FOREIGN PATENT DOCUMENTS

| | | |
|---|---|---|
| EP | 1 004 671 | 5/2000 |
| EP | 1 108 790 | 6/2001 |
| JP | 01-296994 | 11/1989 |
| WO | WO03/046123 | 6/2003 |

OTHER PUBLICATIONS

Miller, S., et al., "Domain organization of the MscS mechanosensitive channel of *Escherichia coli*," The EMBO Journal 2003;22(1):36-46.

Sukharev, S. I., et al., "Mechanosensitive Channels of *Escherichia coli*: The MscL Gene, Protein, and Activities," Annu. Rev. Physiol. 1997;59:633-657.

Notice of Reason for Rejection from Japanese Patent App. No. 2005-379259 (Jun. 21, 2011) with English translation thereof.

Database EMBL [Online] Jan. 22, 2003, "Novel polynucleotide," XP002387853 retrieved from EBI accession No. EM_PAT:BD163602 abstract & JP 2002 191370 A (Kyowa Hakko Kogyo Co. Ltd.) Jul. 9, 2002.

Hoischen, C., et al., "Evidence for an efflux carrier system involved in the secretion of glutamate by *Corynebacterium glutamicum*," Arch. Microbiol. 1989;151:342-347.

Kalinowski, J., et al., "The complete *Corynebacterium glutamicum* ATCC 13032 genome sequence and its impact on the production of L-aspartate-derived amino acids and vitamins," J. Biotechnol. 2003;104:5-25.

Nishio, Y., et al., "Comparative Complete Genome Sequence Analysis of the Amino Acid Replacements Responsible for the Thermostability of *Corynebacterium efficiens*," Genome Res. 2003;13(7):1572-1579.

Nottebrock. D., et al., "Molecular and biochemical characterization of mechanosensitive channels in *Corynebacterium glutamicum*," FEMS Microbiol. Lett. 2003;218:305-309.

Radmacher, E., et al., "Ethambutol, a cell wall inhibitor of *Mycobacterium tuberculosis*, elicits L-glutamate efflux of *Corynebacterium glutamicum*," Microbiol. 2005;151:1359-1368.

Ruffert, S., et al., "Efflux of compatible solutes in *Corynebacterium glutamicum* mediated by osmoregulated channel activity," Eur. J. Biochem. 1997;247:572-580.

Ruffert, S., et al., "Identification of Mechanosensitive Ion Channels in the Cytoplasmic Membrane of *Corynebacterium glutamicum*," J. Bacteriol. 1999;181(5):1673-1676.

(Continued)

Primary Examiner — Kagnew H Gebreyesus
(74) Attorney, Agent, or Firm — Shelly Guest Cermak; Cermak Nakajima LLP

(57) ABSTRACT

A coryneform bacterium that is modified by using a yggB gene so that L-glutamic acid-producing ability is enhanced as compared to a non-modified strains is cultured in a medium to cause accumulation of L-glutamic acid in the medium or bacterial cells, and L-glutamic acid is collected from the medium or cells.

5 Claims, 5 Drawing Sheets

OTHER PUBLICATIONS

Sekine, H., et al., "H$^+$-ATPase defect in *Corynebacterium glutamicum* abolishes glutamic acid production with enhancement of glucose consumption rate," Appl. Microbiol. Biotechnol. 2001;57:534-540.

PCT International Search Report and Written Opinion of the International Searching Authority for PCT Patent App. No. PCT/JP2005/024280 (Jul. 14, 2006).

International Preliminary Report on Patentability for PCT Patent App. No. PCT/JP2005/024280 (Jul. 12, 2007).

Office Action from European Patent App. No. 05824547.3 (Mar. 11, 2008).

Office Action from Peruvian Patent App. No. 00019-2006/OIN (Apr. 23, 2009) with English translation.

IBIS—Integrated Biotechnological Information Services, Database entry: UNIPROT: Q6NJ09, pp. 1-2, 2010.

IBIS—Integrated Biotechnological Information Services, Database entry: GSP: ABU26256, pp. 1-3, 2007.

EBI Dbfetch—UNIPROT: Q8FPX4, pp. 1-2, 2010.

Communication Pursuant to Article 94(3) EPC for EP Patent App. No. 05824547.3 (Nov. 26, 2010).

L-GLUTAMIC ACID-PRODUCING MICROORGANISM AND A METHOD FOR PRODUCING L-GLUTAMIC ACID

This application is a divisional under 35 U.S.C. §120 of U.S. patent application Ser. No. 12/550,929, filed on Aug. 31, 2009, now U.S. Pat. No. 7,927,844 which was a divisional under 35 U.S.C. §120 of U.S. patent application Ser. No. 11/275,346, filed on Dec. 28, 2005, now U.S. Pat. No. 7,794,989, which claims priority under 35 U.S.C. §119(a) to Japanese Patent Application Nos. 2004-378604, filed on Dec. 28, 2004, 2004-378615, filed on Dec. 28, 2004, and 2005-262087, filed on Sep. 9, 2005, and under 35 U.S.C. §119(e) to U.S. Provisional Patent Application Nos. 60/641,079, filed on Jan. 4, 2005, 60/641,080, filed on Jan. 4, 2005, and 60/715,131, filed on Sep. 9, 2005, the entireties of all of which are incorporated by reference. The Sequence Listing on Compact Disk filed herewith is also hereby incorporated by reference in its entirety (File Name: 2011-03-14_US-200D2_Seq_List; File Size: 313 KB; Date Created: Mar. 14, 2011).

BACKGROUND OF THE INVENTION

1. Field of the Invention

The present invention relates to an L-glutamic acid-producing microorganism and a method for producing L-glutamic acid using the microorganism. L-glutamic acid is widely used in the food industry, for example, as a raw material in the production of seasonings.

2. Brief Description of the Related Art

L-glutamic acid has been conventionally produced on an industrial scale by fermentation methods using coryneform bacteria which have L-glutamic acid-producing ability, such as bacteria belonging to the genus *Brevibacterium* or *Corynebacterium*. For this purpose, strains isolated from nature, or artificial mutants thereof, have been used.

Generally, wild-type strains of coryneform bacteria do not produce L-glutamic acid when excess biotin is present. Accordingly, L-glutamic acid production by coryneform bacteria is typically performed under biotin-limited conditions, or a surfactant or penicillin is added to the culture medium (Biosci. Biotech. Biochem., 1997, 61 (7), p 1109-1112). On the other hand, mutant strains that can produce L-glutamic acid in the presence of excess biotin are used for L-glutamic acid production. These strains include a surfactant-temperature-sensitive strain (WO99/02692), a penicillin-sensitive strain (JP-A-55-0124492), and a lysozyme-sensitive strain (WO00/14241). However, such mutant strains may often show a decrease in fatty acid or cell wall synthesis, and there has been some difficulty in producing L-glutamic acid using these strains while maintaining sufficient growth of the strains.

Meanwhile, a genetically modified strain in which a gene encoding α-ketoglutaric acid dehydrogenase (α-KGDH) is disrupted has been used to produce L-glutamic acid in the presence of excess biotin (WO95/34672). However, this α-KGDH gene-deficient strain grows slowly because the TCA cycle is blocked midway, and it is difficult to obtain a sufficient amount of cells required for L-glutamic acid production.

The yggB gene of coryneform bacteria is a homolog of the yggB gene of *Escherichia coli* (FEMS Microbiol Lett. 2003, 218 (2), p305-309, Mol Microbiol. 2004, 54 (2), p420-438), and has been reported to be a kind of mechanosensitive channel (EMBO J. 1999, 18 (7):1730-7). However, its effect on L-glutamic acid production has not been previously reported.

SUMMARY OF THE INVENTION

An object of the present invention is to provide a novel method to improve L-glutamic acid-producing ability of coryneform bacterium.

The inventors of the present invention have made extensive studies to achieve this object, and found that the L-glutamic acid-producing ability of coryneform bacterium can be improved by enhancing expression of the wild-type yggB gene. Furthermore, mutant-type yggB genes which improve L-glutamic acid-producing ability of coryneform bacterium in the presence of excess biotin as well as normal L-glutamic acid-producing conditions were obtained, and thereby accomplished the present invention.

It is an object of the present invention to provide a coryneform bacterium having L-glutamic acid-producing ability, wherein said coryneform bacterium is modified so that L-glutamic acid-producing ability of the strain is enhanced as compared to a non-modified strain, wherein said bacterium is modified in a manner selected from the group consisting of enhancing the expression of a yggB gene or enhancing the activity of the yggB protein, introducing a mutant-type yggB gene, enhancing the expression of a mutant-type yggB gene, and combinations thereof.

It is an object of the present invention to provide the coryneform bacterium as described above, wherein said yggB gene is selected from the group consisting of:

(a) a DNA comprising nucleotides 1437 to 3035 of SEQ ID No: 5, (b) a DNA that is able to hybridize with a nucleotide sequence complementary to the nucleotides 1437 to 3035 of SEQ ID No: 5 or a probe prepared from the nucleotides under stringent conditions, and wherein said DNA increases L-glutamic acid-producing ability of a coryneform bacterium when it is introduced into the coryneform bacterium, (c) a DNA comprising nucleotides 507 to 2093 of SEQ ID No: 61, (d) a DNA that is able to hybridize with a nucleotide sequence complementary to the nucleotides 507 to 2093 of SEQ ID No: 61 or a probe prepared from the nucleotides under stringent conditions, and wherein said DNA increases L-glutamic acid-producing ability of a coryneform bacterium when it is introduced into the coryneform bacterium, (e) a DNA comprising nucleotides 403 to 2001 of SEQ ID No: 67, (f) a DNA that is able to hybridize with a nucleotide sequence complementary to the nucleotides 403 to 2001 of SEQ ID No: 67 or a probe prepared from the nucleotides under stringent conditions, and wherein said DNA increases L-glutamic acid-producing ability of a coryneform bacterium when it is introduced into the coryneform bacterium, (g) a DNA comprising nucleotides 501 to 2099 of SEQ ID No: 83, and (h) a DNA that is able to hybridize with a nucleotide sequence complementary to the nucleotides 501 to 2099 of SEQ ID No: 83 or a probe prepared from the nucleotides under stringent conditions, and wherein said DNA increases L-glutamic acid-producing ability of a coryneform bacterium when it is introduced into the coryneform bacterium.

It is a further object to provide the coryneform bacterium as described above, wherein said yggB gene encodes a protein selected from the group consisting of:

(A) a protein comprising an amino acid sequence selected from the group consisting of SEQ ID NO: 6, 62, 68, 84 and 85, and (B) a protein comprising an amino acid sequence selected from the group consisting of SEQ ID NO: 6, 62, 68, 84 and 85, whereby one or several amino acids in said protein are substituted, deleted, inserted, or added, and said yggB gene increases L-glutamic acid-producing ability of a coryneform bacterium when it is introduced into the coryneform bacterium.

It is a further object to provide the coryneform bacterium as described above, wherein said coryneform bacterium is modified so to enhance expression of the yggB gene as compared to a non-modified strain.

It is a further object to provide the coryneform bacterium as described above, wherein expression of the yggB gene is enhanced by increasing a copy number of the yggB gene or modifying an expression regulating sequence of the yggB gene.

It is a further object to provide the coryneform bacterium as described above, wherein said coryneform bacterium is modified by introducing a mutant-type yggB gene.

It is a further object to provide the coryneform bacterium as described above, wherein said mutant-type yggB gene has a mutation in a region encoding amino acids 419-533 of SEQ ID NO: 6, 68, 84 or 85, or amino acids 419-529 of SEQ ID NO: 62.

It is a further object to provide the coryneform bacterium as described above, wherein said mutation is deletion of said region.

It is a further object to provide the coryneform bacterium as described above, wherein said mutation is insertion of an insertion sequence or transposon into the region.

It is a further object to provide the coryneform bacterium as described above, wherein said mutant-type yggB gene has a mutation which results in replacement of the proline in said region with another amino acid.

It is a further object to provide the coryneform bacterium as described above, wherein said mutant-type yggB gene has a mutation which results in replacement of the proline at position 424 and/or the proline at position 437 in the amino acid sequence of SEQ ID NO: 6, 62, 68, 84 or 85 with another amino acid.

It is a further object to provide the coryneform bacterium as described above, wherein said mutant-type yggB gene has a mutation in the transmembrane-coding region of the yggB protein.

It is a further object to provide the coryneform bacterium as described above, wherein said transmembrane-coding region is selected from the group consisting of amino acids 1-23, amino acids 25-47, amino acids 62-84, amino acids 86-108, and amino acids 110-132 of SEQ ID NO: 6, 62, 68, 84 or 85.

It is a further object to provide the coryneform bacterium as described above, wherein said mutation is introduced without causing a frame-shift.

It is a further object to provide the coryneform bacterium as described above, wherein said mutant-type yggB gene has a mutation which results in replacement of the alanine at position 100 and/or the alanine at position 111 in the amino acid sequence shown in SEQ ID NO: 6, 62, 68, 84 or 85 with another amino acid.

It is a further object to provide the coryneform bacterium as described above, wherein said mutant-type yggB gene has a mutation which results in insertion of at least one amino acid between leucine at position 14 and tryptophan at position 15 in SEQ ID NO: 6, 62, 68, 84 or 85.

It is a further object to provide the coryneform bacterium as described above, wherein resistance to L-glutamic acid analogs of said strain is increased by introduction of the mutant-type yggB gene.

It is a further object to provide the coryneform bacterium as described above, wherein said coryneform bacterium is further modified to inactivate a gene which suppresses a function of said mutant-yggB gene.

It is a further object to provide the coryneform bacterium as described above, wherein said gene which suppresses a function of said mutant-yggB gene is a symA gene and wherein said symA gene is selected from the group consisting of:

(a) a DNA comprising nucleotides 585 to 1121 of SEQ ID No: 86, (b) a DNA that is able to hybridize with a nucleotide sequence complementary to nucleotides 585 to 1121 of SEQ ID No: 86, or a probe prepared from said nucleotides under stringent conditions, and wherein said DNA suppresses a function of said mutant-type yggB gene in the coryneform bacterium.

It is a further object to provide the coryneform bacterium as described above, wherein said coryneform bacterium is further modified so to decrease α-ketoglutarate dehydrogenase activity.

It is a further object to provide the coryneform bacterium as described above, wherein said coryneform bacterium is a bacterium belonging to the genus *Corynebacterium* or the genus *Brevibacterium*.

It is an object of the present invention to provide a method for producing L-glutamic acid comprising culturing the coryneform bacterium as described in a medium so to cause accumulation of L-glutamic acid in the medium or cells, and collecting L-glutamic acid from the medium or the cells.

It is an object of the present invention to provide a mutant-type yggB gene selected from the group consisting of:

(a) a gene encoding amino acid sequence of SEQ ID NO: 8, (b) a gene encoding a protein having a homology of not less than 80% to SEQ ID NO: 8, and having a function to increase L-glutamic acid-producing ability of coryneform bacterium under condition containing excess biotin when it is introduced into the coryneform bacterium, (c) a gene encoding amino acid sequence of SEQ ID NO: 20, (d) a gene encoding a protein having a homology of not less than 80% to SEQ ID NO: 20, and having a function to increase L-glutamic acid-producing ability of coryneform bacterium in the presence of excess biotin when said gene is introduced into the coryneform bacterium, (e) a gene encoding amino acid sequence of SEQ ID NO: 22, (f) a gene encoding a protein having a homology of not less than 80% to SEQ ID NO: 22, and having a function to increase L-glutamic acid-producing ability of coryneform bacterium in the presence of excess biotin when it said gene introduced into the coryneform bacterium, (g) a gene encoding amino acid sequence of SEQ ID NO: 24, (h) a gene encoding a protein having a homology of not less than 80% to SEQ ID NO: 24, and having a function to increase L-glutamic acid-producing ability of coryneform bacterium in the presence of excess biotin when said gene is introduced into the coryneform bacterium, (i) a gene encoding amino acid sequence of SEQ ID NO: 64, (j) a gene encoding a protein having a homology of not less than 80% to SEQ ID NO: 64, and having a function to increase L-glutamic acid-producing ability of coryneform bacterium in the presence of excess biotin when said gene is introduced into the coryneform bacterium, (k) a gene encoding amino acid sequence of SEQ ID NO: 70, (l) a gene encoding a protein having a homology of not less than 80% to SEQ ID NO: 70, and having a function to increase L-glutamic acid-producing ability of coryneform bacterium in the presence of excess biotin when it is introduced into the coryneform bacterium, (m) a gene encoding amino acid sequence of SEQ ID NO: 74, (n) a gene encoding a protein having a homology of not less than 80% to SEQ ID NO: 74, and having a function to increase L-glutamic acid-producing ability of coryneform bacterium in the presence of excess biotin when said gene is introduced into the coryneform bacterium.

It is an object of the present invention to provide a method for producing a coryneform bacterium having a mutant-type yggB gene, comprising inoculating a coryneform bacterium which is deficient in a gene encoding α-ketoglutarate dehydrogenase in a medium containing excess biotin, and selecting a strain that is capable of accumulating L-glutamic acid in the medium as a strain having a mutant-type yggB gene.

It is an object of the present invention to provide a method for producing a coryneform bacterium having a mutant-type yggB gene, comprising inoculating a coryneform bacterium introduced with a yggB gene in which mutation is introduced randomly in vitro in a medium containing excess biotin, and selecting a strain that is capable of accumulating L-glutamic acid in the medium as a strain having a mutant-type yggB gene.

It is an object of the present invention to provide a method for producing a coryneform bacterium having a mutant-type yggB gene, comprising inoculating a coryneform bacterium introduced with a transposable element randomly on a chromosome in a medium containing excess biotin, and selecting a strain that is capable of accumulating L-glutamic acid in the medium as a strain having a mutant-type yggB gene.

It is an object of the present invention to provide a method for producing a coryneform bacterium having a mutant-type yggB gene, comprising inoculating a coryneform bacterium into a medium containing L-glutamic acid analogs, and selecting a strain which grows in said medium.

It is an object of the present invention to provide the method for producing a coryneform bacterium as described above, wherein the strain having the mutant-type yggB gene is a coryneform bacterium as described above.

It is an object of the present invention to provide the method of producing a coryneform bacterium as described above, wherein the medium containing excess biotin is a medium containing 30 μg/l or more of biotin.

DETAILED DESCRIPTION OF EXEMPLARY EMBODIMENTS

Figure 1:
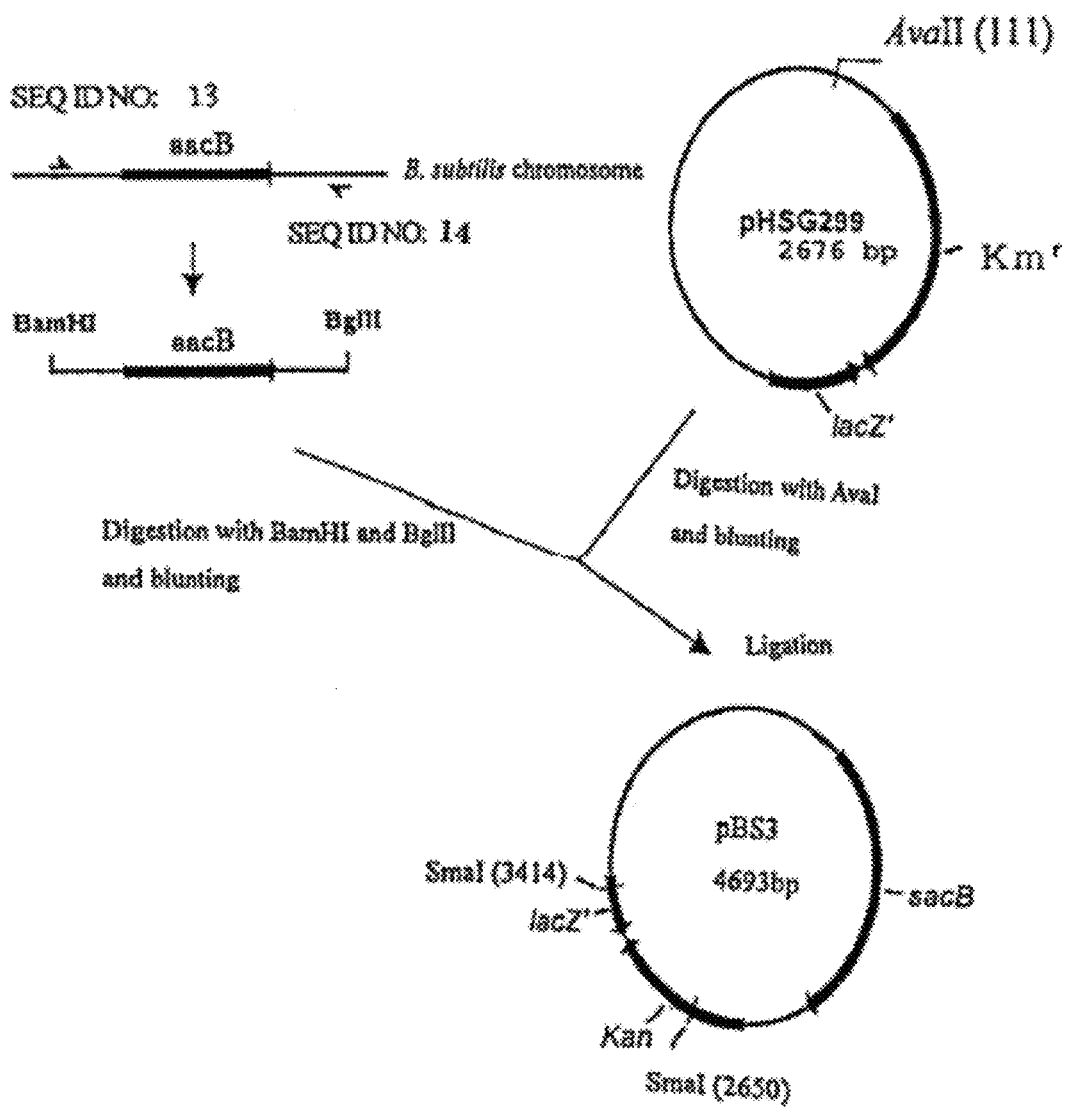
FIG. 1 shows the procedure for constructing plasmid pBS3.

Hereinafter, the present invention is explained in more detail.

<1> Coryneform Bacterium of the Present Invention

The coryneform bacterium of the present invention has L-glutamic acid-producing ability, and is modified using a yggB gene so that the L-glutamic acid-producing ability of the strain is enhanced as compared to a non-modified strain.

In the present invention, examples of coryneform bacterium include conventional coryneform bacteria, and also include bacteria that had been classified into the genus *Brevibacterium*, but are currently classified into the genus *Corynebacterium* (Int. J. Syst. Bacteriol., 41, 255 (1991)), as well as the *Brevibacterium* bacteria that are very close to *Corynebacterium* bacteria. Examples of such coryneform bacterium include the following:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes*
*Brevibacterium album*
*Brevibacterium cerinum*
*Microbacterium ammoniaphilum*

Specific examples of the coryneform bacteria are as follows:

*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, ATCC13032, ATCC13060
*Corynebacterium lilium* ATCC15990
*Corynebacterium melassecola* ATCC17965
*Corynebacterium thermoaminogenes* AJ12340 (FERM BP-1539)
*Corynebacterium herculis* ATCC13868
*Brevibacterium divaricatum* ATCC14020
*Brevibacterium flavum* ATCC13826,
*Brevibacterium flavum* (*Corynebacterium glutamicum*) ATCC14067,
*Brevibacterium flavum* AJ12418 (FERM BP-2205)
*Brevibacterium immariophilum* ATCC14068
*Brevibacterium lactofermentum* (*Corynebacterium glutamicum*) ATCC13869
*Brevibacterium roseum* ATCC13825
*Brevibacterium saccharolyticum* ATCC14066

*Brevibacterium thiogenitalis* ATCC19240
*Brevibacterium ammoniagenes* ATCC6871, ATCC6872
*Brevibacterium album* ATCC15111
*Brevibacterium cerinum* ATCC15112
*Microbacterium ammoniaphilum* ATCC15354

These strains are available from the American Type Culture Collection (ATCC, Address: P.O. Box 1549, Manassas, Va. 20108, United States of America). That is, each strain is given a unique registration number which is listed in the catalogue of the ATCC. Strains can be ordered using this registration number. The AJ12340 strain was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Oct. 27, 1989 under the provisions of the Budapest Treaty and given an accession number of FERM BP-1539. The AJ12418 strain was deposited at National Institute of Bioscience and Human Technology, Agency of Industrial Science and Technology, Ministry of International Trade and Industry on Jan. 5, 1989 under the provisions of the Budapest Treaty and given an accession number of FERM BP-2205.

The coryneform bacterium of the present invention has L-glutamic acid-producing ability. "L-glutamic acid-producing ability" means an ability to cause accumulation of a sufficient amount of L-glutamic acid in a medium when the coryneform bacterium of the present invention is cultured in the medium. L-glutamic acid-producing ability may be a property of a parent strain from which the coryneform bacterium of the present invention is bred, because most of the wild-type strains of coryneform bacterium produce L-glutamic acid under L-glutamic acid-producing conditions as described below. Nevertheless, L-glutamic acid-producing ability may be imparted or enhanced by a mutation, gene recombination technique, etc. as mentioned below. Furthermore, the L-glutamic acid-producing ability may be imparted by enhancing the expression of the yggB gene.

The phrase "L-glutamic acid-producing ability of coryneform bacterium is enhanced" means that the coryneform bacterium of the present invention has an enhanced ability to produce L-glutamic acid compared to a non-modified strain. Examples of non-modified strains include *Corynebacterium glutamicum* ATCC13032, 13869, 14067, and *Corynebacterium melassecola* ATCC 17965. A non-modified strain may also include one which expresses the wild-type yggB gene at the same level as the wild-type strains or one in which a mutation is not introduced into the coding region of a yggB gene.

An example of a method for imparting L-glutamic acid-producing ability includes enhancing expression of a gene encoding an L-glutamic acid biosynthetic enzyme. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Enhancing the expression of these genes can be performed in the same way as enhancing the expression of the yggB gene described below.

Examples of microorganisms which have been modified so that expression of the citrate synthase gene, isocitrate dehydrogenase gene, pyruvate dehydrogenase gene, and/or glutamate dehydrogenase gene is/are enhanced include those microorganisms disclosed in WO00/18935 and JP2000-232890A (EP1010755A).

The modification for imparting L-glutamic acid-producing ability includes decreasing or eliminating an activity of an enzyme that catalyzes a reaction for synthesizing a compound other than L-glutamic acid, and branching from an L-glutamic acid biosynthesis pathway. Examples of such enzymes include isocitrate lyase, α-ketoglutarate dehydrogenase, acetyl phosphate transferase, acetate kinase, acetohydroxy acid synthase, acetolactate synthase, acetyl formate transferase, lactate dehydrogenase, and glutamate decarboxylase. Examples of strains in which α-ketoglutarate dehydrogenase activity is decreased include the following strains:

*Brevibacterium lactofermentum* ΔS strain (WO95/34672)
*Brevibacterium lactofermentum* AJ12821 strain (FERM BP-4172; FR9401748)
*Brevibacterium flavum* AJ12822 strain (FERM BP-4173; FR9401748)
*Brevibacterium glutamicum* AJ12823 strain (FERM BP-4174; FR9401748)

To decrease or eliminate the activity of the enzymes as described above, a mutation or deletion which causes a decrease or loss of the activity of the enzymes may be introduced into the genes of the enzymes on the chromosome. This may be achieved by, for example, disrupting the gene encoding the enzyme on the chromosome, or by modifying an expression control sequence such as a promoter and/or Shine Dargarno (SD) sequence of the gene. In addition, the activities of such enzymes may be decreased or eliminated by introducing a missense mutation which causes an amino acid substitution, a nonsense mutation which generates a stop codon, or a frame shift mutation which adds or deletes one or two nucleotides into a coding region, or by deleting a portion or the entire gene (Journal of biological Chemistry 272:8611-8617 (1997)). For example, activities of such enzymes may be decreased or eliminated by constructing a gene encoding a mutant enzyme in which its coding region is deleted and replacing a chromosomal gene with the resulting gene by homologous recombination, or by introducing a transposon or an IS factor into these genes.

For example, introduction of mutations to decrease or eliminate the activity of the above-described enzymes by gene recombination can be performed as follows. That is, a mutant-type gene is constructed by modifying a partial sequence of a target gene so that a normal enzyme is not produced, and the mutant-type gene is used to transform a coryneform bacterium to cause recombination with the target gene on a chromosome, and thereby, a target gene on a chromosome can be replaced with the mutant-type gene. Such gene disruption by gene substitution utilizing homologous recombination is already established, and includes a method that employs linear DNA or a method that employs a plasmid containing a temperature-sensitive replication origin (U.S. Pat. No. 6,303,383, or JP-A-05-007491). Examples of temperature-sensitive plasmids for coryneform bacteria include p48K and pSFKT2 (U.S. Pat. No. 6,303,383), pHSC4 (France Patent Laid-open Publication No. 2667875, 1992 and JP5-7491A), and so forth. In coryneform bacteria, these plasmids can autonomously replicate at least at a temperature of 25° C., but cannot autonomously replicate at a temperature of 37° C. The AJ12571 strain harboring pHSC4 was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Aug. 26, 1991 under the provisions of the Budapest Treaty and given an accession number of FERM BP-3524.

Gene disruption by gene substitution utilizing the above-mentioned homologous recombination can also be performed by using a plasmid which is not replicable in coryneform bacteria. A plasmid which is not replicable in coryneform bacteria and is replicable in *Escherichia* bacteria is preferably used. Examples of such a plasmid include pHSG299 (Takara Bio) and pHSG399 (Takara Bio).

A chromosomal gene encoding one of the above-mentioned enzymes can be replaced with a deletion-type gene, for example, by homologous recombination using sacB (Schafer, A. et al., Gene 145 (1994) 69-73). The sacB gene encodes levan sucrase and is used to efficiently select strains in which a chromosomal target gene is replaced by a mutant gene, and a vector portion is cured from a chromosome (WO2005/113745, and WO2005/113744).

At first, a recombinant plasmid is prepared by inserting a deletion-type (mutant) gene, a sacB gene, and a selection marker such as a chloramphenicol-resistant gene into a plasmid containing a temperature-sensitive replication origin. The plasmid is then introduced into a host strain of coryneform bacterium. When levan sucrase is expressed in coryneform bacterium, levan generated by the conversion of sucrose is lethal for the bacterium, and hence the bacterium cannot grow on sucrose-containing medium. Therefore, by culturing on a sucrose-containing plate, strains in which substitution occurs between the mutant gene in the plasmid and a chromosomal gene, and from which the other portions of the plasmid are cured from the cell, can be selected.

Examples of the sacB gene include the following:
*Bacillus subilus*: sacB GenBank Accession No. X02730 (SEQ ID NO: 11)
*Bacillus amyloliqufaciens*: sacB GenBank Accession Number X52988
*Zymomonas mobilis*: sacB GenBank Accession Number L33402
*Bacillus stearothermophilus*: surB GenBank Accession Number U34874
*Lactobacillus sanfranciscensis*: frfA GenBank Accession Number AJ508391
*Acetobacter xylinus*: lsxA GenBank Accession Number AB034152
*Gluconacetobacter diazotrophicus*: lsdA GenBank Accession No. L41732

The transformant strain is cultured at a temperature at which the temperature-sensitive replication origin functions (e.g. 25° C.), to obtain a strain into which the plasmid has been introduced. Then, the transformant is cultured at a high temperature at which the temperature-sensitive replication origin does not function (e.g. 34° C.) to cure the temperature-sensitive plasmid, and spread on a plate medium containing an antibiotic drug such as kanamycin. Although strains from which the plasmid is cured cannot grow on a plate containing such an antibiotic drug, a few strains in which the chromosomal gene is replaced with the mutant gene can grow and appear as colonies.

In a strain in which the recombinant DNA containing the mutant gene is integrated into the chromosomal DNA, the recombinant DNA causes recombination with the gene that originally existed on the chromosome, and the fusion genes of the chromosomal gene and the mutant gene are inserted into the chromosome so that the other portions of the recombinant DNA (vector segment, temperature sensitive replication origin and antibiotic resistance marker) are present between the fusion genes. Then, in order to leave only the mutant gene on the chromosomal DNA, one copy of the gene is eliminated together with the vector segment (including the temperature-sensitive replication origin and the antibiotics resistance marker) from the chromosomal DNA. In this case, the native gene is left on the chromosomal DNA and the mutant gene is excised from the chromosomal DNA, or to the contrary, the mutant gene is left on the chromosomal DNA and the native gene is excised from the chromosome DNA. In both cases, the excised DNA is maintained in cells of coryneform bacterium when the coryneform bacterium is cultured at a temperature at which the temperature-sensitive replication origin can function. Then, a gene on the plasmid is cured from the cells along with the plasmid by culturing the coryneform bacterium at a temperature at which the temperature-sensitive replication origin cannot function. In the case of using a sacB gene, strains from which the plasmid is cured can be efficiently obtained by culturing the coryneform bacterium in a sucrose-containing medium. Strains in which a target gene is replaced with a mutant-type or deletion-type gene can be obtained by selecting strains in which a mutation is introduced into the target gene from the plasmid-cured strains.

The L-glutamic acid-producing ability may also be imparted by screening for a strain resistant to organic acid analogs, respiratory inhibitors, or superoxide generators, or by screening for a strain sensitive to inhibitors of cell wall synthesis. Examples of such methods include imparting resistance to monofluoroacetate (JP50-113209A), imparting resistance to adenine or thimine (JP57-065198A), imparting resistance to malonic acid (JP52-038088A), attenuating urease activity ((JP52-038088A), imparting resistance to benzopirone or naphtoquinone (JP56-1889A), imparting resistance to HOQNO (JP56-140895A), imparting resistance to α-ketomalonic acid (JP57-2689A), imparting resistance to guanidine (JP56-35981A), imparting resistance to daunomicin (JP58-158192A), and imparting sensitivity to penicillin (JP04-88994A).

Specific examples of such bacteria include the following strains:
*Brevibacterium flavum* AJ3949 (FERM BP-2632; JP50-113209A)
*Corynebacterium glutamicum* AJ11628 (FERM P-5736; JP57-065198A)
*Brevibacterium flavum* AJ11355 (FERM P-5007; JP56-1889A)
*Corynebacterium glutamicum* AJ11368 (FERM P-5020; JP56-1889A)
*Brevibacterium flavum* AJ11217 (FERM P-4318; JP57-2689A)
*Corynebacterium glutamicum* AJ11218 (FERM P-4319; JP57-2689A)
*Brevibacterium flavum* AJ11564 (FERM P-5472; JP56-140895A)
*Brevibacterium flavum* AJ11439 (FERM P-5136; JP56-35981A)
*Corynebacterium glutamicum* H7684 (FERM BP-3004; JP04-88994A)
*Brevibacterium lactofermentum* AJ11426 (FERM P5123 JP56-048890A)
*Corynebacterium glutamicum* AJ11440 (FERM P5137 JP56-048890A)
*Brevibacterium lactofermentum* AJ11796 (FERM P6402 JP58-158192A)

The coryneform bacterium of the present invention can be obtained by modifying the above-described coryneform bacterium having the L-glutamic acid-producing ability using a yggB gene so that L-glutamic acid-producing ability is further enhanced. Alternatively, modification using a yggB gene may be performed first, followed by additional modification to impart or enhance L-glutamic acid-producing ability.

Modification using a yggB gene includes, but is not limited to, enhancing the expression of a yggB gene in a coryneform bacterium and introducing a mutation into a yggB gene in a coryneform bacterium.

<I> Enhancing Expression of a yggB Gene

A yggB gene encodes a kind of mechanosensitive channel, which is also referred to as "mscS" (FEMS Microbiol Lett. 2003 Jan. 28; 218 (2):305-9).

Enhancing expression of a yggB gene in coryneform bacterium leads to improvement of the L-glutamic acid-producing ability of the coryneform bacterium as compared to a non-modified strain. That is, when a strain of coryneform bacterium which has been modified so that expression of the yggB gene is increased relative to a non-modified strain, such as a wild-type strain, the strain causes accumulation of more L-glutamic acid, or produces L-glutamic acid at a higher rate, than the non-modified strain. It is preferable that enhancing expression of a yggB gene leads to an increase in the amount of L-glutamic acid produced by more than 2% (yield per consumed sugar), more preferably more than 4%, and still more preferably more than 6%, as compared to a non-modified strain. Alternatively, the yield of L-glutamic acid per carbon (sugar), other than carbon used for generation of bacterial cells, may be increased by enhancing expression of a yggB gene.

Although the expression level of a yggB gene may be at any level as long as it is increased relative to a non-modified strain in which expression of the yggB gene is not enhanced, expression is preferably increased not less than 1.5-fold, more preferably not less than 2-fold, and still more preferably not less than 3-fold relative to a non-modified strain. The expression level of the yggB gene can be determined by measuring the amount of mRNA of yggB gene. Methods of determining the expression level include Northern hybridization and RT-PCR (Molecular cloning (Cold Spring Harbor Laboratory Press, Cold Spring Harbor (USA), 2001)). An example of a wild-type coryneform bacterium which can be used as a control includes *Corynebacterium glutamicum* (*Brevibacterium lactofermentum*) ATCC13869, ATCC13032, ATCC14067 and *C. melassecola* ATCC 17965 strain.

The L-glutamic acid-producing ability of the coryneform bacterium which was modified using a yggB gene may be enhanced as compared to a non-modified strain either under L-glutamic acid-producing conditions and/or in the presence of excess biotin. Herein, the "L-glutamic acid producing conditions" include when a substance that induces L-glutamic acid production is added to a conventional medium which contains a carbon source, a nitrogen source, inorganic salts, and a trace amount of organic nutrients, such as amino acids and vitamins, if necessary, and when the amount of a substance that inhibits the L-glutamic acid production is limited in such a conventional medium. The substances that induce L-glutamic acid production include penicillin and surfactants containing saturated fatty acid, such as Tween 40 (Trademark). The substance that inhibits the L-glutamic acid production includes biotin (Amino Acid Fermentation, Japan Scientific Societies Press 1986). The concentration of penicillin in the medium is preferably not less than 0.1 U/ml, more preferably not less than 0.2 U/ml, and still more preferably not less than 0.4 U/ml. The concentration of surfactants in the medium is preferably not less than 0.5 g/L, more preferably not less than 1 g/L, and still more preferably not less than 2 g/L. The concentration of biotin added to the medium under L-glutamic acid-producing conditions is preferably less than 15 μg/L, more preferably less than 10 μg/L, and still more preferably less than 5 μg/L. The L-glutamic acid-producing conditions may not contain biotin at all.

On the other hand, the excess biotin-containing conditions may be conditions containing not less than 30 μg/L biotin, more preferably not less than 40 μg/L, and still more preferably not less than 50 μg/L.

Examples of a yggB gene of coryneform bacteria include a DNA encoding the amino acid sequence of SEQ ID No: 6, a DNA encoding the amino acid sequence of SEQ ID No: 62, a DNA encoding the amino acid sequence of SEQ ID No: 68, and a DNA encoding the amino acid sequence of SEQ ID No: 84. Specific examples of a yggB gene of coryneform bacteria include nucleotides 1437-3035 of SEQ ID No: 5, nucleotides 507 to 2093 of SEQ ID No: 61, nucleotides 403 to 2001 of SEQ ID No: 67, and nucleotides 501 to 2099 of SEQ ID No: 83. The nucleotide sequence of nucleotides 501-2099 of SEQ ID No: 83 is the yggB gene of *Corynebacterium glutamicum* ATCC13032, and corresponds to nucleotide numbers 1336092-1337693 in the genome sequence of GenBank Accession No. NC_003450, and is registered as NCgl 1221 (NP_600492. Reports small-conductance mechanosensitive channel . . . [gi:19552490]). The nucleotide sequence of nucleotides 1437-3035 of SEQ ID No: 5 is the yggB gene of *Corynebacterium glutamicum* ATCC13869. The nucleotide sequence of nucleotides 507-2093 of SEQ ID No: 61 is the yggB gene of *Corynebacterium glutamicum* (*Brevibacterium flavum*) ATCC14067. The nucleotide sequence of nucleotides 403-2001 of SEQ ID No: 67 is the yggB gene of *Corynebacterium melassecola* ATCC17965. Furthermore, since the nucleotide sequence of a yggB gene may differ depending on species and strains, the yggB gene used in the present invention may be a variant of the nucleotide sequence of nucleotides 1437-3035 of SEQ ID No: 5. A variant of the yggB gene may be searched for using the nucleotide sequence of nucleotides 1437-3035 of SEQ ID No: 5, for example, by BLAST (//blast.genome.jp/). A variant of the yggB gene includes a gene obtained by PCR using primers of SEQ ID NOS: 75 and 76. A yggB gene may be a gene derived from other microorganisms so long as it is able to increase the L-glutamic acid-producing ability of coryneform bacteria. A yggB gene may be a mutant-type yggB as described below.

The yggB gene used in the present invention is not limited to a gene encoding a protein having the amino acid sequence shown in SEQ ID NO: 6, 62, 68, or 84, and may also include a gene encoding a protein having the amino acid sequence of SEQ ID NO: 6, 62, 68, or 84, whereby one or more amino acids are replaced, deleted, inserted, or added at one or more positions, while retaining the ability to enhance L-glutamic acid-producing ability of a coryneform bacterium when the gene is introduced into the coryneform bacterium. Although the number of "several" amino acid residues referred to herein may differ depending on positions in the three-dimensional structure or types of amino acid residues of the protein, it may be preferably 2 to 20, more preferably 2 to 10, particularly preferably 2 to 5. The yggB gene preferably encodes a protein which is not less than 80% homologous, more preferably not less than 90% homologous, even more preferably not less than 95% homologous, and particularly preferably not less than 97% homologous, to the amino acid sequence shown in SEQ ID NO: 6, 62, 68, 84 or 85, while maintaining the ability to enhance the L-glutamic acid-producing ability of coryneform bacterium. Homology between amino acid sequences as well as nucleotide sequences may be determined by algorithms including BLAST developed by Karlin and Altschul (Pro. Natl. Acad. Sci. USA, 90, 5873 (1993)) and FASTA developed by Pearson (Methods Enzymol., 183, 63 (1990)). Homology search programs including BLASTN and BLASTP have been developed based on the algorithm (available at www.ncbi.nlm.nih.gov).

The above-mentioned substitution is preferably a conservative substitution. In the case of aromatic amino acids, conservative substitutions include substitutions of phe, trp, and tyr for each other. In the case of hydrophobic amino acids, conservative substitutions include substitutions of leu, ile, and val for each other. In the case of polar amino acids, conservative substitutions include substitutions of gln and asn for each other. In the case of basic amino acids, conservative substitutions include substitutions of arg, lys, and his for each other. In the case of acidic amino acids, conservative substitutions are substitutions of asp and glu for each other. In the case of hydroxyl group-containing amino acids, conservative substitutions are substitutions of ser and thr for each other. The conservative substitutions also include: substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr and substitution of Met, Ile, or Leu for Val.

Especially, the following amino acids may be substituted or deleted in the amino acid sequence of SEQ ID NO: 6. The amino acid sequence of the YggB protein which is conserved among coryneform bacteria is shown in SEQ ID NO: 85, i.e. a consensus sequence. The Xaa residue shown in SEQ ID NO: 85 may be substituted or deleted.

Glu at position 48 (preferably replaced by Arg)
Asp at position 275 (preferably replaced by Ser)
Glu at position 298 (preferably replaced by Ala)
Ala at position 343 (preferably replaced by Val)
Phe at position 396 (preferably replaced by Ile)
Ser at position 438 (preferably replaced by Gly)
Val at position 445 (preferably replaced by Ala)
Ala at position 454 (preferably replaced by Val)
Pro at position 457 (preferably replaced by Ser)
Ser at position 474 (preferably replaced by Asp)
Val at position 517 (preferably deleted)
Glu at position 518 (preferably deleted)
Ala at position 519 (preferably deleted)
Pro at position 520 (preferably deleted) The above-described yggB gene homologue can be obtained by modifying the nucleotide sequence of nucleotides 1437-3035 of SEQ ID No: 5, nucleotides 507 to 2093 of SEQ ID No: 61, nucleotides 403 to 2001 of SEQ ID No: 67, or nucleotides 501 to 2099 of SEQ ID No: 83 by, for example, site-specific mutagenesis, so that substitution, deletion, insertion, or addition of an amino acid residue or residues occurs at a specific site in the encoded protein. Furthermore, such a gene can also be obtained by a conventionally known mutation treatment. Examples of the mutation treatment include treating a gene having the nucleotide sequence of nucleotides 1437-3035 of SEQ ID No: 5, nucleotides 507 to 2093 of SEQ ID No: 61, nucleotides 403 to 2001 of SEQ ID No: 67, or nucleotides 501 to 2099 of SEQ ID No: 83 in vitro with hydroxylamine, and treating a microorganism, for example, an *Escherichia* bacterium, harboring the gene with ultraviolet ray irradiation or a mutagenesis agent typically used in mutation treatments, such as N-methyl-N'-nitro-N-nitrosoguanidine (NTG) or EMS (ethyl methanesulfonate). The mutation for the substitution, deletion, insertion, addition, inversion, or the like of amino acid residues described above also includes a naturally occurring mutation arising from individual differences and differences in species of microorganisms harboring the yggB gene (mutant or variant). Whether these genes are able to enhance the L-glutamic acid-producing ability of coryneform bacterium can be confirmed by, for example, expressing the genes in a wild-type coryneform bacterium and determining if the L-glutamic acid-producing ability of the obtained coryneform bacterium is enhanced relative to a non-modified strain, such as a wild-type strain.

The yggB gene may also be a DNA which is able to hybridize with a DNA having the nucleotide sequence complementary to the nucleotides 1437-3035 of SEQ ID No: 5, nucleotides 507 to 2093 of SEQ ID No: 61, nucleotides 403 to 2001 of SEQ ID No: 67, or nucleotides 501 to 2099 of SEQ ID No: 83, or a probe that can be prepared from any of these nucleotide sequences under stringent conditions and is able to enhance L-glutamic acid-producing ability of coryneform bacterium when it is introduced into the coryneform bacterium.

"Stringent conditions" as used herein are conditions under which a so-called specific hybrid is formed, and a non-specific hybrid is not formed. Examples of stringent conditions include those under which highly homologous DNAs hybridize to each other, for example, DNAs not less than 70% homologous, preferably not less than 80% homologous, more preferably not less than 90% homologous, especially preferably not less than 95% homologous, hybridize to each other, and DNAs lower than 70% homologous do not hybridize to each other, and those under which DNAs hybridize to each other at a salt concentration with washing typical of Southern hybridization, i.e., washing once or preferably 2-3 times with 1×SSC, 0.1% SDS at 60° C., preferably 0.1×SSC, 0.1% SDS at 60° C., more preferably 0.1×SSC, 0.1% SDS at 68° C.

A complementary partial sequence of the yggB gene can also be used as a probe. Such a probe can be prepared by PCR using oligonucleotides which are designed based on the nucleotide sequence of the yggB gene in a manner well known to those skilled in the art. When a DNA fragment having a length of about 300 bp is used as a probe, the washing conditions after hybridization can be exemplified as 2×SSC, 0.1% SDS at 50° C. The oligonucleotides shown in SEQ ID No: 75 and 76 can be used to prepare said probe.

Furthermore, the yggB gene may be a mutant-type yggB gene as described in <II> to <IV> below.

Enhancing the expression of the above-described yggB gene can be attained by increasing the copy number of the yggB gene, modifying an expression regulatory sequence of the yggB gene, amplifying a gene encoding a regulatory factor that increases expression of the yggB gene, or disrupting or attenuating a gene encoding a regulatory factor that reduces expression of the yggB gene, by using transformation with a plasmid or homologous recombination, conjugation, transition, or the like.

For example, a recombinant DNA can be prepared by ligating a gene fragment containing the yggB gene to a vector, preferably a multi-copy vector, which can replicate in coryneform bacterium, and introducing the resulting vector into an L-glutamic acid-producing coryneform bacterium.

The copy number of the yggB gene may also be increased by integrating multiple copies of the yggB gene into a chromosomal DNA of a microorganism. In order to integrate multiple copies of the yggB gene into a chromosomal DNA of a microorganism, homologous recombination can be performed by targeting a sequence which exists in multiple copies on the chromosomal DNA. Repetitive DNA and inverted repeats at an end of a transposon can be used. Alternatively, as disclosed in JP2-109985A, it is also possible to incorporate the yggB gene into a transposon, and transfer it so that multiple copies of the gene are integrated into the chromosomal DNA. Integration of the yggB gene into the chromosome can be confirmed by Southern hybridization using a probe having a partial sequence of the yggB gene.

Hereinafter, an example of a method for constructing a coryneform bacterium which has been modified so that expression of the yggB gene is enhanced is shown. This method can be performed by conventional methods such as those described in Molecular cloning: Cold Spring Harbor Laboratory Press, Cold Spring Harbor (USA), 2001.

At first, the yggB gene is cloned from the chromosomal DNA of a coryneform bacterium. The chromosomal DNA can be prepared from a coryneform microorganism by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992). For PCR, oligonucleotides such as those shown in SEQ ID NO: 75 and 76 can be used as primers.

Then, a recombinant DNA is prepared by ligating the amplified yggB gene to a vector DNA that can function in coryneform bacterium. Vectors which are autonomously replicable in *Escherichia coli* and coryneform bacterium are preferably used for plasmid construction. Examples of vectors which are autonomously replicable in coryneform bacteria include pAM330 (JP58-67699A), pHM1519 (JP58-77895A), pVK7 (US2003-0175912), and pSFK6 (JP2000-262288A), pCRY30 (JP3-210184A), pCRY21, pCRY2KE, pCRY2KX, pCRY31, pCRY3KE, pCRY3KX (JP2-72876A and U.S. Pat. No. 5,185,262), pCRY2, and pCRY3 (JP1-191686), and pAJ655, pAJ611, pAJ1844 (JP58-192900A), pCG1 (JP57-134500A), pCG2 (JP58-35197), pCG4, pCG11 (S57-183799). Examples of vectors autonomously replicable in *Escherichia coli* include pUC19, pUC18, pHSG299, pHSG399, pHSG398, pACYC184, (pHSG and pACYC are available from Takara Bio), RSF1010, pBR322, pMW219 (pMW is available from Nippon Gene), pTrc99A (Amann et al., Gene 69:301-315 (1988), and so forth.

In order to prepare a recombinant DNA by ligating the yggB gene to any of the vectors mentioned above, the vector and a fragment containing the yggB gene are digested with restriction enzymes and ligated to each other, usually by using a ligase such as a T4 DNA ligase.

The recombinant plasmid as prepared above is introduced into the host coryneform bacterium by a conventional transformation method. Examples of transformation methods include treating recipient cells with calcium chloride so to increase permeability of the DNA, which has been reported for *Escherichia coli* K-12 (Mandel, M. and Higa, A., J. Mol. Biol., 53, 159 (1970)), preparing competent cells from cells which are at the growth phase, followed by transformation with DNA, which has been reported for *Bacillus subtilis* (Duncan, C. H., Wilson, G. A. and Young, F. E., Gene, 1, 153 (1977)), and so forth. In addition to these methods, introducing a recombinant DNA into protoplast- or spheroplast-like recipient cells, which have been reported to be applicable to *Bacillus subtilis*, actinomycetes, and yeasts (Chang, S, and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of microorganisms can also be performed by the electric pulse method (JP2-207791A).

The copy number of a yggB gene can also be increased by integrating multiple copies of the gene into a chromosomal DNA of a coryneform bacterium. In order to integrate multiple copies of a yggB gene into a chromosomal DNA of a coryneform bacterium, homologous recombination can be carried out by targeting a sequence which exists in multiple copies on a chromosomal DNA. Repetitive DNA and inverted repeats at the end of a transposon can be used as a sequence which exists in multiple copies on a chromosomal DNA. Alternatively, as disclosed in EP0332488B and Vertes, A. A., Asai, Y., Inui, M., Kobayashi, M., Kurusu, Y. and Yukawa, H.: Mol. Gen. Genet., 245, 397-405 (1994), it is also possible to incorporate a yggB gene into a transposon, and transfer it so that multiple copies of the yggB gene are integrated into the chromosomal DNA.

Furthermore, a yggB gene can also be incorporated into a host chromosome by using Mu phage (EP0332488B) or conjugation method (Biotechnology (NY). 1991 January; 9 (1): 84-7). Furthermore, the copy number of the yggG gene can also be increased by using the artificial transposon described below.

Furthermore, yggB gene may be amplified on a chromosome by inserting the yggB gene into a plasmid which has a replication origin not capable of replicating in a host coryneform bacterium or into a plasmid which has a replication origin not capable of replicating in a host coryneform bacterium and has an ability to transfer by conjugation. Examples of such a plasmid include pSUP301 (Simo et al., Bio/Technology 1, 784-791 (1983)), pK18mob and pK19mob (Schaefer et al., Gene 145, 69-73 (1994)), pGEM-T (Promega corporation, Madison, Wis., USA), pCR2.1-TOPO (Shuman (1994) Journal of Biological Chemistry 269: 32678-84; U.S. Pat. No. 5,487,993), pCR(R)Blunt (Invitrogen, Groningen, Netherlands; Bernard et al., Journal of Molecular Biology, 234: 534-541 (1993)), pEM1 (Schrumpf et al., 1991, Journal of Bacteriology 173: 4510-4516), and pBGS8 (Spratt et al., 1986, Gene, 41:337-342). A plasmid containing a yggB gene is transferred into coryneform bacterium by conjugation or transformation. Gene transfer by conjugation can be performed, for example, by a method described in Schaefer et al. (Applied and Environmental Microbiology 60, 756-759 (1994)). Gene transfer by transformation can be performed, for example, by a method described in Theirbach et al. (Applied Microbiology and Biotechnology 29, 356-362 (1988)), Dunican and Shivinan (Bio/Technology 7, 1067-1070 (1989)), and Tauch et al. (FEMS Microbiological Letters 123, 343-347 (1994)).

Enhancing the expression of a yggB gene can also be attained by replacing an expression regulatory sequence, including a promoter of the yggB gene, on a chromosomal DNA or on a plasmid, with a stronger one, by modifying an element involved in regulating expression of the yggB gene such as an operator and/or a repressor, or by fusing a strong terminator downstream the stop codon of the yggB gene (Hamilton et al.; Journal of Bacteriology 171:4617-4622). For example, the lac promoter, trp promoter, trc promoter, PL promoter, PS2 promoter (Appl Environ Microbiol. 2003 January; 69 (1):358-66; Mol Microbiol. 1993 July; 9 (1):97-109; WO93/03158), and so forth are known as strong promoters. A method for evaluating the strength of promoters and examples of strong promoters are disclosed in Goldstein et al. (Prokaryotic promoters in biotechnology. Biotechnol. Annul. Rev., 1995, 1, 105-128). Moreover, it is also possible to introduce several nucleotide substitutions into the promoter region for the yggB gene so that the promoter is stronger (WO00/18935). For example, the "−35 region" may be replaced with "TTGACA" or "TTGCCA", or the "−10 region" may be replaced with "TATAAT" or "TATAAC". Furthermore, it is known that a spacer sequence between the ribosome binding site (RBS) and translation initiation codon, especially, several nucleotides just upstream of the initiation codon, has a great influence on translation efficiency. Therefore, this sequence may be modified. "Expression regulatory sequence" of yggB gene means a region which influences the expression amount of yggB gene, and an example thereof includes an upstream region of yggB gene. The upstream region suitable for modification to enhance yggB gene expression includes a region upstream of the translation initiation codon of the yggB gene (for example, a region upstream of the nucleotide 1436 of SEQ ID NO: 5), and a preferable example thereof includes a region at least 500 bp upstream of the translation initiation codon, and a more preferable example thereof includes a region at least 300 bp upstream the translation initiation codon.

The substitution of an expression regulatory sequence can also be attained by, for example, using a temperature-sensitive plasmid as described above.

Modifying the expression regulatory sequence may be combined with increasing the copy number of the yggB gene.

<II> Introduction of a Mutant-Type yggB Gene

A modification using the yggB gene may be introducing a mutant-type yggB gene into a coryneform bacterium. Introduction of a mutant-type yggB gene includes introducing a mutation into a chromosomal yggB gene, introducing a plasmid comprising a mutant-type yggB gene, and replacement of a chromosomal yggB gene with a mutant-type yggB gene.

In the present invention, the "mutant-type yggB gene" means a yggB gene comprising a mutation in its coding region which allows the yggB gene to enhance L-glutamic acid-producing ability of a coryneform bacterium in the presence of excess biotin when it is introduced into the coryneform bacterium. A mutant-type yggB gene may be a gene which enhances L-glutamic acid-producing ability of coryneform bacterium under L-glutamic acid-producing conditions as well as in the presence of excess biotin, when it is introduced into the coryneform bacterium.

The phrase "L-glutamic acid-producing ability of coryneform bacterium in the presence of excess biotin is enhanced" means that, when the coryneform bacterium of the present invention is cultured in a medium containing biotin at a concentration which a non-modified strain of coryneform bacterium cannot substantially produce L-glutamic acid, for example, in a medium containing not less than 30 µg/L of biotin, the strain causes accumulation of more L-glutamic acid in the medium than that of a non-modified strain, or the strain produces L-glutamic acid at higher rates than that of the non-modified strain.

Hereinafter, examples of the method of obtaining the mutant-type yggB gene of the present invention and the method of introducing the mutant-type yggB gene are described. However, the method of obtaining the mutant-type yggB gene of the present invention and the method of introducing the mutant-type yggB gene are not limited to these examples.

(II-1) Method of Utilizing odhA Gene-Deficient Strain

The inventors of the present invention have found that a mutant type yggB gene can be efficiently obtained by using an odhA (sucA) gene-disrupted strain in which a gene encoding the E1o subunit of α-ketoglutarate dehydrogenase is disrupted.

In the present invention, α-ketoglutarate dehydrogenase (α-KDGH) activity means an activity to catalyze the oxidative decarboxylating of α-ketoglutaric acid (2-oxoglutaric acid) to generate succinyl-CoA. The reaction is catalyzed by three kinds of enzymes, i.e., α-ketoglutarate dehydrogenase (E1o EC1.2.4.2), dihydrolipoamide-5-succinyltransferase (E2o), and dihydrolipoamide dehydrogenase (E3). α-ketoglutarate dehydrogenase is also called oxoglutarate dehydrogenase (succinyl-transferase) or 2-oxoglutarate dehydrogenase. The α-KGDH activity can be measured by the method of Shiio et al. (Isamu Shiio and Kyoko Ujigawa-Takeda, Agric. Biol. Chem., 44 (8), 1897-1904, 1980).

The nucleotide sequence of the gene encoding the E1o subunit of α-ketoglutarate dehydrogenase (odhA) of coryneform bacterium has already been identified (Microbiology 142, 3347-3354, (1996), GenBank accession No. D84102). The nucleotide sequence of the odhA gene is shown in nucleotides 443-4213 of SEQ ID NO: 43 and the amino acid sequence of the odhA gene is shown in SEQ ID NO: 44.

The odhA gene-disrupted strain can be obtained, for example, by a method using the above-mentioned sacB gene. At first, the internal sequence of odhA gene is amplified by PCR using primers designed based on the nucleotide sequence of the odhA gene, such as those shown in SEQ ID NOS: 1 and 2, and a chromosomal DNA of coryneform bacterium such as ATCCC13869 strain as a template. The internal fragment of the odhA gene is inserted into a plasmid to construct a plasmid for odhA gene-disruption. The plasmids used for gene disruption include temperature-sensitive plasmids for coryneform bacteria (JP-A-05-00791), and pBS3, which is a suicide vector that comprises a sacB gene as described in Example 1.

The obtained plasmid is introduced into a strain that cannot cause accumulation of L-glutamic acid in the presence of excess biotin, for example, a wild-type *C. glutamicum* ATCC13869, ATCC13032 strain, by the electric pulse method (JP-A-2-207791). A single cross-over recombinant is obtained in which homologous recombination between the mutant-type odhA gene on the plasmid and the chromosomal odhA gene has occurred. When the temperature-sensitive plasmid is used, a single cross-over recombinant is obtained at a temperature at which the plasmids cannot replicate. Whether the strain is a single cross-over recombinant or not can be confirmed, for example, by using oligonucleotides of SEQ ID NOS: 3 and 4.

The thus obtained odhA gene-disrupted strain is isolated in a medium containing sugar. In the process of isolation, a spontaneous mutation is introduced into the chromosomal yggB gene at a high frequency. Then, the ability of the isolated strain to produce L-glutamic acid is evaluated by culturing the strain in a medium containing excess biotin. For example, a candidate strain is inoculated in 20 ml of culture medium (30 g/l glucose, 15 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l vitamin B1, 300 µg/l biotin, 0.48 g/l soybean hydrolysates (total nitrogen), adjusted to pH 8.0 with KOH: autoclaved at 115° C. for 10 minutes), followed by addition of 1 g of heat-sterilized calcium carbonate, and the strain is cultured with shaking. After the sugar is completely consumed, the amount of accumulated L-glutamic acid is measured. Strains which produce L-glutamic acid, for example, those which produce not less than 50% (yield per sugar) of L-glutamic acid are selected, and the nucleotide sequence of the yggB gene of the selected strains are determined to obtain a strain in which a mutation is introduced into the yggB gene.

To construct a strain carrying only the mutant-type yggB gene, it is preferable to replace the odhA gene on the chromosome disrupted by the plasmid with a wild-type odhA gene. Strains deficient in the odhA gene grow considerably slower in a medium without sugar. However, when the odhA gene reverts to the wild-type gene, the strain can grow well in a medium without sugar, for example, CM2B medium (10 g/l polypeptone, 10 g/l yeast extract, 5 g/l NaCl, 10 µg/l biotin, 20 g/l agar, adjusted to pH 7.0 with KOH). Therefore, the odhA gene-disrupted strain is spread over a CM2B plate to select growth-improved strains. The thus appeared growth-improved strains are purified on the CM2B plate, and whether the strain has the wild-type odhA gene can be estimated by testing the sensitivity of the strain to antibiotics based on the absence of remaining vectors. Furthermore, the nucleotide sequence of the odhA gene may be determined.

Alternatively, the mutant-type yggB gene may be cloned from the odhA-yggB double mutant strain, and introduced into a wild-type strain. For example, the mutant-type yggB gene can be amplified by performing PCR using the chromosomal DNA of the double mutant strain as a template and the primers shown in SEQ ID NOS: 9 and 10. The amplified product is inserted in a temperature-sensitive plasmid for coryneform bacteria, such as pHSC4 (JP-A-05-007491), or pBS3, a suicide vector described in Example 1 to replace a wild-type yggB gene on a chromosome with the mutant-type yggB gene. Whether a mutation is introduced into the yggB on the chromosome can be confirmed by determining the nucleotide sequence of the yggB gene on the chromosome.

(II-2) Method of Utilizing a Transposable Element

The coryneform bacteria having a mutant-type yggB gene may also be screened for by using a transposable element in coryneform bacteria. The transposable element may include an insertion sequence (IS) and an artificial transposon. The mutant-yggB gene may be a gene having an IS and/or transposon accidentally-inserted into the coding region, or a gene obtained artificially by using the artificial transposon. A strain in which a transposable element is inserted can be selected, for example, based on a decrease in sensitivity to 1-glutamic acid analogs. As an L-glutamic acid analog, 4-fluoroglutamic acid can be used. Furthermore, a strain in which a transposable element is inserted can be selected by randomly selecting antibiotics-resistant strains with an artificial transposon containing an antibiotics-resistant gene, and confirming a length of a yggB gene of the antibiotics-resistant strains by PCR.

The method described in JP-A-09-070291 may be used to introduce the IS into coryneform bacteria. An artificial transposon which includes a structural gene of a transposase and a marker gene sandwiched between inverted repeats (IR) on both sides of the IS may be used. In this case, the structural gene of a transposase may be present together with the marker gene and IS in the same plasmid or may be on a separate plasmid. Alternatively, the function of the transposon that is present on the chromosome of the host coryneform bacterium may be utilized. Examples of genes encoding a transposase derived from coryneform bacterium are shown by GenBank Accession numbers.

1. NCgl0179 Cgl0182; transposase
2. NCgl0235 Cgl0238; putative transposase
3. NCgl0348 Cgl0355; putative transposase
4. NCgl0688 Cgl0718; putative transposase
5. NCgl0919 Cgl0959; transposase
6. NCgl0993 Cgl1037; transposase
7. NCgl1021 Cgl1066; transposase
8. NCgl1464 Cgl1521; putative transposase
9. NCgl1496 Cgl1557; transposase
10. NCgl1662 Cgl1733; putative transposase
11. NCgl1664 Cgl1734; transposase
12. NCgl2131 Cgl2212; transposase
13. NCgl2284 Cgl2367; transposase
14. NCgl2392 Cgl2479; putative transposase
15. NCgl2418 Cgl2504; putative transposase
16. NCgl2420 Cgl2506; putative transposase
17. NCgl2460 Cgl2548; predicted transposase
18. NCgl2542 Cgl2631; predicted transposase
19. NCgl2665 Cgl2761; putative transposase
20. NCgl2748 Cgl2845; putative transposase
21. NCgl2850 Cgl2951; predicted transposase The IS or artificial transposon may be introduced into coryneform bacteria using a suitable vector, for example, a plasmid replicable in coryneform bacteria. Specific examples of the plasmid include pHM1519 (Agric. Biol. Chem., 48, 2901-2903 (1984)), pAM330 (Agric. Biol. Chem., 48, 2901-2903 (1984)), and plasmids obtained by modifying these to carry a drug-resistant gene. Furthermore, to efficiently amplify the IS or artificial transposon on the chromosome, a plasmid having a temperature-sensitive replication origin as described in the above (1) is preferably used (see JP-A-5-7491). The parent strain used for this screening is preferably a strain that cannot cause accumulation of L-glutamic acid in the presence of excess biotin, for example, the ATCC13869 strain, which is a wild-type strain of *C. glutamicum*.

As the method of introducing the plasmid carrying the IS or artificial transposon into coryneform bacteria, conventionally used methods, such as the protoplast method (Gene, 39, 281-286 (1985)), electroporation method (Bio/Technology, 7, 1067-1070 (1989)), and the like may be used.

Introduction of the IS or artificial transposon carried on the temperature-sensitive plasmid into coryneform bacteria can be performed by transforming the coryneform bacteria with the plasmid, culturing the transformants at 25° C. at which the plasmids can replicate to amplify the IS or artificial transposon at several tens to several hundreds copies per cell to enable introduction of the IS or artificial transposon into the chromosome, and then culturing the cells at 34° C. to remove the excess plasmids. Alternatively, a DNA fragment of only IS or artificial transposon or a plasmid vector that cannot replicate in coryneform bacteria (for example, plasmid vector replicable in *Escherichia coli*) may be used to introduce the IS or artificial transposon into the chromosome of the coryneform bacteria (JP-A-7-107976, Vertes, A. A., Asai, Y., Inui, M., Kobayashi, M., Kurusu, Y. and Yukawa, H.: Mol. Gen. Genet., 245, 397-405 (1994)).

The strain which has the IS or artificial transposon on the chromosome is cultured in a medium containing excess biotin so to select a strain that causes accumulation of L-glutamic acid. By determining the nucleotide sequence of the yggB gene on the chromosome of this strain, a coryneform bacterium having a mutant-type yggB gene can be obtained.

(II-3) Method of Randomly Introducing a Mutation into the yggB Gene In Vitro

Furthermore, the mutant-type yggB gene can be obtained by randomly introducing a mutation into the yggB gene in vitro, introducing the mutated gene into coryneform bacterium, and screening for strains which produce L-glutamic acid in the presence of excess biotin as a result of the presence of the mutant-type yggB gene. The parent strain useful for screening is preferably a strain that cannot cause accumulation of L-glutamic acid in the presence of excess biotin, for example, *Corynebacterium glutamicum* ATCC13869 strain, ATCC13032 strain, ATCC14067 strain, and *Corynebacterium melassecola* ATCC17965 strain.

To screen for a mutant-type yggB gene, a yggB-deficient strain is preferably used. The construction of the yggB gene-disrupted strain can be performed by a method similar to the above-mentioned method in which the sacB gene is used. For example, PCR is performed using primers shown in SEQ ID NOS: 39 and 40 and the chromosomal DNA of *C. glutamicum* ATCC13869 as a template to prepare an N-terminal fragment of the yggB gene. Similarly, PCR is performed using synthetic DNAs of SEQ ID NOS: 41 and 42 as primers to prepare a C-terminal fragment. SEQ ID NOS: 40 and 41 are complementary to each other. Subsequently, PCR is performed using a mixture of equimolar amounts of the N-terminal fragment and the C-terminal fragment as a template and synthetic DNAs of SEQ ID NOS: 39 and 42 as primers to prepare a fragment in which an internal sequence of yggB gene is deleted.

The obtained PCR fragment is inserted into a plasmid for gene disruption, for example, pBS4S carrying the levan sucrase gene. The obtained plasmid is introduced into the chromosome of coryneform bacterium, for example, *C. glutamicum* ATCC13869 strain to construct a yggB gene-disrupted strain.

Then, for example, in vitro mutagenesis of the yggB gene can be performed as follows. First, yggB is cloned into a plasmid that can replicate in coryneform bacterium. About 10 µg of the obtained yggB gene-carrying plasmid is dissolved in a buffer containing mutagens, for example, 500 mM phosphate buffer containing 400 mM hydroxylamine and 1 mM EDTA (pH 6.0), and heated at 75° C. for 60 to 90 minutes to introduce a mutation into the yggB gene. After mutagenesis, the plasmid is desalted with SUPREC-02 (Takara Bio INC.) or the like, and then introduced into ATCC13869 ΔyggB strain, and transformants are screened in a medium containing an antibiotic. As a control, yggB gene-carrying plasmid without mutagenesis is introduced into the ATCC13869 ΔyggB strain. The emerged transformants are inoculated into a medium containing excess biotin and cultured with shaking, and then the concentration of accumulated L-glutamic acid is determined. L-glutamic acid does not substantially accumulate in a medium in which the wild-type yggB gene-carrying plasmid-introduced strain is cultured, whereas a significant amount of L-glutamic acid accumulates in a medium in which the mutant-type yggB gene-carrying plasmid-introduced strain is cultured. Whether the strain carries a mutant-type yggB gene or not can be confirmed by extracting a plasmid from the strain and determining the nucleotide sequence of the yggB gene.

Alternatively, a mutant-type yggB gene can be obtained by artificially introducing mutations into the yggB gene by such methods as error prone PCR, DNA shuffling, and StEP-PCR (Firth A E, Patrick W M; Bioinformatics. 2005 Jun. 2; Statistics of protein library construction).

The methods of introducing a mutation into the yggB gene on the chromosome include, besides the above-mentioned method, a method of treating a coryneform bacterium with irradiation of X-rays or ultraviolet rays or with a mutagen such as N-methyl-N'-nitro-N-nitrosoguanidine, and selecting a strain which produces L-glutamic acid in the presence of excess biotin. Whether the mutant-type yggB gene has been introduced or not can be confirmed by determining the nucleotide sequence of the yggB gene on the chromosome.

(II-4) Method of Screening L-Glutamic Acid Analog-Resistant Strains

Mutant-type yggB genes may be obtained by culturing a coryneform bacterium having a wild-type yggB gene in a medium containing an L-glutamic acid analog, and selecting L-glutamic acid analog-resistant strains which can grow in the medium. A parent strain used in this method is preferably a wild-type strain of coryneform bacterium as described above, and may be any strain having a wild-type yggB gene, including a strain having a plasmid containing a wild-type yggB gene.

"L-glutamic acid analogs" as used herein include γ-methyl L-glutamate, α-methyl glutamic acid, β-hydroxyglutamic acid, methioninesulfoximine, glutamic acid-γ-monohydroxamate, 2-amino-4-phosphonobutyric acid, γ-monoethyl L-glutamate, dimethyl L-glutamate, di-t-butyl L-glutamate, monofluoroglutamic acid, diethyl L-glutamate, D-glutamic acid, and 4-fluoroglutamic acid, and among these, 4-fluoroglutamic acid is preferably used. For example, L-glutamic acid analog-resistant strains can be obtained as follows. That is, a coryneform bacterium is inoculated on a minimum medium containing an L-glutamic acid analog, and colonies that have appeared after 24-48 hours are collected. Concentration of the L-glutamic acid analog added to the medium is preferably a concentration at which a strain having a non-mutated yggB gene cannot grow and a strain having a mutated yggB gene can grow. Specifically, the concentration of 4-fluoroglutamic acid is 1.25 mM or more, preferably 2.5 mM or more, and more preferably 5 mM or more. For example, "L-glutamic acid analog-resistant strain" as used herein means that when the strain is cultured in a minimum medium containing 4-fluoroglutamic acid where the viable cell count (number of cells capable of forming colonies) of a wild-type strain is suppressed to not more than 1/100 that of when in the absence of 4-fluoroglutamic acid, the strain exhibits 1/10 or more growth of the strain cultured in the absence of 4-fluoroglutamic acid.

The obtained L-glutamic acid analog-resistant strains are inoculated into a liquid medium containing excess biotin and cultured with shaking, followed by measurement of the concentration of L-glutamic acid which has accumulated in the medium. Whereas a strain having a wild-type yggB gene accumulates little L-glutamic acid, some of the L-glutamic acid analog-resistant strains accumulate a significant amount of L-glutamic acid. The yggB gene is amplified from such a strain and the nucleotide sequence thereof is determined, and thereby, a novel mutant-type yggB gene can be obtained.

(III) Mutant-Type yggB Genes

Hereinafter, specific examples of the mutant-type yggB gene are described. However, the mutant-type yggB gene of the present invention is not limited to these genes.

The mutant type yggB gene obtained by the above-mentioned method is not particularly limited so long as it has a function to enhance the L-glutamic acid-producing ability of a coryneform bacterium in the presence of excess biotin when it is introduced into the coryneform bacterium.

(III-1) Mutation in the C-Terminal Region of the yggB Gene

This mutation is introduced into the region encoding amino acids 419-533 of SEQ ID NO: 6, 68, 84 or 85, or amino acids 419-529 of SEQ ID NO: 62. For example, in SEQ ID NO: 5, this region corresponds to the region consisting of nucleotides 2692 to 3035. This mutation may be of any type, so long as it is introduced into the region, and includes point mutations and insertion of an artificial sequence. Among these, mutations which introduce an insertion sequence (IS) or an artificial transposon are preferable. The mutation may cause amino acid substitution (mis-sense mutation), frame-shift, or stop codon (non-sense mutation) as a result of the point mutation, insertion of IS, or transposon.

(III-1-1) The Mutation by Insertion of Transposable Element (2A-1 Type Mutation)

Examples of a mutation in the C-terminal region include a mutation which inserts a transposable element such as insertion sequence (IS) next to the "G" at position 2691 of SEQ ID NO: 5. The nucleotide sequence of the mutant-type yggB gene having this mutation is shown in SEQ ID NO: 7, and the amino acid sequence of the mutant type YggB protein encoded by the gene is shown in SEQ ID NO: 8. The IS inserted into the nucleotide sequence of SEQ ID NO: 7 has high homology to IS1207 (GenBank accession No. X96962) and IS719 (GenBank accession No. E12759). In the amino acid sequence of SEQ ID NO: 8, the C-terminal region containing the Val at position 419 and thereafter of the Ygg protein (SEQ ID NO: 6) is replaced by a shorter IS-derived sequence. This type of mutation, including the mutations changing or deleting the C-terminal region in the amino acid sequence of SEQ ID NOS: 6, 62, 68, 84 and 85, is named a 2A-1-type mutation.

Furthermore, the 2A-1-type mutation also includes other mutations which introduce another IS or transposon into the same site as the 2A-1 type mutation. The position at which the IS or transposon is inserted may be any position so long as it is located within the above-described region. It is preferable that an IS is inserted into a position where the transposase can readily recognize it, or hot spots where an IS is easy to insert.

(III-1-2) The mutation which results in replacement of the proline with another amino acid (66-type and 22-type mutations) Furthermore, an example of a mutation in the C-terminal region also includes a mutation which results in replacement of the proline in C-terminal region with another amino acid. The prolines at the following positions may be substituted with another amino acid in the amino acid sequence of SEQ ID NO: 6.

Pro at position 424 (424 in SEQ ID NO: 62, 68, 84, 85)
Pro at position 437 (437 in SEQ ID NO: 62, 68, 84, 85)
Pro at position 453 (453 in SEQ ID NO: 62, 68, 84, 85)
Pro at position 457 (457 in SEQ ID NO: 62, 68, 84, 85)
Pro at position 462 (462 in SEQ ID NO: 62, 68, 84, 85)
Pro at position 469 (469 in SEQ ID NO: 62, 68, 84, 85)
Pro at position 484 (484 in SEQ ID NO: 62, 68, 84, 85)
Pro at position 489 (489 in SEQ ID NO: 62, 68, 84, 85)
Pro at position 497 (497 in SEQ ID NO: 62, 68, 84, 85)
Pro at position 515 (515 in SEQ ID NO: 62, 68, 84, 85)
Pro at position 529 (529 in SEQ ID NO: 68, 84, 85, 525 in SEQ ID NO:62)
Pro at position 533 (533 in SEQ ID NO: 68, 84, 85, 529 in SEQ ID NO:62)

It is considered that the proline residues in the C-terminal region of the YggB protein play an important role in maintenance of three-dimensional structure of the YggB protein (Protein Eng. 2002 January; 15 (1):29-33, J Biol Chem. 1991 Dec. 25; 266 (36):24287-94).

Especially, replacing the proline at position 424 and/or the proline at position 437 in SEQ ID NO: 6, 62, 68, 84 or 85 with another amino acid are preferable.

Examples of the other amino acid include Ala, Arg, Asp, Asn, Cys, Glu, Gln, Gly, His, Ile, Met, Leu, Lys, Phe, Ser, Trp, Tyr, Val, and Thr. As the other amino acid replacing the proline at position 424, hydrophobic amino acids such as Ala, Gly, Val, Leu, and Ile are preferable, and amino acids having branched chain such as Leu, Val, and Ile are more preferable. An example of a mutation which replaces Pro at position 424 with Leu includes a mutation which replaces "C" at position 1673 with "T" in SEQ ID NO: 67. The nucleotide sequence of the mutant type yggB gene having this mutation is shown in SEQ ID NO: 69 and the amino acid sequence of the mutant type YggB protein encoded by the gene is shown in SEQ ID NO: 70.

As the other amino acid replacing the proline at position 437, amino acids containing a hydroxyl-group such as Thr, Ser, Tyr are preferable, and amino acids having Ser are more preferable. An example of a mutation which replaces Pro at position 437 with Ser includes a mutation which replaces "C" at position 2745 with "T" in SEQ ID NO:5. Moreover, this mutation may be accompanied by the mutation which replaces the "C" at position 3060 with "T" in SEQ ID NO: 5. The nucleotide sequence of the mutant type yggB gene having this mutation is shown in SEQ ID NO: 73 and the amino acid sequence of the mutant type YggB protein encoded by the gene is shown in SEQ ID NO: 74.

(III-2) Mutation in a Transmembrane Region of the yggB Gene

The YggB protein encoded by the yggB gene is presumed to have five transmembrane regions. In the amino acid sequence of the wild-type YggB protein shown in SEQ ID NOs: 6, 62, 68, 84 and 85, the transmembrane regions correspond to amino acids 1 to 23 (first transmembrane region), amino acids 25 to 47 (second transmembrane region), amino acids 62 to 84 (third transmembrane region), amino acids 86 to 108 (fourth transmembrane region), and amino acids 110 to 132 (fifth transmembrane region). In SEQ ID NO: 5, nucleotides encoding these regions correspond to nucleotides 1437 to 1505, nucleotides 1509 to 1577, nucleotides 1620 to 1688, nucleotides 1692 to 1760, and nucleotides 1764 to 1832, respectively. This type of mutation is preferably introduced into these regions. This kind of mutation preferably introduces a substitution, deletion, addition, insertion, or inversion of one or more amino acids into these regions without causing a frame shift mutation and a translation termination. Among these, mis-sense mutations causing amino acid substitutions in the above-mentioned regions is preferable. The number of "several" amino acids to be substituted, deleted, added, inserted, or inverted means 2 to 20, preferably 2 to 10, more preferably 2 to 5, and still more preferably 2 or 3. The mutations causing insertion and deletion of one or several amino acids without a frame shift are also preferable, and, more preferably, insertion or deletion of 3, 6, 9, 12, 15, 18 or 21 nucleotides, still more preferably, deletion or insertion of 3, 6, or 9 nucleotides, and much more preferably, deletion or insertion of 3 nucleotides.

Specific examples of a mutation in the transmembrane regions include the following:

(III-2-1) Mutation in the First Transmembrane Region (A1-Type Mutation)

This type of mutation includes one which introduces one or more amino acids between the leucine at position 14 and the tryptophan at position 15 in the amino acid sequence shown by SEQ ID NOs: 6, 62, 68, 84 and 85, and more specifically includes a mutation which introduces three amino acids, for example, Cys-Ser-Leu, between the Leu at position 14 and the tryptophan at position 15. This mutation includes insertion of TTCATTGTG next to the G at position 1480 in the wild-type yggB gene of SEQ ID NO: 5. The nucleotide sequence of the mutant-type yggB gene having this mutation is shown in SEQ ID NO: 19 and the amino acid sequence of the mutant type YggB protein encoded by the gene is shown in SEQ ID NO: 20.

(III-2-2) Mutation in the 4Th Transmembrane Region (19-Type Mutation)

This type of mutation includes replacing the Ala at position 100 with another amino acid in the amino acid sequence shown in SEQ ID NOs: 6, 62, 68, 84 and 85. Examples of the other amino acid include Arg, Asp, Asn, Cys, Glu, Gln, Gly, His, Ile, Met, Leu, Lys, Phe, Pro, Ser, Trp, Tyr, Val, and Thr. Of these, amino acids containing a hydroxyl-group such as Thr, Ser, and Tyr are preferable and, threonine is more preferable. A mutation which replaces the Ala at position 100 with Thr includes a mutation which replaces the "G" at position 1734 with "A" of SEQ ID NO: 5.

The nucleotide sequence of the mutant type yggB gene having this mutation is shown in SEQ ID NO: 21 and the amino acid sequence of the mutant type YggB protein encoded by the gene is shown in SEQ ID NO: 22.

(III-2-3) Mutation in the 5Th Transmembrane Region (L30-Type Mutation, 8-Type Mutation)

This type of mutation includes one which replaces the Ala at position 111 with another amino acid in the amino acid sequence shown in SEQ ID NOs: 6, 62, 68, 84 and 85. Examples of the other amino acid include Arg, Asp, Asn, Cys, Glu, Gln, Gly, His, Ile, Met, Leu, Lys, Phe, Pro, Ser, Trp, Tyr, Val, and Thr. Of these, amino acids containing branched chains such as Val, Ile, and Leu, and amino acids containing hydroxyl-group such as Thr, Ser, and Tyr are preferable, and Val or Thr is preferable. This type of mutation includes one which replaces the "C" at position 1768 with a "T" in the nucleotide sequence of SEQ ID NO: 5 (L30-type mutation), and a mutation which replaces the "G" at position 837 with an "A" in the nucleotide sequence of SEQ ID NO: 61 (8-type mutation). The nucleotide sequence of the mutant-type yggB gene having an L30-type mutation is shown in SEQ ID NO: 23 and the amino acid sequence of the mutant type YggB protein encoded by this gene is shown in SEQ ID NO: 24. The nucleotide sequence of the mutant-type yggB gene having 8-type mutation is shown in SEQ ID NO: 63 and the amino acid sequence of the mutant type YggB protein encoded by this gene is shown in SEQ ID NO: 64.

(IV) Equivalents of the Mutant-Type yggB Genes

The "mutant type yggB gene" used in the present invention may be a functionally equivalent gene that is substantially homologous to the above-mentioned "mutant type yggB genes", for example, a mutant type gene comprising a nucleotide sequence that is able to hybridize to a nucleotide sequence complementary to at least one of the nucleotide sequences selected from the group consisting of the nucleotides 1437 to 2705 of SEQ ID NO: 7, the nucleotides 1437 to 3044 of SEQ ID NO: 19, the nucleotides 1437 to 3035 of SEQ ID NO: 21, the nucleotides 507 to 2093 of SEQ ID NO: 63, the nucleotides 403 to 2001 of SEQ ID NO: 69, and the nucleotides 1437 to 3035 of SEQ ID NO: 23, the nucleotides 548 to 2146 of SEQ ID NO: 73 with a probe prepared from these nucleotide sequences under stringent conditions, so long as the gene has a function to enhance L-glutamic acid-producing ability of a coryneform bacterium in the presence of excess biotin.

"Stringent conditions" as used herein are conditions under which a so-called specific hybrid is formed, and a non-specific hybrid is not formed. Examples of stringent conditions include, those under which DNAs having high homology hybridize to each other, for example, DNAs having a homology of not less than 70%, preferably not less than 80%, more preferably not less than 90%, especially preferably not less than 95%, hybridize to each other, and DNAs having homology lower than 70% do not hybridize to each other, and those under which DNAs hybridize to each other at a salt concentration with washing typical of Southern hybridization, i.e., washing once or preferably 2-3 times under 1×SSC, 0.1% SDS at 60° C., preferably 0.1×SSC, 0.1% SDS at 60° C., more preferably 0.1×SSC, 0.1% SDS at 68° C.

The mutant-type yggB gene used in the present invention includes a gene encoding a protein having the amino acid sequence of SEQ ID NOs: 8, 20, 22, 24, 64, 70, or 74 whereby one or more amino acids are replaced, deleted, inserted or added at one or more positions other than the specific amino acid as described above, while maintaining a function to enhance L-glutamic acid-producing ability of a coryneform bacterium in the presence of excess biotin. Although the number of "several" amino acid residues referred to herein may differ depending on positions in the three-dimensional structure or types of amino acid residues of the protein, it may be preferably 2 to 20, more preferably 2 to 10, particularly preferably 2 to 5.

The yggB gene preferably encodes a protein having the above-described specific amino acid substitution or deletion and having homology of not less than 70%, more preferably not less than 80%, further more preferably not less than 90%, particularly preferably not less than 95% to the amino acid sequence shown in SEQ ID NOs: 8, 20, 22 or 24, 64, 70, or 74 while maintaining a function to enhance L-glutamic acid-producing ability of a coryneform bacterium in the presence of excess biotin. The above-mentioned substitution is preferably a conservative substitution (neutral mutation). In the case of aromatic amino acids, conservative substitutions include substitutions of phe, trp, and tyr for each other. In the case of hydrophobic amino acids, conservative substitutions include substitutions of leu, ile, and val for each other. In the case of polar amino acids, conservative substitutions include substitutions of gln and asn for each other. In the case of basic amino acids, conservative substitutions include substitutions of arg, lys, and his for each other. In the case of acidic amino acids, conservative substitutions are substitutions of asp and glu for each other. In the case of hydroxyl group-containing amino acids, conservative substitutions include substitutions of ser and thr for each other. The conservative substitutions also include: substitution of ser or thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Be, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr and substitution of Met, Ile or Leu for Val. As mentioned above, the amino acids shown as Xaa may be substituted in the amino acid sequence of SEQ ID NO: 85.

Especially, the following amino acids may be substituted or deleted in the amino acid sequences of SEQ ID NO: 8, 20, 22, 24, 64, 70, or 74.

Glu at position 48 (preferably replaced by Arg)
Asp at position 275 (preferably replaced by Ser)
Glu at position 298 (preferably replaced by Ala)
Ala at position 343 (preferably replaced by Val)
Phe at position 396 (preferably replaced by Ile)
Ser at position 438 (preferably replaced by Gly)
Val at position 445 (preferably replaced by Ala)
Ala at position 454 (preferably replaced by Val)
Pro at position 457 (preferably replaced by Ser)
Ser at position 474 (preferably replaced by Asp)
Val at position 517 (preferably deleted)
Glu at position 518 (preferably deleted)
Ala at position 519 (preferably deleted)
Pro at position 520 (preferably deleted)

(V) Methods of Introducing the Above-Described Mutant-Type yggB Genes into Coryneform Bacterium The mutant-type yggB gene having the above-mentioned specific mutation can be obtained by conventional methods including a site-directed mutagenesis technique. The site-directed mutagenesis technique includes an overlap extension PCR method that amplifies a mutant gene using a PCR primer having a mutation (Urban, A., Neukirchen, S, and Jaeger, K. E., A rapid and efficient method for site-directed mutagenesis using one-step overlap extension PCR. Nucleic Acids Res, 25, 2227-8. (1997)).

The coryneform bacterium of the present invention having the above-mentioned mutant-type yggB gene can be obtained by introducing the above-mentioned mutant-type yggB gene into a coryneform bacterium. A wild-type yggB gene on a chromosome may be replaced with the mutant-type yggB gene. The mutant-type yggB gene may be introduced into a coryneform bacterium in which a wild-type yggB gene is disrupted. In addition, as in the case of single cross-over recombinants, the mutant type yggB gene may co-exist with a wild-type yggB gene in a coryneform bacterium. For example, the substitution of the yggB gene on the chromosome can be performed by using, for example, a temperature-sensitive plasmid containing a sacB gene encoding the above-mentioned levan sucrase. Furthermore, to introduce the mutant type yggB gene into coryneform bacterium, a vector such as a plasmid replicable in coryneform bacterium or transposon comprising the mutant type yggB gene may be used.

To introduce the mutant type yggB gene into the chromosomal DNA of the coryneform bacteria, it is also possible to perform homologous recombination by targeting a sequence that is present on the chromosomal DNA in multiple copies. Examples of such a sequence include a repetitive DNA and an inverted repeat that is present on the end of a transposable element. The mutant type yggB gene may exist in coryneform bacterium in a single copy or multiple copies. The introduction of the mutant type yggB gene into coryneform bacterium can be confirmed by PCR, Southern hybridization, or the like.

Furthermore, the mutant type yggB gene may be under the control of a potent promoter which is derived from other genes, as described in WO00/18935. For example, lac promoter, trp promoter, trc promoter, PS2 promoter, and so on are known as potent promoters. It is also possible to introduce substitution of nucleotides into the promoter region of the mutant-type yggB gene so that expression of mutant-type yggB gene is enhanced. The substitution of the expression regulating sequence can be performed by using, for example, a temperature-sensitive plasmid.

(VI) L-Glutamic Acid Analog Resistance

Furthermore, the coryneform bacterium of the present invention may have increased resistance to L-glutamic acid analogs as a result of the introduction of the mutant-type yggB gene of the present invention. "L-glutamic acid analogs" as used herein include γ-methyl L-glutamate, α-methyl glutamic acid, β-hydroxyglutamic acid, methioninesulfoximine, glutamic acid-γ-monohydroxamate, 2-amino-4-phosphonobutyric acid, γ-monoethyl L-glutamate, dimethyl L-glutamate, di-t-butyl L-glutamate, monofluoroglutamic acid, diethyl L-glutamate, D-glutamic acid, and 4-fluoroglutamic acid. For example, an increase in resistance to L-glutamic acid analogs is confirmed by the fact that when the strain of the present invention is cultured in a minimum medium containing 4-fluoroglutamic acid at a concentration which the viable cell count (number of cells capable of forming colonies) of the parent strain can be suppressed to not more than 1/100, the strain exhibits 1/10 or more growth as compared to when cultured in the absence of 4-fluoroglutamic acid. Specifically, it is preferable that the strain has a resistance to 1.25 mM or more, preferably 2.5 mM or more, and more preferably 5 mM or more of 4-fluoroglutamic acid.

(VII) Further Modification to Inactivate the Gene which Suppresses the Function of Mutant-Type yggB Gene The coryneform bacterium of the present invention may be further modified so to inactivate a gene which suppresses the function of mutant-type yggB gene. The "gene which suppresses the function of mutant-type yggB gene" means that L-glutamic acid production by a mutant-type yggB gene-introduced strain is suppressed by amplifying the gene in the strain. An example of such a gene includes the symA gene (suppressor of yggB mutation). The symA gene is shown as nucleotide numbers 2051306-2051845 of the genome sequence (Genbank Accession No. NC_003450) of *corynebacterium glutamicum* ATCC13032 strain, and registered as NCgl 1867 (NP_601149. hypothetical prot . . . [gi: 19553147]). The symA gene of *corynebacterium glutamicum* ATCC13869 strain is shown in nucleotides 585-1121 of SEQ ID NO: 86. The symA gene may be a DNA that is able to hybridize with a nucleotide sequence complementary to nucleotides 585 to 1121 of SEQ ID No: 86, or a probe prepared from said nucleotides under stringent conditions, as long as the DNA suppresses a function of said mutant-type yggB gene in the coryneform bacterium.

Gene inactivation can be performed by disrupting the gene, deleting the gene, or modifying it to decrease expression of the gene. Inactivation of the symA gene can be performed using a similar method as the above-described methods for decreasing enzymatic activity.

(VIII) Further Modification to Decrease α-Ketoglutarate Dehydrogenase Activity

In the present invention, a coryneform bacterium is preferably modified so that the activity of α-ketoglutarate dehydrogenase (hereinafter, referred to as "α-KGDH") is decreased in addition to the modification using a yggB gene. The "α-KGDH activity is decreased" means that the α-KGDH activity is decreased as compared with that of the wild-type strain or non-modified strains, such as the parent strain. The α-KGDH activity can be measured according to the method of Shiio et al. (Isamu Shiio and Kyoko Ujigawa-Takeda, Agric. Biol. Chem., 44 (8), 1897-1904, 1980). Although it is sufficient that the α-KGDH activity is decreased as compared to a non-modified strains such as a wild-type strain or a parent strain, it is preferable that the α-KGDH activity is decreased to about ½ time or less, preferably about ¼ time or less, and more preferably about 1/10 time or less with respect to a wild-type or non-modified strain. The coryneform bacterium of the present invention may not have a detectable activity of α-KGDH.

The coryneform bacterium in which the α-KGDH activity is decreased can be constructed in a similar way as described above.

For example, α-KGDH activity may be decreased by introducing a gene encoding the E1o subunit of the α-KGDH complex having a mutation in the thiamine pyrophosphate-binding region (the region encoded by nucleotides 2498 to 2584 of SEQ ID NO: 43 (686Gly-714Asp of SEQ ID NO: 44)).

Examples of the strain having a decreased activity of α-KGDH include *Brevibacterium lactofermentum* ΔS strain (WO95/34672) and *Brevibacterium lactofermentum* AJ12821 (FERM BP-4172) strain (JP-A-06-237779). When using a coryneform bacterium carrying the mutant-type yggB gene and having decreased α-KGDH activity, either decreasing α-KGDH activity or introducing the mutant type yggB gene may be performed first.

<2> Method of Producing L-Glutamic Acid

L-glutamic acid can be produced by culturing the coryneform bacterium of the present invention in a medium to cause accumulation of L-glutamic acid in the medium and/or in the bacterial cells, and collecting the L-glutamic acid from the medium and/or the bacterial cells. In the production method of the present invention, L-glutamic acid is produced preferably by culturing the coryneform bacterium of the present invention, for example, at 25 to 40° C. for 8 to 120 hours.

The culture medium may be an ordinary medium that contains a carbon source, a nitrogen source, an inorganic salt, and optionally organic micronutrients such as amino acids and vitamins. Either a synthetic medium or a natural medium may be used. Any kind of carbon and nitrogen source may be used so long as they can be utilized by the strain being cultured.

Saccharides such as glucose, glycerol, fructose, sucrose, maltose, mannose, galactose, starch hydrolysate, and molasses may be used as the carbon source. In addition, organic acids such as acetic acid and citric acid, and alcohols such as ethanol may also be used alone or in combination as a carbon source. Ammonia, ammonium salts such as ammonium sulfate, ammonium carbonate, ammonium chloride, ammonium phosphate, and ammonium acetate, nitrates, and the like may be used as the nitrogen source. Amino acids, vitamins, fatty acids, nucleic acids, substances containing peptone, casamino acid, yeast extract, and soybean protein decomposition products may be used in a slight amount as the organic nutrients. When an auxotrophic mutant strain that requires an amino acid etc. for growth is used, such a required nutrient is preferably added. Phosphates, magnesium salts, calcium salts, iron salts, manganese salts, and the like can be used as inorganic salts.

Surfactants such as Tween40, penicillin, or biotin may be added in an appropriate amount depending on a strain to be cultured. For example, a strain having a mutant-type yggB gene may be cultured in the presence of excess biotin, although such a strain may also be cultured under L-glutamic conditions containing surfactants or penicillin, or when biotin is limited.

Preferably, aerobic culturing is performed by controlling the fermentation temperature and adjusting the pH of the culture medium to 3 to 9. When the pH decreases during the culture, the medium is neutralized by adding alkali such as calcium carbonate or ammonia gas. Culture for about 10 to about 120 hours results in accumulation of a considerable amount of L-glutamic acid in the medium.

Furthermore, the culture may be performed by using a liquid medium adjusted to conditions under which the produced L-glutamic acid crystallizes and precipitates. The conditions under which L-glutamic acid crystallizes include pH 5.0 to 4.0, preferably pH 4.5 to 4.0, more preferably pH 4.3 to 4.0, particularly preferably pH 4.0 (EP1233069, EP1233070).

Collection of L-glutamic acid from the medium after completion of the culture may be performed by conventional methods. L-glutamic acid may be collected, for example, by removing bacterial cells from the medium and concentrating L-glutamic acid or by using ion exchange chromatography. When the culture is performed under conditions under which L-glutamic acid crystallizes and precipitates, the crystallized L-glutamic acid can be collected, for example, by centrifugation or filtration. In this case, L-glutamic acid dissolved in the medium may also be collected after crystallization of the dissolved L-glutamic acid.

EXAMPLES

Hereinafter, the present invention is specifically explained by referring to the following non-limiting examples.

Example 1

Construction of a Vector for Gene Disruption Carrying the sacB Gene (1-1) Construction of pBS3

Construction of the gene disruption vector carrying the sacB gene was performed by using the method in WO2005/113745 and WO2005/113744. A sacB gene (SEQ ID NO: 11) was obtained by PCR using a chromosomal DNA of Bacillus subtilis as a template and oligonucleotides of SEQ ID NOS: 13 and 14 as primers. The PCR was performed using LA taq (manufactured by TaKaRa) as follows: one cycle of heat retention at 94° C. for 5 minutes; and 25 cycles of denaturing at 94° C. for 30 seconds, annealing at 49° C. for 30 seconds, and elongation at 72° C. for 2 minutes. The obtained PCR product was purified by a conventional method, and then digested with BglII and BamHI and blunt-ended. The fragment was inserted into pHSG299 which had been digested with AvaII and blunt-ended. The obtained DNA was used to transform competent cells of Escherichia coli JM109 (manufactured by TAKARA BIO INC.). Then, the transformed bacterial cells were spread on LB agar medium containing 25 μg/ml Kanamycin (hereinafter, abbreviated as "Km"), and incubated for one night. Thereafter, single colonies were isolated as transformants. Plasmids were extracted from the obtained transformants and the plasmid which had an insert of the object PCR product was named pBS3. FIG. 1 shows the procedure for construction of pBS3.

(1-2) Construction of pBS4S

The SmaI recognition site in the kanamycin-resistant gene on pBS3 was modified by nucleotide substitution using crossover PCR without causing amino acid substitution so that pBS3 is not cut by SmaI endonuclease. First, PCR was performed using pBS3 as a template and synthetic DNAs of SEQ ID NOS: 15 and 16 as primers, to thereby obtain an N-terminal fragment of the kanamycin-resistant gene. On the other hand, to obtain a C-terminal fragment of the kanamycin-resistant gene, PCR was performed using pBS3 as a template and synthetic DNAs of SEQ ID NOS: 17 and 18 as primers. PCR was performed using Pyrobest DNA Polymerase (manufactured by TAKARA BIO INC.) as follows: one cycle of heat retention at 98° C. for 5 minutes; and 25 cycles of denaturing at 98° C. for 10 seconds, annealing at 57° C. for 30 seconds, and elongation at 72° C. for 1 minute, to obtain the objective PCR product. SEQ ID NOS: 16 and 17 are partially complementary to each other and do not contain the SmaI recognition site. Then, to obtain a full-length fragment of the mutant kanamycin-resistant gene without the SmaI recognition site, the above-mentioned N-terminal and C-terminal gene products were mixed together in substantially equimolar amounts. PCR was performed using the gene products as a template and synthetic DNAs of SEQ ID NOS: 15 and 18 as primers to obtain a SmaI site-modified kanamycin-resistant gene fragment. The PCR was performed using Pyrobest DNA Polymerase (manufactured by TAKARA BIO INC.) as follows: one cycle of heat retention at 98° C. for 5 minutes; and 25 cycles of denaturing at 98° C. for 10 seconds, annealing at 57° C. for 30 seconds, and elongation at 72° C. for 1.5 minutes, to thereby obtain the object PCR product.

The PCR product was purified by a conventional method, and then digested with BanII and then inserted into the above-described BanII recognition site of pBS3. The resulting plasmid was used to transform competent cells of Escherichia coli JM109 (available from Takara Bio). That is, the transformed bacterial cells were spread on LB agar medium containing 25 μg/ml of kanamycin, and incubated for one night.

Figure 2:
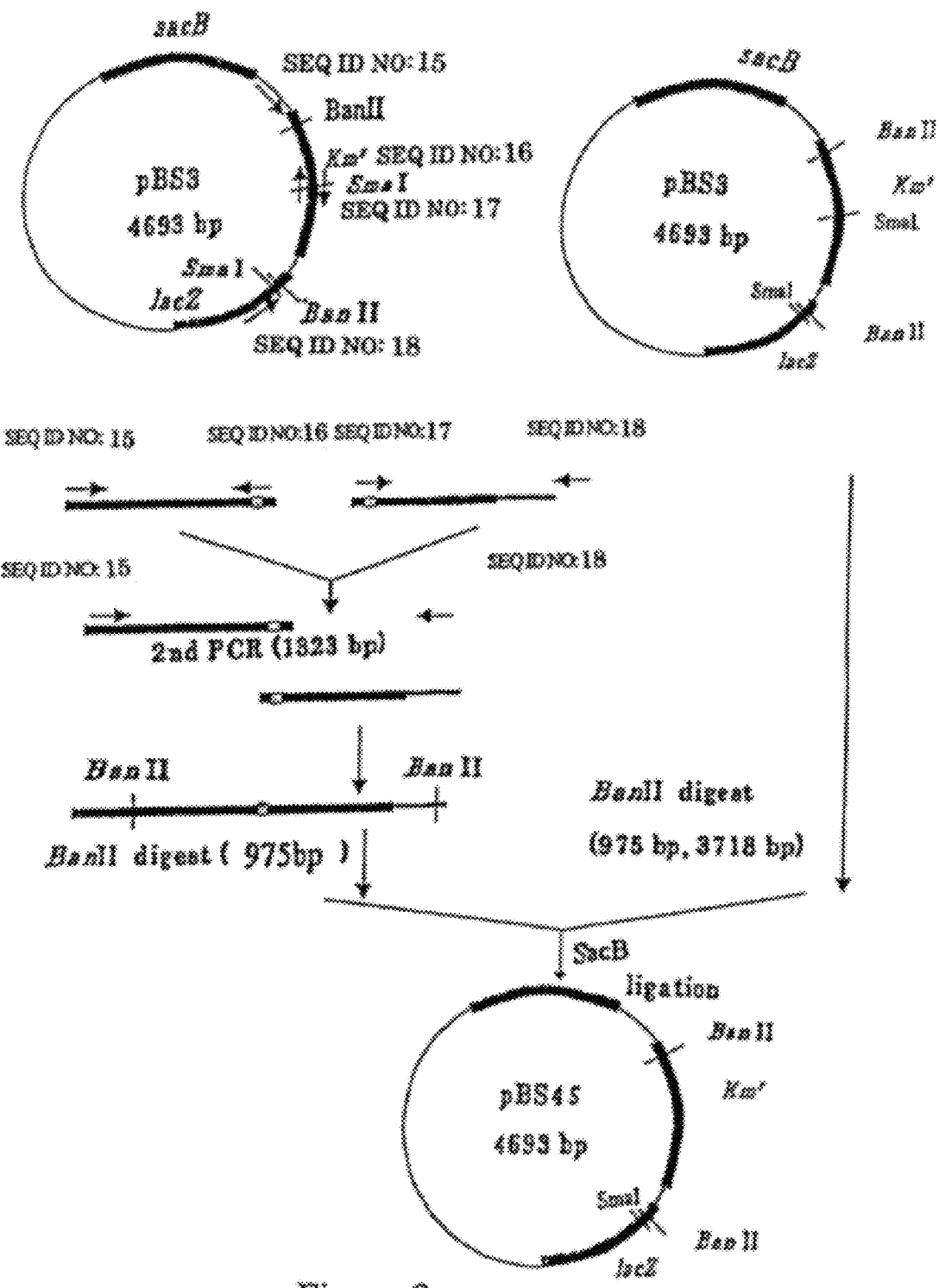
FIG. 2 shows the procedure for constructing plasmid pBS4S.

Thereafter, colonies that appeared were selected as transformants. Plasmids were isolated from the obtained transformants and the plasmid having an insert of the object PCR product was named pBS4S. FIG. 2 shows the procedure for constructing pBS4S.

Example 2

Figure 3:
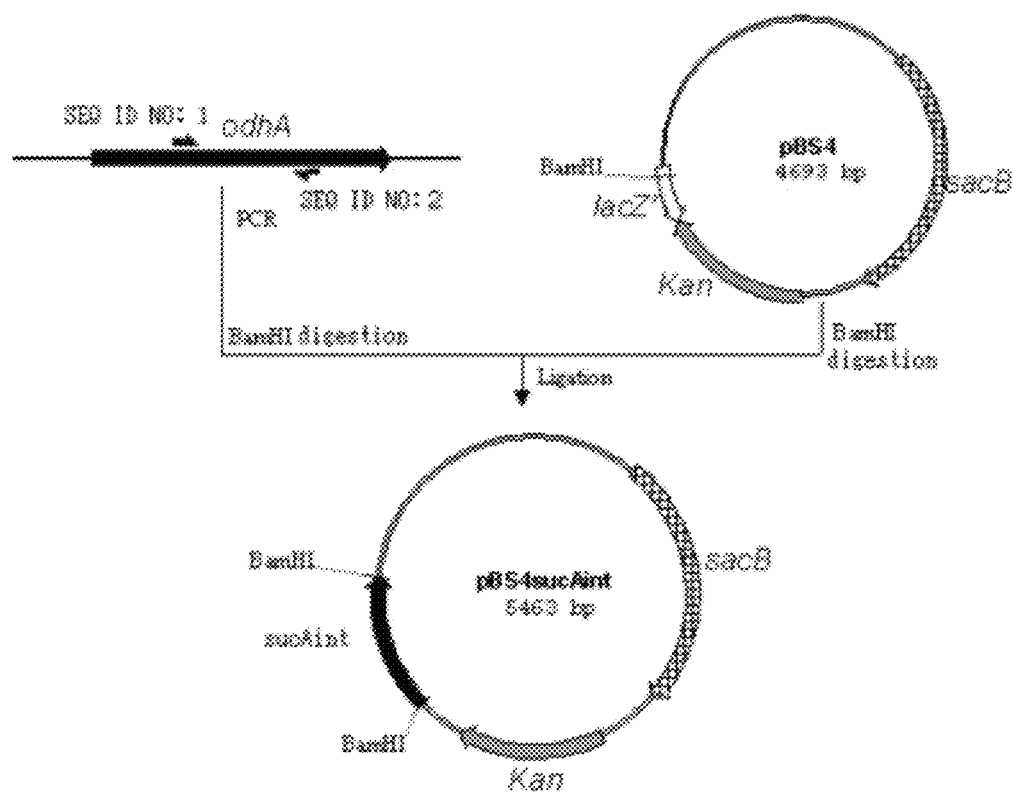
FIG. 3 shows the procedure for constructing plasmid pBS4sucAint.

Construction of an odhA Gene-Disrupted Strain from *C. glutamicum* ATCC13869 Strain The nucleotide sequence of the odhA gene encoding the α-ketoglutarate dehydrogenase of coryneform bacterium has already been identified (Microbiology 142, 3347-3354, (1996), GenBank accession No. D84102). Based on the nucleotide sequence of the odhA gene, the primers described in SEQ ID NOS: 1 and 2 were designed, and PCR was performed using the primers and the chromosomal DNA of the ATCC13869 strain as a template to amplify the internal sequence of the odhA gene. The amplified PCR fragment was completely digested with BamHI and inserted to the BamHI site of pBS4S constructed in Example 1, thereby the plasmid pBS4SΔsucAint was obtained (FIG. 3).

pBS4SΔsucAint was introduced into *C. glutamicum* ATCC13869 strain by the electric pulse method (JP-A-02-207791) and the transformed bacterial cells were spread over CM-Dex agar medium (5 g/l glucose, 10 g/l polypeptone, 10 g/l yeast extract, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 3 g/l urea, 1.2 g/l soybean protein hydrolysate, and 20 g/l agar, adjusted to pH 7.5 with NaOH: autoclaved at 120° C. for 20 minutes) containing 25 μg/ml kanamycin. After culturing at 31.5° C., PCR was performed using each of the chromosomes extracted from strains which appeared to confirm that these strains were single cross-over recombinants in which pBS4SΔsucAint was incorporated by homologous recombination into the chromosome. Primers each having a sequence (SEQ ID NO: 3) specific to pBS4S plasmid and a sequence (SEQ ID NO: 4) complementary to a chromosomal sequence was used for PCR. Since the sequence of pBS4S is absent in a non-recombinant strain, no fragment is amplified from the non-recombinant strain, whereas a single fragment is amplified from a single cross-over recombinant.

The single cross-over recombinant thus obtained was named 2A-1 strain. The wild-type 13869 strain and 2A-1 strain were inoculated in 20 ml of a flask medium (30 g/l glucose, 15 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 μg/l VB1 (vitamin B1), 300 μg/l Biotin, and 0.48 g/l soybean hydrolysates (T-N: total nitrogen), adjusted to pH 8.0 with KOH: autoclaved at 115° C. for 10 minutes), followed by addition of 1 g of heat-sterilized calcium carbonate, and each of the strains was cultured with shaking at 31.5° C. After the sugar was completely consumed, the concentration of L-glutamic acid which had accumulated in the medium was determined. The results are shown in Table 1 (OD620 is turbidity at 620 nm of culture solution diluted to 101 times, and indicates the cell amount, and Glu (g/L) indicates the amount of accumulated L-glutamic acid). It was found that the 2A-1 strain produced L-glutamic acid in the presence of an excess amount of biotin, whereas the parent strain ATTCC 13869 did not produce L-glutamic acid at all.

TABLE 1

| <Amount of L-glutamic acid produced by the control and the 2A-1 strain> | | |
|---|---|---|
| | OD620(×101) | Glu(g/L) |
| ATCC13869 | 0.658 | 0.2 |
| 2A-1 | 0.315 | 17.7 |
| Blank | 0.002 | 0.4 |

Example 3

Construction of an odhA Gene-Revertant Strain from the 2A-1 Strain

In the 2A-1 strain, the odhA gene on the chromosome was disrupted by pBS4SΔsucAint. By curing the plasmid from the chromosome of this strain, the odhA gene could be reverted to the wild-type one. Although the odhA gene-disrupted strain grows very slowly in a medium containing no sugar, the odhA gene-revertant strain in which the odhA gene-revered to the wild-type one grows well in a medium containing no sugar such as CM2B (10 g/l polypeptone, 10 g/l yeast extract, 5 g/l NaCl, 10 μg/l Biotin, 20 g/l agar, adjusted to pH 7.0 with KOH). To obtain such a revertant strain, the 2A-1 strain was spread over CM2B agar medium to select growth-improved strains. The growth-improved strain which appeared was named 2A-1R and isolated on the CM2B agar medium and the kanamycin-sensitivity of the 2A-1R strain was examined. As a result, it was found that all of the selected strains were kanamycin-sensitive and sucrose-resistant. Since the pBS4SΔsucAint contains a kanamycin-resistant gene and the sacB gene encoding levan sucrase, strains harboring pBS4SΔsucAint exhibit kanamycin-resistance and sucrose-sensitivity, while strains from which pBS4SΔsucAint was removed exhibit kanamycin-sensitivity and sucrose-resistance. Therefore, it was considered that the odhA gene reverted to the wild-type one in the 2A-1R strain. Determination of the nucleotide sequence of the odhA gene confirmed that the strain has the wild-type odhA gene.

Figure 4:
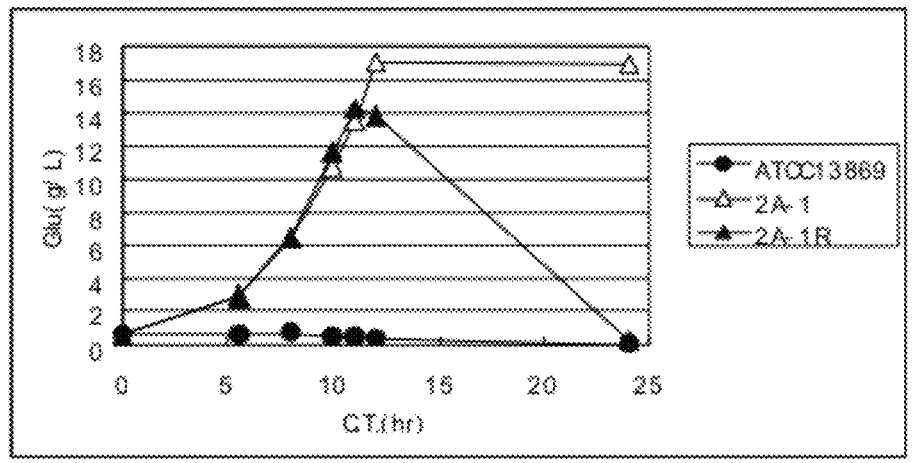
FIG. 4 is a graph showing the accumulation of L-glutamic acid by the mutant-type yggB gene-introduced strain and the control strain.

The ability of 2A-1R strain to produce L-glutamic acid in the presence of an excess amount of biotin was confirmed by the same method as in Example 2. The results are shown in Table 2 (OD620 is turbidity at 620 nm of culture solution diluted to 101 times, and indicates the cell amount, and Glu (g/L) indicates the amount of accumulated L-glutamic acid). Although the accumulation of L-glutamic acid by the 2A-1R strain was slightly decreased as compared to the 2A-1 strain, the 2A-1R strain produced a much higher amount of L-glutamic acid in the presence of an excess amount of biotin than the wild-type ATCC13869 strain (Table 2). In addition, when the shaking culture was continued after the sugar was completely consumed, decomposition of L-glutamic acid was observed in the 2A-1R strain, which proved that the odhA gene had reverted to the wild-type in this strain (FIG. 4).

TABLE 2

| <L-glutamic acid production by the control strain, odhA gene-disrupted strain and odhA gene-revertant strain> | | |
|---|---|---|
| | OD620(×101) | Glu(g/L) |
| ATCC13869 | 0.696 | 0.5 |
| 2A-1 | 0.332 | 17.1 |
| 2A-1R | 0.327 | 14.3 |
| Blank | 0.002 | 0.6 |

Example 4

Isolation of a Gene that is Involved in L-Glutamic Acid Production by the 2A-1R Strain On the CM2B agar medium, the 2A-1R strain could form colonies at substantially the same rate as that of the wild-type strain ATCC13869. However, on the minimum plate medium (20 g/l glucose, 2.64 g/l ammonium sulfate, 0.5 g/l $KH_2PO_4$, 0.5 g/l $K_2HPO_4$, 0.25 g/l $MgSO_4.7H_2O$, 0.01 g/l $FeSO_4.7H_2O$, 0.01 g/l $MnSO_4.7H_2O$, 0.01 g/l $CaCl_2$, 0.02 mg/l $CuSO_4$, 40 g/l MOPS, 30 mg/l protocatechuic acid, 200 µg/l $VB_1$.Hu, 300 µg/l Biotin, 20 g/l agar, adjusted to pH 6.7 with NaOH), the 2A-1R strain showed a considerably decreased colony-forming rate as compared to the wild-type ATCC13869 strain. Accordingly, a gene that can recover the growth of the 2A-1R strain in the minimum medium was found.

The chromosomal DNA of the ATCC13869 strain was partially digested with Sau3AI and ligated to the shuttle vector pVK9 that had been digested with BamHI. The obtained plasmid was precipitated with ethanol and used to transform competent cell of *E. coli* DH5α (TAKARA BIO INC.) by an electric pulse method. pVK9 is a shuttle vector obtained by blunt-ending the AvaII site of pHSG299 (TAKARA BIO INC.) and inserting therein a fragment comprising a sequence automatically replicable in coryneform bacteria excised with BamHI and KpnI from pHK4 (JP-A-05-007491). The transformed cells were spread over an LB agar medium (10 g/l polypeptone, 5 g/l yeast extract, 5 g/l NaCl, 20 g/l agar, adjusted to pH 7.0 with NaOH) containing 25 µg/ml kanamycin, and cultured at 37° C. for one night. On the next day, all of the colonies which appeared were collected from the plate with a platinum loop and plasmids were extracted to construct a plasmid library of the ATCC13869 strain. The plasmid library was transformed to the 2A-1R strain obtained in Example 3 by the electric pulse method, and the transformed cells were applied to a minimum agar medium containing 25 µg/ml kanamycin. The strains that showed an increased colony-forming rate were selected. By extracting a plasmid from the selected strains showing the increased colony-forming rate, it was found that the fragment having a nucleotide sequence shown in SEQ ID NO: 5 was inserted into the BamHI site of pVK9. The obtained plasmid was named pL5k.

Comparison of the nucleotide sequence inserted in the pL5k with the already published genome sequence of *Corynebacterium glutamicum* ATCC13032 (Acc. No. NC_003450) showed that pL5k contained only one ORF encoding the amino acid sequence shown in SEQ ID NO: 6.

The program "SOSUI" available on the Internet (sosui.proteome.bio.tuat.ac.jp/sosuiframe0E.html as of 2004 Oct. 7) was used to predict whether the ORF encodes a membrane protein. Results of analysis of the ORF by using "SOSUI" suggested that five transmembrane regions are present in this amino acid sequence. In the amino acid sequence of SEQ ID NO: 6, the transmembrane regions correspond to the regions of amino acids 1 to 23, amino acids 25 to 47, amino acids 62 to 84, amino acids 86 to 108, and amino acids 110 to 132. DNA sequences encoding these regions correspond to the nucleotides 1437 to 1505, nucleotides 1509 to 1577, nucleotides 1620 to 1688, nucleotides 1692 to 1760, and nucleotides 1764 to 1832 of SEQ ID NO: 5. Each of the amino acid sequences of these regions is shown in SEQ ID NOS: 25 to 29 and Table 3.

TABLE 3

Predicted transmembrane regions of the protein encoded by the inserted gene

| No. | N-terminal position | transmembrane region | C-terminal position | type | length | SEQ ID |
|---|---|---|---|---|---|---|
| 1 | 1 | MILGVPIQYLLYSLWNWIVDTGF | 23 | SECONDARY | 23 | 25 |
| 2 | 25 | VAIILVLAFLIPRIGRLAMRIIK | 47 | PRIMARY | 23 | 26 |
| 3 | 62 | QLAFAGVGVYIAQIVAFFMLAVS | 84 | PRIMARY | 23 | 27 |
| 4 | 86 | MQAFGFSLAGAAIPATIASAAIG | 108 | SECONDARY | 23 | 28 |
| 5 | 110 | GAQSIVADFLAGFFILTEKQFGV | 132 | SECONDARY | 23 | 29 |

A further search of the literature revealed that the ORF is named YggB (NCgl 1221) (FEMS Microbiology letters 218 (2003) 305-309).

Example 5

Figure 5:
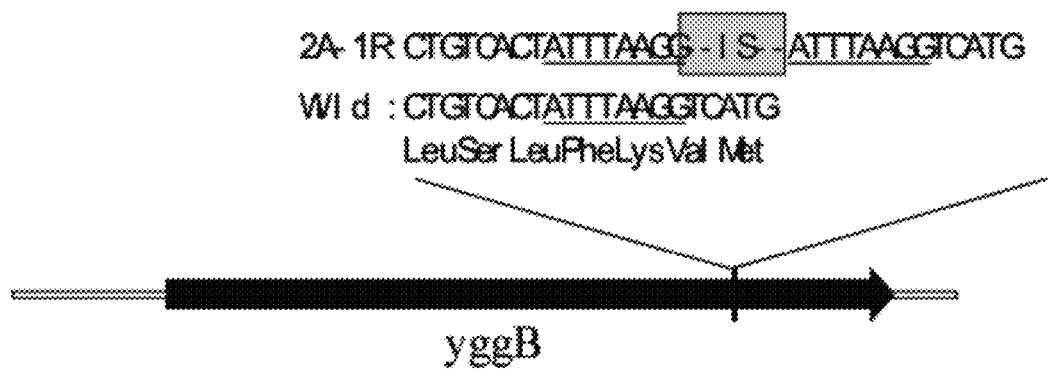
FIG. 5 shows the 2A-1 type mutation in the yggB gene.

Identification of the Mutation Introduced into the yggB Gene of the 2A-1R Strain The yggB gene could recover the growth of the 2A-1R strain in the minimum medium, which suggested the possibility that the yggB gene of the 2A-1R strain has some mutations. Accordingly, the nucleotide sequence of the yggB gene of the 2A-1R strain was determined. The results indicated that in the 2A-1R strain, an IS was inserted into the C-terminal region of the wild-type yggB gene (FIG. 5). The nucleotide sequence of the mutant type yggB gene derived from the 2A-1R strain is shown in SEQ ID NO: 7 and the corresponding amino acid sequence is shown in SEQ ID NO: 8.

This suggested the possibility that the ability of the 2A-1R strain to produce L-glutamic acid in the presence of an excess amount of biotin was due to the mutation in the yggB gene. It should be noted that this mutation was present not only in the 2A-1R strain, but also in the 2A-1 strain. This mutation is presumed to have occurred as a suppressor mutation to stably excrete L-glutamic acid from the cell when the odhA gene was disrupted. The mutation in which an IS was inserted was named the 2A-1 type mutation.

Example 6

Construction of a Strain Having the 2A-1 Type Mutant yggB Gene and Evaluation of L-Glutamic Acid-Producing Ability (6-1) Introduction of the 2A-1 Type Mutation into a Wild-Type Strain and Evaluation of L-Glutamic Acid-Producing Ability (Single Cross-Over Recombinants)

PCR was performed using the chromosomal DNA of the 2A-1 strain as a template and synthetic DNAs shown in SEQ ID NOS: 9 and 10 as primers to amplify the fragment of yggB gene having the 2A-1 type mutation. The amplified product was treated with SacI and inserted into the SacI site of pBS3 obtained in Example 1 to thereby obtain a plasmid containing the 2A-1 type mutant yggB gene (pBS3yggB2A).

The obtained pBS3yggB2A was introduced into *C. glutamicum* ATCC13869 by the electric pulse method and the transformed cells were spread over CM-Dex agar medium containing 25 μg/ml kanamycin. The strains that appeared after culturing at 31.5° C. were evaluated by PCR to confirm that they are single cross-over recombinants in which pBS3yggB2A was incorporated into the chromosome by homologous recombination. The obtained single cross-over recombinant was named 13869-2A. In this strain, both the wild-type yggB gene and mutant-type yggB gene exist and are expressed.

The ability of the obtained mutant-type yggB gene-introduced strain 13869-2A to produce L-glutamic acid in the presence of an excess amount of biotin was evaluated by the method described in Example 2. The results are shown in Table 4 (OD620 is turbidity at 620 nm of culture solution diluted 101 times, and indicates the cell amount, and Glu (g/L) indicates the amount of accumulated L-glutamic acid). The 13869-2A strain produced L-glutamic acid in the presence of an excess amount of biotin when the wild-type ATCC13869 strain cannot produce L-glutamic acid. This indicated that the mutation in the yggB gene could enhance L-glutamic acid production in the presence of an excess amount of biotin. In the case of the 13869-2A strain, both the wild-type yggB gene and mutant type yggB gene were expressed, so that it was revealed that the introduction of the mutant-type yggB gene could impart to a coryneform bacterium an ability to produce L-glutamic acid in high yields even in the presence of the wild type yggB gene on the chromosome.

TABLE 4

<Amount of L-glutamic acid accumulated by the control strain, 2A-1R strain, and the mutant type yggB gene-introduced strain>

|  | OD620(×101) | Glu(g/L) |
|---|---|---|
| ATCC13869 | 0.625 | 0.3 |
| 2A-1R | 0.334 | 15.5 |
| 13869-2A | 0.582 | 3.6 |
| Blank | 0.002 | 0.6 |

(6-2) Introduction of the 2A-1 Type Mutant yggB Gene into the Wild-Type Strain and Evaluation of L-Glutamic Acid-Producing Ability (Double Cross-Over Recombinants)

To construct a strain having only the mutant-type yggB gene, the 13869-2A strain was cultured in the CM-Dex liquid medium for one night and the obtained culture was spread over the S10 agar medium (100 g/l sucrose, 10 g/l polypeptone, 10 g/l yeast extract, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 3 g/l urea, 1.2 g/l soybean protein hydrolysates, 20 g/l agar, adjusted to pH 7.5 with NaOH: autoclaved at 120° C. for 20 minutes) and cultured at 31.5° C. Among the colonies which appeared, the strain exhibiting sensitivity to kanamycin was isolated on CM2B agar medium. Chromosomal DNAs were prepared from the strains. Then, PCR was performed using synthetic DNAs shown in SEQ ID NOS: 9 and 10 as primers to confirm that the strain has only a mutant-type yggB gene. The strain containing the mutant-type yggB gene in which an IS-like sequence was inserted was named 13869-2A-7.

The ability of the obtained 13869-2A-7 strain to produce L-glutamic acid in the presence of an excess amount of biotin was evaluated by the method described in Example 2. The results are shown in Table 5 (OD620 is turbidity at 620 nm of culture solution diluted to 101 times, and indicates the cell amount, and Glu (g/L) indicates the amount of accumulated L-glutamic acid). The 13869-2A-7 strain produced L-glutamic acid equivalent to or higher than the 2A-1R strain, which confirmed that L-glutamic acid production of the coryneform bacterium in the presence of an excess amount of biotin was caused by the mutation in the yggB gene.

TABLE 5

<Amount of L-glutamic acid produced by the control strain, 2A-1R strain and the mutant-type yggB gene-introduced strain>

|  | OD620(×101) | Glu(g/L) |
|---|---|---|
| ATCC13869 | 0.648 | 0.4 |
| 2A-1R | 0.420 | 13.8 |
| 13869-2A-7 | 0.414 | 16.1 |
| Blank | 0.002 | 0.7 |

Example 7

Construction of the A1-Type Mutant yggB Gene-Introduced Strain and Evaluation of L-Glutamic Acid-Producing Ability As a result of the screening using the above-mentioned L-glutamic acid-producing odhA gene-disrupted strain (ΔsucA strain), five kinds of mutations were identified on the yggB gene besides the above-mentioned 2A-1 mutation. Hereinafter, these mutations were named A1-type mutation, 19-type mutation, L30-type mutation, 8-type mutation, and 66-type mutation. The mutant-type yggB genes having each of the A1-type mutation, 19-type mutation, and L30-type mutation were introduced into the chromosome of the ATCC13869 strain, and the effect of each mutation was evaluated. The mutant-type yggB gene having the 8-type mutation was introduced into the chromosome of the ATCC14067 strain, and the effect of the mutation was evaluated. The mutant-type yggB gene having the 66-type mutation was introduced into the chromosome of the *C. melassecola* ATCC17965 strain, and the effect of the mutation was evaluated.

The A1 type mutation is a mutation which inserts "TTCAT-TGTG" next to the "G" at position 1480 of the wild-type yggB gene (the wild-type gene of *C. glutamicum* is shown in nucleotides 1437-3035 of SEQ ID NO: 5), and causes insertion of CysSerLeu between the Leu at position 14 and the Trp at position 15 in the amino acid sequence of SEQ ID NO: 6.

The nucleotide sequence of the mutant type yggB gene in which this mutation was introduced is shown in SEQ ID NO: 19 and the amino acid sequence of the mutant type YggB encoded by this gene is shown in SEQ ID NO: 20.

The A1 type mutant gene can be obtained as follows. PCR is performed by using the synthetic DNAs shown in SEQ ID NOS: 30 and 31 as primers and the chromosomal DNA of ATCC13869 strain as a template to prepare an N-terminal fragment. Similarly, PCR is performed by using the synthetic DNAs shown in SEQ ID NOS: 32 and 33 as primers to prepare a C-terminal fragment. Subsequently, PCR is performed by using an equimolar mixture of the N-terminal fragment and the C-terminal fragment as a template and the synthetic DNAs shown in SEQ ID NOS: 9 and 34 as primers to amplify a partial fragment of the A1 type mutant yggB gene. The obtained mutant-type yggB gene fragment is treated with SacI and inserted into the SacI site of pBS4S to obtain a plasmid for introducing this type of mutation. The pBS4yggBA1 thus obtained is introduced into the chromosome of the ATCC13869 strain in the same manner as described in Example 6 and then only the plasmid portion was cured from the chromosome. The nucleotide sequence of the yggB gene of the obtained kanamycin-sensitive strain is determined and the strain having the A1 type mutant yggB gene is selected. The A1 type mutant yggB gene-introduced strain was named ATCC13869-A1 strain.

The ATCC13869-A1 strain and the control ATCC13869 strain were cultured in the same manner as in Example 2. After completion of the culture, the amount of L-glutamic acid which had accumulated in the culture medium was measured by the known method. It was found that the A1-type mutant yggB gene-introduced strain produced L-glutamic acid in the presence of an excess amount of biotin in a greater amount as compared to the control strain.

TABLE 6

<Amount of L-glutamic acid produced by the control strain, and the mutant-type (A1-type) yggB gene-introduced strain>

| strains | OD620(×101) | Glu(g/L) |
|---|---|---|
| ATCC13869 | 0.650 | 0.5 |
| ATCC13869-A1 | 0.548 | 8.6 |

Example 8

Construction of the 19 Type Mutant yggB Gene-Introduced Strain and Evaluation of L-Glutamic Acid-Producing Ability The 19 type mutation is a mutation which replaces the "G" at position 1734 of the wild type yggB gene (the wild type gene of C. glutamicum is shown in nucleotides 1437-3035 of SEQ ID NO: 5) with an "A", and causes replacement of the Ala at position 100 with Thr in the amino acid sequence of SEQ ID NO: 6. The nucleotide sequence of the mutant type yggB gene having this type of mutation is shown in SEQ ID NO: 21 and the amino acid sequence of the mutant type YggB protein encoded by this gene is shown in SEQ ID NO: 22.

In the same manner as in Example 7, the 19 type mutant yggB gene-introduced strain is constructed. Specifically, PCR is performed by using the synthetic DNAs shown in SEQ ID NOS: 30 and 35 as primers and the chromosomal DNA of the ATCC13869 strain as a template to prepare an N-terminal fragment. Similarly, PCR is performed by using the synthetic DNAs shown in SEQ ID NOS: 33 and 36 as primers to prepare a C-terminal fragment. Subsequently, PCR is performed by using an equimolar mixture of the N-terminal fragment and the C-terminal fragment as a template and the synthetic DNAs shown in SEQ ID NOS: 9 and 34 as primers, to amplify a partial fragment of the 19 type mutant yggB gene. The obtained yggB fragment is treated with SacI and inserted into the SacI site of pBS4S to obtain a plasmid for introducing this mutation. The thus obtained pBS4yggB19 is introduced into the chromosome of the ATCC13869 strain in the same manner as described in Example 6 and then the vector portion is cured from the chromosome. The nucleotide sequence of the yggB gene of the obtained kanamycin-sensitive strain is determined and the strain having the 19 type yggB gene is selected. The 19-type mutant strain was named ATCC13869-19 strain.

The ATCC13869-19 strain and the control ATCC13869 strain were cultured in the same manner as in Example 2. After completion of the culture, the amount of L-glutamic acid which had accumulated in the culture broth was measured by a conventional method. It was found that the 19-type mutant yggB gene-introduced strain produced L-glutamic acid in the presence of an excess amount of biotin in a greater amount as compared to the control strain.

TABLE 7

<Amount of L-glutamic acid produced by the control strain, and the mutant-type (19-type) yggB gene-introduced strain>

| strains | OD620(×101) | Glu(g/L) |
|---|---|---|
| ATCC13869 | 0.650 | 0.5 |
| ATCC13869-19 | 0.614 | 0.7 |

Example 9

Construction of the L30 Type Mutant yggB-Gene Introduced Strain and Evaluation of L-Glutamic Acid-Producing Ability The L30 type mutation is a mutation which replaces the "C" at position 1768 of the wild type yggB gene (the wild type gene of C. glutamicum is shown in SEQ ID NO: 5) with "T", and causes replacement of the Ala at position 111 with Val in the amino acid sequence shown in SEQ ID NO: 6. The nucleotide sequence of the mutant type yggB gene having this type of mutation is shown in SEQ ID NO: 23 and the amino acid sequence of the mutant type YggB protein encoded by this gene is shown in SEQ ID NO: 24.

In the same manner as in Example 7, the L30 type mutant yggB gene-introduced strain was constructed. Specifically, PCR was performed by using the synthetic DNAs shown in SEQ ID NOS: 30 and 37 as primers and the chromosomal DNA of ATCC13869 strain as a template to prepare an N-terminal fragment. Similarly, PCR was performed by using the synthetic DNAs shown in SEQ ID NOS: 34 and 38 as primers to prepare a C-terminal fragment. Subsequently, PCR was performed by using an equimolar mixture of the N-terminal fragment and the C-terminal fragment as a template and the synthetic DNAs shown in SEQ ID NOS: 9 and 34 as primers to amplify a partial fragment of the L30 type mutant yggB gene. The obtained yggB fragment was treated with SacI and inserted into the SacI site of pBS4S to obtain a plasmid for introducing this type of mutation. The thus obtained pBS4yggB-L was introduced into the chromosome of ATCC13869 strain in the same manner as described in Example 6, and then the vector portion was cured from the chromosome. The nucleotide sequence of the yggB gene of the obtained kanamycin-sensitive strain was determined and the strain having L30 type mutant yggB gene was selected. The L30-type mutant yggB gene-introduced strain was named ATCC13869-L30 strain.

The ATCC13869-L30 strain and the control ATCC13869 strain were cultured in the same manner as in Example 2. After completion of the culture, the amount of L-glutamic acid which had accumulated in the culture broth was measured by a conventional method. The results are shown in Table 8 (OD620 is turbidity at 620 nm of culture solution diluted to 101 times, and indicates the cell amount, and Glu (g/L) indicates the amount of accumulated L-glutamic acid). ATCC13869-L30 strain having the L30 type mutant yggB gene caused accumulation of L-glutamic acid in a greater amount as compared to the parent ATCC13869 strain.

TABLE 8

<Amount of L-glutamic acid produced by the control strain and the L30-type mutant yggB gene-introduced strain>

|  | OD620(×101) | Glu(g/L) |
| --- | --- | --- |
| ATCC13869 | 0.650 | 0.5 |
| ATCC13869-L30 | 0.389 | 15.9 |

Example 10

Evaluation of the Mutant-Type yggB Gene-Introduced Strains Under L-Glutamic Acid-Producing Conditions L-glutamic acid production of Coryneform bacterium is induced by addition of surfactants such as Tween40 or by limiting the biotin concentration. Therefore, the ATCC13869 strain and the ATCC13869-19 strain were cultured under a condition containing Tween40 and a condition containing a limited amount of biotin, respectively.

Each of the strains was inoculated into 20 ml of seed culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. The culture solution obtained after complete consumption of sugars was used as a seed culture solution in the following main culture.

For culturing with Tween40, 2 ml of the seed culture solution was inoculated into 20 ml of main culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. When OD620 of culture broth diluted 101-fold reached 0.2, Tween40 was added to a final concentration of 5 g/L and the culture was continued.

For culturing with limited biotin, 1 ml of the seed culture solution was inoculated into 20 ml of main culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. Under these culture conditions, a final concentration of biotin is calculated to be about 2.9 µg/L.

After a 40 hour-culture, the amount of L-glutamic acid which had accumulated in the medium was measured for the Tween40-added culture and the biotin-limited culture. The result is shown in Table 9. It was found that the ATCC13869-19 strain produced L-glutamic acid in an amount greater than the control strain under L-glutamic acid-producing conditions.

TABLE 9

<Amount of L-glutamic acid produced by the control strain and the 19-type mutant yggB gene-introduced strain under L-glutamic acid-producing conditions>

| Strains | OD620 (×101) | Glu (g/L) |
| --- | --- | --- |
| Tween40-added |  |  |
| ATCC13869 | 0.538 | 25.6 |
| ATCC13869-19 | 0.395 | 28.6 |
| biotin-limited |  |  |
| ATCC13869 | 0.462 | 36.0 |
| ATCC13869-19 | 0.431 | 40.0 |

The wild-type ATCC13869 strain, yggB mutant trains ATCC13869-19, ATCC13869-A1, ATCC13869-L30, and a strain having a plasmid containing a wild-type yggB gene (ATCC13869/pL5k-1), and a strain having a control plasmid (ATCC13869/pVK9) were cultured with Tween40. Each of these strains were cultured on a CM-Dex plate medium overnight, and cells collected from 1/6 area of the plate were inoculated in 20 ml of a flask medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, and 0.48 g/l soybean hydrolysates (T-N: total nitrogen), adjusted to pH 8.0 with KOH: autoclaved at 115° C. for 10 minutes), followed by addition of 1 g of heat-sterilized calcium carbonate, and each of the strains was cultured with shaking at 31.5° C. After a 5-hour culture, Tween40 was added to a final concentration of 1 g/L and the culture was continued. Table 10 shows the amount of cells (OD620) and the amount of L-glutamic acid which had accumulated in the medium after 24 hours. It was found that the ATCC13869-19 strain, ATCC13869-A1 strain, ATCC13869-L30 strain, and the strain having a plasmid containing a wild-type yggB gene have an enhanced ability to produce L-glutamic acid under L-glutamic acid-producing conditions.

TABLE 10

|  | OD620(×101) | Glu(g/L) |
| --- | --- | --- |
| ATCC13869 | 0.887 | 12.8 |
| ATCC13869/pVK9 | 0.748 | 12.4 |
| ATCC13869/pL5k-1 | 0.711 | 19.2 |
| ATCC13869-19 | 0.786 | 21.0 |
| ATCC13869-A1 | 0.629 | 34.9 |
| ATCC13869-L30 | 0.649 | 28.3 |
| Blank | 0.001 | 0.5 |

Example 11

Construction of the 8-Type Mutant yggB-Gene Introduced Strain and Evaluation of L-Glutamic Acid-Producing Ability The 8-type mutation is a mutation which replaces the "G" at position 837 of SEQ ID NO: 61 with an "A", and causes replacement of the Ala at position 111 with Thr in the amino acid sequence of SEQ ID NO: 62. The nucleotide sequence of the mutant-type yggB gene having this type of mutation is shown in nucleotides 507-2093 of SEQ ID NO: 63 and the amino acid sequence of the mutant-type YggB protein encoded by this gene is shown in SEQ ID NO: 64.

In the same manner as in Example 7, the 8-type mutant yggB gene-introduced strain is constructed. Specifically, PCR is performed by using the synthetic DNAs shown in SEQ ID NOS: 30 and 65 as primers and the chromosomal DNA of *Brevibacterium flavum* ATCC14067 strain as a template to prepare an N-terminal fragment. Similarly, PCR is performed by using the synthetic DNAs shown in SEQ ID NOS: 34 and 66 as primers to prepare a C-terminal fragment. Subsequently, PCR is performed by using an equimolar mixture of the N-terminal fragment and the C-terminal fragment as a template and the synthetic DNAs shown in SEQ ID NOS: 9 and 34 as primers to amplify a partial fragment of the 8-type mutant yggB gene. The obtained yggB gene fragment is treated with SacI and inserted into the SacI site of pBS4S to obtain a plasmid for introducing this type of mutation. The thus obtained pBS4yggB8 is introduced into the chromosome of ATCC14067 strain in the same manner as described in Example 6 and then the vector portion is cured from the chromosome. The nucleotide sequence of the yggB gene of the obtained kanamycin-sensitive strain is determined and the strain having the 8-type mutant yggB gene was selected. The 8-type mutant yggB gene-introduced strain is named ATCC14067-yggB8 strain.

Example 12

Construction of the 66-Type Mutant yggB-Gene Introduced Strain and Evaluation of L-Glutamic Acid-Producing Ability The 66-type mutation is a mutation which replaces the "C" at position 1673 of SEQ ID NO: 67 with a "T", and causes replacement of the Pro at position 424 with Leu in the amino acid sequence of SEQ ID NO: 68. The nucleotide sequence of the mutant type-yggB gene having this type of mutation is shown in SEQ ID NO: 69 and the amino acid sequence of the mutant type YggB protein encoded by this gene is shown in SEQ ID NO: 70.

In the same manner as in Example 7, the 66-type mutant yggB gene-introduced strain is constructed. Specifically, PCR is performed by using the synthetic DNAs shown in SEQ ID NOS: 30 and 71 as primers and the chromosomal DNA of *C. melassecola* ATCC17965 strain as a template to prepare an N-terminal fragment. Similarly, PCR is performed by using the synthetic DNAs shown in SEQ ID NOS: 34 and 72 as primers to prepare a C-terminal fragment. Subsequently, PCR is performed by using an equimolar mixture of the N-terminal fragment and the C-terminal fragment as a template and the synthetic DNAs shown in SEQ ID NOS: 9 and 34 as primers to amplify a partial fragment of the 66-type mutant yggB gene. The obtained yggB fragment is treated with SacI and inserted into the SacI site of pBS4S to obtain a plasmid for introducing this type of mutation. The thus obtained pBS4yggB66 is introduced into the chromosome of ATCC17965 strain in the same manner as described in Example 6 and then the vector portion is cured from the chromosome. The nucleotide sequence of the yggB gene of the obtained kanamycin-sensitive strain is determined and the strain having the 66-type mutant yggB gene was selected. The 66-type mutant yggB gene-introduced strain is named ATCC17965-yggB66 strain.

Example 13

Screening of the Mutant-Type yggB Genes by In Vitro Mutation

Mutant-type yggB genes may be obtained by introducing a random mutation into the wild-type yggB gene in vitro, transforming a coryneform bacterium with the mutation-introduced yggB gene, and selecting mutant strains capable of producing L-glutamic acid without addition of surfactants or penicillin in the presence of an excess amount of biotin.

(13-1) Construction of a yggB Gene-Disrupted Strain

To perform screening for mutant-type yggB genes, first a yggB gene-disrupted strain was constructed. PCR was performed by using the synthetic DNAs shown in SEQ ID NOS: 39 and 40 as primers and the chromosomal DNA of ATCC13869 strain as a template to prepare an N-terminal fragment. Similarly, PCR was performed by using the synthetic DNAs shown in SEQ ID NOS: 41 and 42 as primers to prepare a C-terminal fragment. SEQ ID NO: 40 and SEQ ID NO: 41 are complementary to each other. Subsequently, PCR was performed by using an equimolar mixture of the N-terminal fragment and the C-terminal fragment as a template and the synthetic DNAs shown in SEQ ID NOS: 39 and 42 as primers to obtain a fragment containing a yggB gene in which the ORF is deleted.

The obtained PCR fragment was treated with SacI and inserted into the SacI site of pBS4S to obtain a plasmid useful for disrupting the yggB gene. The pBS4ΔyggB thus obtained was introduced into the chromosome of ATCC13869 strain in the same manner as described in Example 6 and the vector portion is cured from the chromosome. PCR was performed by using the chromosomal DNA of the obtained kanamycin-sensitive strain as a template and the synthetic DNAs of SEQ ID NOS: 39 and 42 as primers to confirm that the yggB gene was disrupted. The obtained yggB-disrupted strain was named ATCC13869ΔyggB strain.

(13-2) In Vitro Screening of Mutant-Type yggB Genes

Mutagenesis of the yggB gene was performed as follows. First, the above-described pL5k plasmid was treated with XhoI and SalI and self-ligated to remove the region other than the yggB gene, and thereby the plasmid pL5kXS was obtained. A SalI recognition site does not exist on the nucleotide sequence of SEQ ID NO: 5 but is present on the multi-cloning site of pBS3. About 10 μg of the obtained pL5kXS was dissolved in 500 mM phosphate buffer containing 400 mM hydroxylamine and 1 mM EDTA (pH 6.0), and heated at 75° C. for 30 to 90 minutes to introduce a mutation. The plasmid after mutagenesis treatment was desalted using SUPREC-02 (manufactured by TAKARA BIO INC.) and then introduced into ATCC13869ΔyggB strain by the method described in Example 6. Transformed cells were screened on the CM2B medium containing 25 μg/ml of kanamycin. As a control, pL5kXS without mutagenesis treatment was introduced into the ATCC13869ΔyggB strain. The appeared transformants are inoculated into 2 m of a liquid CM2BGU2 medium (CM2B medium described in Example 3 further containing 10 g/l glucose and 15 g/l urea) and cultured at 31.5° C. for 5 hours with shaking, followed by determination of the concentration of L-glutamic acid which had accumulated in the culture broth.

Table 11 shows the result of culturing of the strain obtained by transforming the ATCC13869ΔyggB strain with the mutated pL5kXS on the CM2BGU2 medium. Three strains which cause accumulation of more than 1 g/L of L-glutamic acid were obtained among the transformants transformed with 60, or 90-minute mutated plasmids. The amount of L-glutamic acid contained in the starting medium is 0.16 g/L, and the amount of L-glutamic acid which had accumulated by the control ATCC13869ΔyggB/pL5kXS (without mutagenesis treatment) strain was 0.31 g/L.

Table 12 shows the results of culturing transformants obtained by transforming the ATCC13869ΔyggB strain with mutated pL5kXS on the CM2BGU medium, which has the same composition as the above-mentioned CM2BGU2 medium except that the concentration of urea is 1.5 g/L. One clone which causes accumulation of more than 1 g/L of L-glutamic acid was obtained among the transformants transformed with 90-minute mutated plasmids.

TABLE 11

<Amount of L-glutamic acid production by strains transformed with mutated plasmids>

| Glu accumulation | Number of clones Time of mutagenesis | | |
|---|---|---|---|
| (g/L) | 30 min | 60 min | 90 min |
| Glu ≦ 0.4 | 40 | 36 | 39 |
| 0.4 < Glu ≦ 0.6 | 8 | 11 | 6 |
| 0.6 < Glu ≦ 0.8 | 0 | 0 | 1 |
| 0.8 < Glu ≦ 1 | 0 | 0 | 0 |
| 1 < Glu | 0 | 1 | 2 |

TABLE 12

<Amount of L-glutamic acid production by strains transformed with mutated plasmids>

| Glu accumulation | Number of clones Time of mutagenesis | |
|---|---|---|
| (g/L) | 60 min | 90 min |
| Glu ≦ 0.7 | 45 | 41 |
| 0.7 < Glu ≦ 0.9 | 2 | 7 |
| 0.9 < Glu | 1 | 0 |

A plasmid was extracted from the strain transformed with 60-minute mutated plasmids which produced more than 1 g/L of L-glutamic acid shown in Table 11, and the obtained plasmid was named pL5kXSm-22. A plasmid was also extracted from the strain transformed with 60-minute mutated plasmids which produced more than 0.9 g/L of L-glutamic acid shown in Table 12, and the obtained plasmid was named pL5kXSm-27. ATCC13869 strain was transformed with the plasmids and the obtained strains were named ATCC13869ΔyggB/pL5kXS and ATCC13869ΔyggB/pL5kXSm-27, ATCC13869ΔyggB/pL5kXSm-22, respectively. These strains were cultured under the conditions described in Example 2, and the L-glutamic acid accumulation after a 4-hour culture was analyzed. Table 13 shows the mean value of three independent experiments. It was found that the ATCC13869ΔyggB/pL5kXSm-27 strain and the ATCC13869ΔyggB/pL5kXSm-22 strain produced significantly more L-glutamic acid than the non-mutated plasmid-introduced strain. These results demonstrate that the mutant-type yggB gene of the present invention can be obtained by in vitro random mutagenesis. The nucleotide sequence of the yggB genes contained in pL5kXSm-22 is shown in SEQ ID NOS: 73 and 75, respectively. The pL5kXSm-22 plasmid has a mutation which replaces "C" at position 2745 with "T" in SEQ ID NO: 5 and causes replacement of Pro at position 437 of SEQ ID NO: 6 with Ser. Moreover, this mutation was accompanied by the mutation which replaces "C" at position 3060 with T in SEQ ID NO: 5 (22 type mutation). The nucleotide sequence of the mutant type yggB gene having this mutation is shown in SEQ ID NO: 73 and the amino acid sequence of the mutant type YggB protein encoded by the gene is shown in SEQ ID NO: 74.

TABLE 13

<Amount of L-glutamic acid production by strains transformed with plasmids comprising mutated yggB gene>

| Strains | OD620(×101) | Glu(g/L) |
|---|---|---|
| ATCC13869 Δ yggB/pL5kXS$^{(no\ treatment)}$ | 0.253 | 0.58 |
| ATCC13869 Δ yggB/pL5kXSm22 | 0.232 | 1.10 |
| ATCC13869 Δ yggB/pL5kXSm27 | 0.245 | 0.82 |

(13-3) Introduction of the Mutant-Type yggB Genes into Coryneform Bacteria and Evaluation of L-Glutamic Acid Production The mutant-type yggB gene obtained in (13-2) is introduced into a coryneform bacterium. The method of introducing the gene is as follows.

Each of the mutant-type yggB genes is introduced into pBS4S by the method described in Example 6 and the obtained plasmid is used to obtain a strain in which a wild-type yggB gene on the chromosome is replaced with the mutant-type yggB gene. A strain in which the mutant-type yggB gene is introduced and the control ATCC13869 strain were cultured in the same manner as in Example 2. After completion of the culture, the amount of L-glutamic acid which had accumulated in the culture medium is measured by a known method to confirm that accumulation of L-glutamic acid is increased by introduction of the mutant-type yggB gene. In this manner, a strain having a mutant-type yggB gene-introduced strain with increased ability to produce L-glutamic acid can be obtained.

Example 14

Evaluation of the L-Glutamic Acid Analog-Resistance of the Strains Having the Mutant-Type yggB Gene (14-1) Evaluation of Resistance to 4-Fluoroglutamic Acid on a Solid Medium It was predicted that strains which have enhanced L-glutamic acid-producing ability due to introduction of the mutant-type yggB gene would have decreased sensitivity (increased resistance) to L-glutamic acid analogs. Therefore, sensitivity of the strains to 4-fluoroglutamic acid was analyzed as follows.

Figure 6:
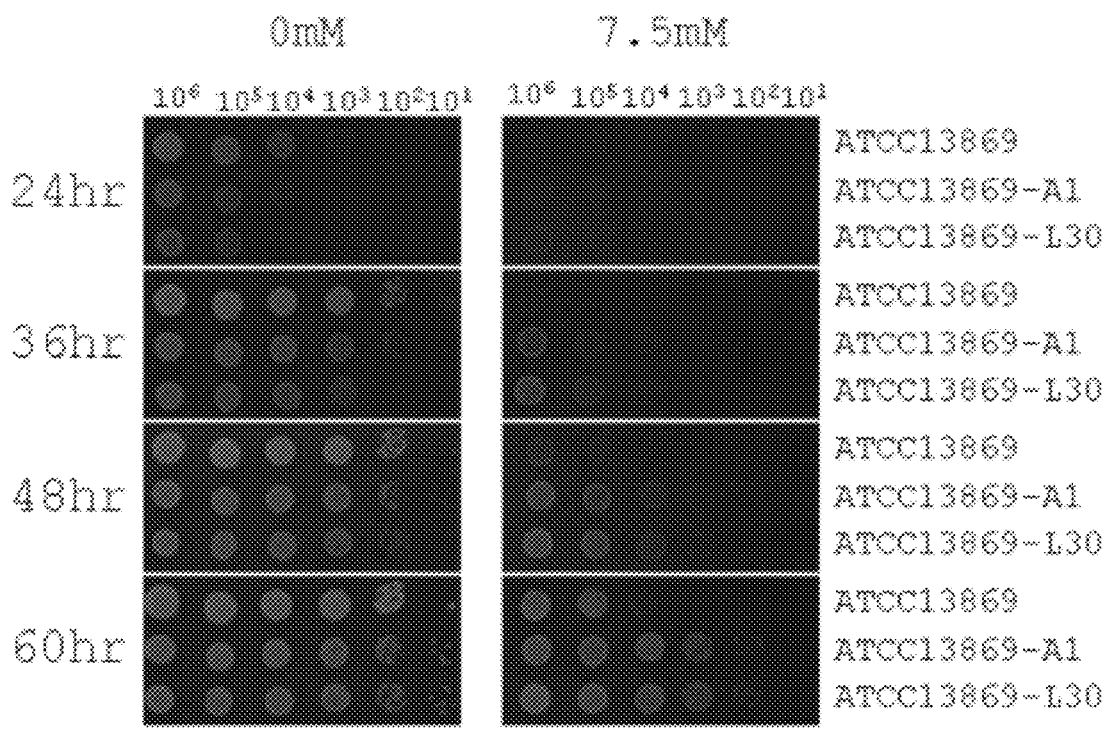
FIG. 6 is a photograph which shows the resistance of the mutant-type yggB gene-introduced strains to 4-fluoro-glutamic acid on CM-Dex plate medium.

4-fluoroglutamic acid solution which was adjusted to pH6.7 with NaOH and sterilized with filtration was added to the minimum medium described in Example 4 so that the final concentration of 4-fluoroglutamic acid was 7.5 mM. Each of the ATCC13869 strain, ATCC13869-L30 strain, and ATCC13869-A1 strain was spread over the CM-Dex plate and cultured overnight. Then, the cells were collected from the plate and washed with sterilized 0.85% NaCl solution, and diluted to the cell concentration described in FIG. 6, spotted onto the plate containing 4-fluoroglutamic acid and a control plate which did not contain 4-fluoroglutamic acid, and cultured at 31.5° C. The time-course of growth of each of strain is shown in FIG. 6. Although the wild-type ATCC13869 strain grows faster than the mutant-type yggB gene-introduced strains in the absence of 4-fluoroglutamic acid, the mutant-type yggB gene-introduced strain grow faster than wild-type ATCC13869 strain in the presence of 4-fluoroglutamic acid.

Figure 7:
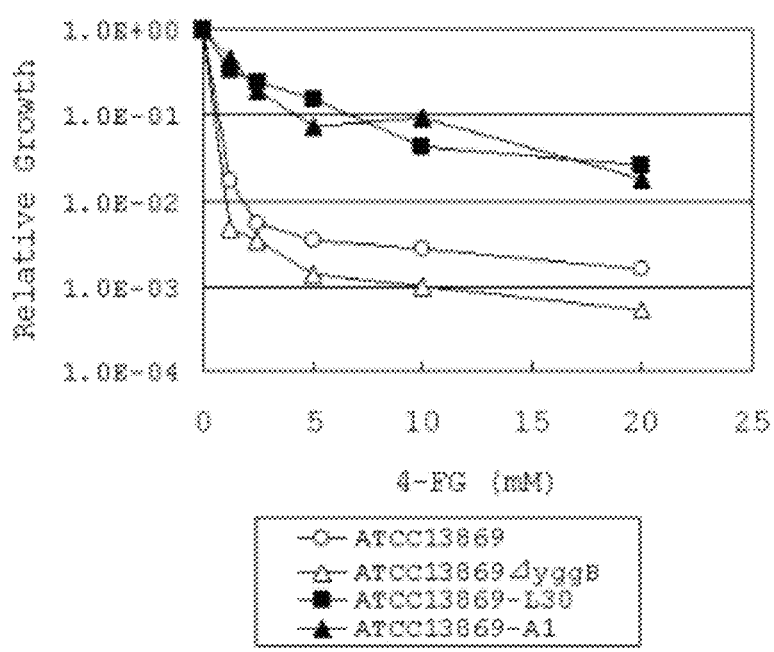
FIG. 7 shows growth of the control strain and the mutant-type yggB gene-introduced strains in a liquid medium containing 4-fluoroglutamic acid.

(14-2) Evaluation of Resistance to 4-Fluoroglutamic Acid in a Liquid Medium 4-fluoroglutamic acid was added into the minimum liquid medium having the same composition as described in Example 4 but not containing agar to the final concentration of 1.25 mM, 2.5 mM, 5 mM, 10 mM, and 20 mM, respectively. Each of the ATCC13869 strain, ATCC13869ΔyggB strain, ATCC13869-L30 strain, and ATCC13869-A1 strain was spread over a CM-Dex plate and cultured at 31.5° C. overnight. Then, cells were collected, and after washing with the sterilized 0.85% NaCl solution, inoculated into the liquid medium and cultured at 31.5° C. with shaking. When the OD660 of each strain cultured without 4-fluoroglutamic acid reached 1.0, the culture was terminated and the obtained culture solution was diluted appropriately and spread over the CM-Dex plate overnight. The number of colonies which appeared were calculated and designated as a viable cell number. FIG. 7 shows the relative cell number at each concentration of 4-fluoroglutamic acid when the cell number of the culture without 4-fluoroglutamic acid was set to 1. It was found that the ATCC13869-A1 strain and the ATCC13869-L30 strain have decreased sensitivity to 4-fluoroglutamic acid.

These results also showed that strains having a mutant-type yggB gene can be obtained by the screening using L-glutamic acid analogs such as 4-fluoroglutamic acid.

Example 15

Construction of the yggB Gene and odhA Gene-Double Mutant Strain

The yggB gene and odhA gene-double mutant strain were prepared by introducing a mutant-type odhA gene into the above-mentioned ATCC13869-L30 strain.

First, each of the mutations shown in Table 14 was introduced into the odhA gene encoding E1o subunit of α-KGDH on the chromosome of the ATCC13869-L30 strain. In Table 14, nucleotide sequences of the region corresponding to nucleotides 2528 to 2562 of SEQ ID NO: 43 in each of the mutant-type odhA gene are shown. In Table 15, amino acid sequences of the region corresponding to amino acids 696 to 707 of SEQ ID NO: 44 in each of the amino acid sequences encoded by the mutant-type odhA genes are shown.

The L30sucA8 strain in which the odhA gene having the nucleotide sequence of SEQ ID NO: 45 is introduced can be obtained as follows. The mutant odhA gene fragment is prepared by PCR using primers of SEQ ID NOS: 53 and 54. The obtained fragment is digested with BamHI and ligated to the BamHI site of plasmid pKF19m which is attached to Mutan-Super Express Km (Takara Bio). Then, PCR is performed using a primer of SEQ ID NO: 55 having a phosphorylated 5'-end and the selection primer of Mutan-Super Express Km, and the obtained PCR product is used to transform sup0-*E. coli* strain, such as MV1184 strain, to obtain a plasmid containing the mutant odhA fragment. This fragment is inserted into the pBS4S plasmid and the obtained plasmid is used to transform the ATCC13869-L30 strain to thereby obtain a strain in which the plasmid is integrated into its chromosome. Then, a strain which is resistant to sucrose and sensitive to kanamycin is selected from these strains. The nucleotide sequence of the odhA gene of the selected strains is determined and the strain in which function of α-KGDH is deficient by a frameshift mutation in the odhA gene is selected as ATCC13869-L30sucA8 (odhA8) strain.

The other odhA mutant strains can be obtained by the similar procedures using the ATCC13869-L30 strain.

The sucA801 strain in which a mutant odhA gene having a nucleotide sequence of SEQ ID NO: 47 is introduced can be obtained by a similar method as described above in which a primer of SEQ ID NO: 56 having a phosphorylated 5'-end is used instead of a primer of SEQ ID NO: 55.

The sucA805 strain in which a mutant odhA gene having a nucleotide sequence of SEQ ID NO: 49 is introduced can be obtained by a similar method as described above in which a primer of SEQ ID NO: 57 having a phosphorylated 5'-end is used instead of a primer of SEQ ID NO: 55.

The sucA77 strain in which a mutant odhA gene having a nucleotide sequence of SEQ ID NO: 51 is introduced can be obtained by a similar method as described above in which a primer of SEQ ID NO: 58 having a phosphorylated 5'-end is used instead of a primer of SEQ ID NO: 55.

The L30sucA8 strain does not have intracellular α-KGDH because the sucA8 mutation is a frame-shift mutation which causes an immature truncation of the α-KGDH protein. On the other hand, sucA801 strain, sucA805 strain, and sucA77 strain have decreased but some α-KGDH activity because these mutations are not frame-shift mutations and do not cause immature truncation of the α-KGDH protein.

TABLE 14 partial nucleotide acid sequence of odhA mutant genes

| Strains | Nucleotide sequence of odhA gene |
|---|---|
| ATCC13869-L30 | CTG GCT AAG CTG CGT GGC TAC GAC GTC GGA GGC ACC |
| L30sucA8 | CTG GCT AAG CTG CGT     C GAC GTC GGA GGC ACC |
| L30sucA801 | CTG GCT AAG CTG CGT    CTC GAC GTC GGA GGC ACC |
| L30sucA805 | CTG GCT AAA AGC TGC    GTC GAC GTC GGA GGC ACC |
| L30sucA77 | CTG GCT ATA AGC TGC    GTC GAC GTC GGA GGC ACC |

TABLE 15 amino acid sequence of odhA mutants

| Strains | Amino acid sequence of E1o subunit |
|---|---|
| Wild | Leu Ala Lys Leu Arg Gly Tyr Asp Val Gly Gly Thr |
| L30sucA8 (ΔsucA) | Leu Ala Lys Leu Arg         Arg Arg Arg Arg His |
| L30sucA801 | Leu Ala Lys Leu Arg --- Leu Asp Val Gly Gly Thr |
| L30sucA805 | Leu Ala Lys Ser Cys --- Val Asp Val Gly Gly Thr |
| L30sucA77 | Leu Ala Ile Ser Cys --- Val Asp Val Gly Gly Thr |

<L-Glutamic Acid Production Using the yggB Gene and the odhA Gene-Double Mutant Strain L-glutamic acid productivity of the obtained ygg gene and odhA gene-double mutant strain was evaluated by culturing these strains in a Sakaguchi flask. Each of the strains listed in Table 14 was cultured at 31.5° C. overnight on CM-Dex agar medium, and then 1/6 of the culture was transferred to 20 ml of a medium containing 60 g/l glucose, 22.5 g/l $(NH_4)_2SO_4$, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l vitamin B1, 0.48 g/l soybean protein hydrolysate, and 300 µg/l biotin (adjusted to pH 8.0 with KOH), added with $CaCO_3$ and cultured with stirring at 115 rpm at 31.5° C. The amount of accumulated L-glutamic acid after 19 hours of culture is shown in Table 16. The sucA801, sucA805, and sucA77 strains exhibited higher L-glutamic acid productivity than the ATCC13869-L30 strain carrying a wild-type odhA gene and the sucA8 strain carrying odhA gene with a frame-shift mutation. These results showed that L-glutamic acid is efficiently produced by regulating α-KGDH activity by introducing mutations into the proximate of thiamine pyrophosphate binding region of the odhA gene.

TABLE 16

L-glutamic acid production by odhA mutant strains

| Strain | L-glutamic acid (g/L) |
|---|---|
| ATCC13869-L30 | 4.9 |
| L30sucA8 | 19.8 |
| L30sucA801 | 22.1 |
| L30sucA805 | 23.8 |
| L30sucA77 | 21.6 |

Example 16

Disruption of the odhA Gene in the ATCC14067yggB8 Strain

The odhA gene was disrupted in the ATCC14067 strain and the ATCC14067yggB8 strain, respectively and the obtained strains were cultured. First, a plasmid for disrupting the odhA gene was constructed. PCR was performed using the synthetic oligonucleotides shown in SEQ ID NOS: 77 and 78 as primers and chromosomal DNA of ATCC14067 strain as a template to amplify a fragment covering the N-terminal region of the odhA gene. Another PCR was performed using the synthetic oligonucleotides shown in SEQ ID NOS: 79 and 80 as primers and chromosomal DNA of ATCC14067 strain as a template to amplify a fragment covering C-terminal region of the odhA gene. Subsequently, PCR was performed using a mixture of equimolar amounts of the N-terminal fragment and the C-terminal fragment as a template and synthetic DNAs of SEQ ID NOS: 81 and 82 as primers to prepare a fragment in which an internal sequence of the odhA gene is deleted. The obtained PCR product was digested with BamHI and inserted into the pBS4S constructed in Example 1 to obtain a plasmid pBSΔsucA47.

ATCC14067 strain and ATCC14067yggB8 of Example 11 were transformed with the pBSΔsucA47 in the same way as described in Example 6 to introduce the deletion-type odhA gene into the chromosome and remove only the vector portion. Strains in which the odhA gene was disrupted were selected from kanamycin-sensitive strains by PCR using the primers of SEQ ID NOS: 77 and 80. The thus obtained strains were named ATCC14067ΔodhA strain and ATCC14067ΔodhA yggB8 strain, respectively.

Table 17 shows the results of cultivation of the ATCC14067ΔodhA strain and the ATCC14067ΔodhA yggB8 strain according to the method described in Example 3. It was found that introduction of the 8-type mutant yggB gene enhanced L-glutamic acid producing ability of the odhA gene-disrupted strain.

TABLE 17

<L-glutamic acid production of the odhA gene-disrupted strain and the odhA-disrupted and 8-type mutant yggB gene-introduced strain>

| | OD620(×101) | Glu(g/L) |
|---|---|---|
| ATCC14067 Δ odhA | 0.270 | 5.8 |
| ATCC14067 Δ odhA yggB8 | 0.242 | 22.0 |

Example 17

Disruption of the symA Gene in the yggB-Mutant Strain

The symA gene was disrupted in the 2A-1R strain constructed in Example 3 and having an IS inserted into the yggB gene, and the obtained strain was cultured in comparison with the 2A-1R strain. The nucleotide sequence of the symA gene from the ATCC13869 strain is shown in SEQ ID NO: 86, and the amino acid sequence is shown in SEQ ID NO: 87. First, a plasmid for the purpose of disrupting the symA gene was constructed. PCR was performed using the synthetic oligonucleotides shown in SEQ ID NOS: 88 and 89 as primers and chromosomal DNA of ATCC13869 strain as a template to amplify a fragment covering N-terminal region of the symA gene. Another PCR was performed using the synthetic oligonucleotides shown in SEQ ID NOS: 90 and 91 as primers and chromosomal DNA of ATCC13869 strain as a template to amplify a fragment covering the C-terminal region of the symA gene. Subsequently, PCR was performed using a mixture of equimolar amounts of the N-terminal fragment and the C-terminal fragment as a template and synthetic DNAs of SEQ ID NOS: 88 and 91 as primers to prepare a fragment in which an internal sequence of the SymA gene is deleted. The obtained PCR product was digested with BamHI and inserted into the pBS4S constructed in Example 1 to obtain a plasmid pBSΔ1867.

The 2A-1R strain was transformed with the pBSΔ1867 in the same way as described in Example 6 to introduce the deletion-type SymA gene into the chromosome and remove only the vector portion. Strains in which the SymA gene was disrupted were selected from kanamycin-sensitive strains by PCR using the primers of SEQ ID NOS: 88 and 91. The thus obtained strains were named 2A-1RΔSymA strain.

Table 18 shows the results of cultivation of the 2A-1RΔSymA strain and the 2A-1R strain according to the method described in Example 3. It was found that deletion of the SymA gene further enhanced L-glutamic acid producing ability of the mutant-type yggB gene-introduced strain.

TABLE 18

<L-glutamic acid production of the 2A-1R strain and the symA gene-disrupted 2A-1R strain>

| | OD620(×51) | Glu (g/L) |
|---|---|---|
| 2A-1R | 0.846 | 12.4 |
| 2A-1R Δ symA | 0.709 | 15.8 |

Example 18

Construction of a Wild-Type yggB Gene-Amplified Strain pL5k containing a wild-type yggB gene of a coryneform bacterium was used to introduce the wild-type yggB gene into coryneform bacterium. A plasmid having a similar structure as pL5k can also be constructed by performing PCR using primers of SEQ ID Nos: 59 and 60 and chromosomal DNA of ATCC13869 strain as a template, digesting the amplified product with BamHI, and inserting the resulting fragment into the BamHI site of pVK9. pVK9 is a shuttle vector which was obtained by blunt-ending the AvaII site of pHSG299 (Takara Bio) and inserting therein a fragment involved in autonomous replication in coryneform bacteria excised from pHK4 (JP-A-05-007491) with BamHI and KpnI.

A *Corynebacterium glutamicum* ATCC13869 strain was transformed with pL5k by the electric pulse method (JP-A-2-207791). The transformed cells were spread over a CM2B plate medium (10 g/l polypeptone, 10 g/l yeast extract, 5 g/l NaCl, 20 g/l agar, adjusted to pH 7.0 with KOH) and cultured at 31.5° C. for one night. On the next day, colonies which appeared were purified on a CM2B plate medium containing 25 µg/ml kanamycin to obtain a wild-type yggB-gene amplified strain. Plasmids were extracted from the transformants by a conventional method to confirm that the target plasmid was introduced. The wild-type yggB-gene amplified strain thus obtained was named ATCC13869/pL5k. As a control strain, ATCC13869/pVK9 introduced with pVK9 was constructed in the same manner as described above.

Example 19

Evaluation of a Wild-Type yggB Gene-Amplified Strain (2-1) Evaluation Under Biotin-Limited Culture Conditions Three clones were isolated from each of the wild-type yggB gene-amplified strain and control strain constructed in Example 17, and each clone was inoculated into 20 ml of a seed culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by shaking culture at 31.5° C. After complete consumption of sugars, 2 ml of the culture was inoculated into 20 ml of main culture medium containing no biotin (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. After the complete consumption of sugars, the concentration of L-glutamic acid in the medium was determined. As a result, it was found that the wild-type yggB gene-amplified strain (ATCC13869/pL5k) caused accumulation of more L-glutamic acid than the vector-introduced strain. (In Table 19, OD620 is turbidity at 620 nm of culture solution diluted to 101 times, and indicates the cell amount and GH (g/L) indicates the amount of L-glutamic acid which had accumulated.)

TABLE 19

<Amount of L-glutamic acid which had accumulated under biotin limited conditions

| | OD620 | GH(g/L) |
|---|---|---|
| ATCC13869/pVK9-1 | 51.4 | 43.6 |
| ATCC13869/pVK9-2 | 51.3 | 43.8 |
| ATCC13869/pVK9-3 | 52.6 | 43.0 |
| ATCC13869/pL5k-1 | 44.7 | 46.0 |
| ATCC13869/pL5k-2 | 47.2 | 45.2 |
| ATCC13869/pL5k-3 | 43.9 | 45.8 |
| Blank | 0 | 0.4 |

(2-2) Evaluation Under Surfactant-Added Conditions

The same clones used in the above (2-1) were inoculated into 20 ml of a seed culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. After the complete consumption of sugars, 2 ml of the culture was inoculated into 20 ml of main culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. After 2 hours from the beginning of the culture, Tween 40 was added to a final concentration of 5 g/L, and the culture was continued. After the complete consumption of sugars, the concentration of L-glutamic acid in the medium was determined. As a result, it was found that the wild-type yggB gene-amplified strain (ATCC13869/pL5k) caused accumulation of more L-glutamic acid than the vector-introduced strain.

TABLE 20

Amount of L-glutamic acid which had accumulated under surfactant-added conditions

|  | OD620 | GH(g/L) |
|---|---|---|
| ATCC13869/pVK9-1 | 50.7 | 40.0 |
| ATCC13869/pVK9-2 | 50.7 | 39.3 |
| ATCC13869/pVK9-3 | 51.7 | 38.7 |
| ATCC13869/pL5k-1 | 38.6 | 42.1 |
| ATCC13869/pL5k-2 | 40.6 | 46.0 |
| ATCC13869/pL5k-3 | 39.1 | 45.5 |
| Blank | 0 | 0.4 |

(OD620 is turbidity at 620 nm of culture solution diluted 101 times, and indicates the cell amount and GH indicates the amount of L-glutamic acid which had accumulated.)

(2-3) Evaluation Under Penicillin G-Added Conditions

The same clones used in the above (2-1) were inoculated into 20 ml of a seed culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. After the complete consumption of sugars, 2 ml of the culture was inoculated into 20 ml of main culture medium (80 g/l glucose, 30 g/l ammonium sulfate, 1 g/l $KH_2PO_4$, 0.4 g/l $MgSO_4.7H_2O$, 0.01 g/l $FeSO_4.7H_2O$, 0.01 g/l $MnSO_4.4-5H_2O$, 200 µg/l VB1, 60 µg/l biotin, 0.48 g/l soybean hydrolysate (T-N), adjusted to pH 8.0 with KOH: autoclaved at 115° C. for 10 minutes), and then 1 g of sterilized calcium carbonate was added thereto, followed by a shaking culture at 31.5° C. After 2 hours of the culture, penicillin G was added to a final concentration of 0.5 U/ml and the culture was continued. After the complete consumption of sugars, the concentration of L-glutamic acid in the medium was determined. As a result, it was found that the wild-type yggB gene-amplified strain (ATCC13869/pL5k) caused accumulation of more L-glutamic acid than the vector-introduced strain. (Table 21)

TABLE 21

Amount of L-glutamic acid accumulated under penicillin G-added conditions

|  | OD620 | GH(g/L) |
|---|---|---|
| ATCC13869/pVK9-1 | 66.4 | 24.4 |
| ATCC13869/pVK9-2 | 65.5 | 24.0 |
| ATCC13869/pVK9-3 | 66.9 | 24.4 |
| ATCC13869/pL5k-1 | 59.5 | 30.8 |
| ATCC13869/pL5k-2 | 59.6 | 29.8 |
| ATCC13869/pL5k-3 | 60.1 | 29.4 |
| Blank | 0 | 0.4 |

(OD620 is turbidity at 620 nm of culture solution diluted 101 times, and indicates the cell amount and GH indicates the amount of L-glutamic acid which had accumulated.)

INDUSTRIAL APPLICABILITY

According to the present invention, L-glutamic acid is efficiently produced by using a strain modified by using yggB genes.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing a coryneform bacterium comprising a mutant-type yggB gene, said method comprising:
   a) introducing a random mutation into a wild-type yggB gene in vitro, resulting in a mutant-type yggB gene,
   b) modifying a coryneform bacterium by transforming said coryneform bacterium with the mutant-type yggB gene;
   c) inoculating a said coryneform bacterium of step b) into a medium containing not less than 30 μg/l of biotin, and
   d) selecting coryneform bacteria that show increased accumulation of L-glutamic acid-in the medium as compared to a non-modified coryneform bacterium.

2. A method for producing a coryneform bacterium comprising a mutant-type yggB gene, said method comprising:
   a) modifying a coryneform bacterium by randomly introducing a transposable element into the chromosome of said coryneform bacterium,
   b) inoculating said coryneform bacterium of step (a) into a medium containing not less than 30 μg/1 of biotin,
   c) screening for coryneform bacteria that show increased accumulation of L-glutamic acid in the medium as compared to a non-modified coryneform bacterium, and d) selecting coryneform bacteria comprising a mutant-type yggB by determining the nucleotide sequence of the yggB gene on the chromosome of the bacteria.

3. A method for producing a coryneform bacterium comprising a mutant type yggB gene, said method comprising:
   a) inoculating a coryneform bacterium into a medium containing L-glutamic acid analogs,
   b) screening for coryneform bacteria which grows on the medium containing L-glutamic acid analogs, and
   c) selecting coryneform bacteria comprising a mutant-type yggB gene by determining the nucleotide sequence of the yggB gene.

4. A method for producing a coryneform bacterium comprising a mutant-type yggB gene, said method comprising:
   a) modifying a coryneform bacterium by inoculating said coryneform bacterium which is deficient in a gene encoding α-ketoglutarate dehydrogenase into a medium containing not less than 30 μg/l of biotin, and
   b) selecting coryneform bacteria that show increased accumulation of L-glutamic acid in the medium as compared to a non-modified coryneform bacterium;
   c) selecting coryneform bacteria comprising a mutant-type yggB gene by determining the nucleotide sequence of the mutant-type yggB gene in coryneform bacteria selected in step (b).

5. The method according to claim 1, said method further comprising a step of determining the nucleotide sequence of the yggB gene in coryneform bacteria selected in step (d).

* * * * *

SEQUENCE LISTING

```
<160> NUMBER OF SEQ ID NOS: 91

<210> SEQ ID NO 1
<211> LENGTH: 33
<212> TYPE: DNA
<213> ORGANISM: Artificial sequence
<220> FEATURE:
<223> OTHER INFORMATION: odhA primer

<400> SEQUENCE: 1
ggggatccat cggtatgcca caccgtggtc gcc                                33

<210> SEQ ID NO 2
<211> LENGTH: 33
<212> TYPE: DNA
<213> ORGANISM: Artificial sequence
<220> FEATURE:
<223> OTHER INFORMATION: odhA primer

<400> SEQUENCE: 2
ggggatccac gactgcttct gcatcttcgt tgg                                33

<210> SEQ ID NO 3
<211> LENGTH: 17
<212> TYPE: DNA
<213> ORGANISM: Artificial sequence
<220> FEATURE:
```

```
<223> OTHER INFORMATION: M1 primer

<400> SEQUENCE: 3
gtaaaacgac ggccagt                                                    17

<210> SEQ ID NO 4
<211> LENGTH: 25
<212> TYPE: DNA
<213> ORGANISM: Artificial sequence
<220> FEATURE:
<223> OTHER INFORMATION: odhA primer

<400> SEQUENCE: 4
cagaaggaat catcggtgag caggc                                           25

<210> SEQ ID NO 5
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)
<223> OTHER INFORMATION: yggB

<400> SEQUENCE: 5
gatcttgccg atttcggcag gatcaatgtc ggcgtgaatg atcttggcat caggtgcgaa     60
agtgtcaacg tcaccggtga cgcggtcatc aaagcgggag ccgatagcaa tcagcaggtc    120
gctgcgctgc agtgcaccaa cagcggacac agtgccatgc atgcctggca tacccatgtg    180
cagctcgtgg gactctggga aggttcccag cgccatcaat gtggtgacaa ctggaatgcc    240
ggtgtgctca gcgaacgcac gaagctcttc gtgggcatca gccttgataa cgccgccgcc    300
aacgtaaagg acaggcttct tagactcacc gatcagtttg acagcctgct caatctgtcg    360
agcatgcggt gttgaaactg ggcggtagcc tggcaggtcg atctttggtg gccagacgaa    420
atccaattca gcgttctgaa catccttggg gatatccact agaacaggac cagggcgacc    480
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg gccggtgatg caaccatgg gaacggagtc     660 caagtttgca tcagcgattg gggtaaccaa gttggttgcg cctgggccag aggttgcaat    720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc aggggcggcg atcgaccac ggcttgcaac     960 cgtggcggga gtgggctgtt gagaagctgc cacattcacg actttctggc tcctttacta   1020
aataaggatt tcacaggac ccgtccaagc caagccgatt tcaactcagc ctaaagacaa    1080
agccctcatt taaaattgtt ccgacgcgga tgcgtgtgca cgcagtgcga cagatgtctg   1140
ttgcaaagtt ggctacttgg gtcataacca acaagaaagc cctcgttcca acactgtggt   1200
gagtgttgtc gagggcgctt gacgagacga cttggaaggc cgttacggca ggcgccgcgc   1260
ggttactact acaagtcgaa taatggtcat ggtgtgtcat gctacacaca tcgagtttcc   1320
aattccacaa cgcacgaaaa ttcccacccc caaaactccc ccacttcggt taaggaatca   1380
ggattctcac aaagttcagg caggctcccg ctactttca gcgctaatct tggctc atg    1439
                                                                     Met
                                                                       1
```

```
att tta ggc gta ccc att caa tat ttg ctc tat tca ttg tgg aat tgg    1487
Ile Leu Gly Val Pro Ile Gln Tyr Leu Leu Tyr Ser Leu Trp Asn Trp
         5                  10                  15 att gtc gat acc ggt ttt gat gta gca att atc ctg gtc ttg gcg ttt    1535
Ile Val Asp Thr Gly Phe Asp Val Ala Ile Ile Leu Val Leu Ala Phe
             20                  25                  30 ttg att cca cgt atc ggc cga ctg gcc atg cgt att atc aag cag cga    1583
Leu Ile Pro Arg Ile Gly Arg Leu Ala Met Arg Ile Ile Lys Gln Arg
         35                  40                  45 gtg gag tct gca gcc gat gcg gac acc act aag aac cag ctc gcg ttc    1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt    1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg    1727
Ala Val Ser Ala Met Gln Ala Phe Gly Phe Ser Leu Ala Gly Ala Ala
             85                  90                  95 att ccg gca acc att gcg tca gct gcc att ggt ctt ggt gcg cag tcg    1775
Ile Pro Ala Thr Ile Ala Ser Ala Ala Ile Gly Leu Gly Ala Gln Ser
         100                 105                 110 att gtt gcg gac ttc ttg gcc gga ttt ttc atc ctg acg gaa aag caa    1823
Ile Val Ala Asp Phe Leu Ala Gly Phe Phe Ile Leu Thr Glu Lys Gln
     115                 120                 125 ttc ggc gtg ggt gac tgg gtg cgc ttt gag ggc aac ggc atc gtt gtt    1871
Phe Gly Val Gly Asp Trp Val Arg Phe Glu Gly Asn Gly Ile Val Val
130                 135                 140                 145 gaa ggc acc gtc att gag atc acc atg cgc gcg acc aaa att cgc acg    1919
Glu Gly Thr Val Ile Glu Ile Thr Met Arg Ala Thr Lys Ile Arg Thr
                 150                 155                 160 att gca caa gag acc gtg atc atc ccg aac tcc acg gcg aaa gtg tgc    1967
Ile Ala Gln Glu Thr Val Ile Ile Pro Asn Ser Thr Ala Lys Val Cys
             165                 170                 175 atc aac aat tct aat aac tgg tcg cgt gcg gtt gtc gtt att ccg atc    2015
Ile Asn Asn Ser Asn Asn Trp Ser Arg Ala Val Val Val Ile Pro Ile
         180                 185                 190 ccc atg ttg ggt tct gaa aac atc aca gat gtc atc gcg cgc tct gaa    2063
Pro Met Leu Gly Ser Glu Asn Ile Thr Asp Val Ile Ala Arg Ser Glu
     195                 200                 205 gct gcg act cgt cgc gca ctt ggc cag gag aaa atc gca ccg gaa atc    2111
Ala Ala Thr Arg Arg Ala Leu Gly Gln Glu Lys Ile Ala Pro Glu Ile
210                 215                 220                 225 ctc ggt gaa ctc gat gtg cac cca gcc acg gaa gtc aca ccg cca acg    2159
Leu Gly Glu Leu Asp Val His Pro Ala Thr Glu Val Thr Pro Pro Thr
                 230                 235                 240 gtg gtc ggc atg ccg tgg atg gtc acc atg cgt ttc ctc gtg caa gtc    2207
Val Val Gly Met Pro Trp Met Val Thr Met Arg Phe Leu Val Gln Val
             245                 250                 255 acc gcc ggc aat caa tgg ctg gtc gaa cgc gcc atc cgc aca gaa atc    2255
Thr Ala Gly Asn Gln Trp Leu Val Glu Arg Ala Ile Arg Thr Glu Ile
         260                 265                 270 atc aac gaa ttc tgg gaa gaa tac ggc agc gca acc act aca tcg gga    2303
Ile Asn Glu Phe Trp Glu Glu Tyr Gly Ser Ala Thr Thr Thr Ser Gly
     275                 280                 285 acc ctc att gat tcc tta cac gtt gag cat gaa gag cca aag acc tcg    2351
Thr Leu Ile Asp Ser Leu His Val Glu His Glu Glu Pro Lys Thr Ser
290                 295                 300                 305 ctt atc gac gcc tcc ccc cag gct ctt aag gaa ccg aag ccg gag gct    2399
Leu Ile Asp Ala Ser Pro Gln Ala Leu Lys Glu Pro Lys Pro Glu Ala
                 310                 315                 320
```

```
gcg gcg acg gtt gca tcg cta gct gca tcg tct aac gac gat gca gac      2447
Ala Ala Thr Val Ala Ser Leu Ala Ala Ser Ser Asn Asp Asp Ala Asp
        325                 330                 335 aat gca gac gcc tcg gcg atc aat gca ggc aat cca gag aag gaa ctt      2495
Asn Ala Asp Ala Ser Ala Ile Asn Ala Gly Asn Pro Glu Lys Glu Leu
            340                 345                 350 gat tcc gat gtg ctg gaa caa gaa ctc tcc agc gaa gaa ccg gaa gaa      2543
Asp Ser Asp Val Leu Glu Gln Glu Leu Ser Ser Glu Glu Pro Glu Glu
        355                 360                 365 aca gca aaa cca gat cac tct ctc cga ggc ttc ttc cgc act gat tac      2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc      2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt      2687
Met Ser Thr Ser Leu Leu Leu Gly Ala Leu Leu Leu Leu Ser Leu Phe
            405                 410                 415 aag gtc atg act gtg gaa cca agt gag aat tgg caa aac tcc agt gga      2735
Lys Val Met Thr Val Glu Pro Ser Glu Asn Trp Gln Asn Ser Ser Gly
        420                 425                 430 tgg ctg tca cca agc act gcc acc tca act gcg gtg acc acc tcc gaa      2783
Trp Leu Ser Pro Ser Thr Ala Thr Ser Thr Ala Val Thr Thr Ser Glu
    435                 440                 445 act tcc gcg cca gca agc acg cct tcg atg aca gtg ccc act acg gtg      2831
Thr Ser Ala Pro Ala Ser Thr Pro Ser Met Thr Val Pro Thr Thr Val
450                 455                 460                 465 gag gag acc cca acg atg gaa tct agc gtc gaa acg cag cag gaa acc      2879
Glu Glu Thr Pro Thr Met Glu Ser Ser Val Glu Thr Gln Gln Glu Thr
                470                 475                 480 tca acc cct gca acc gca acg ccc cag cga gcc gac acc atc gaa ccg      2927
Ser Thr Pro Ala Thr Ala Thr Pro Gln Arg Ala Asp Thr Ile Glu Pro
            485                 490                 495 acc gag gaa gcc acg tcg cag gag gaa acg act gca tcg cag acg cag      2975
Thr Glu Glu Ala Thr Ser Gln Glu Glu Thr Thr Ala Ser Gln Thr Gln
        500                 505                 510 tct cca gca gtg gaa gca cca acc gcg gtc caa gaa aca gtt gcg ccg      3023
Ser Pro Ala Val Glu Ala Pro Thr Ala Val Gln Glu Thr Val Ala Pro
    515                 520                 525 acg tcc acc cct taggacgctg attacagacg tgtcccattt ctttactact           3075
Thr Ser Thr Pro
530 attggaaatt atgagttcag acgcagaaaa ggcatccgtg agctttccg aaaaatttca      3135 cccagaacgc acccatattt tgggcgccgt tgttttggc ctgatctcat tattagtcat     3195 cggcgcagcc cctcagtacc tgttttggct gctcgcgctc cctgtcatct tcggttactg    3255 ggttctaaaa tcatccacga tcgttgatga acagggcatc accgcaaact acgccttcaa    3315 gggcaaaaag gttgtggcct gggaagacct cgcaggaatc ggattcaagg gtgcccgcac    3375 tttcgctcgc accacctccg atgcagaagt caccctcccc ggcgtcacct tcaactccct    3435 tccccgcctt gaagctgctt cccacggccg catccccgat gcgatc                   3481

<210> SEQ ID NO 6
<211> LENGTH: 533
<212> TYPE: PRT
<213> ORGANISM: Corynebacterium glutamicum

<400> SEQUENCE: 6

Met Ile Leu Gly Val Pro Ile Gln Tyr Leu Leu Tyr Ser Leu Trp Asn
1               5                   10                  15
```

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
            35                  40                  45

Arg Val Glu Ser Ala Ala Asp Ala Asp Thr Thr Lys Asn Gln Leu Ala
50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ile Gly Leu Gly Ala Gln
                100                 105                 110

Ser Ile Val Ala Asp Phe Leu Ala Gly Phe Phe Ile Leu Thr Glu Lys
                115                 120                 125

Gln Phe Gly Val Gly Asp Trp Val Arg Phe Glu Gly Asn Gly Ile Val
130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
                180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
            210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Pro Glu
            355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser

```
                    435                 440                 445
Glu Thr Ser Ala Pro Ala Ser Thr Pro Ser Met Thr Val Pro Thr Thr
            450                 455                 460
Val Glu Glu Thr Pro Thr Met Glu Ser Ser Val Glu Thr Gln Gln Glu
465                 470                 475                 480
Thr Ser Thr Pro Ala Thr Ala Thr Pro Gln Arg Ala Asp Thr Ile Glu
                485                 490                 495
Pro Thr Glu Glu Ala Thr Ser Gln Glu Glu Thr Thr Ala Ser Gln Thr
            500                 505                 510
Gln Ser Pro Ala Val Glu Ala Pro Thr Ala Val Gln Glu Thr Val Ala
        515                 520                 525
Pro Thr Ser Thr Pro
    530

<210> SEQ ID NO 7
<211> LENGTH: 4934
<212> TYPE: DNA
<213> ORGANISM: Corynebacterium glutamicum
<220> FEATURE:
<221> NAME/KEY: CDS
<222> LOCATION: (1437)..(2705)
<223> OTHER INFORMATION: 2A-1

<400> SEQUENCE: 7
```

| | | | | | |
|---|---|---|---|---|---|
| gatcttgccg | atttcggcag | gatcaatgtc | ggcgtgaatg | atcttggcat | caggtgcgaa | 60 |
| agtgtcaacg | tcaccggtga | cgcggtcatc | aaagcgggag | ccgatagcaa | tcagcaggtc | 120 |
| gctgcgctgc | agtgcaccaa | cagcggacac | agtgccatgc | atgcctggca | tacccatgtg | 180 |
| cagctcgtgg | gactctggga | aggttcccag | cgccatcaat | gtggtgacaa | ctggaatgcc | 240 |
| ggtgtgctca | gcgaacgcac | gaagctcttc | gtgggcatca | gccttgataa | cgccgccgcc | 300 |
| aacgtaaagg | acaggcttct | tagactcacc | gatcagtttg | acagcctgct | caatctgtcg | 360 |
| agcatgcggt | gttgaaactg | gcggtagcc | tggcaggtcg | atctttggtg | ccagacgaa | 420 |
| atccaattca | gcgttctgaa | catccttggg | gatatccact | agaacaggac | cagggcgacc | 480 |
| agtaatcgcg | aggtggaatg | cctcagccaa | tgcctgtgga | atgtcgttgg | ggttggtgac | 540 |
| catgaagttg | tgcttggtca | ctggcatggt | gatgccgcgg | atatcggctt | cctggaaagc | 600 |
| atcggtaccc | agcaggctac | ttccgacctg | gccggtgatg | gcaaccatgg | gaacggagtc | 660 |
| caagtttgca | tcagcgattg | gggtaaccaa | gttggttgcg | cctgggccag | aggttgcaat | 720 |
| gcagacgcca | acgcgtccag | taacctgcgc | gtagccggtt | gctgcgtggc | ctgcgccctg | 780 |
| ctcgtggcgc | actaggacgt | ggcgcacctt | tgtggaggaa | tagagcgggt | catacaccgg | 840 |
| tagcaccgca | ccaccaggaa | taccgaacac | gatgtcggcg | ttaagctcct | cgagcgatcg | 900 |
| aacaattgcc | tgtgcacctg | tcatccgctc | aggggcggcg | atcgaccac | ggcttgcaac | 960 |
| cgtggcggga | gtgggctgtt | gagaagctgc | cacattcacg | actttctggc | tcctttacta | 1020 |
| aataaggatt | tcacaggac | ccgtccaagc | caagccgatt | tcaactcagc | ctaaagacaa | 1080 |
| agccctcatt | taaaattgtt | ccgacgcgga | tgcgtgtgca | cgcagtgcga | cagatgtctg | 1140 |
| ttgcaaagtt | ggctacttgg | gtcataacca | acaagaaagc | cctcgttcca | acactgtggt | 1200 |
| gagtgttgtc | gagggcgctt | gacgagacga | cttggaaggc | cgttacggca | ggcgccgcgc | 1260 |
| ggttactact | acaagtcgaa | taatggtcat | ggtgtgtcat | gctacacaca | tcgagtttcc | 1320 |
| aattccacaa | cgcacgaaaa | ttcccacccc | caaaactccc | ccacttcggt | taaggaatca | 1380 |
| ggattctcac | aaagttcagg | caggctcccg | ctactttca | gcgctaatct | tggctc atg | 1439 |
| | | | | | Met | |

-continued

| | |
|---|---|
| att tta ggc gta ccc att caa tat ttg ctc tat tca ttg tgg aat tgg<br>Ile Leu Gly Val Pro Ile Gln Tyr Leu Leu Tyr Ser Leu Trp Asn Trp<br>5                           10                 15 | 1487 |
| att gtc gat acc ggt ttt gat gta gca att atc ctg gtc ttg gcg ttt<br>Ile Val Asp Thr Gly Phe Asp Val Ala Ile Ile Leu Val Leu Ala Phe<br>20                      25                    30 | 1535 |
| ttg att cca cgt atc ggc cga ctg gcc atg cgt att atc aag cag cga<br>Leu Ile Pro Arg Ile Gly Arg Leu Ala Met Arg Ile Ile Lys Gln Arg<br>35                      40                 45 | 1583 |
| gtg gag tct gca gcc gat gcg gac acc act aag aac cag ctc gcg ttc<br>Val Glu Ser Ala Ala Asp Ala Asp Thr Thr Lys Asn Gln Leu Ala Phe<br>50                      55                   60               65 | 1631 |
| gct ggc gtt ggc gtt tat atc gcg caa att gtg gcg ttt ttc atg ctt<br>Ala Gly Val Gly Val Tyr Ile Ala Gln Ile Val Ala Phe Phe Met Leu<br>70                      75                   80 | 1679 |
| gcc gtc tcc gcg atg cag gct ttt ggt ttc tct ctc gcg ggc gct gcg<br>Ala Val Ser Ala Met Gln Ala Phe Gly Phe Ser Leu Ala Gly Ala Ala<br>85                      90                 95 | 1727 |
| att ccg gca acc att gcg tca gct gcc att ggt ctt ggt gcg cag tcg<br>Ile Pro Ala Thr Ile Ala Ser Ala Ala Ile Gly Leu Gly Ala Gln Ser<br>100                  105               110 | 1775 |
| att gtt gcg gac ttc ttg gcc gga ttt ttc atc ctg acg gaa aag caa<br>Ile Val Ala Asp Phe Leu Ala Gly Phe Phe Ile Leu Thr Glu Lys Gln<br>115                 120               125 | 1823 |
| ttc ggc gtg ggt gac tgg gtg cgc ttt gag ggc aac ggc atc gtt gtt<br>Phe Gly Val Gly Asp Trp Val Arg Phe Glu Gly Asn Gly Ile Val Val<br>130                 135               140              145 | 1871 |
| gaa ggc acc gtc att gag atc acc atg cgc gcg acc aaa att cgc acg<br>Glu Gly Thr Val Ile Glu Ile Thr Met Arg Ala Thr Lys Ile Arg Thr<br>150                 155               160 | 1919 |
| att gca caa gag acc gtg atc atc ccg aac tcc acg gcg aaa gtg tgc<br>Ile Ala Gln Glu Thr Val Ile Ile Pro Asn Ser Thr Ala Lys Val Cys<br>165                 170               175 | 1967 |
| atc aac aat tct aat aac tgg tcg cgt gcg gtt gtc gtt att ccg atc<br>Ile Asn Asn Ser Asn Asn Trp Ser Arg Ala Val Val Val Ile Pro Ile<br>180                 185               190 | 2015 |
| ccc atg ttg ggt tct gaa aac atc aca gat gtc atc gcg cgc tct gaa<br>Pro Met Leu Gly Ser Glu Asn Ile Thr Asp Val Ile Ala Arg Ser Glu<br>195                 200               205 | 2063 |
| gct gcg act cgt cgc gca ctt ggc cag gag aaa atc gca ccg gaa atc<br>Ala Ala Thr Arg Arg Ala Leu Gly Gln Glu Lys Ile Ala Pro Glu Ile<br>210                 215               220              225 | 2111 |
| ctc ggt gaa ctc gat gtg cac cca gcc acg gaa gtc aca ccg cca acg<br>Leu Gly Glu Leu Asp Val His Pro Ala Thr Glu Val Thr Pro Pro Thr<br>230                 235               240 | 2159 |
| gtg gtc ggc atg ccg tgg atg gtc acc atg cgt ttc ctc gtg caa gtc<br>Val Val Gly Met Pro Trp Met Val Thr Met Arg Phe Leu Val Gln Val<br>245                 250               255 | 2207 |
| acc gcc ggc aat caa tgg ctg gtc gaa cgc gcc atc cgc aca gaa atc<br>Thr Ala Gly Asn Gln Trp Leu Val Glu Arg Ala Ile Arg Thr Glu Ile<br>260                 265               270 | 2255 |
| atc aac gaa ttc tgg gaa gaa tac ggc agc gca acc act aca tcg gga<br>Ile Asn Glu Phe Trp Glu Glu Tyr Gly Ser Ala Thr Thr Thr Ser Gly<br>275                 280               285 | 2303 |
| acc ctc att gat tcc tta cac gtt gag cat gaa gag cca aag acc tcg<br>Thr Leu Ile Asp Ser Leu His Val Glu His Glu Glu Pro Lys Thr Ser<br>290                 295               300              305 | 2351 |
| ctt atc gac gcc tcc ccc cag gct ctt aag gaa ccg aag ccg gag gct<br>Leu Ile Asp Ala Ser Pro Gln Ala Leu Lys Glu Pro Lys Pro Glu Ala | 2399 |

```
                     310                 315                 320
gcg gcg acg gtt gca tcg cta gct gca tcg tct aac gac gat gca gac    2447
Ala Ala Thr Val Ala Ser Leu Ala Ala Ser Ser Asn Asp Asp Ala Asp
            325                 330                 335 aat gca gac gcc tcg gcg atc aat gca ggc aat cca gag aag gaa ctt    2495
Asn Ala Asp Ala Ser Ala Ile Asn Ala Gly Asn Pro Glu Lys Glu Leu
            340                 345                 350 gat tcc gat gtg ctg gaa caa gaa ctc tcc agc gaa gaa ccg gaa gaa    2543
Asp Ser Asp Val Leu Glu Gln Glu Leu Ser Ser Glu Glu Pro Glu Glu
        355                 360                 365 aca gca aaa cca gat cac tct ctc cga ggc ttc ttc cgc act gat tac    2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc    2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt    2687
Met Ser Thr Ser Leu Leu Leu Gly Ala Leu Leu Leu Leu Ser Leu Phe
            405                 410                 415 aag ggg ctc ttc ctg ttt tagagtgcat tgatcttatg gaccaactgc           2735
Lys Gly Leu Phe Leu Phe
            420 cctgaatgga taaggcaccg cagaatgtag tggttcaaat tacggaaacc tagagcaatc    2795 ccacgcaaat gctccaaccg tccgttgatc gcttcgaccg gaccgttgga gacaccaaca    2855 tcgaaatacg ccaacacatc accaagtcgt ttaaacaaac tacgacccaa ctgcgcgagt    2915 tccttattcg gccccttcaa cacccgaagc tgatcaataa tggtccgcat tttcttcttc    2975 gcttcacgct tattacccat ctgataacaa tcaataatcg cctgatacgc aagccacgca    3035 agctttaaca ccccgtagtc tttgtcatac gcccacaact gctccaagct ttcttgctga    3095 cgaggactca accacttgtg cgtggtcaac aaggtcttcc ggttttatata caacggatcc    3155 tggcttaaac cacgacgctg gtatttctcc cgctggaggc gttgccggca ggcggtgagc    3215 ttgtcaccag caagccgcac aacatggaat ggatccatca gcgcgacgagc agaaggaatg    3275 agttctttac ttgctgtggc gtagccttgg aacccatcca tggacacgat ccgtatctga    3335 ttgcggaact gttcaccgcg ggaaccaagc caggaccgta agcatcagc actacgacct    3395 gggacgacat ctaataaccg ggcaggacac cgtgagtcat accgatgccc ggtcatatcg    3455 acaatcacgg tgacaaaccc atcaccatgc ttagccctat tatgtgacca cttatgctca    3515 tccaccccaa tgcatacac tccatcaaga tggtgaggat cgttatagac cagctcacgg      3575 cacatatcga gggctagttg gcaggttaaa tcccacccta gcccaagtgc tttcgcggtt    3635 gcgtgaacac tcatccggtc aatagcaagg cgttgcaaaa tccagcgggt gacccggtgg    3695 gtgaccttt taccgtggtc agcgcagctt agttctgctt ggaaatactt ttgcttacat    3755 gtcgggttgg tgcagcggta gcgaggtaga cggataaaca gtttggtggg aaacccgacg    3815 atgggtaaat caatgagcat ccggtgggtg tgatgacgaa acaccccagg ttgggagcat    3875 tctgggcagg tggaggtata gtcgagtgcg tctgcttcga tcagggtgta atcacctgca    3935 tcggaagcgc cggtgatggt gagtcctagt tccgcagtgc ggcagatggt gtcagcgatg    3995 atgttgccgg tagacttcat gggtagagcc ttttgttggt gtttggttag cttagatacc    4055 taaaccttaa ccctgacaaa aggctcgttt attttcgggt ctacaccgct agcccaggtt    4115 ctgtgatgta cccaaaaacc ggaagggcct catgactgtg gaaccaagtg agaattggca    4175 aaactccagt ggatggctgt caccaagcac tgccacctca actgcggtga ccacctccga    4235
```

```
aacttccgcg ccagcaagca cgccttcgat gacagtgccc actacggtgg aggagacccc    4295
aacgatggaa tctagcgtcg aaacgcagca ggaaacctca accccctgcaa ccgcaacgcc    4355 ccagcgagcc gacaccatcg aaccgaccga ggaagccacg tcgcaggagg aaacgactgc    4415
atcgcagacg cagtctccag cagtggaagc accaaccgcg gtccaagaaa cagttgcgcc    4475
gacgtccacc ccttaggacg ctgattacag acgtgtccca tttctttact actattggaa    4535
attatgagtt cagacgcaga aaaggcatcc gtggagcttt ccgaaaaatt tcacccagaa    4595
cgcacccata ttttgggcgc cgttgttttt ggcctgatct cattattagt catcggcgca    4655
gcccctcagt acctgttttg gctgctcgcg ctccctgtca tcttcggtta ctgggttcta    4715
aaatcatcca cgatcgttga tgaacagggc atcaccgcaa actacgcctt caagggcaaa    4775
aaggttgtgg cctgggaaga cctcgcagga atcggattca agggtgcccg cactttcgct    4835
cgcaccacct ccgatgcaga agtcaccctc cccggcgtca ccttcaactc ccttccccgc    4895
cttgaagctg cttcccacgg ccgcatcccc gatgcgatc                           4934
```

```
<210> SEQ ID NO 8
<211> LENGTH: 423
<212> TYPE: PRT
<213> ORGANISM: Corynebacterium glutamicum

<400> SEQUENCE: 8

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255
```

```
Val Thr Ala Gly Asn Gln Trp Leu Val Glu Arg Ala Ile Arg Thr Glu
            260                 265                 270

Ile Ile Asn Glu Phe Trp Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Gly Leu Phe Leu Phe
            420

<210> SEQ ID NO 9
<211> LENGTH: 28
<212> TYPE: DNA
<213> ORGANISM: Artificial sequence
<220> FEATURE:
<223> OTHER INFORMATION: primer

<400> SEQUENCE: 9
gggagctcga ctttctggct cctttact                                      28

<210> SEQ ID NO 10
<211> LENGTH: 28
<212> TYPE: DNA
<213> ORGANISM: Artificial sequence
<220> FEATURE:
<223> OTHER INFORMATION: primer

<400> SEQUENCE: 10
gggagctcgc cgatgactaa taatgaga                                      28

<210> SEQ ID NO 11
<211> LENGTH: 2014
<212> TYPE: DNA
<213> ORGANISM: Bacillus subtilis
<220> FEATURE:
<221> NAME/KEY: CDS
<222> LOCATION: (464)..(1885)
<223> OTHER INFORMATION: sacB

<400> SEQUENCE: 11
gatccttttt aacccatcac atatacctgc cgttcactat tatttagtga aatgagatat     60
tatgatattt tctgaattgt gattaaaaag gcaactttat gcccatgcaa cagaaactat    120
aaaaaataca gagaatgaaa agaaacagat agatttttta gttctttagg cccgtagtct    180
gcaaatcctt ttatgatttt ctatcaaaca aagaggaaaa atagaccagt tgcaatccaa    240
acgagagtct aatagaatga ggtcgaaaag taaatcgcgc gggtttgtta ctgataaagc    300
aggcaagacc taaaatgtgt aaagggcaaa gtgtatactt tggcgtcacc ccttacatat    360
```

```
tttaggtctt tttttattgt gcgtaactaa cttgccatct tcaaacagga gggctggaag      420
aagcagaccg ctaacacagt acataaaaaa ggagacatga acg atg aac atc aaa       475
                                              Met Asn Ile Lys
                                              1 aag ttt gca aaa caa gca aca gta tta acc ttt act acc gca ctg ctg       523
Lys Phe Ala Lys Gln Ala Thr Val Leu Thr Phe Thr Thr Ala Leu Leu
 5                10                  15                  20 gca gga ggc gca act caa gcg ttt gcg aaa gaa acg aac caa aag cca       571
Ala Gly Gly Ala Thr Gln Ala Phe Ala Lys Glu Thr Asn Gln Lys Pro
                25                  30                  35 tat aag gaa aca tac ggc att tcc cat att aca cgc cat gat atg ctg       619
Tyr Lys Glu Thr Tyr Gly Ile Ser His Ile Thr Arg His Asp Met Leu
        40                  45                  50 caa atc cct gaa cag caa aaa aat gaa aaa tat caa gtt cct gaa ttc       667
Gln Ile Pro Glu Gln Gln Lys Asn Glu Lys Tyr Gln Val Pro Glu Phe
            55                  60                  65 gat tcg tcc aca att aaa aat atc tct tct gca aaa ggc ctg gac gtt       715
Asp Ser Ser Thr Ile Lys Asn Ile Ser Ser Ala Lys Gly Leu Asp Val
 70                  75                  80 tgg gac agc tgg cca tta caa aac gct gac ggc act gtc gca aac tat       763
Trp Asp Ser Trp Pro Leu Gln Asn Ala Asp Gly Thr Val Ala Asn Tyr
85                  90                  95                 100 cac ggc tac cac atc gtc ttt gca tta gcc gga gat cct aaa aat gcg       811
His Gly Tyr His Ile Val Phe Ala Leu Ala Gly Asp Pro Lys Asn Ala
                105                 110                 115 gat gac aca tcg att tac atg ttc tat caa aaa gtc ggc gaa act tct       859
Asp Asp Thr Ser Ile Tyr Met Phe Tyr Gln Lys Val Gly Glu Thr Ser
            120                 125                 130 att gac agc tgg aaa aac gct ggc cgc gtc ttt aaa gac agc gac aaa       907
Ile Asp Ser Trp Lys Asn Ala Gly Arg Val Phe Lys Asp Ser Asp Lys
        135                 140                 145 ttc gat gca aat gat tct atc cta aaa gac caa aca caa gaa tgg tca       955
Phe Asp Ala Asn Asp Ser Ile Leu Lys Asp Gln Thr Gln Glu Trp Ser
150                 155                 160 ggt tca gcc aca ttt aca tct gac gga aaa atc cgt tta ttc tac act      1003
Gly Ser Ala Thr Phe Thr Ser Asp Gly Lys Ile Arg Leu Phe Tyr Thr
165                 170                 175                 180 gat ttc tcc ggt aaa cat tac ggc aaa caa aca ctg aca act gca caa      1051
Asp Phe Ser Gly Lys His Tyr Gly Lys Gln Thr Leu Thr Thr Ala Gln
                185                 190                 195 gtt aac gta tca gca tca gac agc tct ttg aac atc aac ggt gta gag      1099
Val Asn Val Ser Ala Ser Asp Ser Ser Leu Asn Ile Asn Gly Val Glu
            200                 205                 210 gat tat aaa tca atc ttt gac ggt gac gga aaa acg tat caa aat gta      1147
Asp Tyr Lys Ser Ile Phe Asp Gly Asp Gly Lys Thr Tyr Gln Asn Val
        215                 220                 225 cag cag ttc atc gat gaa ggc aac tac agc tca ggc gac aac cat acg      1195
Gln Gln Phe Ile Asp Glu Gly Asn Tyr Ser Ser Gly Asp Asn His Thr
    230                 235                 240 ctg aga gat cct cac tac gta gaa gat aaa ggc cac aaa tac tta gta      1243
Leu Arg Asp Pro His Tyr Val Glu Asp Lys Gly His Lys Tyr Leu Val
245                 250                 255                 260 ttt gaa gca aac act gga act gaa gat ggc tac caa ggc gaa gaa tct      1291
Phe Glu Ala Asn Thr Gly Thr Glu Asp Gly Tyr Gln Gly Glu Glu Ser
                265                 270                 275 tta ttt aac aaa gca tac tat ggc aaa agc aca tca ttc ttc cgt caa      1339
Leu Phe Asn Lys Ala Tyr Tyr Gly Lys Ser Thr Ser Phe Phe Arg Gln
            280                 285                 290 gaa agt caa aaa ctt ctg caa agc gat aaa aaa cgc acg gct gag tta      1387
```

```
Glu Ser Gln Lys Leu Leu Gln Ser Asp Lys Arg Thr Ala Glu Leu
            295                 300                 305 gca aac ggc gct ctc ggt atg att gag cta aac gat gat tac aca ctg      1435
Ala Asn Gly Ala Leu Gly Met Ile Glu Leu Asn Asp Asp Tyr Thr Leu
310                 315                 320 aaa aaa gtg atg aaa ccg ctg att gca tct aac aca gta aca gat gaa      1483
Lys Lys Val Met Lys Pro Leu Ile Ala Ser Asn Thr Val Thr Asp Glu
325                 330                 335                 340 att gaa cgc gcg aac gtc ttt aaa atg aac ggc aaa tgg tac ctg ttc      1531
Ile Glu Arg Ala Asn Val Phe Lys Met Asn Gly Lys Trp Tyr Leu Phe
            345                 350                 355 act gac tcc cgc gga tca aaa atg acg att gac ggc att acg tct aac      1579
Thr Asp Ser Arg Gly Ser Lys Met Thr Ile Asp Gly Ile Thr Ser Asn
            360                 365                 370 gat att tac atg ctt ggt tat gtt tct aat tct tta act ggc cca tac      1627
Asp Ile Tyr Met Leu Gly Tyr Val Ser Asn Ser Leu Thr Gly Pro Tyr
            375                 380                 385 aag ccg ctg aac aaa act ggc ctt gtg tta aaa atg gat ctt gat cct      1675
Lys Pro Leu Asn Lys Thr Gly Leu Val Leu Lys Met Asp Leu Asp Pro
390                 395                 400 aac gat gta acc ttt act tac tca cac ttc gct gta cct caa gcg aaa      1723
Asn Asp Val Thr Phe Thr Tyr Ser His Phe Ala Val Pro Gln Ala Lys
405                 410                 415                 420 gga aac aat gtc gtg att aca agc tat atg aca aac aga gga ttc tac      1771
Gly Asn Asn Val Val Ile Thr Ser Tyr Met Thr Asn Arg Gly Phe Tyr
            425                 430                 435 gca gac aaa caa tca acg ttt gcg cca agc ttc ctg ctg aac atc aaa      1819
Ala Asp Lys Gln Ser Thr Phe Ala Pro Ser Phe Leu Leu Asn Ile Lys
            440                 445                 450 ggc aag aaa aca tct gtt gtc aaa gac agc atc ctt gaa caa gga caa      1867
Gly Lys Lys Thr Ser Val Val Lys Asp Ser Ile Leu Glu Gln Gly Gln
            455                 460                 465 tta aca gtt aac aaa taa aaacgcaaaa gaaaatgccg atatcctatt            1915
Leu Thr Val Asn Lys
    470 ggcattttct tttatttctt atcaacataa aggtgaatcc catatgaact atataaaagc    1975 aggcaaatgg ctaaccgtat tcctaacctt ttgaagatc                          2014

<210> SEQ ID NO 12
<211> LENGTH: 473
<212> TYPE: PRT
<213> ORGANISM: Bacillus subtilis

<400> SEQUENCE: 12

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
                20                  25                  30

Asn Gln Lys Pro Tyr Lys Glu Thr Tyr Gly Ile Ser His Ile Thr Arg
            35                  40                  45

His Asp Met Leu Gln Ile Pro Glu Gln Gln Lys Asn Glu Lys Tyr Gln
        50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110
```

Pro Lys Asn Ala Asp Asp Thr Ser Ile Tyr Met Phe Tyr Gln Lys Val
            115                 120                 125

Gly Glu Thr Ser Ile Asp Ser Trp Lys Asn Ala Gly Arg Val Phe Lys
        130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
450                 455                 460

Glu Gln Gly Gln Leu Thr Val Asn Lys
465                 470

<210> SEQ ID NO 13
<211> LENGTH: 24
<212> TYPE: DNA
<213> ORGANISM: Artificial sequence
<220> FEATURE:
<223> OTHER INFORMATION: sacB primer

<400> SEQUENCE: 13
cgggatcctt tttaacccat caca                                          24

```
<210> SEQ ID NO 14
<211> LENGTH: 29
<212> TYPE: DNA
<213> ORGANISM: Artificial sequence
<220> FEATURE:
<223> OTHER INFORMATION: sacB primer

<400> SEQUENCE: 14
gaagatcttc aaaaggttag gaatacggt                                    29

<210> SEQ ID NO 15
<211> LENGTH: 23
<212> TYPE: DNA
<213> ORGANISM: Artificial sequence
<220> FEATURE:
<223> OTHER INFORMATION: sacB primer

<400> SEQUENCE: 15 cctttttgaag atcgaccagt tgg                                         23

<210> SEQ ID NO 16
<211> LENGTH: 44
<212> TYPE: DNA
<213> ORGANISM: Artificial sequence
<220> FEATURE:
<223> OTHER INFORMATION: sacB primer

<400> SEQUENCE: 16
tacctggaat gctgttttcc cagggatcgc agtggtgagt aacc                   44

<210> SEQ ID NO 17
<211> LENGTH: 28
<212> TYPE: DNA
<213> ORGANISM: Artificial sequence
<220> FEATURE:
<223> OTHER INFORMATION: sacB primer

<400> SEQUENCE: 17
cctgggaaaa cagcattcca ggtattag                                     28

<210> SEQ ID NO 18
<211> LENGTH: 23
<212> TYPE: DNA
<213> ORGANISM: Artificial sequence
<220> FEATURE:
<223> OTHER INFORMATION: sacB primer

<400> SEQUENCE: 18
tgcaggtcga ctctagagga tcc                                          23

<210> SEQ ID NO 19
<211> LENGTH: 3490
<212> TYPE: DNA
<213> ORGANISM: Corynebacterium glutamicum
<220> FEATURE:
<221> NAME/KEY: CDS
<222> LOCATION: (1437)..(3044)
<223> OTHER INFORMATION: A1

<400> SEQUENCE: 19
gatcttgccg atttcggcag gatcaatgtc ggcgtgaatg atcttggcat caggtgcgaa     60
agtgtcaacg tcaccggtga cgcggtcatc aaagcgggag ccgatagcaa tcagcaggtc    120
gctgcgctgc agtgcaccaa cagcggacac agtgccatgc atgcctggca tacccatgtg    180
cagctcgtgg gactctggga aggttcccag cgccatcaat gtggtgacaa ctggaatgcc    240
```

-continued

```
ggtgtgctca gcgaacgcac gaagctcttc gtgggcatca gccttgataa cgccgccgcc    300
aacgtaaagg acaggcttct tagactcacc gatcagtttg acagcctgct caatctgtcg    360
agcatgcggt gttgaaactg gcggtagcc tggcaggtcg atctttggtg gccagacgaa     420
atccaattca gcgttctgaa catccttggg gatatccact agaacaggac cagggcgacc    480
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg gccggtgatg caaccatgg gaacggagtc     660
caagtttgca tcagcgattg ggtaaccaa gttggttgcg cctgggccag aggttgcaat     720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc aggggcggcg gatcgaccac ggcttgcaac    960
cgtggcggga gtgggctgtt gagaagctgc acattcacg actttctggc tcctttacta   1020
aataaggatt ttcacaggac ccgtccaagc caagccgatt tcaactcagc ctaaagacaa   1080
agccctcatt taaaattgtt ccgacgcgga tgcgtgtgca cgcagtgcga cagatgtctg   1140
ttgcaaagtt ggctacttgg gtcataacca acaagaaagc cctcgttcca acactgtggt   1200
gagtgttgtc gagggcgctt gacgagacga cttggaaggc cgttacggca ggcgccgcgc   1260
ggttactact acaagtcgaa taatggtcat ggtgtgtcat gctacacaca tcgagtttcc   1320
aattccacaa cgcacgaaaa ttcccacccc caaaactccc ccacttcggt taaggaatca   1380
ggattctcac aaagttcagg caggctcccg ctactttca gcgctaatct tggctc atg    1439
                                                                  Met
                                                                   1 att tta ggc gta ccc att caa tat ttg ctc tat tca ttg tgt tca ttg    1487
Ile Leu Gly Val Pro Ile Gln Tyr Leu Leu Tyr Ser Leu Cys Ser Leu
      5                  10                  15 tgg aat tgg att gtc gat acc ggt ttt gat gta gca att atc ctg gtc    1535
Trp Asn Trp Ile Val Asp Thr Gly Phe Asp Val Ala Ile Ile Leu Val
 20                  25                  30 ttg gcg ttt ttg att cca cgt atc ggc cga ctg gcc atg cgt att atc    1583
Leu Ala Phe Leu Ile Pro Arg Ile Gly Arg Leu Ala Met Arg Ile Ile
 35                  40                  45 aag cag cga gtg gag tct gca gcc gat gcg gac acc act aag aac cag    1631
Lys Gln Arg Val Glu Ser Ala Ala Asp Ala Asp Thr Thr Lys Asn Gln
50                  55                  60                  65 ctc gcg ttc gct ggc gtt ggc gtt tat atc gcg caa att gtg gcg ttt    1679
Leu Ala Phe Ala Gly Val Gly Val Tyr Ile Ala Gln Ile Val Ala Phe
              70                  75                  80 ttc atg ctt gcc gtc tcc gcg atg cag gct ttt ggt ttc tct ctc gcg    1727
Phe Met Leu Ala Val Ser Ala Met Gln Ala Phe Gly Phe Ser Leu Ala
             85                  90                  95 ggc gct gcg att ccg gca acc att gcg tca gct gcc att ggt ctt ggt    1775
Gly Ala Ala Ile Pro Ala Thr Ile Ala Ser Ala Ala Ile Gly Leu Gly
        100                 105                 110 gcg cag tcg att gtt gcg gac ttc ttg gcc gga ttt ttc atc ctg acg    1823
Ala Gln Ser Ile Val Ala Asp Phe Leu Ala Gly Phe Phe Ile Leu Thr
    115                 120                 125 gaa aag caa ttc ggc gtg ggt gac tgg gtg cgc ttt gag ggc aac ggc    1871
Glu Lys Gln Phe Gly Val Gly Asp Trp Val Arg Phe Glu Gly Asn Gly
130                 135                 140                 145 atc gtt gtt gaa ggc acc gtc att gag atc acc atg cgc gcg acc aaa    1919
```

```
Ile Val Val Glu Gly Thr Val Ile Glu Ile Thr Met Arg Ala Thr Lys
            150                 155                 160 att cgc acg att gca caa gag acc gtg atc atc ccg aac tcc acg gcg    1967
Ile Arg Thr Ile Ala Gln Glu Thr Val Ile Ile Pro Asn Ser Thr Ala
            165                 170                 175 aaa gtg tgc atc aac aat tct aat aac tgg tcg cgt gcg gtt gtc gtt    2015
Lys Val Cys Ile Asn Asn Ser Asn Asn Trp Ser Arg Ala Val Val Val
            180                 185                 190 att ccg atc ccc atg ttg ggt tct gaa aac atc aca gat gtc atc gcg    2063
Ile Pro Ile Pro Met Leu Gly Ser Glu Asn Ile Thr Asp Val Ile Ala
            195                 200                 205 cgc tct gaa gct gcg act cgt cgc gca ctt ggc cag gag aaa atc gca    2111
Arg Ser Glu Ala Ala Thr Arg Arg Ala Leu Gly Gln Glu Lys Ile Ala
210                 215                 220                 225 ccg gaa atc ctc ggt gaa ctc gat gtg cac cca gcc acg gaa gtc aca    2159
Pro Glu Ile Leu Gly Glu Leu Asp Val His Pro Ala Thr Glu Val Thr
                230                 235                 240 ccg cca acg gtg gtc ggc atg ccg tgg atg gtc acc atg cgt ttc ctc    2207
Pro Pro Thr Val Val Gly Met Pro Trp Met Val Thr Met Arg Phe Leu
            245                 250                 255 gtg caa gtc acc gcc ggc aat caa tgg ctg gtc gaa cgc gcc atc cgc    2255
Val Gln Val Thr Ala Gly Asn Gln Trp Leu Val Glu Arg Ala Ile Arg
            260                 265                 270 aca gaa atc atc aac gaa ttc tgg gaa gaa tac ggc agc gca acc act    2303
Thr Glu Ile Ile Asn Glu Phe Trp Glu Glu Tyr Gly Ser Ala Thr Thr
275                 280                 285 aca tcg gga acc ctc att gat tcc tta cac gtt gag cat gaa gag cca    2351
Thr Ser Gly Thr Leu Ile Asp Ser Leu His Val Glu His Glu Glu Pro
290                 295                 300                 305 aag acc tcg ctt atc gac gcc tcc ccc cag gct ctt aag gaa ccg aag    2399
Lys Thr Ser Leu Ile Asp Ala Ser Pro Gln Ala Leu Lys Glu Pro Lys
            310                 315                 320 ccg gag gct gcg gcg acg gtt gca tcg cta gct gca tcg tct aac gac    2447
Pro Glu Ala Ala Ala Thr Val Ala Ser Leu Ala Ala Ser Ser Asn Asp
            325                 330                 335 gat gca gac aat gca gac gcc tcg gcg atc aat gca ggc aat cca gag    2495
Asp Ala Asp Asn Ala Asp Ala Ser Ala Ile Asn Ala Gly Asn Pro Glu
            340                 345                 350 aag gaa ctt gat tcc gat gtg ctg gaa caa gaa ctc tcc agc gaa gaa    2543
Lys Glu Leu Asp Ser Asp Val Leu Glu Gln Glu Leu Ser Ser Glu Glu
            355                 360                 365 ccg gaa gaa aca gca aaa cca gat cac tct ctc cga ggc ttc ttc cgc    2591
Pro Glu Glu Thr Ala Lys Pro Asp His Ser Leu Arg Gly Phe Phe Arg
370                 375                 380                 385 act gat tac tac cca aat cgg tgg cag aag atc ctg tcg ttt ggc gga    2639
Thr Asp Tyr Tyr Pro Asn Arg Trp Gln Lys Ile Leu Ser Phe Gly Gly
                390                 395                 400 cgt gtc cgc atg agc act tcc ctg ttg ttg ggt gcg ctc ctc ttg ctg    2687
Arg Val Arg Met Ser Thr Ser Leu Leu Leu Gly Ala Leu Leu Leu Leu
            405                 410                 415 tca cta ttt aag gtc atg act gtg gaa cca agt gag aat tgg caa aac    2735
Ser Leu Phe Lys Val Met Thr Val Glu Pro Ser Glu Asn Trp Gln Asn
            420                 425                 430 tcc agt gga tgg ctg tca cca agc act gcc acc tca act gcg gtg acc    2783
Ser Ser Gly Trp Leu Ser Pro Ser Thr Ala Thr Ser Thr Ala Val Thr
            435                 440                 445 acc tcc gaa act tcc gcg cca gca agc acg cct tcg atg aca gtg ccc    2831
Thr Ser Glu Thr Ser Ala Pro Ala Ser Thr Pro Ser Met Thr Val Pro
450                 455                 460                 465 act acg gtg gag gag acc cca acg atg gaa tct agc gtc gaa acg cag    2879
```

```
            Thr Thr Val Glu Glu Thr Pro Thr Met Glu Ser Ser Val Glu Thr Gln
                        470                 475                 480 cag gaa acc tca acc cct gca acc gca acg ccc cag cga gcc gac acc          2927
Gln Glu Thr Ser Thr Pro Ala Thr Ala Thr Pro Gln Arg Ala Asp Thr
            485                 490                 495 atc gaa ccg acc gag gaa gcc acg tcg cag gag gaa acg act gca tcg          2975
Ile Glu Pro Thr Glu Glu Ala Thr Ser Gln Glu Glu Thr Thr Ala Ser
            500                 505                 510 cag acg cag tct cca gca gtg gaa gca cca acc gcg gtc caa gaa aca          3023
Gln Thr Gln Ser Pro Ala Val Glu Ala Pro Thr Ala Val Gln Glu Thr
            515                 520                 525 gtt gcg ccg acg tcc acc cct taggacgctg attacagacg tgtcccattt             3074
Val Ala Pro Thr Ser Thr Pro
530                 535 ctttactact attggaaatt atgagttcag acgcagaaaa ggcatccgtg gagctttccg         3134
aaaaatttca cccagaacgc acccatattt tgggcgccgt tgttttttggc ctgatctcat       3194 tattagtcat cggcgcagcc cctcagtacc tgttttggct gctcgcgctc cctgtcatct        3254
tcggttactg ggttctaaaa tcatccacga tcgttgatga acagggcatc accgcaaact        3314
acgccttcaa gggcaaaaag gttgtggcct gggaagacct cgcaggaatc ggattcaagg        3374
gtgcccgcac tttcgctcgc accacctccg atgcagaagt caccctcccc ggcgtcacct       3434
tcaactccct tccccgcctt gaagctgctt cccacggccg catccccgat gcgatc            3490

<210> SEQ ID NO 20
<211> LENGTH: 536
<212> TYPE: PRT
<213> ORGANISM: Corynebacterium glutamicum

<400> SEQUENCE: 20

Met Ile Leu Gly Val Pro Ile Gln Tyr Leu Leu Tyr Ser Leu Cys Ser
1               5                   10                  15

Leu Trp Asn Trp Ile Val Asp Thr Gly Phe Asp Val Ala Ile Ile Leu
            20                  25                  30

Val Leu Ala Phe Leu Ile Pro Arg Ile Gly Arg Leu Ala Met Arg Ile
        35                  40                  45

Ile Lys Gln Arg Val Glu Ser Ala Ala Asp Ala Asp Thr Thr Lys Asn
    50                  55                  60

Gln Leu Ala Phe Ala Gly Val Gly Val Tyr Ile Ala Gln Ile Val Ala
65                  70                  75                  80

Phe Phe Met Leu Ala Val Ser Ala Met Gln Ala Phe Gly Phe Ser Leu
                85                  90                  95

Ala Gly Ala Ala Ile Pro Ala Thr Ile Ala Ser Ala Ala Ile Gly Leu
            100                 105                 110

Gly Ala Gln Ser Ile Val Ala Asp Phe Leu Ala Gly Phe Phe Ile Leu
        115                 120                 125

Thr Glu Lys Gln Phe Gly Val Gly Asp Trp Val Arg Phe Glu Gly Asn
    130                 135                 140

Gly Ile Val Val Glu Gly Thr Val Ile Glu Ile Thr Met Arg Ala Thr
145                 150                 155                 160

Lys Ile Arg Thr Ile Ala Gln Glu Thr Val Ile Pro Asn Ser Thr
                165                 170                 175

Ala Lys Val Cys Ile Asn Asn Ser Asn Asn Trp Ser Arg Ala Val Val
            180                 185                 190

Val Ile Pro Ile Pro Met Leu Gly Ser Glu Asn Ile Thr Asp Val Ile
        195                 200                 205
```

```
Ala Arg Ser Glu Ala Ala Thr Arg Arg Ala Leu Gly Gln Glu Lys Ile
    210                 215                 220

Ala Pro Glu Ile Leu Gly Glu Leu Asp Val His Pro Ala Thr Glu Val
225                 230                 235                 240

Thr Pro Pro Thr Val Val Gly Met Pro Trp Met Val Thr Met Arg Phe
                245                 250                 255

Leu Val Gln Val Thr Ala Gly Asn Gln Trp Leu Val Glu Arg Ala Ile
            260                 265                 270

Arg Thr Glu Ile Ile Asn Glu Phe Trp Glu Tyr Gly Ser Ala Thr
        275                 280                 285

Thr Thr Ser Gly Thr Leu Ile Asp Ser Leu His Val Glu His Glu Glu
    290                 295                 300

Pro Lys Thr Ser Leu Ile Asp Ala Ser Pro Gln Ala Leu Lys Glu Pro
305                 310                 315                 320

Lys Pro Glu Ala Ala Ala Thr Val Ala Ser Leu Ala Ala Ser Ser Asn
                325                 330                 335

Asp Asp Ala Asp Asn Ala Asp Ala Ser Ala Ile Asn Ala Gly Asn Pro
            340                 345                 350

Glu Lys Glu Leu Asp Ser Asp Val Leu Glu Gln Glu Leu Ser Ser Glu
        355                 360                 365

Glu Pro Glu Glu Thr Ala Lys Pro Asp His Ser Leu Arg Gly Phe Phe
    370                 375                 380

Arg Thr Asp Tyr Tyr Pro Asn Arg Trp Gln Lys Ile Leu Ser Phe Gly
385                 390                 395                 400

Gly Arg Val Arg Met Ser Thr Ser Leu Leu Gly Ala Leu Leu Leu
                405                 410                 415

Leu Ser Leu Phe Lys Val Met Thr Val Glu Pro Ser Glu Asn Trp Gln
            420                 425                 430

Asn Ser Ser Gly Trp Leu Ser Pro Ser Thr Ala Thr Ser Thr Ala Val
        435                 440                 445

Thr Thr Ser Glu Thr Ser Ala Pro Ala Ser Thr Pro Ser Met Thr Val
    450                 455                 460

Pro Thr Thr Val Glu Glu Thr Pro Thr Met Glu Ser Ser Val Glu Thr
465                 470                 475                 480

Gln Gln Glu Thr Ser Thr Pro Ala Thr Ala Thr Pro Gln Arg Ala Asp
                485                 490                 495

Thr Ile Glu Pro Thr Glu Glu Ala Thr Ser Gln Glu Glu Thr Thr Ala
            500                 505                 510

Ser Gln Thr Gln Ser Pro Ala Val Glu Ala Pro Thr Ala Val Gln Glu
        515                 520                 525

Thr Val Ala Pro Thr Ser Thr Pro
    530                 535

<210> SEQ ID NO 21
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)
<223> OTHER INFORMATION: 19

<400> SEQUENCE: 21
gatcttgccg atttcggcag gatcaatgtc ggcgtgaatg atcttggcat caggtgcgaa      60
agtgtcaacg tcaccggtga cgcggtcatc aaagcgggag ccgatagcaa tcagcaggtc     120
gctgcgctgc agtgcaccaa cagcggacac agtgccatgc atgcctggca tacccatgtg     180
```

```
cagctcgtgg gactctggga aggttcccag cgccatcaat gtggtgacaa ctggaatgcc      240
ggtgtgctca gcgaacgcac gaagctcttc gtgggcatca gccttgataa cgccgccgcc      300
aacgtaaagg acaggcttct tagactcacc gatcagtttg acagcctgct caatctgtcg      360
agcatgcggt gttgaaactg gcggtagcc tggcaggtcg atctttggtg ccagacgaa       420 atccaattca gcgttctgaa catccttggg gatatccact agaacaggac cagggcgacc      480
agtaatcgcg aggtggaatg cctcagccaa tgcctgtgga atgtcgttgg ggttggtgac      540
catgaagttg tgcttggtca ctggcatggt gatgccgcgg atatcggctt cctggaaagc      600
atcggtaccc agcaggctac ttccgacctg gccggtgatg gcaaccatgg aacggagtc       660 caagtttgca tcagcgattg gggtaaccaa gttggttgcg cctgggccag aggttgcaat      720
gcagacgcca acgcgtccag taacctgcgc gtagccggtt gctgcgtggc ctgcgccctg      780
ctcgtggcgc actaggacgt ggcgcacctt tgtggaggaa tagagcgggt catacaccgg      840
tagcaccgca ccaccaggaa taccgaacac gatgtcggcg ttaagctcct cgagcgatcg      900
aacaattgcc tgtgcacctg tcatccgctc aggggcggcg gatcgaccac ggcttgcaac      960
cgtggcggga gtgggctgtt gagaagctgc cacattcacg actttctggc tcctttacta    1020
aataaggatt ttcacaggac ccgtccaagc caagccgatt tcaactcagc ctaaagacaa    1080
agccctcatt taaaattgtt ccgacgcgga tgcgtgtgca cgcagtgcga cagatgtctg    1140
ttgcaaagtt ggctacttgg gtcataacca acaagaaagc cctcgttcca acactgtggt    1200
gagtgttgtc gagggcgctt gacgagacga cttggaaggc cgttacggca ggcgccgcgc    1260
ggttactact acaagtcgaa taatggtcat ggtgtgtcat gctacacaca tcgagtttcc    1320
aattccacaa cgcacgaaaa ttcccacccc caaaactccc ccacttcggt taaggaatca    1380
ggattctcac aaagttcagg caggctcccg ctactttca gcgctaatct tggctc atg    1439
                                                             Met
                                                              1 att tta ggc gta ccc att caa tat ttg ctc tat tca ttg tgg aat tgg      1487
Ile Leu Gly Val Pro Ile Gln Tyr Leu Leu Tyr Ser Leu Trp Asn Trp
           5                  10                  15 att gtc gat acc ggt ttt gat gta gca att atc ctg gtc ttg gcg ttt      1535
Ile Val Asp Thr Gly Phe Asp Val Ala Ile Ile Leu Val Leu Ala Phe
         20                  25                  30 ttg att cca cgt atc ggc cga ctg gcc atg cgt att atc aag cag cga      1583
Leu Ile Pro Arg Ile Gly Arg Leu Ala Met Arg Ile Ile Lys Gln Arg
     35                  40                  45 gtg gag tct gca gcc gat gcg gac acc act aag aac cag ctc gcg ttc      1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt      1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg      1727
Ala Val Ser Ala Met Gln Ala Phe Gly Phe Ser Leu Ala Gly Ala Ala
             85                  90                  95 att ccg aca acc att gcg tca gct gcc att ggt ctt ggt gcg cag tcg      1775
Ile Pro Thr Thr Ile Ala Ser Ala Ala Ile Gly Leu Gly Ala Gln Ser
         100                 105                 110 att gtt gcg gac ttc ttg gcc gga ttt ttc atc ctg acg gaa aag caa      1823
Ile Val Ala Asp Phe Leu Ala Gly Phe Phe Ile Leu Thr Glu Lys Gln
     115                 120                 125 ttc ggc gtg ggt gac tgg gtg cgc ttt gag ggc aac ggc atc gtt gtt      1871
Phe Gly Val Gly Asp Trp Val Arg Phe Glu Gly Asn Gly Ile Val Val
130                 135                 140                 145
```

```
gaa ggc acc gtc att gag atc acc atg cgc gcg acc aaa att cgc acg    1919
Glu Gly Thr Val Ile Glu Ile Thr Met Arg Ala Thr Lys Ile Arg Thr
            150                 155                 160 att gca caa gag acc gtg atc atc ccg aac tcc acg gcg aaa gtg tgc    1967
Ile Ala Gln Glu Thr Val Ile Ile Pro Asn Ser Thr Ala Lys Val Cys
        165                 170                 175 atc aac aat tct aat aac tgg tcg cgt gcg gtt gtc gtt att ccg atc    2015
Ile Asn Asn Ser Asn Asn Trp Ser Arg Ala Val Val Val Ile Pro Ile
    180                 185                 190 ccc atg ttg ggt tct gaa aac atc aca gat gtc atc gcg cgc tct gaa    2063
Pro Met Leu Gly Ser Glu Asn Ile Thr Asp Val Ile Ala Arg Ser Glu
195                 200                 205 gct gcg act cgt cgc gca ctt ggc cag gag aaa atc gca ccg gaa atc    2111
Ala Ala Thr Arg Arg Ala Leu Gly Gln Glu Lys Ile Ala Pro Glu Ile
210                 215                 220                 225 ctc ggt gaa ctc gat gtg cac cca gcc acg gaa gtc aca ccg cca acg    2159
Leu Gly Glu Leu Asp Val His Pro Ala Thr Glu Val Thr Pro Pro Thr
                230                 235                 240 gtg gtc ggc atg ccg tgg atg gtc acc atg cgt ttc ctc gtg caa gtc    2207
Val Val Gly Met Pro Trp Met Val Thr Met Arg Phe Leu Val Gln Val
            245                 250                 255 acc gcc ggc aat caa tgg ctg gtc gaa cgc gcc atc cgc aca gaa atc    2255
Thr Ala Gly Asn Gln Trp Leu Val Glu Arg Ala Ile Arg Thr Glu Ile
        260                 265                 270 atc aac gaa ttc tgg gaa gaa tac ggc agc gca acc act aca tcg gga    2303
Ile Asn Glu Phe Trp Glu Glu Tyr Gly Ser Ala Thr Thr Thr Ser Gly
    275                 280                 285 acc ctc att gat tcc tta cac gtt gag cat gaa gag cca aag acc tcg    2351
Thr Leu Ile Asp Ser Leu His Val Glu His Glu Glu Pro Lys Thr Ser
290                 295                 300                 305 ctt atc gac gcc tcc ccc cag gct ctt aag gaa ccg aag ccg gag gct    2399
Leu Ile Asp Ala Ser Pro Gln Ala Leu Lys Glu Pro Lys Pro Glu Ala
                310                 315                 320 gcg gcg acg gtt gca tcg cta gct gca tcg tct aac gac gat gca gac    2447
Ala Ala Thr Val Ala Ser Leu Ala Ala Ser Ser Asn Asp Asp Ala Asp
            325                 330                 335 aat gca gac gcc tcg gcg atc aat gca ggc aat cca gag aag gaa ctt    2495
Asn Ala Asp Ala Ser Ala Ile Asn Ala Gly Asn Pro Glu Lys Glu Leu
        340                 345                 350 gat tcc gat gtg ctg gaa caa gaa ctc tcc agc gaa gaa ccg gaa gaa    2543
Asp Ser Asp Val Leu Glu Gln Glu Leu Ser Ser Glu Glu Pro Glu Glu
    355                 360                 365 aca gca aaa cca gat cac tct ctc cga ggc ttc ttc cgc act gat tac    2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc    2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt    2687
Met Ser Thr Ser Leu Leu Leu Gly Ala Leu Leu Leu Ser Leu Phe
            405                 410                 415 aag gtc atg act gtg gaa cca agt gag aat tgg caa aac tcc agt gga    2735
Lys Val Met Thr Val Glu Pro Ser Glu Asn Trp Gln Asn Ser Ser Gly
        420                 425                 430 tgg ctg tca cca agc act gcc acc tca act gcg gtg acc acc tcc gaa    2783
Trp Leu Ser Pro Ser Thr Ala Thr Ser Thr Ala Val Thr Thr Ser Glu
    435                 440                 445 act tcc gcg cca gca agc acg cct tcg atg aca gtg ccc act acg gtg    2831
Thr Ser Ala Pro Ala Ser Thr Pro Ser Met Thr Val Pro Thr Thr Val
450                 455                 460                 465
```

```
gag gag acc cca acg atg gaa tct agc gtc gaa acg cag cag gaa acc    2879
Glu Glu Thr Pro Thr Met Glu Ser Ser Val Glu Thr Gln Gln Glu Thr
            470                 475                 480 tca acc cct gca acc gca acg ccc cag cga gcc gac acc atc gaa ccg    2927
Ser Thr Pro Ala Thr Ala Thr Pro Gln Arg Ala Asp Thr Ile Glu Pro
            485                 490                 495 acc gag gaa gcc acg tcg cag gag gaa acg act gca tcg cag acg cag    2975
Thr Glu Glu Ala Thr Ser Gln Glu Glu Thr Thr Ala Ser Gln Thr Gln
            500                 505                 510 tct cca gca gtg gaa gca cca acc gcg gtc caa gaa aca gtt gcg ccg    3023
Ser Pro Ala Val Glu Ala Pro Thr Ala Val Gln Glu Thr Val Ala Pro
            515                 520                 525 acg tcc acc cct taggacgctg attacagacg tgtcccattt ctttactact        3075
Thr Ser Thr Pro
530 attggaaatt atgagttcag acgcagaaaa ggcatccgtg gagctttccg aaaaatttca  3135 cccagaacgc acccatattt tgggcgccgt tgttttttggc ctgatctcat tattagtcat 3195 cggcgcagcc cctcagtacc tgtttttggct gctcgcgctc cctgtcatct tcggttactg 3255 ggttctaaaa tcatccacga tcgttgatga acagggcatc accgcaaact acgccttcaa 3315 gggcaaaaag gttgtggcct gggaagacct cgcaggaatc ggattcaagg gtgcccgcac 3375 tttcgctcgc accacctccg atgcagaagt caccctcccc ggcgtcacct tcaactccct 3435 tccccgcctt gaagctgctt cccacggccg catccccgat gcgatc                3481

<210> SEQ ID NO 22
<211> LENGTH: 533
<212> TYPE: PRT
<213> ORGANISM: Corynebacterium glutamicum

<400> SEQUENCE: 22

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Thr Thr Ile Ala Ser Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
```

195                 200                 205
Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
        370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Ala Ser Thr Pro Ser Met Thr Val Pro Thr Thr
        450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530

<210> SEQ ID NO 23
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)
<223> OTHER INFORMATION: L30

<400> SEQUENCE: 23
gatcttgccg atttcggcag gatcaatgtc ggcgtgaatg atcttggcat caggtgcgaa    60
agtgtcaacg tcaccggtga cgcggtcatc aaagcgggag ccgatagcaa tcagcaggtc   120

-continued

```
gctgcgctgc agtgcaccaa cagcggacac agtgccatgc atgcctggca tacccatgtg      180
cagctcgtgg gactctggga aggttcccag cgccatcaat gtggtgacaa ctggaatgcc      240
ggtgtgctca gcgaacgcac gaagctcttc gtgggcatca gccttgataa cgccgccgcc      300
aacgtaaagg acaggcttct tagactcacc gatcagtttg acagcctgct caatctgtcg      360
agcatgcggt gttgaaactg gcggtagcc tggcaggtcg atctttggtg gccagacgaa       420
atccaattca gcgttctgaa catccttggg gatatccact agaacaggac cagggcgacc      480
agtaatcgcg aggtggaatg cctcagccaa tgcctgtgga atgtcgttgg ggttggtgac      540
catgaagttg tgcttggtca ctggcatggt gatgccgcgg atatcggctt cctggaaagc      600
atcggtaccc agcaggctac ttccgacctg gccggtgatg gcaaccatgg gaacggagtc      660
caagtttgca tcagcgattg gggtaaccaa gttggttgcg cctgggccag aggttgcaat      720
gcagacgcca acgcgtccag taacctgcgc gtagccggtt gctgcgtggc ctgcgccctg      780
ctcgtggcgc actaggacgt ggcgcacctt tgtggaggaa tagagcgggt catacaccgg      840
tagcaccgca ccaccaggaa taccgaacac gatgtcggcg ttaagctcct cgagcgatcg      900
aacaattgcc tgtgcacctg tcatccgctc aggggcggcg atcgaccac ggcttgcaac       960 cgtggcggga gtgggctgtt gagaagctgc cacattcacg actttctggc tcctttacta     1020
aataaggatt ttcacaggac ccgtccaagc caagccgatt tcaactcagc ctaaagacaa     1080
agccctcatt taaaattgtt ccgacgcgga tgcgtgtgca cgcagtgcga cagatgtctg     1140
ttgcaaagtt ggctacttgg gtcataacca acaagaaagc cctcgttcca acactgtggt     1200
gagtgttgtc gagggcgctt gacgagacga cttggaaggc cgttacggca ggcgccgcgc     1260
ggttactact acaagtcgaa taatggtcat ggtgtgtcat gctacacaca tcgagtttcc     1320
aattccacaa cgcacgaaaa ttcccacccc caaaactccc ccacttcggt taaggaatca     1380
ggattctcac aaagttcagg caggctcccg ctactttca gcgctaatct tggctc atg      1439
                                                                 Met
                                                                  1 att tta ggc gta ccc att caa tat ttg ctc tat tca ttg tgg aat tgg      1487
Ile Leu Gly Val Pro Ile Gln Tyr Leu Leu Tyr Ser Leu Trp Asn Trp
         5                  10                  15 att gtc gat acc ggt ttt gat gta gca att atc ctg gtc ttg gcg ttt      1535
Ile Val Asp Thr Gly Phe Asp Val Ala Ile Ile Leu Val Leu Ala Phe
     20                  25                  30 ttg att cca cgt atc ggc cga ctg gcc atg cgt att atc aag cag cga      1583
Leu Ile Pro Arg Ile Gly Arg Leu Ala Met Arg Ile Ile Lys Gln Arg
 35                  40                  45 gtg gag tct gca gcc gat gcg gac acc act aag aac cag ctc gcg ttc      1631
Val Glu Ser Ala Ala Asp Ala Asp Thr Thr Lys Asn Gln Leu Ala Phe
 50                  55                  60                  65 gct ggc gtt ggc gtt tat atc gcg caa att gtg gcg ttt ttc atg ctt      1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg      1727
Ala Val Ser Ala Met Gln Ala Phe Gly Phe Ser Leu Ala Gly Ala Ala
             85                  90                  95 att ccg gca acc att gcg tca gct gcc att ggt ctt ggt gtg cag tcg      1775
Ile Pro Ala Thr Ile Ala Ser Ala Ala Ile Gly Leu Gly Val Gln Ser
        100                 105                 110 att gtt gcg gac ttc ttg gcc gga ttt ttc atc ctg acg gaa aag caa      1823
Ile Val Ala Asp Phe Leu Ala Gly Phe Phe Ile Leu Thr Glu Lys Gln
    115                 120                 125 ttc ggc gtg ggt gac tgg gtg cgc ttt gag ggc aac ggc atc gtt gtt      1871
```

```
                Phe Gly Val Gly Asp Trp Val Arg Phe Glu Gly Asn Gly Ile Val Val
                130                 135                 140                 145 gaa ggc acc gtc att gag atc acc atg cgc gcg acc aaa att cgc acg         1919
Glu Gly Thr Val Ile Glu Ile Thr Met Arg Ala Thr Lys Ile Arg Thr
            150                 155                 160 att gca caa gag acc gtg atc atc ccg aac tcc acg gcg aaa gtg tgc         1967
Ile Ala Gln Glu Thr Val Ile Ile Pro Asn Ser Thr Ala Lys Val Cys
                165                 170                 175 atc aac aat tct aat aac tgg tcg cgt gcg gtt gtc gtt att ccg atc         2015
Ile Asn Asn Ser Asn Asn Trp Ser Arg Ala Val Val Val Ile Pro Ile
            180                 185                 190 ccc atg ttg ggt tct gaa aac atc aca gat gtc atc gcg cgt tct gaa         2063
Pro Met Leu Gly Ser Glu Asn Ile Thr Asp Val Ile Ala Arg Ser Glu
    195                 200                 205 gct gcg act cgt cgc gca ctt ggc cag gag aaa atc gca ccg gaa atc         2111
Ala Ala Thr Arg Arg Ala Leu Gly Gln Glu Lys Ile Ala Pro Glu Ile
210                 215                 220                 225 ctc ggt gaa ctc gat gtg cac cca gcc acg gaa gtc aca ccg cca acg         2159
Leu Gly Glu Leu Asp Val His Pro Ala Thr Glu Val Thr Pro Pro Thr
                230                 235                 240 gtg gtc ggc atg ccg tgg atg gtc acc atg cgt ttc ctc gtg caa gtc         2207
Val Val Gly Met Pro Trp Met Val Thr Met Arg Phe Leu Val Gln Val
            245                 250                 255 acc gcc ggc aat caa tgg ctg gtc gaa cgc gcc atc cgc aca gaa atc         2255
Thr Ala Gly Asn Gln Trp Leu Val Glu Arg Ala Ile Arg Thr Glu Ile
        260                 265                 270 atc aac gaa ttc tgg gaa gaa tac ggc agc gca acc act aca tcg gga         2303
Ile Asn Glu Phe Trp Glu Glu Tyr Gly Ser Ala Thr Thr Thr Ser Gly
    275                 280                 285 acc ctc att gat tcc tta cac gtt gag cat gaa gag cca aag acc tcg         2351
Thr Leu Ile Asp Ser Leu His Val Glu His Glu Glu Pro Lys Thr Ser
290                 295                 300                 305 ctt atc gac gcc tcc ccc cag gct ctt aag gaa ccg aag ccg gag gct         2399
Leu Ile Asp Ala Ser Pro Gln Ala Leu Lys Glu Pro Lys Pro Glu Ala
                310                 315                 320 gcg gcg acg gtt gca tcg cta gct gca tcg tct aac gac gat gca gac         2447
Ala Ala Thr Val Ala Ser Leu Ala Ala Ser Ser Asn Asp Asp Ala Asp
            325                 330                 335 aat gca gac gcc tcg gcg atc aat gca ggc aat cca gag aag gaa ctt         2495
Asn Ala Asp Ala Ser Ala Ile Asn Ala Gly Asn Pro Glu Lys Glu Leu
        340                 345                 350 gat tcc gat gtg ctg gaa caa gaa ctc tcc agc gaa gaa ccg gaa gaa         2543
Asp Ser Asp Val Leu Glu Gln Glu Leu Ser Ser Glu Glu Pro Glu Glu
    355                 360                 365 aca gca aaa cca gat cac tct ctc cga ggc ttc ttc cgc act gat tac         2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc         2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt         2687
Met Ser Thr Ser Leu Leu Leu Gly Ala Leu Leu Leu Leu Ser Leu Phe
            405                 410                 415 aag gtc atg act gtg gaa cca agt gag aat tgg caa aac tcc agt gga         2735
Lys Val Met Thr Val Glu Pro Ser Glu Asn Trp Gln Asn Ser Ser Gly
        420                 425                 430 tgg ctg tca cca agc act gcc acc tca act gcg gtg acc acc tcc gaa         2783
Trp Leu Ser Pro Ser Thr Ala Thr Ser Thr Ala Val Thr Thr Ser Glu
    435                 440                 445 act tcc gcg cca gca agc acg cct tcg atg aca gtg ccc act acg gtg         2831
```

```
Thr Ser Ala Pro Ala Ser Thr Pro Ser Met Thr Val Pro Thr Thr Val
450                 455                 460                 465 gag gag acc cca acg atg gaa tct agc gtc gaa acg cag cag gaa acc      2879
Glu Glu Thr Pro Thr Met Glu Ser Ser Val Glu Thr Gln Gln Glu Thr
                        470                 475                 480 tca acc cct gca acc gca acg ccc cag cga gcc gac acc atc gaa ccg      2927
Ser Thr Pro Ala Thr Ala Thr Pro Gln Arg Ala Asp Thr Ile Glu Pro
                485                 490                 495 acc gag gaa gcc acg tcg cag gag gaa acg act gca tcg cag acg cag      2975
Thr Glu Glu Ala Thr Ser Gln Glu Glu Thr Thr Ala Ser Gln Thr Gln
            500                 505                 510 tct cca gca gtg gaa gca cca acc gcg gtc caa gaa aca gtt gcg ccg      3023
Ser Pro Ala Val Glu Ala Pro Thr Ala Val Gln Glu Thr Val Ala Pro
        515                 520                 525 acg tcc acc cct taggacgctg attacagacg tgtcccattt ctttactact          3075
Thr Ser Thr Pro
530 attggaaatt atgagttcag acgcagaaaa ggcatccgtg agctttccg aaaaatttca     3135 cccagaacgc acccatattt tgggcgccgt tgtttttggc ctgatctcat tattagtcat    3195 cggcgcagcc cctcagtacc tgttttggct gctcgcgctc cctgtcatct tcggttactg    3255 ggttctaaaa tcatccacga tcgttgatga acagggcatc accgcaaact acgccttcaa   3315 gggcaaaaag gttgtggcct gggaagacct cgcaggaatc ggattcaagg gtgcccgcac    3375 tttcgctcgc accacctccg atgcagaagt caccctcccc ggcgtcacct tcaactccct   3435 tccccgcctt gaagctgctt cccacggccg catccccgat gcgatc                   3481

<210> SEQ ID NO 24
<211> LENGTH: 533
<212> TYPE: PRT
<213> ORGANISM: Corynebacterium glutamicum

<400> SEQUENCE: 24

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Val Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190
```

```
Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Tyr Gly Ser Ala Thr Thr Thr Ser
        275                 280                 285

Gly Thr Leu Ile Asp Ser Leu His Val Glu His Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Pro Glu
    355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
    435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Gly Thr Val Ala
    515                 520                 525

Pro Thr Ser Thr Pro
    530

<210> SEQ ID NO 25
<211> LENGTH: 23
<212> TYPE: PRT
<213> ORGANISM: Corynebacterium glutamicum

<400> SEQUENCE: 25

Met Ile Leu Gly Val Pro Ile Gln Tyr Leu Leu Tyr Ser Leu Trp Asn
1               5                   10                  15

Trp Ile Val Asp Thr Gly Phe
            20
```

```
<210> SEQ ID NO 26
<211> LENGTH: 23
<212> TYPE: PRT
<213> ORGANISM: Corynebacterium glutamicum

<400> SEQUENCE: 26

Val Ala Ile Ile Leu Val Leu Ala Phe Leu Ile Pro Arg Ile Gly Arg
1               5                   10                  15

Leu Ala Met Arg Ile Ile Lys
            20

<210> SEQ ID NO 27
<211> LENGTH: 23
<212> TYPE: PRT
<213> ORGANISM: Corynebacterium glutamicum

<400> SEQUENCE: 27

Gln Leu Ala Phe Ala Gly Val Gly Val Tyr Ile Ala Gln Ile Val Ala
1               5                   10                  15

Phe Phe Met Leu Ala Val Ser
            20

<210> SEQ ID NO 28
<211> LENGTH: 23
<212> TYPE: PRT
<213> ORGANISM: Corynebacterium glutamicum

<400> SEQUENCE: 28

Met Gln Ala Phe Gly Phe Ser Leu Ala Gly Ala Ala Ile Pro Ala Thr
1               5                   10                  15

Ile Ala Ser Ala Ala Ile Gly
            20

<210> SEQ ID NO 29
<211> LENGTH: 23
<212> TYPE: PRT
<213> ORGANISM: Corynebacterium glutamicum

<400> SEQUENCE: 29

Gly Ala Gln Ser Ile Val Ala Asp Phe Leu Ala Gly Phe Phe Ile Leu
1               5                   10                  15

Thr Glu Lys Gln Phe Gly Val
            20

<210> SEQ ID NO 30
<211> LENGTH: 20
<212> TYPE: DNA
<213> ORGANISM: Artificial sequence
<220> FEATURE:
<223> OTHER INFORMATION: primer

<400> SEQUENCE: 30
ggctgttgag aagctgccac                                            20

<210> SEQ ID NO 31
<211> LENGTH: 40
<212> TYPE: DNA
<213> ORGANISM: Artificial sequence
<220> FEATURE:
<223> OTHER INFORMATION: primer

<400> SEQUENCE: 31
ccaattccac aatgaacaca atgaatagag caaatattga                      40
```

<210> SEQ ID NO 32
<211> LENGTH: 40
<212> TYPE: DNA
<213> ORGANISM: Artificial sequence
<220> FEATURE:
<223> OTHER INFORMATION: primer

<400> SEQUENCE: 32
tcaatatttg ctctattcat tgtgttcatt gtggaattgg                          40

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
ttcggttcct taagagcctg                                                20

<210> SEQ ID NO 34
<211> LENGTH: 28
<212> TYPE: DNA
<213> ORGANISM: Artificial sequence
<220> FEATURE:
<223> OTHER INFORMATION: primer

<400> SEQUENCE: 34
gggagctcca cggcatgccg accaccgt                                       28

<210> SEQ ID NO 35
<211> LENGTH: 23
<212> TYPE: DNA
<213> ORGANISM: Artificial sequence
<220> FEATURE:
<223> OTHER INFORMATION: primer

<400> SEQUENCE: 35
gacgcaatgg ttgtcggaat cgc                                            23

<210> SEQ ID NO 36
<211> LENGTH: 23
<212> TYPE: DNA
<213> ORGANISM: Artificial sequence
<220> FEATURE:
<223> OTHER INFORMATION: primer

<400> SEQUENCE: 36
gcgattccga caaccattgc gtc                                            23

<210> SEQ ID NO 37
<211> LENGTH: 29
<212> TYPE: DNA
<213> ORGANISM: Artificial sequence
<220> FEATURE:
<223> OTHER INFORMATION: primer

<400> SEQUENCE: 37
ccgcaacaat cgactgcaca ccaagacca                                      29

<210> SEQ ID NO 38
<211> LENGTH: 29
<212> TYPE: DNA
<213> ORGANISM: Artificial sequence
<220> FEATURE:
<223> OTHER INFORMATION: primer

```
<400> SEQUENCE: 38
tggtcttggt gtgcagtcga ttgttgcgg                                    29

<210> SEQ ID NO 39
<211> LENGTH: 28
<212> TYPE: DNA
<213> ORGANISM: Artificial sequence
<220> FEATURE:
<223> OTHER INFORMATION: primer

<400> SEQUENCE: 39
gggagctcac ctttgtggag gaatagag                                     28

<210> SEQ ID NO 40
<211> LENGTH: 46
<212> TYPE: DNA
<213> ORGANISM: Artificial sequence
<220> FEATURE:
<223> OTHER INFORMATION: primer

<400> SEQUENCE: 40
gggacacgtc tgtaatcagc gtcctagagc caagattagc gctgaa                 46

<210> SEQ ID NO 41
<211> LENGTH: 46
<212> TYPE: DNA
<213> ORGANISM: Artificial sequence
<220> FEATURE:
<223> OTHER INFORMATION: primer

<400> SEQUENCE: 41
ttcagcgcta atcttggctc taggacgctg attacagacg tgtccc                 46

<210> SEQ ID NO 42
<211> LENGTH: 28
<212> TYPE: DNA
<213> ORGANISM: Artificial sequence
<220> FEATURE:
<223> OTHER INFORMATION: primer

<400> SEQUENCE: 42
gggagctcag tactcttcct tggacatc                                     28

<210> SEQ ID NO 43
<211> LENGTH: 4400
<212> TYPE: DNA
<213> ORGANISM: Corynebacterium glutamicum
<220> FEATURE:
<221> NAME/KEY: CDS
<222> LOCATION: (443)..(4213)
<223> OTHER INFORMATION: odhA

<400> SEQUENCE: 43
gtcgacaagc aaaatcgaag cggcagcacg ccgcgtcgga gccttaaacg ccatcgccgc   60
catccctgat ggtttcaacc atcaagtcgg tgaacgcggg cgcaacctgt catccggaca   120
gcgccaactg atcgcgctgg cgcgcgccga acttatcgag ccttccatca tgcttctcga   180
cgaagccacc tccacccctc gaccccgcca cgaagccgtt atcctcaacg cctccgatcg   240
agtcactaag gacgcacca gcatcatcgt cgcgcaccgc ttggcaaccg ctaaaagggc   300
cgaccgtatt cttgttgttg aacaaggacg tatcattgag gacggatctc acgacgcgtt   360
gttgtctgct aacggcacct acgccgcat gtggcattta atggcctgac acgttatttt   420
taggagaact gtcaacaaat ta atg cta caa ctg ggg ctt agg cat aat cag   472
```

-continued

```
                    Met Leu Gln Leu Gly Leu Arg His Asn Gln
                     1               5                  10 cca acg acc aac gtt aca gtg gat aaa aca aag ctc aat aaa ccc tca    520
Pro Thr Thr Asn Val Thr Val Asp Lys Thr Lys Leu Asn Lys Pro Ser
             15                  20                  25 aga agc aag gaa aag agg cga gta cct gcc gtg agc agc gct agt act    568
Arg Ser Lys Glu Lys Arg Arg Val Pro Ala Val Ser Ser Ala Ser Thr
         30                  35                  40 ttc ggc cag aat gcg tgg ctg gta gac gag atg ttc cag cag ttc cag    616
Phe Gly Gln Asn Ala Trp Leu Val Asp Glu Met Phe Gln Gln Phe Gln
             45                  50                  55 aag gac ccc aag tcc gtg gac aag gaa tgg aga gaa ctc ttt gag gcg    664
Lys Asp Pro Lys Ser Val Asp Lys Glu Trp Arg Glu Leu Phe Glu Ala
 60                  65                  70 cag ggg gga cca aat act acc ccc gct aca aca gaa gca cag cct tca    712
Gln Gly Gly Pro Asn Thr Thr Pro Ala Thr Thr Glu Ala Gln Pro Ser
 75              80                  85                  90 gcg ccc aag gag tct gcg aaa cca gca cca aag gct gcc cct gca gcc    760
Ala Pro Lys Glu Ser Ala Lys Pro Ala Pro Lys Ala Ala Pro Ala Ala
                 95                 100                 105 aag gca gca ccg cgc gta gaa acc aag ccg gcc gac aag acc gcc cct    808
Lys Ala Ala Pro Arg Val Glu Thr Lys Pro Ala Asp Lys Thr Ala Pro
             110                 115                 120 aag gcc aag gag tcc tca gtg cca cag caa cct aag ctt ccg gag cca    856
Lys Ala Lys Glu Ser Ser Val Pro Gln Gln Pro Lys Leu Pro Glu Pro
         125                 130                 135 gga caa acc cca atc agg ggt att ttc aag tcc atc gcg aag aac atg    904
Gly Gln Thr Pro Ile Arg Gly Ile Phe Lys Ser Ile Ala Lys Asn Met
     140                 145                 150 gat atc tcc ctg gaa atc cca acc gca acc tcg gtt cgc gat atg cca    952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag   1000
Ala Arg Leu Met Phe Glu Asn Arg Ala Met Val Asn Asp Gln Leu Lys
                 175                 180                 185 cgc acc cgc ggt ggc aag atc tcc ttc acc cac atc att ggc tac gcc   1048
Arg Thr Arg Gly Gly Lys Ile Ser Phe Thr His Ile Ile Gly Tyr Ala
             190                 195                 200 atg gtg aag gca gtc atg gct cac ccg gac atg aac aac tcc tac gac   1096
Met Val Lys Ala Val Met Ala His Pro Asp Met Asn Asn Ser Tyr Asp
         205                 210                 215 gtc atc gac ggc aag cca acc ctg atc gtg cct gag cac atc aac ctg   1144
Val Ile Asp Gly Lys Pro Thr Leu Ile Val Pro Glu His Ile Asn Leu
     220                 225                 230 ggc ctt gct atc gac ctt cct cag aag gac ggc tcc cgc gca ctt gtc   1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc   1240
Val Ala Ala Ile Lys Glu Thr Glu Lys Met Asn Phe Ser Glu Phe Leu
                 255                 260                 265 gca gcc tac gaa gac atc gtg gca cgc tcc cgc aag ggc aag ctc acc   1288
Ala Ala Tyr Glu Asp Ile Val Ala Arg Ser Arg Lys Gly Lys Leu Thr
             270                 275                 280 atg gat gac tac cag ggc gtt acc gtt tcc ttg acc aac cca ggt ggc   1336
Met Asp Asp Tyr Gln Gly Val Thr Val Ser Leu Thr Asn Pro Gly Gly
         285                 290                 295 atc ggt acc cgc cac tct gtt cca cgt cta acc aag ggc cag ggc acc   1384
Ile Gly Thr Arg His Ser Val Pro Arg Leu Thr Lys Gly Gln Gly Thr
     300                 305                 310 atc atc ggt gtc ggt tcc atg gat tac cca gca gag ttc cag ggc gct   1432
```

```
                                    -continued

Ile Ile Gly Val Gly Ser Met Asp Tyr Pro Ala Glu Phe Gln Gly Ala
315             320                 325                 330 tca gaa gac cgc ctt gca gag ctc ggc gtt ggc aaa ctt gtc acc atc     1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa     1528
Thr Ser Thr Tyr Asp His Arg Val Ile Gln Gly Ala Val Ser Gly Glu
            350                 355                 360 ttc ctg cgc acc atg tct cgc ctg ctc acc gat gat tcc ttc tgg gat     1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca     1624
Glu Ile Phe Asp Ala Met Asn Val Pro Tyr Thr Pro Met Arg Trp Ala
    380                 385                 390 cag gac gtt cca aac acc ggt gtt gat aag aac acc cgc gtc atg cag     1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac     1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac     1768
Pro Leu Ser Trp Val Gln Pro Gly Met Pro Val Pro Asp His Arg Asp
            430                 435                 440 ctc gac atc gag acc cac aac ctg acc atc tgg gat ctg gac cgt acc     1816
Leu Asp Ile Glu Thr His Asn Leu Thr Ile Trp Asp Leu Asp Arg Thr
        445                 450                 455 ttc aac gtc ggt ggc ttc ggc ggc aag gag acc atg acc ctg cgc gag     1864
Phe Asn Val Gly Gly Phe Gly Gly Lys Glu Thr Met Thr Leu Arg Glu
    460                 465                 470 gta ctg tcc cgc ctc cgc gct gcg tac acc ctc aag gtc ggc tcc gaa     1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc     1960
Tyr Thr His Ile Leu Asp Arg Asp Glu Arg Thr Trp Leu Gln Asp Arg
                495                 500                 505 ctc gag gcc gga atg cca aag cca acc cag gca gag cag aag tac atc     2008
Leu Glu Ala Gly Met Pro Lys Pro Thr Gln Ala Glu Gln Lys Tyr Ile
            510                 515                 520 ctg cag aag ctg aac gcc gcg gag gct ttc gag aac ttc ctg cag acc     2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gca ctt     2104
Lys Tyr Val Gly Gln Lys Arg Phe Ser Leu Glu Gly Ala Glu Ala Leu
    540                 545                 550 atc cca ctg atg gac tcc gcc atc gac acc gcc gca ggc caa ggc ctc     2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg     2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa     2248
Phe Asn Ile Val Gly Lys Pro Leu Ala Ser Ile Phe Asn Glu Phe Glu
            590                 595                 600 ggc caa atg gag cag ggc cag atc ggt ggc tcc ggt gac gtg aag tac     2296
Gly Gln Met Glu Gln Gly Gln Ile Gly Gly Ser Gly Asp Val Lys Tyr
        605                 610                 615 cac ctc ggt tcc gaa ggc cag cac ctg cag atg ttc ggc gac ggc gag     2344
His Leu Gly Ser Glu Gly Gln His Leu Gln Met Phe Gly Asp Gly Glu
    620                 625                 630 atc aag gtc tcc ctg act gct aac ccg tcc cac ctg gaa gct gtt aac     2392
```

```
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag       2440
Pro Val Met Glu Gly Ile Val Arg Ala Lys Gln Asp Tyr Leu Asp Lys
            655                 660                 665 ggc gta gac ggc aag act gtt gtg cca ctg ctc cac ggt gac gct           2488
Gly Val Asp Gly Lys Thr Val Val Pro Leu Leu Leu His Gly Asp Ala
            670                 675                 680 gca ttc gca ggc ctg ggc atc gtg cca gaa acc atc aac ctg gct aag       2536
Ala Phe Ala Gly Leu Gly Ile Val Pro Glu Thr Ile Asn Leu Ala Lys
            685                 690                 695 ctg cgt ggc tac gac gtc ggc ggc acc atc cac atc gtg gtg aac aac       2584
Leu Arg Gly Tyr Asp Val Gly Gly Thr Ile His Ile Val Val Asn Asn
    700                 705                 710 cag atc ggc ttc acc acc acc cca gac tcc agc cgc tcc atg cac tac       2632
Gln Ile Gly Phe Thr Thr Thr Pro Asp Ser Ser Arg Ser Met His Tyr
715                 720                 725                 730 gca acc gac tac gcc aag gca ttc ggc tgc cca gtc ttc cac gtc aac       2680
Ala Thr Asp Tyr Ala Lys Ala Phe Gly Cys Pro Val Phe His Val Asn
                735                 740                 745 ggc gac gac cca gag gca gtt gtc tgg gtt ggc cag ctg gcc acc gag       2728
Gly Asp Asp Pro Glu Ala Val Val Trp Val Gly Gln Leu Ala Thr Glu
            750                 755                 760 tac cgt cgt cgc ttc ggc aag gac gtc ttc atc gac ctc gtc tgc tac       2776
Tyr Arg Arg Arg Phe Gly Lys Asp Val Phe Ile Asp Leu Val Cys Tyr
            765                 770                 775 cgc ctc cgc ggc cac aac gaa gct gat gat cct tcc atg acc cag cca       2824
Arg Leu Arg Gly His Asn Glu Ala Asp Asp Pro Ser Met Thr Gln Pro
            780                 785                 790 aag atg tat gag ctc atc acc ggc cgc gag acc gtt cgt gct cag tac       2872
Lys Met Tyr Glu Leu Ile Thr Gly Arg Glu Thr Val Arg Ala Gln Tyr
795                 800                 805                 810 acc gaa gac ctg ctc gga cgt gga gac ctc tcc aac gaa gat gca gaa       2920
Thr Glu Asp Leu Leu Gly Arg Gly Asp Leu Ser Asn Glu Asp Ala Glu
            815                 820                 825 gca gtc gtc cgc gac ttc cac gac cag atg gaa tct gtg ttc aac gaa       2968
Ala Val Val Arg Asp Phe His Asp Gln Met Glu Ser Val Phe Asn Glu
            830                 835                 840 gtc aag gaa ggc ggc aag aag cag gct gag gca cag acc ggc atc acc       3016
Val Lys Glu Gly Gly Lys Lys Gln Ala Glu Ala Gln Thr Gly Ile Thr
        845                 850                 855 ggc tcc cag aag ctt cca cac ggc ctt gag acc aac atc tcc cgt gaa       3064
Gly Ser Gln Lys Leu Pro His Gly Leu Glu Thr Asn Ile Ser Arg Glu
        860                 865                 870 gag ctc ctg gaa ctg gga cag gct ttc gcc aac acc cca gaa ggc ttc       3112
Glu Leu Leu Glu Leu Gly Gln Ala Phe Ala Asn Thr Pro Glu Gly Phe
875                 880                 885                 890 aac tac cac cca cgt gtg gct ccc gtt gct aag aag cgc gtc tcc tct       3160
Asn Tyr His Pro Arg Val Ala Pro Val Ala Lys Lys Arg Val Ser Ser
            895                 900                 905 gtc acc gaa ggt ggc atc gac tgg gca tgg ggc gag ctc ctc gcc ttc       3208
Val Thr Glu Gly Gly Ile Asp Trp Ala Trp Gly Glu Leu Leu Ala Phe
            910                 915                 920 ggt tcc ctg gct aac tcc ggc cgc ttg gtt cgc ctt gca ggt gaa gat       3256
Gly Ser Leu Ala Asn Ser Gly Arg Leu Val Arg Leu Ala Gly Glu Asp
        925                 930                 935 tcc cgc cgc ggt acc ttc acc cag cgc cac gca gtt gcc atc gac cca       3304
Ser Arg Arg Gly Thr Phe Thr Gln Arg His Ala Val Ala Ile Asp Pro
        940                 945                 950 gcg acc gct gaa gag ttc aac cca ctc cac gag ctt gca cag tcc aag       3352
```

```
                                                                             -continued
Ala Thr Ala Glu Glu Phe Asn Pro Leu His Glu Leu Ala Gln Ser Lys
955                 960                 965                 970 ggc aac aac ggt aag ttc ctg gtc tac aac tcc gca ctg acc gag tac      3400
Gly Asn Asn Gly Lys Phe Leu Val Tyr Asn Ser Ala Leu Thr Glu Tyr
                975                 980                 985 gca ggc atg ggc ttc gag tac ggc tac tcc gta gga aac gaa gac tcc      3448
Ala Gly Met Gly Phe Glu Tyr Gly Tyr Ser Val Gly Asn Glu Asp Ser
        990                 995                 1000 atc gtt gca tgg gaa gca cag ttc ggc gac ttc gcc aac ggc gct          3493
Ile Val Ala Trp Glu Ala Gln Phe Gly Asp Phe Ala Asn Gly Ala
    1005                1010                1015 cag acc atc atc gat gag tac gtc tcc tca ggc gaa gct aag tgg          3538
Gln Thr Ile Ile Asp Glu Tyr Val Ser Ser Gly Glu Ala Lys Trp
    1020                1025                1030 ggc cag acc tcc aag ctg atc ctt ctg ctg cct cac ggc tac gaa          3583
Gly Gln Thr Ser Lys Leu Ile Leu Leu Leu Pro His Gly Tyr Glu
    1035                1040                1045 ggc cag ggc cca gac cac tct tcc gca cgt atc gag cgc ttc ctg          3628
Gly Gln Gly Pro Asp His Ser Ser Ala Arg Ile Glu Arg Phe Leu
    1050                1055                1060 cag ctg tgc gct gag ggt tcc atg act gtt gct cag cca tcc acc          3673
Gln Leu Cys Ala Glu Gly Ser Met Thr Val Ala Gln Pro Ser Thr
    1065                1070                1075 cca gca aac cac ttc cac cta ctg cgt cgt cac gct ctg tcc gac          3718
Pro Ala Asn His Phe His Leu Leu Arg Arg His Ala Leu Ser Asp
    1080                1085                1090 ctg aag cgt cca ctg gtt atc ttc acc ccg aag tcc atg ctg cgt          3763
Leu Lys Arg Pro Leu Val Ile Phe Thr Pro Lys Ser Met Leu Arg
    1095                1100                1105 aac aag gct gct gcc tcc gca cca gaa gac ttc act gag gtc acc          3808
Asn Lys Ala Ala Ala Ser Ala Pro Glu Asp Phe Thr Glu Val Thr
    1110                1115                1120 aag ttc cag tcc gtg atc aac gat cca aac gtt gca gat gca gcc          3853
Lys Phe Gln Ser Val Ile Asn Asp Pro Asn Val Ala Asp Ala Ala
    1125                1130                1135 aag gtg aag aag gtc atg ctg gtc tcc ggc aag ctg tac tac gaa          3898
Lys Val Lys Lys Val Met Leu Val Ser Gly Lys Leu Tyr Tyr Glu
    1140                1145                1150 ttg gca aag cgc aag gag aag gac gga cgc gac gac atc gcg atc          3943
Leu Ala Lys Arg Lys Glu Lys Asp Gly Arg Asp Asp Ile Ala Ile
    1155                1160                1165 gtt cgt atc gaa atg ctc cac cca att ccg ttc aac cgc atc tcc          3988
Val Arg Ile Glu Met Leu His Pro Ile Pro Phe Asn Arg Ile Ser
    1170                1175                1180 gag gct ctt gcc ggc tac cct aac gct gag gaa gtc ctc ttc gtt          4033
Glu Ala Leu Ala Gly Tyr Pro Asn Ala Glu Glu Val Leu Phe Val
    1185                1190                1195 cag gat gag cca gca aac cag ggc cca tgg ccg ttc tac cag gag          4078
Gln Asp Glu Pro Ala Asn Gln Gly Pro Trp Pro Phe Tyr Gln Glu
    1200                1205                1210 cac ctc cca gag ctg atc ccg aac atg cca aag atg cgc cgc gtt          4123
His Leu Pro Glu Leu Ile Pro Asn Met Pro Lys Met Arg Arg Val
    1215                1220                1225 tcc cgc cgc gct cag tcc tcc acc gca act ggt gtt gcc aag gtg          4168
Ser Arg Arg Ala Gln Ser Ser Thr Ala Thr Gly Val Ala Lys Val
    1230                1235                1240 cac cag ctg gag gag aag cag ctt atc gac gag gct ttc gag gct          4213
His Gln Leu Glu Glu Lys Gln Leu Ile Asp Glu Ala Phe Glu Ala
    1245                1250                1255 taagtcttta tagtcctgca ctagcctaga agggccttat gccgtgtgaa tcacacagca    4273
```

```
tacggcccu tttgctgccg tggttgccta aggtggaagg tatgaaacga atctgtgcgg    4333
tcgcgatctc ttcagtactt ttgttaagtg gctgctcctc cacttccaca acgcagctcg    4393
agggatt                                                               4400
```

<210> SEQ ID NO 44
<211> LENGTH: 1257
<212> TYPE: PRT
<213> ORGANISM: Corynebacterium glutamicum

<400> SEQUENCE: 44

```
Met Leu Gln Leu Gly Leu Arg His Asn Gln Pro Thr Thr Asn Val Thr
1               5                   10                  15

Val Asp Lys Thr Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Thr
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Asp Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Ala Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350
```

```
Arg Val Ile Gln Gly Ala Val Ser Gly Glu Phe Leu Arg Thr Met Ser
            355                 360                 365

Arg Leu Leu Thr Asp Asp Ser Phe Trp Asp Glu Ile Phe Asp Ala Met
        370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Asn Leu Thr Ile Trp Asp Leu Asp Arg Thr Phe Asn Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
    530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu His Gly Asp Ala Ala Phe Ala Gly Leu Gly
        675                 680                 685

Ile Val Pro Glu Thr Ile Asn Leu Ala Lys Leu Arg Gly Tyr Asp Val
    690                 695                 700

Gly Gly Thr Ile His Ile Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
            740                 745                 750

Val Val Trp Val Gly Gln Leu Ala Thr Glu Tyr Arg Arg Phe Gly
        755                 760                 765

Lys Asp Val Phe Ile Asp Leu Val Cys Tyr Arg Leu Arg Gly His Asn
```

```
                    770              775              780
Glu Ala Asp Asp Pro Ser Met Thr Gln Pro Lys Met Tyr Glu Leu Ile
785              790              795              800

Thr Gly Arg Glu Thr Val Arg Ala Gln Tyr Thr Glu Asp Leu Leu Gly
             805              810              815

Arg Gly Asp Leu Ser Asn Glu Asp Ala Glu Ala Val Val Arg Asp Phe
             820              825              830

His Asp Gln Met Glu Ser Val Phe Asn Glu Val Lys Glu Gly Gly Lys
             835              840              845

Lys Gln Ala Glu Ala Gln Thr Gly Ile Thr Gly Ser Gln Lys Leu Pro
850              855              860

His Gly Leu Glu Thr Asn Ile Ser Arg Glu Glu Leu Leu Glu Leu Gly
865              870              875              880

Gln Ala Phe Ala Asn Thr Pro Glu Gly Phe Asn Tyr His Pro Arg Val
             885              890              895

Ala Pro Val Ala Lys Lys Arg Val Ser Ser Val Thr Gly Gly Ile
             900              905              910

Asp Trp Ala Trp Gly Glu Leu Leu Ala Phe Gly Ser Leu Ala Asn Ser
             915              920              925

Gly Arg Leu Val Arg Leu Ala Gly Glu Asp Ser Arg Arg Gly Thr Phe
930              935              940

Thr Gln Arg His Ala Val Ala Ile Asp Pro Ala Thr Ala Glu Glu Phe
945              950              955              960

Asn Pro Leu His Glu Leu Ala Gln Ser Lys Gly Asn Asn Gly Lys Phe
             965              970              975

Leu Val Tyr Asn Ser Ala Leu Thr Glu Tyr Ala Gly Met Gly Phe Glu
             980              985              990

Tyr Gly Tyr Ser Val Gly Asn Glu Asp Ser Ile Val Ala Trp Glu Ala
             995             1000             1005

Gln Phe Gly Asp Phe Ala Asn Gly Ala Gln Thr Ile Ile Asp Glu
            1010             1015             1020

Tyr Val Ser Ser Gly Glu Ala Lys Trp Gly Gln Thr Ser Lys Leu
            1025             1030             1035

Ile Leu Leu Leu Pro His Gly Tyr Glu Gly Gln Gly Pro Asp His
            1040             1045             1050

Ser Ser Ala Arg Ile Glu Arg Phe Leu Gln Leu Cys Ala Glu Gly
            1055             1060             1065

Ser Met Thr Val Ala Gln Pro Ser Thr Pro Ala Asn His Phe His
            1070             1075             1080

Leu Leu Arg Arg His Ala Leu Ser Asp Leu Lys Arg Pro Leu Val
            1085             1090             1095

Ile Phe Thr Pro Lys Ser Met Leu Arg Asn Lys Ala Ala Ala Ser
            1100             1105             1110

Ala Pro Glu Asp Phe Thr Glu Val Thr Lys Phe Gln Ser Val Ile
            1115             1120             1125

Asn Asp Pro Asn Val Ala Asp Ala Ala Lys Val Lys Lys Val Met
            1130             1135             1140

Leu Val Ser Gly Lys Leu Tyr Tyr Glu Leu Ala Lys Arg Lys Glu
            1145             1150             1155

Lys Asp Gly Arg Asp Asp Ile Ala Ile Val Arg Ile Glu Met Leu
            1160             1165             1170

His Pro Ile Pro Phe Asn Arg Ile Ser Glu Ala Leu Ala Gly Tyr
            1175             1180             1185
```

-continued

```
Pro Asn Ala Glu Glu Val Leu Phe Val Gln Asp Glu Pro Ala Asn
    1190                1195                1200

Gln Gly Pro Trp Pro Phe Tyr Gln Glu His Leu Pro Glu Leu Ile
    1205                1210                1215

Pro Asn Met Pro Lys Met Arg Arg Val Ser Arg Arg Ala Gln Ser
    1220                1225                1230

Ser Thr Ala Thr Gly Val Ala Lys Val His Gln Leu Glu Glu Lys
    1235                1240                1245

Gln Leu Ile Asp Glu Ala Phe Glu Ala
    1250                1255
```

<210> SEQ ID NO 45
<211> LENGTH: 4389
<212> TYPE: DNA
<213> ORGANISM: Corynebacterium glutamicum
<220> FEATURE:
<221> NAME/KEY: CDS
<222> LOCATION: (443)..(2542)
<223> OTHER INFORMATION: sucA8

<400> SEQUENCE: 45

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccacccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag      472
                         Met Leu Gln Leu Gly Leu Arg His Asn Gln
                           1               5                  10 cca acg acc aac gtt aca gtg gat aaa ata aag ctc aat aaa ccc tca      520
Pro Thr Thr Asn Val Thr Val Asp Lys Ile Lys Leu Asn Lys Pro Ser
        15                  20                  25 aga agc aag gaa aag agg cga gta cct gcc gtg agc agc gct agt act      568
Arg Ser Lys Glu Lys Arg Arg Val Pro Ala Val Ser Ser Ala Ser Thr
    30                  35                  40 ttc ggc cag aat gcg tgg ctg gta gac gag atg ttc cag cag ttc cag      616
Phe Gly Gln Asn Ala Trp Leu Val Asp Glu Met Phe Gln Gln Phe Gln
45                  50                  55 aag gac ccc aag tcc gtg gac aag gaa tgg aga gaa ctc ttt gag gcg      664
Lys Asp Pro Lys Ser Val Asp Lys Glu Trp Arg Glu Leu Phe Glu Ala
    60                  65                  70 cag ggg gga cca aat gct acc ccc gct aca aca gaa gca cag cct tca      712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc      760
Ala Pro Lys Glu Ser Ala Lys Pro Ala Pro Lys Ala Ala Pro Ala Ala
                95                  100                 105 aag gca gca ccg cgc gta gaa acc aag ccg gcc gcc aag acc gcc cct      808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca      856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
    140                 145                 150
```

```
gat atc tcc ctg gaa atc cca acc gca acc tcg gtt cgc gat atg cca     952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag    1000
Ala Arg Leu Met Phe Glu Asn Arg Ala Met Val Asn Asp Gln Leu Lys
            175                 180                 185 cgc acc cgc ggt ggc aag atc tcc ttc acc cac atc att ggc tac gcc    1048
Arg Thr Arg Gly Gly Lys Ile Ser Phe Thr His Ile Ile Gly Tyr Ala
        190                 195                 200 atg gtg aag gca gtc atg gct cac ccg gac atg aac aac tcc tac gac    1096
Met Val Lys Ala Val Met Ala His Pro Asp Met Asn Asn Ser Tyr Asp
205                 210                 215 gtc atc gac ggc aag cca acc ctg atc gtg cct gag cac atc aac ctg    1144
Val Ile Asp Gly Lys Pro Thr Leu Ile Val Pro Glu His Ile Asn Leu
220                 225                 230 ggc ctt gcc atc gac ctt cct cag aag gac ggc tcc cgc gca ctt gtc    1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc    1240
Val Ala Ala Ile Lys Glu Thr Glu Lys Met Asn Phe Ser Glu Phe Leu
            255                 260                 265 gca gca tac gaa gac atc gtg aca cgc tcc cgc aag ggc aag ctc acc    1288
Ala Ala Tyr Glu Asp Ile Val Thr Arg Ser Arg Lys Gly Lys Leu Thr
        270                 275                 280 atg gat gac tac cag ggc gtt acc gtt tcc ttg acc aac cca ggt ggc    1336
Met Asp Asp Tyr Gln Gly Val Thr Val Ser Leu Thr Asn Pro Gly Gly
285                 290                 295 atc ggt acc cgc cac tct gtc cca cgt ctg acc aag ggc cag ggc acc    1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct    1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc    1480
Ser Glu Asp Arg Leu Ala Glu Leu Gly Val Gly Lys Leu Val Thr Ile
            335                 340                 345 acc tcc acc tac gat cac cgc gtg atc cag ggt gct gtg tcc ggt gaa    1528
Thr Ser Thr Tyr Asp His Arg Val Ile Gln Gly Ala Val Ser Gly Glu
        350                 355                 360 ttc ctg cgt acc atg tct cgc ctg ctc acc gat gat tcc ttc tgg gat    1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca    1624
Glu Ile Phe Asp Ala Met Asn Val Pro Tyr Thr Pro Met Arg Trp Ala
        380                 385                 390 cag gac gtt cca aac acc ggt gtt gat aag aac acc cgc gtc atg cag    1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac    1720
Leu Ile Glu Ala Tyr Arg Ser Arg Gly His Leu Ile Ala Asp Thr Asn
            415                 420                 425 cca ctt tca tgg gtt cag cct ggc atg cca gtt cca gac cac cgc gac    1768
Pro Leu Ser Trp Val Gln Pro Gly Met Pro Val Pro Asp His Arg Asp
        430                 435                 440 ctc gac atc gag acc cac agc ctg acc atc tgg gat ctg gac cgt acc    1816
Leu Asp Ile Glu Thr His Ser Leu Thr Ile Trp Asp Leu Asp Arg Thr
        445                 450                 455 ttc agc gtc ggt ggc ttc ggc ggc aag gag acc atg acc ctg cgc gag    1864
Phe Ser Val Gly Gly Phe Gly Gly Lys Glu Thr Met Thr Leu Arg Glu
460                 465                 470
```

| | |
|---|---|
| gta ctg tcc cgc ctg cgc gct gcc tac acc ttg aag gtc ggc tcc gaa<br>Val Leu Ser Arg Leu Arg Ala Ala Tyr Thr Leu Lys Val Gly Ser Glu<br>475                      480                     485                  490 | 1912 |
| tac acc cac atc ctg gac cgc gac gag cgc acc tgg ctg cag gac cgc<br>Tyr Thr His Ile Leu Asp Arg Asp Glu Arg Thr Trp Leu Gln Asp Arg<br>                495                     500                     505 | 1960 |
| ctc gaa gcc gga atg cca aag cca acc cag gca gag cag aag tac atc<br>Leu Glu Ala Gly Met Pro Lys Pro Thr Gln Ala Glu Gln Lys Tyr Ile<br>           510                     515                     520 | 2008 |
| ctg cag aag ctg aac gcc gca gag gct ttc gag aac ttc ctg cag acc<br>Leu Gln Lys Leu Asn Ala Ala Glu Ala Phe Glu Asn Phe Leu Gln Thr<br>525                      530                     535 | 2056 |
| aag tac gtc ggc cag aag cgc ttc tcc ctc gaa ggt gca gaa gct ctc<br>Lys Tyr Val Gly Gln Lys Arg Phe Ser Leu Glu Gly Ala Glu Ala Leu<br>        540                     545                     550 | 2104 |
| atc cca ctg atg gac tcc gcc atc gac acc gcc gca ggc cag ggc ctc<br>Ile Pro Leu Met Asp Ser Ala Ile Asp Thr Ala Ala Gly Gln Gly Leu<br>555                      560                     565              570 | 2152 |
| gac gaa gtt gtc atc ggt atg cca cac cgt ggt cgc ctc aac gtg ctg<br>Asp Glu Val Val Ile Gly Met Pro His Arg Gly Arg Leu Asn Val Leu<br>                575                     580                     585 | 2200 |
| ttc aac atc gtg ggc aag cca ctg gca tcc atc ttc aac gag ttt gaa<br>Phe Asn Ile Val Gly Lys Pro Leu Ala Ser Ile Phe Asn Glu Phe Glu<br>           590                     595                     600 | 2248 |
| ggc caa atg gag cag ggc cag atc ggt ggc tcc ggt gac gtg aag tac<br>Gly Gln Met Glu Gln Gly Gln Ile Gly Gly Ser Gly Asp Val Lys Tyr<br>        605                     610                     615 | 2296 |
| cac ctc ggt tcc gaa ggc cag cac ctg cag atg ttc ggc gac ggc gag<br>His Leu Gly Ser Glu Gly Gln His Leu Gln Met Phe Gly Asp Gly Glu<br>           620                     625                     630 | 2344 |
| atc aag gtc tcc ctg act gct aac ccg tcc cac ctg gaa gct gtt aac<br>Ile Lys Val Ser Leu Thr Ala Asn Pro Ser His Leu Glu Ala Val Asn<br>635                      640                     645              650 | 2392 |
| cca gtg atg gaa ggt atc gtc cgc gca aag cag gac tac ctg gac aag<br>Pro Val Met Glu Gly Ile Val Arg Ala Lys Gln Asp Tyr Leu Asp Lys<br>                655                     660                     665 | 2440 |
| ggc gta gac ggc aag act gtt gtg cca ctg ctg ctc cac ggt gac gct<br>Gly Val Asp Gly Lys Thr Val Val Pro Leu Leu Leu His Gly Asp Ala<br>           670                     675                     680 | 2488 |
| gca ttc gca ggc ctg ggc atc gtg cca gaa acc atc aac ctg gct aag<br>Ala Phe Ala Gly Leu Gly Ile Val Pro Glu Thr Ile Asn Leu Ala Lys<br>        685                     690                     695 | 2536 |
| ctg cgt cgacgtcgga ggcaccatcc acatcgtggt gaacaaccag atcggcttca<br>Leu Arg<br>700 | 2592 |
| ccaccacccc agactccagc cgctccatgc actacgcaac cgactacgcc aaggcattcg | 2652 |
| gctgcccagt cttccacgtc aatggtgatg acccagaggc agttgtctgg gttggccagc | 2712 |
| tggcaaccga gtaccgtcgt cgcttcggca aggacgtctt catcgacctc gtttgctacc | 2772 |
| gcctccgcgg ccacaacgaa gctgatgatc cttccatgac ccagccaaag atgtatgagc | 2832 |
| tcatcaccgg ccgcgagacc gttcgtgctc agtacaccga agacctgctc ggacgtggag | 2892 |
| acctctccaa cgaagatgca gaagcagtcg tccgcgactt ccacgaccag atggaatctg | 2952 |
| tgttcaacga agtcaaggaa ggcggcaaga agcaggctga ggcacagacc ggcatcaccg | 3012 |
| gctcccagaa gcttccacac ggccttgaga ccaacatctc ccgtgaagag ctcctggaac | 3072 |
| tgggacaggc tttcgccaac accccagaag gcttcaacta ccaccacgt gtggctccag | 3132 |
| ttgctaagaa gcgcgtctcc tctgtcaccg aaggtggcat cgactgggca tggggcgagc | 3192 |

-continued

```
tcctcgcctt cggttccctg gctaactccg gccgcttggt tcgccttgca ggtgaagatt    3252
cccgccgcgg taccttcacc cagcgccacg cagttgccat cgacccagcg accgctgaag    3312
agttcaaccc actccacgag cttgcacagt ccaagggcaa caacggtaag ttcctggtct    3372
acaactccgc actgaccgag tacgcaggca tgggcttcga gtacggctac tccgtaggaa    3432
acgaagactc cgtcgttgca tgggaagcac agttcggcga cttcgccaac ggcgctcaga    3492
ccatcatcga tgagtacgtc tcctcaggcg aagctaagtg gggccagacc tccaagctga    3552
tccttctgct gcctcacggc tacgaaggcc agggcccaga ccactcttcc gcacgtatcg    3612
agcgcttcct gcagctgtgc gctgagggtt ccatgactgt tgctcagcca tccaccccag    3672
caaaccactt ccacctgctg cgtcgtcacg ctctgtccga cctgaagcgt ccactggtta    3732
tcttcacccc gaagtccatg ctgcgtaaca aggctgctgc ctccgcacca gaagacttca    3792
ctgaggtcac caagttccaa tccgtgatcg acgatccaaa cgttgcagat gcagccaagg    3852
tgaagaaggt catgctggtc tccggcaagc tgtactacga attggcaaag cgcaaggaga    3912
aggacggacg cgacgacatc gcgatcgttc gtatcgaaat gctccaccca attccgttca    3972
accgcatctc cgaggctctt gccggctacc taacgctga ggaagtcctc ttcgttcagg    4032
atgagccagc aaaccagggc ccatggccgt tctaccagga gcacctccca gagctgatcc    4092
cgaacatgcc aaagatgcgc gcgtttccc gccgcgctca gtcctccacc gcaactggtg    4152
ttgctaaggt gcaccagctg gaggagaagc agcttatcga cgaggctttc gaggcttaag    4212
tctttatagt cctgcactag cctagagggc cttatgcagt gtgaatcaca cagcataagg    4272
ccctttttgc tgccgtggtt gcctaaggtg gaaggcatga aacgaatctg tgcggtcacg    4332
atctcttcag tacttttgct aagtggctgc tcctccactt ccaccacgca gctcgag       4389
```

<210> SEQ ID NO 46
<211> LENGTH: 700
<212> TYPE: PRT
<213> ORGANISM: Corynebacterium glutamicum

<400> SEQUENCE: 46

```
Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
```

```
                    165                 170                 175
Asn Arg Ala Met Val Asn Asp Gln Leu Lys Arg Thr Arg Gly Gly Lys
                180                 185                 190

Ile Ser Phe Thr His Ile Ile Gly Tyr Ala Met Val Lys Ala Val Met
            195                 200                 205

Ala His Pro Asp Met Asn Asn Ser Tyr Asp Val Ile Asp Gly Lys Pro
        210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
            290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
        370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Ser Leu Thr Ile Trp Asp Leu Asp Arg Thr Phe Ser Val Gly Gly Phe
        450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
        530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590
```

```
        Pro Leu Ala Ser Ile Phe Asn Glu Phe Glu Gly Gln Met Glu Gln Gly
            595                 600                 605

Gln Ile Gly Gly Ser Gly Asp Val Lys Tyr His Leu Gly Ser Glu Gly
            610                 615                 620

Gln His Leu Gln Met Phe Gly Asp Gly Glu Ile Lys Val Ser Leu Thr
        625                 630                 635                 640

Ala Asn Pro Ser His Leu Glu Ala Val Asn Pro Val Met Glu Gly Ile
                        645                 650                 655

Val Arg Ala Lys Gln Asp Tyr Leu Asp Lys Gly Val Asp Gly Lys Thr
                    660                 665                 670

Val Val Pro Leu Leu His Gly Asp Ala Ala Phe Ala Gly Leu Gly
                675                 680                 685

Ile Val Pro Glu Thr Ile Asn Leu Ala Lys Leu Arg
            690                 695                 700

<210> SEQ ID NO 47
<211> LENGTH: 4391
<212> TYPE: DNA
<213> ORGANISM: Corynebacterium glutamicum
<220> FEATURE:
<221> NAME/KEY: CDS
<222> LOCATION: (443)..(4210)
<223> OTHER INFORMATION: sucA801

<400> SEQUENCE: 47
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccacccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag     472
                          Met Leu Gln Leu Gly Leu Arg His Asn Gln
                           1               5                  10 cca acg acc aac gtt aca gtg gat aaa ata aag ctc aat aaa ccc tca     520
Pro Thr Thr Asn Val Thr Val Asp Lys Ile Lys Leu Asn Lys Pro Ser
             15                  20                  25 aga agc aag gaa aag agg cga gta cct gcc gtg agc agc gct agt act     568
Arg Ser Lys Glu Lys Arg Arg Val Pro Ala Val Ser Ser Ala Ser Thr
         30                  35                  40 ttc ggc cag aat gcg tgg ctg gta gac gag atg ttc cag cag ttc cag     616
Phe Gly Gln Asn Ala Trp Leu Val Asp Glu Met Phe Gln Gln Phe Gln
     45                  50                  55 aag gac ccc aag tcc gtg gac aag gaa tgg aga gaa ctc ttt gag gcg     664
Lys Asp Pro Lys Ser Val Asp Lys Glu Trp Arg Glu Leu Phe Glu Ala
 60                  65                  70 cag ggg gga cca aat gct acc ccc gct aca aca gaa gca cag cct tca     712
Gln Gly Gly Pro Asn Ala Thr Pro Ala Thr Thr Glu Ala Gln Pro Ser
 75                  80                  85                  90 gcg ccc aag gag tct gcg aaa cca gca cca aag gct gcc cct gca gcc     760
Ala Pro Lys Glu Ser Ala Lys Pro Ala Pro Lys Ala Ala Pro Ala Ala
             95                 100                 105 aag gca gca ccg cgc gta gaa acc aag ccg gcc gcc aag acc gcc cct     808
Lys Ala Ala Pro Arg Val Glu Thr Lys Pro Ala Ala Lys Thr Ala Pro
         110                 115                 120 aag gcc aag gag tcc tca gtg cca cag caa cct aag ctt ccg gag cca     856
```

```
                Lys Ala Lys Glu Ser Ser Val Pro Gln Gln Pro Lys Leu Pro Glu Pro
                        125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
        140                 145                 150 gat atc tcc ctg gaa atc cca acc gca acc tcg gtt cgc gat atg cca      952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag     1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc     1048
Arg Thr Arg Gly Gly Lys Ile Ser Phe Thr His Ile Ile Gly Tyr Ala
                190                 195                 200 atg gtg aag gca gtc atg gct cac ccg gac atg aac aac tcc tac gac     1096
Met Val Lys Ala Val Met Ala His Pro Asp Met Asn Asn Ser Tyr Asp
        205                 210                 215 gtc atc gac ggc aag cca acc ctg atc gtg cct gag cac atc aac ctg     1144
Val Ile Asp Gly Lys Pro Thr Leu Ile Val Pro Glu His Ile Asn Leu
220                 225                 230 ggc ctt gcc atc gac ctt cct cag aag gac ggc tcc cgc gca ctt gtc     1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc     1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc     1288
Ala Ala Tyr Glu Asp Ile Val Thr Arg Ser Arg Lys Gly Lys Leu Thr
                270                 275                 280 atg gat gac tac cag ggc gtt acc gtt tcc ttg acc aac cca ggt ggc     1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc     1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct     1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc     1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa     1528
Thr Ser Thr Tyr Asp His Arg Val Ile Gln Gly Ala Val Ser Gly Glu
                350                 355                 360 ttc ctg cgt acc atg tct cgc ctg ctc acc gat gat tcc ttc tgg gat     1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca     1624
Glu Ile Phe Asp Ala Met Asn Val Pro Tyr Thr Pro Met Arg Trp Ala
        380                 385                 390 cag gac gtt cca aac acc ggt gtt gat aag aac acc cgc gtc atg cag     1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac     1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac     1768
Pro Leu Ser Trp Val Gln Pro Gly Met Pro Val Pro Asp His Arg Asp
        430                 435                 440 ctc gac atc gag acc cac agc ctg acc atc tgg gat ctg gac cgt acc     1816
```

```
                Leu Asp Ile Glu Thr His Ser Leu Thr Ile Trp Asp Leu Asp Arg Thr
                                445                 450                 455 ttc agc gtc ggt ggc ttc ggc ggc aag gag acc atg acc ctg cgc gag           1864
Phe Ser Val Gly Gly Phe Gly Gly Lys Glu Thr Met Thr Leu Arg Glu
460                 465                 470 gta ctg tcc cgc ctg cgc gct gcc tac acc ttg aag gtc ggc tcc gaa           1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc           1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc           2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc           2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gct ctc           2104
Lys Tyr Val Gly Gln Lys Arg Phe Ser Leu Glu Gly Ala Glu Ala Leu
540                 545                 550 atc cca ctg atg gac tcc gcc atc gac acc gcc gca ggc cag ggc ctc           2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg           2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa           2248
Phe Asn Ile Val Gly Lys Pro Leu Ala Ser Ile Phe Asn Glu Phe Glu
            590                 595                 600 ggc caa atg gag cag ggc cag atc ggt ggc tcc ggt gac gtg aag tac           2296
Gly Gln Met Glu Gln Gly Gln Ile Gly Gly Ser Gly Asp Val Lys Tyr
        605                 610                 615 cac ctc ggt tcc gaa ggc cag cac ctg cag atg ttc ggc gac ggc gag           2344
His Leu Gly Ser Glu Gly Gln His Leu Gln Met Phe Gly Asp Gly Glu
620                 625                 630 atc aag gtc tcc ctg act gct aac ccg tcc cac ctg gaa gct gtt aac           2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag           2440
Pro Val Met Glu Gly Ile Val Arg Ala Lys Gln Asp Tyr Leu Asp Lys
                655                 660                 665 ggc gta gac ggc aag act gtt gtg cca ctg ctg ctc cac ggt gac gct           2488
Gly Val Asp Gly Lys Thr Val Val Pro Leu Leu Leu His Gly Asp Ala
            670                 675                 680 gca ttc gca ggc ctg ggc atc gtg cca gaa acc atc aac ctg gct aag           2536
Ala Phe Ala Gly Leu Gly Ile Val Pro Glu Thr Ile Asn Leu Ala Lys
        685                 690                 695 ctg cgt ctc gac gtc gga ggc acc atc cac atc gtg gtg aac aac cag           2584
Leu Arg Leu Asp Val Gly Gly Thr Ile His Ile Val Val Asn Asn Gln
700                 705                 710 atc ggc ttc acc acc acc cca gac tcc agc cgc tcc atg cac tac gca           2632
Ile Gly Phe Thr Thr Thr Pro Asp Ser Ser Arg Ser Met His Tyr Ala
715                 720                 725                 730 acc gac tac gcc aag gca ttc ggc tgc cca gtc ttc cac gtc aat ggt           2680
Thr Asp Tyr Ala Lys Ala Phe Gly Cys Pro Val Phe His Val Asn Gly
                735                 740                 745 gat gac cca gag gca gtt gtc tgg gtt ggc cag ctg gca acc gag tac           2728
Asp Asp Pro Glu Ala Val Val Trp Val Gly Gln Leu Ala Thr Glu Tyr
            750                 755                 760 cgt cgt cgc ttc ggc aag gac gtc ttc atc gac ctc gtt tgc tac cgc           2776
```

```
                    -continued

Arg Arg Arg Phe Gly Lys Asp Val Phe Ile Asp Leu Val Cys Tyr Arg
        765                 770                 775 ctc cgc ggc cac aac gaa gct gat gat cct tcc atg acc cag cca aag    2824
Leu Arg Gly His Asn Glu Ala Asp Asp Pro Ser Met Thr Gln Pro Lys
        780                 785                 790 atg tat gag ctc atc acc ggc cgc gag acc gtt cgt gct cag tac acc    2872
Met Tyr Glu Leu Ile Thr Gly Arg Glu Thr Val Arg Ala Gln Tyr Thr
795                 800                 805                 810 gaa gac ctg ctc gga cgt gga gac ctc tcc aac gaa gat gca gaa gca    2920
Glu Asp Leu Leu Gly Arg Gly Asp Leu Ser Asn Glu Asp Ala Glu Ala
            815                 820                 825 gtc gtc cgc gac ttc cac gac cag atg gaa tct gtg ttc aac gaa gtc    2968
Val Val Arg Asp Phe His Asp Gln Met Glu Ser Val Phe Asn Glu Val
                830                 835                 840 aag gaa ggc ggc aag aag cag gct gag gca cag acc ggc atc acc ggc    3016
Lys Glu Gly Gly Lys Lys Gln Ala Glu Ala Gln Thr Gly Ile Thr Gly
845                 850                 855 tcc cag aag ctt cca cac ggc ctt gag acc aac atc tcc cgt gaa gag    3064
Ser Gln Lys Leu Pro His Gly Leu Glu Thr Asn Ile Ser Arg Glu Glu
        860                 865                 870 ctc ctg gaa ctg gga cag gct ttc gcc aac acc cca gaa ggc ttc aac    3112
Leu Leu Glu Leu Gly Gln Ala Phe Ala Asn Thr Pro Glu Gly Phe Asn
875                 880                 885                 890 tac cac cca cgt gtg gct cca gtt gct aag aag cgc gtc tcc tct gtc    3160
Tyr His Pro Arg Val Ala Pro Val Ala Lys Lys Arg Val Ser Ser Val
                895                 900                 905 acc gaa ggt ggc atc gac tgg gca tgg ggc gag ctc ctc gcc ttc ggt    3208
Thr Glu Gly Gly Ile Asp Trp Ala Trp Gly Glu Leu Leu Ala Phe Gly
                    910                 915                 920 tcc ctg gct aac tcc ggc cgc ttg gtt cgc ctt gca ggt gaa gat tcc    3256
Ser Leu Ala Asn Ser Gly Arg Leu Val Arg Leu Ala Gly Glu Asp Ser
            925                 930                 935 cgc cgc ggt acc ttc acc cag cgc cac gca gtt gcc atc gac cca gcg    3304
Arg Arg Gly Thr Phe Thr Gln Arg His Ala Val Ala Ile Asp Pro Ala
940                 945                 950 acc gct gaa gag ttc aac cca ctc cac gag ctt gca cag tcc aag ggc    3352
Thr Ala Glu Glu Phe Asn Pro Leu His Glu Leu Ala Gln Ser Lys Gly
955                 960                 965                 970 aac aac ggt aag ttc ctg gtc tac aac tcc gca ctg acc gag tac gca    3400
Asn Asn Gly Lys Phe Leu Val Tyr Asn Ser Ala Leu Thr Glu Tyr Ala
                975                 980                 985 ggc atg ggc ttc gag tac ggc tac tcc gta gga aac gaa gac tcc gtc    3448
Gly Met Gly Phe Glu Tyr Gly Tyr Ser Val Gly Asn Glu Asp Ser Val
                990                 995                1000 gtt gca tgg gaa gca cag ttc ggc gac ttc gcc aac ggc gct cag        3493
Val Ala Trp Glu Ala Gln Phe Gly Asp Phe Ala Asn Gly Ala Gln
        1005                1010                1015 acc atc atc gat gag tac gtc tcc tca ggc gaa gct aag tgg ggc        3538
Thr Ile Ile Asp Glu Tyr Val Ser Ser Gly Glu Ala Lys Trp Gly
        1020                1025                1030 cag acc tcc aag ctg atc ctt ctg ctg cct cac ggc tac gaa ggc        3583
Gln Thr Ser Lys Leu Ile Leu Leu Leu Pro His Gly Tyr Glu Gly
        1035                1040                1045 cag ggc cca gac cac tct tcc gca cgt atc gag cgc ttc ctg cag        3628
Gln Gly Pro Asp His Ser Ser Ala Arg Ile Glu Arg Phe Leu Gln
        1050                1055                1060 ctg tgc gct gag ggt tcc atg act gtt gct cag cca tcc acc cca        3673
Leu Cys Ala Glu Gly Ser Met Thr Val Ala Gln Pro Ser Thr Pro
        1065                1070                1075 gca aac cac ttc cac ctg ctg cgt cgt cac gct ctg tcc gac ctg        3718
```

```
Ala Asn His Phe His Leu Leu Arg Arg His Ala Leu Ser Asp Leu
        1080                1085                1090 aag cgt cca ctg gtt atc ttc acc ccg aag tcc atg ctg cgt aac     3763
Lys Arg Pro Leu Val Ile Phe Thr Pro Lys Ser Met Leu Arg Asn
        1095                1100                1105 aag gct gct gcc tcc gca cca gaa gac ttc act gag gtc acc aag     3808
Lys Ala Ala Ala Ser Ala Pro Glu Asp Phe Thr Glu Val Thr Lys
        1110                1115                1120 ttc caa tcc gtg atc gac gat cca aac gtt gca gat gca gcc aag     3853
Phe Gln Ser Val Ile Asp Asp Pro Asn Val Ala Asp Ala Ala Lys
        1125                1130                1135 gtg aag aag gtc atg ctg gtc tcc ggc aag ctg tac tac gaa ttg     3898
Val Lys Lys Val Met Leu Val Ser Gly Lys Leu Tyr Tyr Glu Leu
        1140                1145                1150 gca aag cgc aag gag aag gac gga cgc gac gac atc gcg atc gtt     3943
Ala Lys Arg Lys Glu Lys Asp Gly Arg Asp Asp Ile Ala Ile Val
        1155                1160                1165 cgt atc gaa atg ctc cac cca att ccg ttc aac cgc atc tcc gag     3988
Arg Ile Glu Met Leu His Pro Ile Pro Phe Asn Arg Ile Ser Glu
        1170                1175                1180 gct ctt gcc ggc tac cct aac gct gag gaa gtc ctc ttc gtt cag     4033
Ala Leu Ala Gly Tyr Pro Asn Ala Glu Glu Val Leu Phe Val Gln
        1185                1190                1195 gat gag cca gca aac cag ggc cca tgg ccg ttc tac cag gag cac     4078
Asp Glu Pro Ala Asn Gln Gly Pro Trp Pro Phe Tyr Gln Glu His
        1200                1205                1210 ctc cca gag ctg atc ccg aac atg cca aag atg cgc cgc gtt tcc     4123
Leu Pro Glu Leu Ile Pro Asn Met Pro Lys Met Arg Arg Val Ser
        1215                1220                1225 cgc cgc gct cag tcc tcc acc gca act ggt gtt gct aag gtg cac     4168
Arg Arg Ala Gln Ser Ser Thr Ala Thr Gly Val Ala Lys Val His
        1230                1235                1240 cag ctg gag gag aag cag ctt atc gac gag gct ttc gag gct         4210
Gln Leu Glu Glu Lys Gln Leu Ile Asp Glu Ala Phe Glu Ala
        1245                1250                1255 taagtcttta tagtcctgca ctagcctaga gggccttatg cagtgtgaat cacacagcat 4270
aaggcccttt tgctgccgt ggttgcctaa ggtggaaggc atgaaacgaa tctgtgcggt  4330
cacgatctct tcagtacttt tgctaagtgg ctgctcctcc acttccacca cgcagctcga 4390
g                                                                 4391

<210> SEQ ID NO 48
<211> LENGTH: 1256
<212> TYPE: PRT
<213> ORGANISM: Corynebacterium glutamicum

<400> SEQUENCE: 48

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
                20                  25                  30

Arg Val Pro Ala Val Ser Ser Ala Ser Thr Phe Gly Gln Asn Ala Trp
            35                  40                  45

Leu Val Asp Glu Met Phe Gln Gln Phe Gln Lys Asp Pro Lys Ser Val
        50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95
```

```
Lys Pro Ala Pro Lys Ala Ala Pro Ala Ala Lys Ala Ala Pro Arg Val
            100                 105                 110
Glu Thr Lys Pro Ala Ala Lys Thr Ala Pro Lys Ala Lys Glu Ser Ser
            115                 120                 125
Val Pro Gln Gln Pro Lys Leu Pro Glu Pro Gly Gln Thr Pro Ile Arg
130                 135                 140
Gly Ile Phe Lys Ser Ile Ala Lys Asn Met Asp Ile Ser Leu Glu Ile
145                 150                 155                 160
Pro Thr Ala Thr Ser Val Arg Asp Met Pro Ala Arg Leu Met Phe Glu
                165                 170                 175
Asn Arg Ala Met Val Asn Asp Gln Leu Lys Arg Thr Arg Gly Gly Lys
            180                 185                 190
Ile Ser Phe Thr His Ile Ile Gly Tyr Ala Met Val Lys Ala Val Met
            195                 200                 205
Ala His Pro Asp Met Asn Asn Ser Tyr Asp Val Ile Asp Gly Lys Pro
210                 215                 220
Thr Leu Ile Val Pro Glu His Ile Asn Leu Gly Leu Ala Ile Asp Leu
225                 230                 235                 240
Pro Gln Lys Asp Gly Ser Arg Ala Leu Val Val Ala Ala Ile Lys Glu
                245                 250                 255
Thr Glu Lys Met Asn Phe Ser Glu Phe Leu Ala Ala Tyr Glu Asp Ile
            260                 265                 270
Val Thr Arg Ser Arg Lys Gly Lys Leu Thr Met Asp Asp Tyr Gln Gly
            275                 280                 285
Val Thr Val Ser Leu Thr Asn Pro Gly Gly Ile Gly Thr Arg His Ser
            290                 295                 300
Val Pro Arg Leu Thr Lys Gly Gln Gly Thr Ile Ile Gly Val Gly Ser
305                 310                 315                 320
Met Asp Tyr Pro Ala Glu Phe Gln Gly Ala Ser Glu Asp Arg Leu Ala
                325                 330                 335
Glu Leu Gly Val Gly Lys Leu Val Thr Ile Thr Ser Thr Tyr Asp His
            340                 345                 350
Arg Val Ile Gln Gly Ala Val Ser Gly Glu Phe Leu Arg Thr Met Ser
            355                 360                 365
Arg Leu Leu Thr Asp Asp Ser Phe Trp Asp Glu Ile Phe Asp Ala Met
            370                 375                 380
Asn Val Pro Tyr Thr Pro Met Arg Trp Ala Gln Asp Val Pro Asn Thr
385                 390                 395                 400
Gly Val Asp Lys Asn Thr Arg Val Met Gln Leu Ile Glu Ala Tyr Arg
                405                 410                 415
Ser Arg Gly His Leu Ile Ala Asp Thr Asn Pro Leu Ser Trp Val Gln
            420                 425                 430
Pro Gly Met Pro Val Pro Asp His Arg Asp Leu Asp Ile Glu Thr His
            435                 440                 445
Ser Leu Thr Ile Trp Asp Leu Asp Arg Thr Phe Ser Val Gly Gly Phe
450                 455                 460
Gly Gly Lys Glu Thr Met Thr Leu Arg Glu Val Leu Ser Arg Leu Arg
465                 470                 475                 480
Ala Ala Tyr Thr Leu Lys Val Gly Ser Glu Tyr Thr His Ile Leu Asp
                485                 490                 495
Arg Asp Glu Arg Thr Trp Leu Gln Asp Arg Leu Glu Ala Gly Met Pro
            500                 505                 510
Lys Pro Thr Gln Ala Glu Gln Lys Tyr Ile Leu Gln Lys Leu Asn Ala
```

```
                515                 520                 525
Ala Glu Ala Phe Glu Asn Phe Leu Gln Thr Lys Tyr Val Gly Gln Lys
530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
                580                 585                 590

Pro Leu Ala Ser Ile Phe Asn Glu Phe Glu Gly Gln Met Glu Gln Gly
            595                 600                 605

Gln Ile Gly Gly Ser Gly Asp Val Lys Tyr His Leu Gly Ser Glu Gly
        610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu Leu His Gly Asp Ala Ala Phe Ala Gly Leu Gly
            675                 680                 685

Ile Val Pro Glu Thr Ile Asn Leu Ala Lys Leu Arg Leu Asp Val Gly
690                 695                 700

Gly Thr Ile His Ile Val Val Asn Asn Gln Ile Gly Phe Thr Thr Thr
705                 710                 715                 720

Pro Asp Ser Ser Arg Ser Met His Tyr Ala Thr Asp Tyr Ala Lys Ala
                725                 730                 735

Phe Gly Cys Pro Val Phe His Val Asn Gly Asp Asp Pro Glu Ala Val
                740                 745                 750

Val Trp Val Gly Gln Leu Ala Thr Glu Tyr Arg Arg Arg Phe Gly Lys
            755                 760                 765

Asp Val Phe Ile Asp Leu Val Cys Tyr Arg Leu Arg Gly His Asn Glu
            770                 775                 780

Ala Asp Asp Pro Ser Met Thr Gln Pro Lys Met Tyr Glu Leu Ile Thr
785                 790                 795                 800

Gly Arg Glu Thr Val Arg Ala Gln Tyr Thr Glu Asp Leu Leu Gly Arg
                805                 810                 815

Gly Asp Leu Ser Asn Glu Asp Ala Glu Ala Val Val Arg Asp Phe His
            820                 825                 830

Asp Gln Met Glu Ser Val Phe Asn Glu Val Lys Glu Gly Gly Lys Lys
            835                 840                 845

Gln Ala Glu Ala Gln Thr Gly Ile Thr Gly Ser Gln Lys Leu Pro His
        850                 855                 860

Gly Leu Glu Thr Asn Ile Ser Arg Glu Glu Leu Leu Glu Leu Gly Gln
865                 870                 875                 880

Ala Phe Ala Asn Thr Pro Glu Gly Phe Asn Tyr His Pro Arg Val Ala
                885                 890                 895

Pro Val Ala Lys Lys Arg Val Ser Ser Val Thr Glu Gly Gly Ile Asp
            900                 905                 910

Trp Ala Trp Gly Glu Leu Leu Ala Phe Gly Ser Leu Ala Asn Ser Gly
            915                 920                 925

Arg Leu Val Arg Leu Ala Gly Glu Asp Ser Arg Arg Gly Thr Phe Thr
930                 935                 940
```

-continued

```
Gln Arg His Ala Val Ala Ile Asp Pro Ala Thr Ala Glu Glu Phe Asn
945                 950                 955                 960

Pro Leu His Glu Leu Ala Gln Ser Lys Gly Asn Asn Gly Lys Phe Leu
            965                 970                 975

Val Tyr Asn Ser Ala Leu Thr Glu Tyr Ala Gly Met Gly Phe Glu Tyr
        980                 985                 990

Gly Tyr Ser Val Gly Asn Glu Asp  Ser Val Val Ala Trp Glu Ala Gln
    995                 1000                1005

Phe Gly Asp Phe Ala Asn Gly  Ala Gln Thr Ile Ile  Asp Glu Tyr
1010                1015                1020

Val Ser Ser Gly Glu Ala Lys  Trp Gly Gln Thr Ser  Lys Leu Ile
1025                1030                1035

Leu Leu Leu Pro His Gly Tyr  Glu Gly Gln Gly Pro  Asp His Ser
1040                1045                1050

Ser Ala Arg Ile Glu Arg Phe  Leu Gln Leu Cys Ala  Glu Gly Ser
1055                1060                1065

Met Thr Val Ala Gln Pro Ser  Thr Pro Ala Asn His  Phe His Leu
1070                1075                1080

Leu Arg Arg His Ala Leu Ser  Asp Leu Lys Arg Pro  Leu Val Ile
1085                1090                1095

Phe Thr Pro Lys Ser Met Leu  Arg Asn Lys Ala Ala  Ala Ser Ala
1100                1105                1110

Pro Glu Asp Phe Thr Glu Val  Thr Lys Phe Gln Ser  Val Ile Asp
1115                1120                1125

Asp Pro Asn Val Ala Asp Ala  Ala Lys Val Lys Lys  Val Met Leu
1130                1135                1140

Val Ser Gly Lys Leu Tyr Tyr  Glu Leu Ala Lys Arg  Lys Glu Lys
1145                1150                1155

Asp Gly Arg Asp Asp Ile Ala  Ile Val Arg Ile Glu  Met Leu His
1160                1165                1170

Pro Ile Pro Phe Asn Arg Ile  Ser Glu Ala Leu Ala  Gly Tyr Pro
1175                1180                1185

Asn Ala Glu Glu Val Leu Phe  Val Gln Asp Glu Pro  Ala Asn Gln
1190                1195                1200

Gly Pro Trp Pro Phe Tyr Gln  Glu His Leu Pro Glu  Leu Ile Pro
1205                1210                1215

Asn Met Pro Lys Met Arg Arg  Val Ser Arg Ala Gln  Ser Ser
1220                1225                1230

Thr Ala Thr Gly Val Ala Lys  Val His Gln Leu Glu  Glu Lys Gln
1235                1240                1245

Leu Ile Asp Glu Ala Phe Glu  Ala
1250                1255
```

<210> SEQ ID NO 49
<211> LENGTH: 4391
<212> TYPE: DNA
<213> ORGANISM: Corynebacterium glutamicum
<220> FEATURE:
<221> NAME/KEY: CDS
<222> LOCATION: (443)..(4210)
<223> OTHER INFORMATION: sucA805

<400> SEQUENCE: 49

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
```

```
cgaagccacc tccaccctcg accccgccac cgaagccgtt atcctcaacg cctccgatcg        240
agtcactaag ggacgcacca gcatcatcgt cgcgcaccgc ttggcaaccg ctaaaagggc        300
cgaccgtatt cttgttgttg aacaaggacg tatcattgag gacggatctc acgacgcgtt        360
gttgtctgct aacggcacct acgccgcat gtggcattta atggcctgac acgttatttt        420
taggagaact gtcaacaaat ta atg cta caa ctg ggg ctt agg cat aat cag        472
                         Met Leu Gln Leu Gly Leu Arg His Asn Gln
                           1               5                  10 cca acg acc aac gtt aca gtg gat aaa ata aag ctc aat aaa ccc tca        520
Pro Thr Thr Asn Val Thr Val Asp Lys Ile Lys Leu Asn Lys Pro Ser
                15                  20                  25 aga agc aag gaa aag agg cga gta cct gcc gtg agc agc gct agt act        568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag        616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg        664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca        712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc        760
Ala Pro Lys Glu Ser Ala Lys Pro Ala Pro Lys Ala Ala Pro Ala Ala
                95                 100                 105 aag gca gca ccg cgc gta gaa acc aag ccg gcc gcc aag acc gcc cct        808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca        856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg        904
Gly Gln Thr Pro Ile Arg Gly Ile Phe Lys Ser Ile Ala Lys Asn Met
    140                 145                 150 gat atc tcc ctg gaa atc cca acc gca acc tcg gtt cgc gat atg cca        952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag        1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc        1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac        1096
Met Val Lys Ala Val Met Ala His Pro Asp Met Asn Asn Ser Tyr Asp
        205                 210                 215 gtc atc gac ggc aag cca acc ctg atc gtg cct gag cac atc aac ctg        1144
Val Ile Asp Gly Lys Pro Thr Leu Ile Val Pro Glu His Ile Asn Leu
    220                 225                 230 ggc ctt gcc atc gac ctt cct cag aag gac ggc tcc cgc gca ctt gtc        1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc        1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc        1288
Ala Ala Tyr Glu Asp Ile Val Thr Arg Ser Arg Lys Gly Lys Leu Thr
            270                 275                 280
```

```
atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
            285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
            350                 355                 360 ttc ctg cgt acc atg tct cgc ctc ctc acc gat gat tcc ttc tgg gat      1576
Phe Leu Arg Thr Met Ser Arg Leu Leu Thr Asp Asp Ser Phe Trp Asp
365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac      1768
Pro Leu Ser Trp Val Gln Pro Gly Met Pro Val Pro Asp His Arg Asp
            430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
460                 465                 470 gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc      1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc      2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc      2056
Leu Gln Lys Leu Asn Ala Ala Glu Ala Phe Glu Asn Phe Leu Gln Thr
525                 530                 535 aag tac gtc ggc cag aag cgc ttc tcc ctc gaa ggt gca gaa gct ctc      2104
Lys Tyr Val Gly Gln Lys Arg Phe Ser Leu Glu Gly Ala Glu Ala Leu
540                 545                 550 atc cca ctg atg gac tcc gcc atc gac acc gcc gca ggc cag ggc ctc      2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg      2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa      2248
Phe Asn Ile Val Gly Lys Pro Leu Ala Ser Ile Phe Asn Glu Phe Glu
            590                 595                 600
```

| | | | | | | | | | | | | | | | | |
|---|---|---|---|---|---|---|---|---|---|---|---|---|---|---|---|---|
| ggc | caa | atg | gag | cag | ggc | cag | atc | ggt | ggc | tcc | ggt | gac | gtg | aag | tac | 2296 |
| Gly | Gln | Met | Glu | Gln | Gly | Gln | Ile | Gly | Gly | Ser | Gly | Asp | Val | Lys | Tyr | |
| | | 605 | | | | 610 | | | | 615 | | | | | | |
| cac | ctc | ggt | tcc | gaa | ggc | cag | cac | ctg | cag | atg | ttc | ggc | gac | ggc | gag | 2344 |
| His | Leu | Gly | Ser | Glu | Gly | Gln | His | Leu | Gln | Met | Phe | Gly | Asp | Gly | Glu | |
| | 620 | | | | | 625 | | | | | 630 | | | | | |
| atc | aag | gtc | tcc | ctg | act | gct | aac | ccg | tcc | cac | ctg | gaa | gct | gtt | aac | 2392 |
| Ile | Lys | Val | Ser | Leu | Thr | Ala | Asn | Pro | Ser | His | Leu | Glu | Ala | Val | Asn | |
| 635 | | | | | 640 | | | | | 645 | | | | | 650 | |
| cca | gtg | atg | gaa | ggt | atc | gtc | cgc | gca | aag | cag | gac | tac | ctg | gac | aag | 2440 |
| Pro | Val | Met | Glu | Gly | Ile | Val | Arg | Ala | Lys | Gln | Asp | Tyr | Leu | Asp | Lys | |
| | | | | 655 | | | | | 660 | | | | | 665 | | |
| ggc | gta | gac | ggc | aag | act | gtt | gtg | cca | ctg | ctc | cac | ggt | gac | gct | | 2488 |
| Gly | Val | Asp | Gly | Lys | Thr | Val | Val | Pro | Leu | Leu | Leu | His | Gly | Asp | Ala | |
| | | | 670 | | | | | 675 | | | | | 680 | | | |
| gca | ttc | gca | ggc | ctg | ggc | atc | gtg | cca | gaa | acc | atc | aac | ctg | gct | aaa | 2536 |
| Ala | Phe | Ala | Gly | Leu | Gly | Ile | Val | Pro | Glu | Thr | Ile | Asn | Leu | Ala | Lys | |
| | | | 685 | | | | | 690 | | | | | 695 | | | |
| agc | tgc | gtc | gac | gtc | gga | ggc | acc | atc | cac | atc | gtg | gtg | aac | aac | cag | 2584 |
| Ser | Cys | Val | Asp | Val | Gly | Gly | Thr | Ile | His | Ile | Val | Val | Asn | Asn | Gln | |
| | 700 | | | | | 705 | | | | | 710 | | | | | |
| atc | ggc | ttc | acc | acc | acc | cca | gac | tcc | agc | cgc | tcc | atg | cac | tac | gca | 2632 |
| Ile | Gly | Phe | Thr | Thr | Thr | Pro | Asp | Ser | Ser | Arg | Ser | Met | His | Tyr | Ala | |
| 715 | | | | | 720 | | | | | 725 | | | | | 730 | |
| acc | gac | tac | gcc | aag | gca | ttc | ggc | tgc | cca | gtc | ttc | cac | gtc | aat | ggt | 2680 |
| Thr | Asp | Tyr | Ala | Lys | Ala | Phe | Gly | Cys | Pro | Val | Phe | His | Val | Asn | Gly | |
| | | | | 735 | | | | | 740 | | | | | 745 | | |
| gat | gac | cca | gag | gca | gtt | gtc | tgg | gtt | ggc | cag | ctg | gca | acc | gag | tac | 2728 |
| Asp | Asp | Pro | Glu | Ala | Val | Val | Trp | Val | Gly | Gln | Leu | Ala | Thr | Glu | Tyr | |
| | | | 750 | | | | | 755 | | | | | 760 | | | |
| cgt | cgt | cgc | ttc | ggc | aag | gac | gtc | ttc | atc | gac | ctc | gtt | tgc | tac | cgc | 2776 |
| Arg | Arg | Arg | Phe | Gly | Lys | Asp | Val | Phe | Ile | Asp | Leu | Val | Cys | Tyr | Arg | |
| | | 765 | | | | | 770 | | | | | 775 | | | | |
| ctc | cgc | ggc | cac | aac | gaa | gct | gat | gat | cct | tcc | atg | acc | cag | cca | aag | 2824 |
| Leu | Arg | Gly | His | Asn | Glu | Ala | Asp | Asp | Pro | Ser | Met | Thr | Gln | Pro | Lys | |
| | | 780 | | | | | 785 | | | | | 790 | | | | |
| atg | tat | gag | ctc | atc | acc | ggc | cgc | gag | acc | gtt | cgt | gct | cag | tac | acc | 2872 |
| Met | Tyr | Glu | Leu | Ile | Thr | Gly | Arg | Glu | Thr | Val | Arg | Ala | Gln | Tyr | Thr | |
| 795 | | | | | 800 | | | | | 805 | | | | | 810 | |
| gaa | gac | ctg | ctc | gga | cgt | gga | gac | ctc | tcc | aac | gaa | gat | gca | gaa | gca | 2920 |
| Glu | Asp | Leu | Leu | Gly | Arg | Gly | Asp | Leu | Ser | Asn | Glu | Asp | Ala | Glu | Ala | |
| | | | | 815 | | | | | 820 | | | | | 825 | | |
| gtc | gtc | cgc | gac | ttc | cac | gac | cag | atg | gaa | tct | gtg | ttc | aac | gaa | gtc | 2968 |
| Val | Val | Arg | Asp | Phe | His | Asp | Gln | Met | Glu | Ser | Val | Phe | Asn | Glu | Val | |
| | | | 830 | | | | | 835 | | | | | 840 | | | |
| aag | gaa | ggc | ggc | aag | aag | cag | gct | gag | gca | cag | acc | ggc | atc | acc | ggc | 3016 |
| Lys | Glu | Gly | Gly | Lys | Lys | Gln | Ala | Glu | Ala | Gln | Thr | Gly | Ile | Thr | Gly | |
| | | 845 | | | | | 850 | | | | | 855 | | | | |
| tcc | cag | aag | ctt | cca | cac | ggc | ctt | gag | acc | aac | atc | tcc | cgt | gaa | gag | 3064 |
| Ser | Gln | Lys | Leu | Pro | His | Gly | Leu | Glu | Thr | Asn | Ile | Ser | Arg | Glu | Glu | |
| | 860 | | | | | 865 | | | | | 870 | | | | | |
| ctc | ctg | gaa | ctg | gga | cag | gct | ttc | gcc | aac | acc | cca | gaa | ggc | ttc | aac | 3112 |
| Leu | Leu | Glu | Leu | Gly | Gln | Ala | Phe | Ala | Asn | Thr | Pro | Glu | Gly | Phe | Asn | |
| 875 | | | | | 880 | | | | | 885 | | | | | 890 | |
| tac | cac | cca | cgt | gtg | gct | cca | gtt | gct | aag | aag | cgc | gtc | tcc | tct | gtc | 3160 |
| Tyr | His | Pro | Arg | Val | Ala | Pro | Val | Ala | Lys | Lys | Arg | Val | Ser | Ser | Val | |
| | | | | 895 | | | | | 900 | | | | | 905 | | |
| acc | gaa | ggt | ggc | atc | gac | tgg | gca | tgg | ggc | gag | ctc | ctc | gcc | ttc | ggt | 3208 |
| Thr | Glu | Gly | Gly | Ile | Asp | Trp | Ala | Trp | Gly | Glu | Leu | Leu | Ala | Phe | Gly | |
| | | | | 910 | | | | | 915 | | | | | 920 | | |

| | |
|---|---|
| tcc ctg gct aac tcc ggc cgc ttg gtt cgc ctt gca ggt gaa gat tcc<br>Ser Leu Ala Asn Ser Gly Arg Leu Val Arg Leu Ala Gly Glu Asp Ser<br>925                   930                   935 | 3256 |
| cgc cgc ggt acc ttc acc cag cgc cac gca gtt gcc atc gac cca gcg<br>Arg Arg Gly Thr Phe Thr Gln Arg His Ala Val Ala Ile Asp Pro Ala<br>940                     945                   950 | 3304 |
| acc gct gaa gag ttc aac cca ctc cac gag ctt gca cag tcc aag ggc<br>Thr Ala Glu Glu Phe Asn Pro Leu His Glu Leu Ala Gln Ser Lys Gly<br>955                   960                   965                   970 | 3352 |
| aac aac ggt aag ttc ctg gtc tac aac tcc gca ctg acc gag tac gca<br>Asn Asn Gly Lys Phe Leu Val Tyr Asn Ser Ala Leu Thr Glu Tyr Ala<br>                 975                   980                   985 | 3400 |
| ggc atg ggc ttc gag tac ggc tac tcc gta gga aac gaa gac tcc gtc<br>Gly Met Gly Phe Glu Tyr Gly Tyr Ser Val Gly Asn Glu Asp Ser Val<br>                 990                   995                 1000 | 3448 |
| gtt gca tgg gaa gca cag ttc ggc gac ttc gcc aac ggc gct cag<br>Val Ala Trp Glu Ala Gln Phe Gly Asp Phe Ala Asn Gly Ala Gln<br>1005                 1010                 1015 | 3493 |
| acc atc atc gat gag tac gtc tcc tca ggc gaa gct aag tgg ggc<br>Thr Ile Ile Asp Glu Tyr Val Ser Ser Gly Glu Ala Lys Trp Gly<br>1020                 1025                 1030 | 3538 |
| cag acc tcc aag ctg atc ctt ctg ctg cct cac ggc tac gaa ggc<br>Gln Thr Ser Lys Leu Ile Leu Leu Leu Pro His Gly Tyr Glu Gly<br>1035                 1040                 1045 | 3583 |
| cag ggc cca gac cac tct tcc gca cgt atc gag cgc ttc ctg cag<br>Gln Gly Pro Asp His Ser Ser Ala Arg Ile Glu Arg Phe Leu Gln<br>1050                 1055                 1060 | 3628 |
| ctg tgc gct gag ggt tcc atg act gtt gct cag cca tcc acc cca<br>Leu Cys Ala Glu Gly Ser Met Thr Val Ala Gln Pro Ser Thr Pro<br>1065                 1070                 1075 | 3673 |
| gca aac cac ttc cac ctg ctg cgt cgt cac gct ctg tcc gac ctg<br>Ala Asn His Phe His Leu Leu Arg Arg His Ala Leu Ser Asp Leu<br>1080                 1085                 1090 | 3718 |
| aag cgt cca ctg gtt atc ttc acc ccg aag tcc atg ctg cgt aac<br>Lys Arg Pro Leu Val Ile Phe Thr Pro Lys Ser Met Leu Arg Asn<br>1095                 1100                 1105 | 3763 |
| aag gct gct gcc tcc gca cca gaa gac ttc act gag gtc acc aag<br>Lys Ala Ala Ala Ser Ala Pro Glu Asp Phe Thr Glu Val Thr Lys<br>1110                 1115                 1120 | 3808 |
| ttc caa tcc gtg atc gac gat cca aac gtt gca gat gca gcc aag<br>Phe Gln Ser Val Ile Asp Asp Pro Asn Val Ala Asp Ala Ala Lys<br>1125                 1130                 1135 | 3853 |
| gtg aag aag gtc atg ctg gtc tcc ggc aag ctg tac tac gaa ttg<br>Val Lys Lys Val Met Leu Val Ser Gly Lys Leu Tyr Tyr Glu Leu<br>1140                 1145                 1150 | 3898 |
| gca aag cgc aag gag aag gac gga cgc gac gac atc gcg atc gtt<br>Ala Lys Arg Lys Glu Lys Asp Gly Arg Asp Asp Ile Ala Ile Val<br>1155                 1160                 1165 | 3943 |
| cgt atc gaa atg ctc cac cca att ccg ttc aac cgc atc tcc gag<br>Arg Ile Glu Met Leu His Pro Ile Pro Phe Asn Arg Ile Ser Glu<br>1170                 1175                 1180 | 3988 |
| gct ctt gcc ggc tac cct aac gct gag gaa gtc ctc ttc gtt cag<br>Ala Leu Ala Gly Tyr Pro Asn Ala Glu Glu Val Leu Phe Val Gln<br>1185                 1190                 1195 | 4033 |
| gat gag cca gca aac cag ggc cca tgg ccg ttc tac cag gag cac<br>Asp Glu Pro Ala Asn Gln Gly Pro Trp Pro Phe Tyr Gln Glu His<br>1200                 1205                 1210 | 4078 |
| ctc cca gag ctg atc ccg aac atg cca aag atg cgc cgc gtt tcc<br>Leu Pro Glu Leu Ile Pro Asn Met Pro Lys Met Arg Arg Val Ser<br>1215                 1220                 1225 | 4123 |

```
cgc cgc gct cag tcc tcc acc gca act ggt gtt gct aag gtg cac      4168
Arg Arg Ala Gln Ser Ser Thr Ala Thr Gly Val Ala Lys Val His
        1230                1235                1240 cag ctg gag gag aag cag ctt atc gac gag gct ttc gag gct          4210
Gln Leu Glu Glu Lys Gln Leu Ile Asp Glu Ala Phe Glu Ala
    1245                1250                1255 taagtcttta tagtcctgca ctagcctaga gggccttatg cagtgtgaat cacacagcat 4270
aaggcccttt ttgctgccgt ggttgcctaa ggtggaaggc atgaaacgaa tctgtgcggt 4330
cacgatctct tcagtacttt tgctaagtgg ctgctcctcc acttccacca cgcagctcga 4390
g                                                                4391

<210> SEQ ID NO 50
<211> LENGTH: 1256
<212> TYPE: PRT
<213> ORGANISM: Corynebacterium glutamicum

<400> SEQUENCE: 50

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
```

```
                290                 295                 300
Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
                340                 345                 350

Arg Val Ile Gln Gly Ala Val Ser Gly Glu Phe Leu Arg Thr Met Ser
                355                 360                 365

Arg Leu Leu Thr Asp Asp Ser Phe Trp Asp Glu Ile Phe Asp Ala Met
                370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
                420                 425                 430

Pro Gly Met Pro Val Pro Asp His Arg Asp Leu Asp Ile Glu Thr His
                435                 440                 445

Ser Leu Thr Ile Trp Asp Leu Asp Arg Thr Phe Ser Val Gly Gly Phe
450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
                500                 505                 510

Lys Pro Thr Gln Ala Glu Gln Lys Tyr Ile Leu Gln Lys Leu Asn Ala
                515                 520                 525

Ala Glu Ala Phe Glu Asn Phe Leu Gln Thr Lys Tyr Val Gly Gln Lys
                530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
                580                 585                 590

Pro Leu Ala Ser Ile Phe Asn Glu Phe Glu Gly Gln Met Glu Gln Gly
                595                 600                 605

Gln Ile Gly Gly Ser Gly Asp Val Lys Tyr His Leu Gly Ser Glu Gly
                610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
                660                 665                 670

Val Val Pro Leu Leu Leu His Gly Asp Ala Ala Phe Ala Gly Leu Gly
                675                 680                 685

Ile Val Pro Glu Thr Ile Asn Leu Ala Lys Ser Cys Val Asp Val Gly
                690                 695                 700

Gly Thr Ile His Ile Val Val Asn Asn Gln Ile Gly Phe Thr Thr Thr
705                 710                 715                 720
```

-continued

```
Pro Asp Ser Ser Arg Ser Met His Tyr Ala Thr Asp Tyr Ala Lys Ala
            725                 730                 735

Phe Gly Cys Pro Val Phe His Val Asn Gly Asp Pro Glu Ala Val
        740                 745                 750

Val Trp Val Gly Gln Leu Ala Thr Glu Tyr Arg Arg Arg Phe Gly Lys
        755                 760                 765

Asp Val Phe Ile Asp Leu Val Cys Tyr Arg Leu Arg Gly His Asn Glu
    770                 775                 780

Ala Asp Asp Pro Ser Met Thr Gln Pro Lys Met Tyr Glu Leu Ile Thr
785                 790                 795                 800

Gly Arg Glu Thr Val Arg Ala Gln Tyr Thr Glu Asp Leu Leu Gly Arg
                805                 810                 815

Gly Asp Leu Ser Asn Glu Asp Ala Glu Ala Val Val Arg Asp Phe His
                820                 825                 830

Asp Gln Met Glu Ser Val Phe Asn Glu Val Lys Glu Gly Gly Lys Lys
            835                 840                 845

Gln Ala Glu Ala Gln Thr Gly Ile Thr Gly Ser Gln Lys Leu Pro His
        850                 855                 860

Gly Leu Glu Thr Asn Ile Ser Arg Glu Glu Leu Leu Glu Leu Gly Gln
865                 870                 875                 880

Ala Phe Ala Asn Thr Pro Glu Gly Phe Asn Tyr His Pro Arg Val Ala
                885                 890                 895

Pro Val Ala Lys Lys Arg Val Ser Ser Val Thr Glu Gly Gly Ile Asp
                900                 905                 910

Trp Ala Trp Gly Glu Leu Leu Ala Phe Gly Ser Leu Ala Asn Ser Gly
            915                 920                 925

Arg Leu Val Arg Leu Ala Gly Glu Asp Ser Arg Arg Gly Thr Phe Thr
        930                 935                 940

Gln Arg His Ala Val Ala Ile Asp Pro Ala Thr Ala Glu Glu Phe Asn
945                 950                 955                 960

Pro Leu His Glu Leu Ala Gln Ser Lys Gly Asn Asn Gly Lys Phe Leu
                965                 970                 975

Val Tyr Asn Ser Ala Leu Thr Glu Tyr Ala Gly Met Gly Phe Glu Tyr
            980                 985                 990

Gly Tyr Ser Val Gly Asn Glu Asp Ser Val Val Ala Trp Glu Ala Gln
        995                 1000                1005

Phe Gly Asp Phe Ala Asn Gly Ala Gln Thr Ile Ile Asp Glu Tyr
    1010                1015                1020

Val Ser Ser Gly Glu Ala Lys Trp Gly Gln Thr Ser Lys Leu Ile
    1025                1030                1035

Leu Leu Leu Pro His Gly Tyr Glu Gly Gln Gly Pro Asp His Ser
    1040                1045                1050

Ser Ala Arg Ile Glu Arg Phe Leu Gln Leu Cys Ala Glu Gly Ser
    1055                1060                1065

Met Thr Val Ala Gln Pro Ser Thr Pro Ala Asn His Phe His Leu
    1070                1075                1080

Leu Arg Arg His Ala Leu Ser Asp Leu Lys Arg Pro Leu Val Ile
    1085                1090                1095

Phe Thr Pro Lys Ser Met Leu Arg Asn Lys Ala Ala Ala Ser Ala
    1100                1105                1110

Pro Glu Asp Phe Thr Glu Val Thr Lys Phe Gln Ser Val Ile Asp
    1115                1120                1125

Asp Pro Asn Val Ala Asp Ala Ala Lys Val Lys Lys Val Met Leu
    1130                1135                1140
```

| | | | | | | | | | | |
|---|---|---|---|---|---|---|---|---|---|---|
|Val|Ser|Gly|Lys|Leu|Tyr|Tyr|Glu|Leu|Ala|Lys|Arg|Lys|Glu|Lys|
| |1145| | | |1150| | | | |1155| | | | |

| | | | | | | | | | | |
|---|---|---|---|---|---|---|---|---|---|---|
|Asp|Gly|Arg|Asp|Asp|Ile|Ala|Ile|Val|Arg|Ile|Glu|Met|Leu|His|
| |1160| | | |1165| | | | |1170| | | | |

| | | | | | | | | | | |
|---|---|---|---|---|---|---|---|---|---|---|
|Pro|Ile|Pro|Phe|Asn|Arg|Ile|Ser|Glu|Ala|Leu|Ala|Gly|Tyr|Pro|
| |1175| | | |1180| | | | |1185| | | | |

| | | | | | | | | | | |
|---|---|---|---|---|---|---|---|---|---|---|
|Asn|Ala|Glu|Glu|Val|Leu|Phe|Val|Gln|Asp|Glu|Pro|Ala|Asn|Gln|
| |1190| | | |1195| | | | |1200| | | | |

| | | | | | | | | | | |
|---|---|---|---|---|---|---|---|---|---|---|
|Gly|Pro|Trp|Pro|Phe|Tyr|Gln|Glu|His|Leu|Pro|Glu|Leu|Ile|Pro|
| |1205| | | |1210| | | | |1215| | | | |

| | | | | | | | | | | |
|---|---|---|---|---|---|---|---|---|---|---|
|Asn|Met|Pro|Lys|Met|Arg|Arg|Val|Ser|Arg|Arg|Ala|Gln|Ser|Ser|
| |1220| | | |1225| | | | |1230| | | | |

| | | | | | | | | | | |
|---|---|---|---|---|---|---|---|---|---|---|
|Thr|Ala|Thr|Gly|Val|Ala|Lys|Val|His|Gln|Leu|Glu|Glu|Lys|Gln|
| |1235| | | |1240| | | | |1245| | | | |

| | | | | | |
|---|---|---|---|---|---|
|Leu|Ile|Asp|Glu|Ala|Phe|Glu|Ala|
| |1250| | | |1255| | |

<210> SEQ ID NO 51
<211> LENGTH: 4391
<212> TYPE: DNA
<213> ORGANISM: Corynebacterium glutamicum
<220> FEATURE:
<221> NAME/KEY: CDS
<222> LOCATION: (443)..(4210)
<223> OTHER INFORMATION: sucA77

<400> SEQUENCE: 51

```
gtcgacaagc aaaatcgaag cggcagcacg ccgcgtcgga gccttaaacg ccatcgccgc       60
catccctgat ggtttcaatc atcaagtcgg tgaacgcggg cgcaacctgt catccggaca      120
gcgccaactg atcgcgctgg cgcgcgccga actcatcgag ccttccatca tgcttctcga      180
cgaagccacc tccaccctcg accccgccac cgaagccgtt atcctcaacg cctccgatcg      240
agtcactaag ggacgcacca gcatcatcgt cgcgcaccgc ttggcaaccg ctaaaagggc      300
cgaccgtatt cttgttgttg aacaaggacg tatcattgag gacggatctc acgacgcgtt      360
gttgtctgct aacggcacct acgcccgcat gtggcattta atggcctgac acgttatttt      420
taggagaact gtcaacaaat ta atg cta caa ctg ggg ctt agg cat aat cag       472
                         Met Leu Gln Leu Gly Leu Arg His Asn Gln
                          1               5                  10
```

| | | | | | | | | | | |
|---|---|---|---|---|---|---|---|---|---|---|
|cca|acg|acc|aac|gtt|aca|gtg|gat|aaa|ata|aag|ctc|aat|aaa|ccc|tca|520|
|Pro|Thr|Thr|Asn|Val|Thr|Val|Asp|Lys|Ile|Lys|Leu|Asn|Lys|Pro|Ser| |
| | | | |15| | | | |20| | | | |25| | |

| | | | | | | | | | | |
|---|---|---|---|---|---|---|---|---|---|---|
|aga|agc|aag|gaa|aag|agg|cga|gta|cct|gcc|gtg|agc|agc|gct|agt|act|568|
|Arg|Ser|Lys|Glu|Lys|Arg|Arg|Val|Pro|Ala|Val|Ser|Ser|Ala|Ser|Thr| |
| | |30| | | | |35| | | | |40| | | | |

| | | | | | | | | | | |
|---|---|---|---|---|---|---|---|---|---|---|
|ttc|ggc|cag|aat|gcg|tgg|ctg|gta|gac|gag|atg|ttc|cag|cag|ttc|cag|616|
|Phe|Gly|Gln|Asn|Ala|Trp|Leu|Val|Asp|Glu|Met|Phe|Gln|Gln|Phe|Gln| |
| | |45| | | | |50| | | | |55| | | | |

| | | | | | | | | | | |
|---|---|---|---|---|---|---|---|---|---|---|
|aag|gac|ccc|aag|tcc|gtg|gac|aag|gaa|tgg|aga|gaa|ctc|ttt|gag|gcg|664|
|Lys|Asp|Pro|Lys|Ser|Val|Asp|Lys|Glu|Trp|Arg|Glu|Leu|Phe|Glu|Ala| |
| | |60| | | | |65| | | | |70| | | | |

| | | | | | | | | | | |
|---|---|---|---|---|---|---|---|---|---|---|
|cag|ggg|gga|cca|aat|gct|acc|ccc|gct|aca|aca|gaa|gca|cag|cct|tca|712|
|Gln|Gly|Gly|Pro|Asn|Ala|Thr|Pro|Ala|Thr|Thr|Glu|Ala|Gln|Pro|Ser| |
|75| | | | |80| | | | |85| | | | |90| |

| | | | | | | | | | | |
|---|---|---|---|---|---|---|---|---|---|---|
|gcg|ccc|aag|gag|tct|gcg|aaa|cca|gca|cca|aag|gct|gcc|cct|gca|gcc|760|
|Ala|Pro|Lys|Glu|Ser|Ala|Lys|Pro|Ala|Pro|Lys|Ala|Ala|Pro|Ala|Ala| |
| | | |95| | | | |100| | | | |105| | | |

| | | | | | | | | | | |
|---|---|---|---|---|---|---|---|---|---|---|
|aag|gca|gca|ccg|cgc|gta|gaa|acc|aag|ccg|gcc|gcc|aag|acc|gcc|cct|808|

```
                                    -continued

Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca       856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg       904
Gly Gln Thr Pro Ile Arg Gly Ile Phe Lys Ser Ile Ala Lys Asn Met
        140                 145                 150 gat atc tcc ctg gaa atc cca acc gca acc tcg gtt cgc gat atg cca       952
Asp Ile Ser Leu Glu Ile Pro Thr Ala Thr Ser Val Arg Asp Met Pro
155                 160                 165                 170 gct cgc ctc atg ttc gaa aac cgc gcg atg gtc aac gat cag ctc aag      1000
Ala Arg Leu Met Phe Glu Asn Arg Ala Met Val Asn Asp Gln Leu Lys
                175                 180                 185 cgc acc cgc ggt ggc aag atc tcc ttc acc cac atc att ggc tac gcc      1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac      1096
Met Val Lys Ala Val Met Ala His Pro Asp Met Asn Asn Ser Tyr Asp
            205                 210                 215 gtc atc gac ggc aag cca acc ctg atc gtg cct gag cac atc aac ctg      1144
Val Ile Asp Gly Lys Pro Thr Leu Ile Val Pro Glu His Ile Asn Leu
        220                 225                 230 ggc ctt gcc atc gac ctt cct cag aag gac ggc tcc cgc gca ctt gtc      1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc      1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc      1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
        300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat      1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
        380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac      1768
```

-continued

```
                Pro Leu Ser Trp Val Gln Pro Gly Met Pro Val Pro Asp His Arg Asp
                            430                 435                 440 ctc gac atc gag acc cac agc ctg acc atc tgg gat ctg gac cgt acc           1816
Leu Asp Ile Glu Thr His Ser Leu Thr Ile Trp Asp Leu Asp Arg Thr
            445                 450                 455 ttc agc gtc ggt ggc ttc ggc ggc aag gag acc atg acc ctg cgc gag           1864
Phe Ser Val Gly Gly Phe Gly Gly Lys Glu Thr Met Thr Leu Arg Glu
        460                 465                 470 gta ctg tcc cgc ctg cgc gct gcc tac acc ttg aag gtc ggc tcc gaa           1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc           1960
Tyr Thr His Ile Leu Asp Arg Asp Glu Arg Thr Trp Leu Gln Asp Arg
                495                 500                 505 ctc gaa gcc gga atg cca aag cca acc cag gca gag cag aag tac atc           2008
Leu Glu Ala Gly Met Pro Lys Pro Thr Gln Ala Glu Gln Lys Tyr Ile
            510                 515                 520 ctg cag aag ctg aac gcc gca gag gct ttc gag aac ttc ctg cag acc           2056
Leu Gln Lys Leu Asn Ala Ala Glu Ala Phe Glu Asn Phe Leu Gln Thr
        525                 530                 535 aag tac gtc ggc cag aag cgc ttc tcc ctc gaa ggt gca gaa gct ctc           2104
Lys Tyr Val Gly Gln Lys Arg Phe Ser Leu Glu Gly Ala Glu Ala Leu
540                 545                 550 atc cca ctg atg gac tcc gcc atc gac acc gcc gca ggc cag ggc ctc           2152
Ile Pro Leu Met Asp Ser Ala Ile Asp Thr Ala Ala Gly Gln Gly Leu
555                 560                 565                 570 gac gaa gtt gtc atc ggt atg cca cac cgt ggt cgc ctc aac gtg ctg           2200
Asp Glu Val Val Ile Gly Met Pro His Arg Gly Arg Leu Asn Val Leu
                575                 580                 585 ttc aac atc gtg ggc aag cca ctg gca tcc atc ttc aac gag ttt gaa           2248
Phe Asn Ile Val Gly Lys Pro Leu Ala Ser Ile Phe Asn Glu Phe Glu
            590                 595                 600 ggc caa atg gag cag ggc cag atc ggt ggc tcc ggt gac gtg aag tac           2296
Gly Gln Met Glu Gln Gly Gln Ile Gly Gly Ser Gly Asp Val Lys Tyr
        605                 610                 615 cac ctc ggt tcc gaa ggc cag cac ctg cag atg ttc ggc gac ggc gag           2344
His Leu Gly Ser Glu Gly Gln His Leu Gln Met Phe Gly Asp Gly Glu
    620                 625                 630 atc aag gtc tcc ctg act gct aac ccg tcc cac ctg gaa gct gtt aac           2392
Ile Lys Val Ser Leu Thr Ala Asn Pro Ser His Leu Glu Ala Val Asn
635                 640                 645                 650 cca gtg atg gaa ggt atc gtc cgc gca aag cag gac tac ctg gac aag           2440
Pro Val Met Glu Gly Ile Val Arg Ala Lys Gln Asp Tyr Leu Asp Lys
                655                 660                 665 ggc gta gac ggc aag act gtt gtg cca ctg ctc ctc cac ggt gac gct           2488
Gly Val Asp Gly Lys Thr Val Val Pro Leu Leu Leu His Gly Asp Ala
            670                 675                 680 gca ttc gca ggc ctg ggc atc gtg cca gaa acc atc aac ctg gct ata           2536
Ala Phe Ala Gly Leu Gly Ile Val Pro Glu Thr Ile Asn Leu Ala Ile
        685                 690                 695 agc tgc gtc gac gtc gga ggc acc atc cac atc gtg gtg aac aac cag           2584
Ser Cys Val Asp Val Gly Gly Thr Ile His Ile Val Val Asn Asn Gln
    700                 705                 710 atc ggc ttc acc acc acc cca gac tcc agc cgc tcc atg cac tac gca           2632
Ile Gly Phe Thr Thr Thr Pro Asp Ser Ser Arg Ser Met His Tyr Ala
715                 720                 725                 730 acc gac tac gcc aag gca ttc ggc tgc cca gtc ttc cac gtc aat ggt           2680
Thr Asp Tyr Ala Lys Ala Phe Gly Cys Pro Val Phe His Val Asn Gly
                735                 740                 745 gat gac cca gag gca gtt gtc tgg gtt ggc cag ctg gca acc gag tac           2728
Asp Asp Pro Glu Ala Val Val Trp Val Gly Gln Leu Ala Thr Glu Tyr
```

-continued

```
              Asp Asp Pro Glu Ala Val Val Trp Val Gly Gln Leu Ala Thr Glu Tyr
                      750                 755                 760 cgt cgt cgc ttc ggc aag gac gtc ttc atc gac ctc gtt tgc tac cgc         2776
Arg Arg Arg Phe Gly Lys Asp Val Phe Ile Asp Leu Val Cys Tyr Arg
        765                 770                 775 ctc cgc ggc cac aac gaa gct gat gat cct tcc atg acc cag cca aag         2824
Leu Arg Gly His Asn Glu Ala Asp Asp Pro Ser Met Thr Gln Pro Lys
        780                 785                 790 atg tat gag ctc atc acc ggc cgc gag acc gtt cgt gct cag tac acc         2872
Met Tyr Glu Leu Ile Thr Gly Arg Glu Thr Val Arg Ala Gln Tyr Thr
795                 800                 805                 810 gaa gac ctg ctc gga cgt gga gac ctc tcc aac gaa gat gca gaa gca         2920
Glu Asp Leu Leu Gly Arg Gly Asp Leu Ser Asn Glu Asp Ala Glu Ala
            815                 820                 825 gtc gtc cgc gac ttc cac gac cag atg gaa tct gtg ttc aac gaa gtc         2968
Val Val Arg Asp Phe His Asp Gln Met Glu Ser Val Phe Asn Glu Val
            830                 835                 840 aag gaa ggc ggc aag aag cag gct gag gca cag acc ggc atc acc ggc         3016
Lys Glu Gly Gly Lys Lys Gln Ala Glu Ala Gln Thr Gly Ile Thr Gly
        845                 850                 855 tcc cag aag ctt cca cac ggc ctt gag acc aac atc tcc cgt gaa gag         3064
Ser Gln Lys Leu Pro His Gly Leu Glu Thr Asn Ile Ser Arg Glu Glu
        860                 865                 870 ctc ctg gaa ctg gga cag gct ttc gcc aac acc cca gaa ggc ttc aac         3112
Leu Leu Glu Leu Gly Gln Ala Phe Ala Asn Thr Pro Glu Gly Phe Asn
875                 880                 885                 890 tac cac cca cgt gtg gct cca gtt gct aag aag cgc gtc tcc tct gtc         3160
Tyr His Pro Arg Val Ala Pro Val Ala Lys Lys Arg Val Ser Ser Val
            895                 900                 905 acc gaa ggt ggc atc gac tgg gca tgg ggc gag ctc ctc gcc ttc ggt         3208
Thr Glu Gly Gly Ile Asp Trp Ala Trp Gly Glu Leu Leu Ala Phe Gly
            910                 915                 920 tcc ctg gct aac tcc ggc cgc ttg gtt cgc ctt gca ggt gaa gat tcc         3256
Ser Leu Ala Asn Ser Gly Arg Leu Val Arg Leu Ala Gly Glu Asp Ser
        925                 930                 935 cgc cgc ggt acc ttc acc cag cgc cac gca gtt gcc atc gac cca gcg         3304
Arg Arg Gly Thr Phe Thr Gln Arg His Ala Val Ala Ile Asp Pro Ala
    940                 945                 950 acc gct gaa gag ttc aac cca ctc cac gag ctt gca cag tcc aag ggc         3352
Thr Ala Glu Glu Phe Asn Pro Leu His Glu Leu Ala Gln Ser Lys Gly
955                 960                 965                 970 aac aac ggt aag ttc ctg gtc tac aac tcc gca ctg acc gag tac gca         3400
Asn Asn Gly Lys Phe Leu Val Tyr Asn Ser Ala Leu Thr Glu Tyr Ala
            975                 980                 985 ggc atg ggc ttc gag tac ggc tac tcc gta gga aac gaa gac  tcc gtc       3448
Gly Met Gly Phe Glu Tyr Gly Tyr Ser Val Gly Asn Glu Asp  Ser Val
            990                 995                1000 gtt gca tgg  gaa gca cag ttc ggc  gac ttc gcc aac ggc  gct cag          3493
Val Ala Trp  Glu Ala Gln Phe Gly  Asp Phe Ala Asn Gly  Ala Gln
           1005                1010                1015 acc atc atc  gat gag tac gtc tcc  tca ggc gaa gct aag  tgg ggc          3538
Thr Ile Ile  Asp Glu Tyr Val Ser  Ser Gly Glu Ala Lys  Trp Gly
           1020                1025                1030 cag acc tcc  aag ctg atc ctt ctg  ctg cct cac ggc tac  gaa ggc          3583
Gln Thr Ser  Lys Leu Ile Leu Leu  Leu Pro His Gly Tyr  Glu Gly
           1035                1040                1045 cag ggc cca  gac cac tct tcc gca  cgt atc gag cgc ttc  ctg cag          3628
Gln Gly Pro  Asp His Ser Ser Ala  Arg Ile Glu Arg Phe  Leu Gln
           1050                1055                1060 ctg tgc gct  gag ggt tcc atg act  gtt gct cag cca tcc  acc cca          3673
```

```
Leu Cys Ala Glu Gly Ser Met Thr Val Ala Gln Pro Ser Thr Pro
        1065                1070                1075 gca aac cac ttc cac ctg ctg cgt cgt cac gct ctg tcc gac ctg       3718
Ala Asn His Phe His Leu Leu Arg Arg His Ala Leu Ser Asp Leu
        1080                1085                1090 aag cgt cca ctg gtt atc ttc acc ccg aag tcc atg ctg cgt aac       3763
Lys Arg Pro Leu Val Ile Phe Thr Pro Lys Ser Met Leu Arg Asn
        1095                1100                1105 aag gct gct gcc tcc gca cca gaa gac ttc act gag gtc acc aag       3808
Lys Ala Ala Ala Ser Ala Pro Glu Asp Phe Thr Glu Val Thr Lys
        1110                1115                1120 ttc caa tcc gtg atc gac gat cca aac gtt gca gat gca gcc aag       3853
Phe Gln Ser Val Ile Asp Asp Pro Asn Val Ala Asp Ala Ala Lys
        1125                1130                1135 gtg aag aag gtc atg ctg gtc tcc ggc aag ctg tac tac gaa ttg       3898
Val Lys Lys Val Met Leu Val Ser Gly Lys Leu Tyr Tyr Glu Leu
        1140                1145                1150 gca aag cgc aag gag aag gac gga cgc gac gac atc gcg atc gtt       3943
Ala Lys Arg Lys Glu Lys Asp Gly Arg Asp Asp Ile Ala Ile Val
        1155                1160                1165 cgt atc gaa atg ctc cac cca att ccg ttc aac cgc atc tcc gag       3988
Arg Ile Glu Met Leu His Pro Ile Pro Phe Asn Arg Ile Ser Glu
        1170                1175                1180 gct ctt gcc ggc tac cct aac gct gag gaa gtc ctc ttc gtt cag       4033
Ala Leu Ala Gly Tyr Pro Asn Ala Glu Glu Val Leu Phe Val Gln
        1185                1190                1195 gat gag cca gca aac cag ggc cca tgg ccg ttc tac cag gag cac       4078
Asp Glu Pro Ala Asn Gln Gly Pro Trp Pro Phe Tyr Gln Glu His
        1200                1205                1210 ctc cca gag ctg atc ccg aac atg cca aag atg cgc cgc gtt tcc       4123
Leu Pro Glu Leu Ile Pro Asn Met Pro Lys Met Arg Arg Val Ser
        1215                1220                1225 cgc cgc gct cag tcc tcc acc gca act ggt gtt gct aag gtg cac       4168
Arg Arg Ala Gln Ser Ser Thr Ala Thr Gly Val Ala Lys Val His
        1230                1235                1240 cag ctg gag gag aag cag ctt atc gac gag gct ttc gag gct           4210
Gln Leu Glu Glu Lys Gln Leu Ile Asp Glu Ala Phe Glu Ala
        1245                1250                1255 taagtcttta tagtcctgca ctagcctaga gggcccttatg cagtgtgaat cacacagcat 4270
aaggcccttt ttgctgccgt ggttgcctaa ggtggaaggc atgaaacgaa tctgtgcggt   4330
cacgatctct tcagtacttt tgctaagtgg ctgctcctcc acttccacca cgcagctcga  4390
g                                                                  4391

<210> SEQ ID NO 52
<211> LENGTH: 1256
<212> TYPE: PRT
<213> ORGANISM: Corynebacterium glutamicum

<400> SEQUENCE: 52

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
                20                  25                  30

Arg Val Pro Ala Val Ser Ser Ala Ser Thr Phe Gly Gln Asn Ala Trp
            35                  40                  45

Leu Val Asp Glu Met Phe Gln Gln Phe Gln Lys Asp Pro Lys Ser Val
        50                  55                  60

Asp Lys Glu Trp Arg Glu Leu Phe Glu Ala Gln Gly Gly Pro Asn Ala
```

```
                65                  70                  75                  80
Thr Pro Ala Thr Thr Glu Ala Gln Pro Ser Ala Pro Lys Glu Ser Ala
                    85                  90                  95
Lys Pro Ala Pro Lys Ala Ala Pro Ala Lys Ala Ala Pro Arg Val
                    100                 105                 110
Glu Thr Lys Pro Ala Ala Lys Thr Ala Pro Lys Ala Lys Glu Ser Ser
                    115                 120                 125
Val Pro Gln Gln Pro Lys Leu Pro Glu Pro Gly Gln Thr Pro Ile Arg
            130                 135                 140
Gly Ile Phe Lys Ser Ile Ala Lys Asn Met Asp Ile Ser Leu Glu Ile
145                 150                 155                 160
Pro Thr Ala Thr Ser Val Arg Asp Met Pro Ala Arg Leu Met Phe Glu
                    165                 170                 175
Asn Arg Ala Met Val Asn Asp Gln Leu Lys Arg Thr Arg Gly Gly Lys
                    180                 185                 190
Ile Ser Phe Thr His Ile Ile Gly Tyr Ala Met Val Lys Ala Val Met
                195                 200                 205
Ala His Pro Asp Met Asn Asn Ser Tyr Asp Val Ile Asp Gly Lys Pro
            210                 215                 220
Thr Leu Ile Val Pro Glu His Ile Asn Leu Gly Leu Ala Ile Asp Leu
225                 230                 235                 240
Pro Gln Lys Asp Gly Ser Arg Ala Leu Val Val Ala Ala Ile Lys Glu
                245                 250                 255
Thr Glu Lys Met Asn Phe Ser Glu Phe Leu Ala Ala Tyr Glu Asp Ile
                260                 265                 270
Val Thr Arg Ser Arg Lys Gly Lys Leu Thr Met Asp Asp Tyr Gln Gly
            275                 280                 285
Val Thr Val Ser Leu Thr Asn Pro Gly Gly Ile Gly Thr Arg His Ser
290                 295                 300
Val Pro Arg Leu Thr Lys Gly Gln Gly Thr Ile Ile Gly Val Gly Ser
305                 310                 315                 320
Met Asp Tyr Pro Ala Glu Phe Gln Gly Ala Ser Glu Asp Arg Leu Ala
                325                 330                 335
Glu Leu Gly Val Gly Lys Leu Val Thr Ile Thr Ser Thr Tyr Asp His
            340                 345                 350
Arg Val Ile Gln Gly Ala Val Ser Gly Glu Phe Leu Arg Thr Met Ser
            355                 360                 365
Arg Leu Leu Thr Asp Asp Ser Phe Trp Asp Glu Ile Phe Asp Ala Met
        370                 375                 380
Asn Val Pro Tyr Thr Pro Met Arg Trp Ala Gln Asp Val Pro Asn Thr
385                 390                 395                 400
Gly Val Asp Lys Asn Thr Arg Val Met Gln Leu Ile Glu Ala Tyr Arg
                405                 410                 415
Ser Arg Gly His Leu Ile Ala Asp Thr Asn Pro Leu Ser Trp Val Gln
                420                 425                 430
Pro Gly Met Pro Val Pro Asp His Arg Asp Leu Asp Ile Glu Thr His
            435                 440                 445
Ser Leu Thr Ile Trp Asp Leu Asp Arg Thr Phe Ser Val Gly Gly Phe
    450                 455                 460
Gly Gly Lys Glu Thr Met Thr Leu Arg Glu Val Leu Ser Arg Leu Arg
465                 470                 475                 480
Ala Ala Tyr Thr Leu Lys Val Gly Ser Glu Tyr Thr His Ile Leu Asp
                485                 490                 495
```

```
Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
            515                 520                 525

Ala Glu Ala Phe Glu Asn Phe Leu Gln Thr Lys Tyr Val Gly Gln Lys
        530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu Leu His Gly Asp Ala Ala Phe Ala Gly Leu Gly
        675                 680                 685

Ile Val Pro Glu Thr Ile Asn Leu Ala Ile Ser Cys Val Asp Val Gly
    690                 695                 700

Gly Thr Ile His Ile Val Val Asn Asn Gln Ile Gly Phe Thr Thr Thr
705                 710                 715                 720

Pro Asp Ser Ser Arg Ser Met His Tyr Ala Thr Asp Tyr Ala Lys Ala
                725                 730                 735

Phe Gly Cys Pro Val Phe His Val Asn Gly Asp Asp Pro Glu Ala Val
            740                 745                 750

Val Trp Val Gly Gln Leu Ala Thr Glu Tyr Arg Arg Arg Phe Gly Lys
        755                 760                 765

Asp Val Phe Ile Asp Leu Val Cys Tyr Arg Leu Arg Gly His Asn Glu
    770                 775                 780

Ala Asp Asp Pro Ser Met Thr Gln Pro Lys Met Tyr Glu Leu Ile Thr
785                 790                 795                 800

Gly Arg Glu Thr Val Arg Ala Gln Tyr Thr Glu Asp Leu Leu Gly Arg
                805                 810                 815

Gly Asp Leu Ser Asn Glu Asp Ala Glu Ala Val Val Arg Asp Phe His
            820                 825                 830

Asp Gln Met Glu Ser Val Phe Asn Glu Val Lys Glu Gly Gly Lys Lys
        835                 840                 845

Gln Ala Glu Ala Gln Thr Gly Ile Thr Gly Ser Gln Lys Leu Pro His
    850                 855                 860

Gly Leu Glu Thr Asn Ile Ser Arg Glu Glu Leu Leu Glu Leu Gly Gln
865                 870                 875                 880

Ala Phe Ala Asn Thr Pro Glu Gly Phe Asn Tyr His Pro Arg Val Ala
                885                 890                 895

Pro Val Ala Lys Lys Arg Val Ser Ser Val Thr Glu Gly Gly Ile Asp
            900                 905                 910

Trp Ala Trp Gly Glu Leu Leu Ala Phe Gly Ser Leu Ala Asn Ser Gly
        915                 920                 925
```

```
Arg Leu Val Arg Leu Ala Gly Glu Asp Ser Arg Gly Thr Phe Thr
    930                 935                 940

Gln Arg His Ala Val Ala Ile Asp Pro Ala Thr Ala Glu Glu Phe Asn
945                 950                 955                 960

Pro Leu His Glu Leu Ala Gln Ser Lys Gly Asn Asn Gly Lys Phe Leu
                965                 970                 975

Val Tyr Asn Ser Ala Leu Thr Glu Tyr Ala Gly Met Gly Phe Glu Tyr
            980                 985                 990

Gly Tyr Ser Val Gly Asn Glu Asp Ser Val Val Ala Trp Glu Ala Gln
        995                1000                1005

Phe Gly Asp Phe Ala Asn Gly Ala Gln Thr Ile Ile Asp Glu Tyr
    1010                1015                1020

Val Ser Ser Gly Glu Ala Lys Trp Gly Gln Thr Ser Lys Leu Ile
    1025                1030                1035

Leu Leu Leu Pro His Gly Tyr Glu Gly Gln Gly Pro Asp His Ser
    1040                1045                1050

Ser Ala Arg Ile Glu Arg Phe Leu Gln Leu Cys Ala Glu Gly Ser
    1055                1060                1065

Met Thr Val Ala Gln Pro Ser Thr Pro Ala Asn His Phe His Leu
    1070                1075                1080

Leu Arg Arg His Ala Leu Ser Asp Leu Lys Arg Pro Leu Val Ile
    1085                1090                1095

Phe Thr Pro Lys Ser Met Leu Arg Asn Lys Ala Ala Ala Ser Ala
    1100                1105                1110

Pro Glu Asp Phe Thr Glu Val Thr Lys Phe Gln Ser Val Ile Asp
    1115                1120                1125

Asp Pro Asn Val Ala Asp Ala Ala Lys Val Lys Lys Val Met Leu
    1130                1135                1140

Val Ser Gly Lys Leu Tyr Tyr Glu Leu Ala Lys Arg Lys Glu Lys
    1145                1150                1155

Asp Gly Arg Asp Asp Ile Ala Ile Val Arg Ile Glu Met Leu His
    1160                1165                1170

Pro Ile Pro Phe Asn Arg Ile Ser Glu Ala Leu Ala Gly Tyr Pro
    1175                1180                1185

Asn Ala Glu Glu Val Leu Phe Val Gln Asp Glu Pro Ala Asn Gln
    1190                1195                1200

Gly Pro Trp Pro Phe Tyr Gln Glu His Leu Pro Glu Leu Ile Pro
    1205                1210                1215

Asn Met Pro Lys Met Arg Arg Val Ser Arg Arg Ala Gln Ser Ser
    1220                1225                1230

Thr Ala Thr Gly Val Ala Lys Val His Gln Leu Glu Glu Lys Gln
    1235                1240                1245

Leu Ile Asp Glu Ala Phe Glu Ala
    1250                1255

<210> SEQ ID NO 53
<211> LENGTH: 40
<212> TYPE: DNA
<213> ORGANISM: Artificial sequence
<220> FEATURE:
<223> OTHER INFORMATION: primer

<400> SEQUENCE: 53
gccgggatcc ctgtgtgatt cacactgcat aaggccctct                          40
```

```
<210> SEQ ID NO 54
<211> LENGTH: 40
<212> TYPE: DNA
<213> ORGANISM: Artificial sequence
<220> FEATURE:
<223> OTHER INFORMATION: primer

<400> SEQUENCE: 54
gccgggatcc ccatcgccgc catccctgat ggtttcaatc                              40

<210> SEQ ID NO 55
<211> LENGTH: 28
<212> TYPE: DNA
<213> ORGANISM: Artificial sequence
<220> FEATURE:
<223> OTHER INFORMATION: sucA8primer

<400> SEQUENCE: 55
ctgcgtcgac gtcggaggca ccatccac                                           28

<210> SEQ ID NO 56
<211> LENGTH: 30
<212> TYPE: DNA
<213> ORGANISM: Artificial sequence
<220> FEATURE:
<223> OTHER INFORMATION: sucA801primer

<400> SEQUENCE: 56
ctgcgtctcg acgtcggagg caccatccac                                         30

<210> SEQ ID NO 57
<211> LENGTH: 36
<212> TYPE: DNA
<213> ORGANISM: Artificial sequence
<220> FEATURE:
<223> OTHER INFORMATION: sucA805primer

<400> SEQUENCE: 57
gctaaaagct gcgtcgacgt cggaggcacc atccac                                  36

<210> SEQ ID NO 58
<211> LENGTH: 36
<212> TYPE: DNA
<213> ORGANISM: Artificial sequence
<220> FEATURE:
<223> OTHER INFORMATION: sucA77

<400> SEQUENCE: 58
gctataagct gcgtcgacgt cggaggcacc atccac                                  36

<210> SEQ ID NO 59
<211> LENGTH: 33
<212> TYPE: DNA
<213> ORGANISM: Artificial sequence
<220> FEATURE:
<223> OTHER INFORMATION: yggB primer-N

<400> SEQUENCE: 59
ggggatcctg ccgatttcgg caggatcaat gtc                                     33

<210> SEQ ID NO 60
<211> LENGTH: 31
<212> TYPE: DNA
<213> ORGANISM: Artificial sequence
<220> FEATURE:
<223> OTHER INFORMATION: yggB primer-C

<400> SEQUENCE: 60
```

```
ttccttgctt gcggggatcc catcggggat g                                  31
```

<210> SEQ ID NO 61
<211> LENGTH: 2432
<212> TYPE: DNA
<213> ORGANISM: Corynebacterium glutamicum
<220> FEATURE:
<221> NAME/KEY: CDS
<222> LOCATION: (507)..(2093)

<400> SEQUENCE: 61

| | |
|---|---:|
| agggggcggcg gatcgaccac ggcttgcaac cgtggcggga gtgggctgtt gagaagctgc | 60 |
| cacattcacg actttctggc tcctttacta aataaggatt ttcacaggac ccgtccaagc | 120 |
| caagccgatt tcaactcagc ctaaagacaa agccctcatt taaaattgtt ccgacgcgga | 180 |
| tgcgtgtgca cgcagtgcga cagatgtctg ttgcaaagtt ggctacttgg gtcataacca | 240 |
| acaagaaagc cctcgttcca acactgtggt gagtgttgtc gagggcgctt gacgagacga | 300 |
| cttggaaggc cgttacggca ggcgccgcgc ggttactact acaagtcgaa taatggtcat | 360 |
| ggtgtgtcat gctacacaca tcgagtttcc aattccacaa cgcacgaaaa ttcccacccc | 420 |
| caaaactccc ccacttcggt taaggaatca ggattctcac aaagttcagg caggctcccg | 480 |

```
ctacttttca gcgctaatct tggctc atg att tta ggc gta ccc att caa tat    533
                              Met Ile Leu Gly Val Pro Ile Gln Tyr
                                1               5 ttg ctc tat tca ttg tgg aat tgg att gtc gat acc ggt ttt gat gta    581
Leu Leu Tyr Ser Leu Trp Asn Trp Ile Val Asp Thr Gly Phe Asp Val
 10              15                  20                  25 gca att atc ctg gtc ttg gcg ttt ttg att cca cgt atc ggc cga ctg    629
Ala Ile Ile Leu Val Leu Ala Phe Leu Ile Pro Arg Ile Gly Arg Leu
             30                  35                  40 gcc atg cgt att atc aag cgg cga gtg gag tct gca gcc gat gcg gac    677
Ala Met Arg Ile Ile Lys Arg Arg Val Glu Ser Ala Ala Asp Ala Asp
         45                  50                  55 acc act aag aac cag ctc gcg ttc gct ggc gtt ggc gtt tat atc gcg    725
Thr Thr Lys Asn Gln Leu Ala Phe Ala Gly Val Gly Val Tyr Ile Ala
     60                  65                  70 caa att gtg gcg ttt ttc atg ctt gcc gtc tcc gcg atg cag gct ttt    773
Gln Ile Val Ala Phe Phe Met Leu Ala Val Ser Ala Met Gln Ala Phe
 75                  80                  85 ggt ttc tct ctc gcg ggc gct gcg att ccg gca acc att gcg tca gct    821
Gly Phe Ser Leu Ala Gly Ala Ala Ile Pro Ala Thr Ile Ala Ser Ala
 90                  95                 100                 105 gcc att ggc ctt ggt gcg cag tcg att gtt gcg gac ttc ttg gcc gga    869
Ala Ile Gly Leu Gly Ala Gln Ser Ile Val Ala Asp Phe Leu Ala Gly
                110                 115                 120 ttt ttc atc ctg acg gaa aag caa ttc ggc gtg ggt gac tgg gtg cgt    917
Phe Phe Ile Leu Thr Glu Lys Gln Phe Gly Val Gly Asp Trp Val Arg
            125                 130                 135 ttt gag ggc aac ggc atc gtt gtc gaa ggc acc gtc att gag atc acc    965
Phe Glu Gly Asn Gly Ile Val Val Glu Gly Thr Val Ile Glu Ile Thr
        140                 145                 150 atg cgc gcg acc aaa att cgc acg att gca caa gag acc gtg atc atc   1013
Met Arg Ala Thr Lys Ile Arg Thr Ile Ala Gln Glu Thr Val Ile Ile
    155                 160                 165 ccc aac tcc acg gcg aaa gtg tgc atc aac aat tct aat aac tgg tcg   1061
Pro Asn Ser Thr Ala Lys Val Cys Ile Asn Asn Ser Asn Asn Trp Ser
170                 175                 180                 185 cgt gcg gtt gtc gtt att ccg atc ccc atg ttg ggt tct gaa aac atc   1109
Arg Ala Val Val Val Ile Pro Ile Pro Met Leu Gly Ser Glu Asn Ile
```

-continued

```
                    190                 195                 200
aca gat gtc atc gcg cgc tct gaa gct gcg act cgt cgc gca ctt ggc        1157
Thr Asp Val Ile Ala Arg Ser Glu Ala Ala Thr Arg Arg Ala Leu Gly
            205                 210                 215 cag gag aaa atc gca ccg gaa atc ctc ggt gaa ctc gat gtg cac cca        1205
Gln Glu Lys Ile Ala Pro Glu Ile Leu Gly Glu Leu Asp Val His Pro
        220                 225                 230 gcc acg gaa gtc aca ccg cca acg gtg gtc ggc atg ccg tgg atg gtc        1253
Ala Thr Glu Val Thr Pro Pro Thr Val Val Gly Met Pro Trp Met Val
    235                 240                 245 acc atg cgt ttc ctc gtg caa gtc acc gcc ggc aat caa tgg ctg gtc        1301
Thr Met Arg Phe Leu Val Gln Val Thr Ala Gly Asn Gln Trp Leu Val
250                 255                 260                 265 gaa cgc gcc atc cgc aca gaa atc atc aac gaa ttc tgg gaa gaa tac        1349
Glu Arg Ala Ile Arg Thr Glu Ile Ile Asn Glu Phe Trp Glu Glu Tyr
                270                 275                 280 ggc agc gca acc act aca tcg gga acc ctc att gat tcc tta cac gtt        1397
Gly Ser Ala Thr Thr Thr Ser Gly Thr Leu Ile Asp Ser Leu His Val
            285                 290                 295 gag cat gaa gag cca aag acc tcg ctt atc gac gcc tcc ccc cag gct        1445
Glu His Glu Glu Pro Lys Thr Ser Leu Ile Asp Ala Ser Pro Gln Ala
        300                 305                 310 ctt aag gaa ccg aag ccg gag gct gcg gcg acg gtt gca tcg cta gct        1493
Leu Lys Glu Pro Lys Pro Glu Ala Ala Ala Thr Val Ala Ser Leu Ala
    315                 320                 325 gca tcg tct aac gac gat gca gac aat gca gac gcc tcg gcg atc aat        1541
Ala Ser Ser Asn Asp Asp Ala Asp Asn Ala Asp Ala Ser Ala Ile Asn
330                 335                 340                 345 gca ggc aat cca gag aag gaa ctt gat tcc gat gtg ctg gaa caa gaa        1589
Ala Gly Asn Pro Glu Lys Glu Leu Asp Ser Asp Val Leu Glu Gln Glu
                350                 355                 360 ctc tcc agc gaa gaa ccg gaa gaa aca gca aaa cca gat cac tct ctc        1637
Leu Ser Ser Glu Glu Pro Glu Glu Thr Ala Lys Pro Asp His Ser Leu
            365                 370                 375 cga ggc ttc ttc cgc act gat tac tac cca aat cgg tgg cag aag atc        1685
Arg Gly Phe Phe Arg Thr Asp Tyr Tyr Pro Asn Arg Trp Gln Lys Ile
        380                 385                 390 ctg tcg ttt ggc gga cgt gtc cgc atg agc act tcc ctg ttg ttg ggt        1733
Leu Ser Phe Gly Gly Arg Val Arg Met Ser Thr Ser Leu Leu Leu Gly
    395                 400                 405 gcg ctc ctc ttg ctg tca cta ttt aag gtc atg act gtg gaa cca agt        1781
Ala Leu Leu Leu Leu Ser Leu Phe Lys Val Met Thr Val Glu Pro Ser
410                 415                 420                 425 gag aat tgg caa aac tcc agt gga tgg ctg tca cca agc act gcc acc        1829
Glu Asn Trp Gln Asn Ser Ser Gly Trp Leu Ser Pro Ser Thr Ala Thr
                430                 435                 440 tca act gcg gtg acc acc tcc gaa act tcc gcg cca gta agc act tct        1877
Ser Thr Ala Val Thr Thr Ser Glu Thr Ser Ala Pro Val Ser Thr Ser
            445                 450                 455 tcg atg aca gtg ccc act acg gtg gag gag acc cca acg atg gaa tct        1925
Ser Met Thr Val Pro Thr Thr Val Glu Glu Thr Pro Thr Met Glu Ser
        460                 465                 470 agc gtc gaa acg cag cag gaa acc tca acc cct gca acc gca acg ccc        1973
Ser Val Glu Thr Gln Gln Glu Thr Ser Thr Pro Ala Thr Ala Thr Pro
    475                 480                 485 cag cga gcc gac acc atc gaa ccg acc gag gaa gcc acg tcg cag gag        2021
Gln Arg Ala Asp Thr Ile Glu Pro Thr Glu Glu Ala Thr Ser Gln Glu
490                 495                 500                 505 gaa acg act gcg tcg cag acg cag tct cca gca acc gcg gtt caa gag        2069
Glu Thr Thr Ala Ser Gln Thr Gln Ser Pro Ala Thr Ala Val Gln Glu
```

```
                    510             515             520
aca gtt gcg ccg acg tcc acc cct taggacgctg attacagacg tgtcccattt    2123
Thr Val Ala Pro Thr Ser Thr Pro
                525 ctttactact attggaaatt atgagttcag acgcagaaaa ggcatccgtg gagctttccg    2183 aaaaatttca cccagaacgc acccatattt tgggcgccgt tgttttggc ctgatctcat     2243 tattagtcat cggcgcagcc cctcagtacc tgttttggct gctcgcgctc cctgtcatct    2303 tcggttactg ggttctaaaa tcatccacga tcgttgatga acagggcatc accgcaaact    2363 acgccttcaa gggcaaaaag gttgtggcct gggaagacct cgcaggaatc ggattcaagg    2423 gtgcccgca                                                            2432

<210> SEQ ID NO 62
<211> LENGTH: 529
<212> TYPE: PRT
<213> ORGANISM: Corynebacterium glutamicum

<400> SEQUENCE: 62

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
                20                  25                  30

Phe Leu Ile Pro Arg Ile Gly Arg Leu Ala Met Arg Ile Lys Arg
            35                  40                  45

Arg Val Glu Ser Ala Ala Asp Ala Asp Thr Thr Lys Asn Gln Leu Ala
        50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Ser
        275                 280                 285
```

```
Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Val Ser Thr Ser Ser Met Thr Val Pro Thr Thr
450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Thr Ala Val Gln Glu Thr Val Ala Pro Thr Ser Thr
            515                 520                 525

Pro

<210> SEQ ID NO 63
<211> LENGTH: 2432
<212> TYPE: DNA
<213> ORGANISM: Corynebacterium glutamicum
<220> FEATURE:
<221> NAME/KEY: CDS
<222> LOCATION: (507)..(2093)

<400> SEQUENCE: 63 agggcggcg  gatcgaccac  ggcttgcaac  cgtggcggga  gtgggctgtt  gagaagctgc      60
cacattcacg  actttctggc  tcctttacta  aataaggatt  ttcacaggac  ccgtccaagc    120
caagccgatt  tcaactcagc  ctaaagacaa  agccctcatt  taaaattgtt  ccgacgcgga    180
tgcgtgtgca  cgcagtgcga  cagatgtctg  ttgcaaagtt  ggctacttgg  gtcataacca    240
acaagaaagc  cctcgttcca  acactgtggt  gagtgttgtc  gagggcgctt  gacgagacga    300
cttggaaggc  cgttacggca  ggcgccgcgc  ggttactact  acaagtcgaa  taatggtcat    360
ggtgtgtcat  gctacacaca  tcgagtttcc  aattccacaa  cgcacgaaaa  ttcccacccc    420
caaaactccc  ccactttcggt  taaggaatca  ggattctcac  aaagttcagg  caggctcccg    480
ctacttttca  gcgctaatct  tggctc atg att tta ggc gta ccc att caa tat         533
                              Met Ile Leu Gly Val Pro Ile Gln Tyr
                                1               5 ttg ctc tat tca ttg tgg aat tgg att gtc gat acc ggt ttt gat gta             581
Leu Leu Tyr Ser Leu Trp Asn Trp Ile Val Asp Thr Gly Phe Asp Val
```

```
                10                  15                  20                  25
gca att atc ctg gtc ttg gcg ttt ttg att cca cgt atc ggc cga ctg       629
Ala Ile Ile Leu Val Leu Ala Phe Leu Ile Pro Arg Ile Gly Arg Leu
                30                  35                  40 gcc atg cgt att atc aag cgg cga gtg gag tct gcc gcc gat gcg gac       677
Ala Met Arg Ile Ile Lys Arg Arg Val Glu Ser Ala Ala Asp Ala Asp
            45                  50                  55 acc act aag aac cag ctc gcg ttc gct ggc gtt ggc gtt tat atc gcg       725
Thr Thr Lys Asn Gln Leu Ala Phe Ala Gly Val Gly Val Tyr Ile Ala
            60                  65                  70 caa att gtg gcg ttt ttc atg ctt gcc gtc tcc gcg atg cag gct ttt       773
Gln Ile Val Ala Phe Phe Met Leu Ala Val Ser Ala Met Gln Ala Phe
            75                  80                  85 ggt ttc tct ctc gcg ggc gct gcg att ccg gca acc att gcg tca gct       821
Gly Phe Ser Leu Ala Gly Ala Ala Ile Pro Ala Thr Ile Ala Ser Ala
90                  95                  100                 105 gcc att ggc ctt ggt acg cag tcg att gtt gcg gac ttc ttg gcc gga       869
Ala Ile Gly Leu Gly Thr Gln Ser Ile Val Ala Asp Phe Leu Ala Gly
                110                 115                 120 ttt ttc atc ctg acg gaa aag caa ttc ggc gtg ggt gac tgg gtg cgt       917
Phe Phe Ile Leu Thr Glu Lys Gln Phe Gly Val Gly Asp Trp Val Arg
                125                 130                 135 ttt gag ggc aac ggc atc gtt gtc gaa ggc acc gtc att gag atc acc       965
Phe Glu Gly Asn Gly Ile Val Val Glu Gly Thr Val Ile Glu Ile Thr
                140                 145                 150 atg cgc gcg acc aaa att cgc acg att gca caa gag acc gtg atc atc      1013
Met Arg Ala Thr Lys Ile Arg Thr Ile Ala Gln Glu Thr Val Ile Ile
            155                 160                 165 ccc aac tcc acg gcg aaa gtg tgc atc aac aat tct aat aac tgg tcg      1061
Pro Asn Ser Thr Ala Lys Val Cys Ile Asn Asn Ser Asn Asn Trp Ser
170                 175                 180                 185 cgt gcg gtt gtc gtt att ccg atc ccc atg ttg ggt tct gaa aac atc      1109
Arg Ala Val Val Val Ile Pro Ile Pro Met Leu Gly Ser Glu Asn Ile
                190                 195                 200 aca gat gtc atc gcg cgc tct gaa gct gcg act cgt cgc gca ctt ggc      1157
Thr Asp Val Ile Ala Arg Ser Glu Ala Ala Thr Arg Arg Ala Leu Gly
                205                 210                 215 cag gag aaa atc gca ccg gaa atc ctc ggt gaa ctc gat gtg cac cca      1205
Gln Glu Lys Ile Ala Pro Glu Ile Leu Gly Glu Leu Asp Val His Pro
                220                 225                 230 gcc acg gaa gtc aca ccg cca acg gtg gtc ggc atg ccg tgg atg gtc      1253
Ala Thr Glu Val Thr Pro Pro Thr Val Val Gly Met Pro Trp Met Val
            235                 240                 245 acc atg cgt ttc ctc gtg caa gtc acc gcc ggc aat caa tgg ctg gtc      1301
Thr Met Arg Phe Leu Val Gln Val Thr Ala Gly Asn Gln Trp Leu Val
250                 255                 260                 265 gaa cgc gcc atc cgc aca gaa atc atc aac gaa ttc tgg gaa gaa tac      1349
Glu Arg Ala Ile Arg Thr Glu Ile Ile Asn Glu Phe Trp Glu Glu Tyr
                270                 275                 280 ggc agc gca acc act aca tcg gga acc ctc att gat tcc tta cac gtt      1397
Gly Ser Ala Thr Thr Thr Ser Gly Thr Leu Ile Asp Ser Leu His Val
            285                 290                 295 gag cat gaa gag cca aag acc tcg ctt atc gac gcc tcc ccc cag gct      1445
Glu His Glu Glu Pro Lys Thr Ser Leu Ile Asp Ala Ser Pro Gln Ala
            300                 305                 310 ctt aag gaa ccg aag ccg gag gct gcg gcg acg gtt gca tcg cta gct      1493
Leu Lys Glu Pro Lys Pro Glu Ala Ala Ala Thr Val Ala Ser Leu Ala
            315                 320                 325 gca tcg tct aac gac gat gca gac aat gca gac gcc tcg gcg atc aat      1541
Ala Ser Ser Asn Asp Asp Ala Asp Asn Ala Asp Ala Ser Ala Ile Asn
```

| | | | | | | | | | | | | | | |
|---|---|---|---|---|---|---|---|---|---|---|---|---|---|---|
| gca | ggc | aat | cca | gag | aag | gaa | ctt | gat | tcc | gat | gtg | ctg | gaa | caa | gaa | 1589 |
| Ala | Gly | Asn | Pro | Glu | Lys | Glu | Leu | Asp | Ser | Asp | Val | Leu | Glu | Gln | Glu |
| | | | 350 | | | | | 355 | | | | | 360 | | |

```
                330                 335                 340                 345 gca ggc aat cca gag aag gaa ctt gat tcc gat gtg ctg gaa caa gaa         1589
Ala Gly Asn Pro Glu Lys Glu Leu Asp Ser Asp Val Leu Glu Gln Glu
                350                 355                 360 ctc tcc agc gaa gaa ccg gaa gaa aca gca aaa cca gat cac tct ctc         1637
Leu Ser Ser Glu Glu Pro Glu Glu Thr Ala Lys Pro Asp His Ser Leu
            365                 370                 375 cga ggc ttc ttc cgc act gat tac tac cca aat cgg tgg cag aag atc         1685
Arg Gly Phe Phe Arg Thr Asp Tyr Tyr Pro Asn Arg Trp Gln Lys Ile
        380                 385                 390 ctg tcg ttt ggc gga cgt gtc cgc atg agc act tcc ctg ttg ttg ggt         1733
Leu Ser Phe Gly Gly Arg Val Arg Met Ser Thr Ser Leu Leu Leu Gly
    395                 400                 405 gcg ctg ctc ttg ctg tca cta ttt aag gtc atg act gtg gaa cca agt         1781
Ala Leu Leu Leu Leu Ser Leu Phe Lys Val Met Thr Val Glu Pro Ser
410                 415                 420                 425 gag aat tgg caa aac tcc agt gga tgg ctg tca cca agc act gcc acc         1829
Glu Asn Trp Gln Asn Ser Ser Gly Trp Leu Ser Pro Ser Thr Ala Thr
                430                 435                 440 tca act gcg gtg acc acc tcc gaa act tcc gcg cca gta agc act tct         1877
Ser Thr Ala Val Thr Thr Ser Glu Thr Ser Ala Pro Val Ser Thr Ser
            445                 450                 455 tcg atg aca gtg ccc act acg gtg gag gag acc cca acg atg gaa tct         1925
Ser Met Thr Val Pro Thr Thr Val Glu Glu Thr Pro Thr Met Glu Ser
        460                 465                 470 agc gtc gaa acg cag cag gaa acc tca acc cct gca acc gca acg ccc         1973
Ser Val Glu Thr Gln Gln Glu Thr Ser Thr Pro Ala Thr Ala Thr Pro
    475                 480                 485 cag cga gcc gac acc atc gaa ccg acc gag gaa gcc acg tcg cag gag         2021
Gln Arg Ala Asp Thr Ile Glu Pro Thr Glu Glu Ala Thr Ser Gln Glu
490                 495                 500                 505 gaa acg act gcg tcg cag acg cag tct cca gca acc gcg gtt caa gag         2069
Glu Thr Thr Ala Ser Gln Thr Gln Ser Pro Ala Thr Ala Val Gln Glu
                510                 515                 520 aca gtt gcg ccg acg tcc acc cct taggacgctg attacagacg tgtcccattt       2123
Thr Val Ala Pro Thr Ser Thr Pro
            525 ctttactact attggaaatt atgagttcag acgcagaaaa ggcatccgtg gagctttccg       2183 aaaaatttca cccagaacgc acccatattt gggcgccgt tgttttggc ctgatctcat        2243 tattagtcat cggcgcagcc cctcagtacc tgttttggct gctcgcgctc cctgtcatct      2303 tcggttactg ggttctaaaa tcatccacga tcgttgatga acagggcatc accgcaaact      2363 acgccttcaa gggcaaaaag gttgtggcct gggaagacct cgcaggaatc ggattcaagg      2423 gtgcccgca                                                              2432
```

<210> SEQ ID NO 64
<211> LENGTH: 529
<212> TYPE: PRT
<213> ORGANISM: Corynebacterium glutamicum

<400> SEQUENCE: 64

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Leu Val Leu Ala
                20                  25                  30

Phe Leu Ile Pro Arg Ile Gly Arg Leu Ala Met Arg Ile Ile Lys Arg
            35                  40                  45

Arg Val Glu Ser Ala Ala Asp Ala Asp Thr Thr Lys Asn Gln Leu Ala
```

```
           50                  55                  60
Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ala Ile Gly Leu Gly Thr Gln
            100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
        130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
                195                 200                 205

Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Tyr Gly Ser Ala Thr Thr Thr Ser
            275                 280                 285

Gly Thr Leu Ile Asp Ser Leu His Val Glu His Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Pro Glu
        355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Val Ser Thr Ser Ser Met Thr Val Pro Thr Thr
    450                 455                 460

Val Glu Glu Thr Pro Thr Met Glu Ser Ser Val Glu Thr Gln Gln Glu
465                 470                 475                 480
```

```
Thr Ser Thr Pro Ala Thr Ala Thr Pro Gln Arg Ala Asp Thr Ile Glu
                485                 490                 495

Pro Thr Glu Glu Ala Thr Ser Gln Glu Gly Thr Thr Ala Ser Gln Thr
            500                 505                 510

Gln Ser Pro Ala Thr Ala Val Gln Glu Thr Val Ala Pro Thr Ser Thr
            515                 520                 525

Pro

<210> SEQ ID NO 65
<211> LENGTH: 29
<212> TYPE: DNA
<213> ORGANISM: Artificial sequence
<220> FEATURE:
<223> OTHER INFORMATION: 5'-primer for 8-type mutation

<400> SEQUENCE: 65
tggccttggt acgcagtcga ttgttgcgg                                     29

<210> SEQ ID NO 66
<211> LENGTH: 29
<212> TYPE: DNA
<213> ORGANISM: Artificial sequence
<220> FEATURE:
<223> OTHER INFORMATION: 3'-primer for 8-type mutation

<400> SEQUENCE: 66
ccgcaacaat cgactgcgta ccaaggcca                                     29

<210> SEQ ID NO 67
<211> LENGTH: 2131
<212> TYPE: DNA
<213> ORGANISM: Corynebacterium melassecola
<220> FEATURE:
<221> NAME/KEY: CDS
<222> LOCATION: (403)..(2001)

<400> SEQUENCE: 67
caggacccgt ccaagccaag ccgatttcaa ctcagcctaa agacaaagcc ctcatttaaa     60
attgttccga cgcggatgcg tgtgcacgca gtgcgacaga tgtctgttgc aaagttggct    120
acttgggtca taaccaacaa gaaagccctc gttccaacac tgtggtgagt gttgtcgagg    180
gcgcttgacg agacgacttg gaaggccgtt acggcaggcg ccgcgcggtt actactacaa    240
gtcgaataat ggtcatgatg tgtcatgcta cacacatcga gtttccaatt ccacaacgca    300
cgaaaattcc caccccaaa actccccac ttcggttaag gaatcaggat tctcacaaag    360
ttcaggcagg ctcccgctac ttttcagcgc taatcttggc tc atg att tta ggc       414
                                              Met Ile Leu Gly
                                                1 gta ccc att caa tat ttg ctc tat tca ttg tgg aat tgg att gtc gat     462
Val Pro Ile Gln Tyr Leu Leu Tyr Ser Leu Trp Asn Trp Ile Val Asp
 5                  10                  15                  20 acc ggt ttt gat gta gca att atc ctg gtc ttg gcg ttt ttg att cca     510
Thr Gly Phe Asp Val Ala Ile Ile Leu Val Leu Ala Phe Leu Ile Pro
                 25                  30                  35 cgt atc ggc cga ctg gcc atg cgt att atc aag cgc cga gtg gag tct     558
Arg Ile Gly Arg Leu Ala Met Arg Ile Ile Lys Arg Arg Val Glu Ser
         40                  45                  50 gca gcc gat gcg gac acc act aag aac cag ctc gcg ttc gct ggc gtt     606
Ala Ala Asp Ala Asp Thr Thr Lys Asn Gln Leu Ala Phe Ala Gly Val
     55                  60                  65 ggc gtt tat atc gcg caa att gtg gcg ttt ttc atg ctt gcc gtc tcc     654
Gly Val Tyr Ile Ala Gln Ile Val Ala Phe Phe Met Leu Ala Val Ser
 70                  75                  80
```

-continued

```
            70                  75                  80
gcg atg cag gct ttt ggt ttc tct ctc gcg ggc gct gcg att ccg gca    702
Ala Met Gln Ala Phe Gly Phe Ser Leu Ala Gly Ala Ala Ile Pro Ala
85                  90                  95                 100 acc att gcg tca gct gcc att ggt ctt ggt gcg cag tcg att gtt gcg    750
Thr Ile Ala Ser Ala Ala Ile Gly Leu Gly Ala Gln Ser Ile Val Ala
                105                 110                 115 gac ttc ttg gcc gga ttt ttc atc ctg acg gaa aag caa ttc ggc gtg   798
Asp Phe Leu Ala Gly Phe Phe Ile Leu Thr Glu Lys Gln Phe Gly Val
        120                 125                 130 ggt gac tgg gtg cgt ttt gag ggc aac ggc atc gtt gtt gaa ggc acc   846
Gly Asp Trp Val Arg Phe Glu Gly Asn Gly Ile Val Val Glu Gly Thr
            135                 140                 145 gtc att gag atc acc atg cgc gcg acc aaa att cgc acg att gca caa   894
Val Ile Glu Ile Thr Met Arg Ala Thr Lys Ile Arg Thr Ile Ala Gln
150                 155                 160 gag acc gtg atc atc ccc aac tcc acg gcg aaa gtg tgc atc aac aat   942
Glu Thr Val Ile Ile Pro Asn Ser Thr Ala Lys Val Cys Ile Asn Asn
165                 170                 175                 180 tct aat aac tgg tcg cgt gcg gtt gtc gtt att ccg atc ccc atg ttg   990
Ser Asn Asn Trp Ser Arg Ala Val Val Val Ile Pro Ile Pro Met Leu
                185                 190                 195 ggt tct gaa aac atc aca gat gtc atc gcg cgc tct gaa gct gcg act  1038
Gly Ser Glu Asn Ile Thr Asp Val Ile Ala Arg Ser Glu Ala Ala Thr
        200                 205                 210 cgt cgc gca ctt ggc cag gag aaa atc gca ccg gaa atc ctc ggt gaa  1086
Arg Arg Ala Leu Gly Gln Glu Lys Ile Ala Pro Glu Ile Leu Gly Glu
            215                 220                 225 ctc gat gtg cac cca gcc acg gaa gtc aca ccg cca acg gtg gtc ggc  1134
Leu Asp Val His Pro Ala Thr Glu Val Thr Pro Pro Thr Val Val Gly
230                 235                 240 atg ccg tgg atg gtc acc atg cgt ttc ctc gtg caa gtc acc gcc ggc  1182
Met Pro Trp Met Val Thr Met Arg Phe Leu Val Gln Val Thr Ala Gly
245                 250                 255                 260 aat caa tgg ctg gtc gaa cgc gcc atc cgc aca gaa atc atc aac gaa  1230
Asn Gln Trp Leu Val Glu Arg Ala Ile Arg Thr Glu Ile Ile Asn Glu
                265                 270                 275 ttc tgg gaa gaa tac ggc agc gca acc act aca tcg gga acc ctc att  1278
Phe Trp Glu Glu Tyr Gly Ser Ala Thr Thr Thr Ser Gly Thr Leu Ile
        280                 285                 290 gat tcc tta cac gtt gcg cat gaa gag cca aag acc tcg ctt atc gac  1326
Asp Ser Leu His Val Ala His Glu Glu Pro Lys Thr Ser Leu Ile Asp
            295                 300                 305 gcc tcc ccc cag gct ctt aag gaa ccg aag ccg gag gct gcg gcg acg  1374
Ala Ser Pro Gln Ala Leu Lys Glu Pro Lys Pro Glu Ala Ala Ala Thr
310                 315                 320 gtt gca tcg cta gct gca tcg tct aac gac gat gca gac aat gca gac  1422
Val Ala Ser Leu Ala Ala Ser Ser Asn Asp Asp Ala Asp Asn Ala Asp
325                 330                 335                 340 gcc tcg gcg atc aat gca ggc aat cca gag aag gaa ctt gat tcc gat  1470
Ala Ser Ala Ile Asn Ala Gly Asn Pro Glu Lys Glu Leu Asp Ser Asp
                345                 350                 355 gtg ctg gaa caa gaa ctc tcc agc gaa gaa ccg gaa gaa aca gca aaa  1518
Val Leu Glu Gln Glu Leu Ser Ser Glu Glu Pro Glu Glu Thr Ala Lys
        360                 365                 370 cca gat cac tct ctc cga ggc ttc ttc cgc act gat tac tac cca aat  1566
Pro Asp His Ser Leu Arg Gly Phe Phe Arg Thr Asp Tyr Tyr Pro Asn
            375                 380                 385 cgg tgg cag aag atc ctg tcg atc ggc gga cgt gtc cgc atg agc acg  1614
Arg Trp Gln Lys Ile Leu Ser Ile Gly Gly Arg Val Arg Met Ser Thr
```

```
                390             395             400
tcc ctg ctg ttg ggt gcg ctc cta ttt ctg tca ctg ttt aag gtc atg    1662
Ser Leu Leu Leu Gly Ala Leu Leu Leu Ser Leu Phe Lys Val Met
405             410             415             420 act gtg gaa cca agt gag aat tgg caa aac tcc agt gga tgg ctg tca    1710
Thr Val Glu Pro Ser Glu Asn Trp Gln Asn Ser Ser Gly Trp Leu Ser
                425             430             435 cca ggc act gcc acc tca act gcg gcg acc acc tcc gaa act tcc gcg    1758
Pro Gly Thr Ala Thr Ser Thr Ala Ala Thr Thr Ser Glu Thr Ser Ala
            440             445             450 cca gta agc acg cct tcg atg aca gtg ccc act acg gtg gag gag acc    1806
Pro Val Ser Thr Pro Ser Met Thr Val Pro Thr Thr Val Glu Glu Thr
        455             460             465 cca acg atg gaa tct agc gtc gaa acg cag cag gaa acc tca acc cct    1854
Pro Thr Met Glu Ser Ser Val Glu Thr Gln Gln Glu Thr Ser Thr Pro
    470             475             480 gca acc gca acg ccg cag cga gcc gac acc atc gaa ccg acc gag gaa    1902
Ala Thr Ala Thr Pro Gln Arg Ala Asp Thr Ile Glu Pro Thr Glu Glu
485             490             495             500 gcc acg tcg cag gag gaa acg act gcg tcg cag acg cag tct cca gca    1950
Ala Thr Ser Gln Glu Glu Thr Thr Ala Ser Gln Thr Gln Ser Pro Ala
                505             510             515 gtg gaa gca cca acc gcg gtc caa gag aca gtt gcg ccg acg tcc acc    1998
Val Glu Ala Pro Thr Ala Val Gln Glu Thr Val Ala Pro Thr Ser Thr
            520             525             530 cct taggacgctg attacagacg tgtcccattt ctttactact attggaaatt        2051
Pro atgagttcag acgcagaaaa ggcatccgtg gagctttccg aaaaatttca cccagaacgc  2111
acccatattt tgggcgccgt                                             2131

<210> SEQ ID NO 68
<211> LENGTH: 533
<212> TYPE: PRT
<213> ORGANISM: Corynebacterium melassecola

<400> SEQUENCE: 68

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
```

```
                 165                 170                 175
Cys Ile Asn Asn Ser Asn Asn Trp Ser Arg Ala Val Val Ile Pro
            180                 185                 190
Ile Pro Met Leu Gly Ser Glu Asn Ile Thr Asp Val Ile Ala Arg Ser
        195                 200                 205
Glu Ala Ala Thr Arg Arg Ala Leu Gly Gln Glu Lys Ile Ala Pro Glu
    210                 215                 220
Ile Leu Gly Glu Leu Asp Val His Pro Ala Thr Glu Val Thr Pro Pro
225                 230                 235                 240
Thr Val Val Gly Met Pro Trp Met Val Thr Met Arg Phe Leu Val Gln
                245                 250                 255
Val Thr Ala Gly Asn Gln Trp Leu Val Glu Arg Ala Ile Arg Thr Glu
            260                 265                 270
Ile Ile Asn Glu Phe Trp Glu Tyr Gly Ser Ala Thr Thr Thr Ser
        275                 280                 285
Gly Thr Leu Ile Asp Ser Leu His Val Ala His Glu Glu Pro Lys Thr
    290                 295                 300
Ser Leu Ile Asp Ala Ser Pro Gln Ala Leu Lys Glu Pro Lys Pro Glu
305                 310                 315                 320
Ala Ala Ala Thr Val Ala Ser Leu Ala Ala Ser Ser Asn Asp Asp Ala
                325                 330                 335
Asp Asn Ala Asp Ala Ser Ala Ile Asn Ala Gly Asn Pro Glu Lys Glu
            340                 345                 350
Leu Asp Ser Asp Val Leu Glu Gln Glu Leu Ser Ser Glu Gly Pro Glu
        355                 360                 365
Glu Thr Ala Lys Pro Asp His Ser Leu Arg Gly Phe Phe Arg Thr Asp
    370                 375                 380
Tyr Tyr Pro Asn Arg Trp Gln Lys Ile Leu Ser Ile Gly Gly Arg Val
385                 390                 395                 400
Arg Met Ser Thr Ser Leu Leu Leu Gly Ala Leu Leu Leu Ser Leu
                405                 410                 415
Phe Lys Val Met Thr Val Glu Pro Ser Glu Asn Trp Gln Asn Ser Ser
            420                 425                 430
Gly Trp Leu Ser Pro Gly Thr Ala Thr Ser Thr Ala Ala Thr Thr Ser
        435                 440                 445
Glu Thr Ser Ala Pro Val Ser Thr Pro Ser Met Thr Val Pro Thr Thr
    450                 455                 460
Val Glu Glu Thr Pro Thr Met Glu Ser Ser Val Glu Thr Gln Gln Glu
465                 470                 475                 480
Thr Ser Thr Pro Ala Thr Ala Thr Pro Gln Arg Ala Asp Thr Ile Glu
                485                 490                 495
Pro Thr Glu Glu Ala Thr Ser Gln Glu Glu Thr Thr Ala Ser Gln Thr
            500                 505                 510
Gln Ser Pro Ala Val Glu Ala Pro Thr Ala Val Gln Glu Thr Val Ala
        515                 520                 525
Pro Thr Ser Thr Pro
    530

<210> SEQ ID NO 69
<211> LENGTH: 2131
<212> TYPE: DNA
<213> ORGANISM: Corynebacterium melassecola
<220> FEATURE:
<221> NAME/KEY: CDS
<222> LOCATION: (403)..(2001)
```

<400> SEQUENCE: 69

```
caggaccccgt ccaagccaag ccgatttcaa ctcagcctaa agacaaagcc ctcatttaaa    60
attgttccga cgcggatgcg tgtgcacgca gtgcgacaga tgtctgttgc aaagttggct   120
acttgggtca taaccaacaa gaaagccctc gttccaacac tgtggtgagt gttgtcgagg   180
gcgcttgacg agacgacttg gaaggccgtt acggcaggcg ccgcgcggtt actactacaa   240
gtcgaataat ggtcatgatg tgtcatgcta cacacatcga gtttccaatt ccacaacgca   300
cgaaaattcc caccccccaaa actcccccac ttcggttaag gaatcaggat tctcacaaag   360
ttcaggcagg ctcccgctac ttttcagcgc taatcttggc tc atg att tta ggc      414
                                              Met Ile Leu Gly
                                                1
```

| | | | | | | | | | | | | | | | | |
|---|---|---|---|---|---|---|---|---|---|---|---|---|---|---|---|---|
| gta | ccc | att | caa | tat | ttg | ctc | tat | tca | ttg | tgg | aat | tgg | att | gtc | gat | 462 |
| Val | Pro | Ile | Gln | Tyr | Leu | Leu | Tyr | Ser | Leu | Trp | Asn | Trp | Ile | Val | Asp | |
| 5 | | | | 10 | | | | | 15 | | | | | 20 | | |

| | | | | | | | | | | | | | | | | |
|---|---|---|---|---|---|---|---|---|---|---|---|---|---|---|---|---|
| acc | ggt | ttt | gat | gta | gca | att | atc | ctg | gtc | ttg | gcg | ttt | ttg | att | cca | 510 |
| Thr | Gly | Phe | Asp | Val | Ala | Ile | Ile | Leu | Val | Leu | Ala | Phe | Leu | Ile | Pro | |
| | | | | 25 | | | | 30 | | | | | 35 | | | |

| | | | | | | | | | | | | | | | | |
|---|---|---|---|---|---|---|---|---|---|---|---|---|---|---|---|---|
| cgt | atc | ggc | cga | ctg | gcc | atg | cgt | att | atc | aag | cgc | cga | gtg | gag | tct | 558 |
| Arg | Ile | Gly | Arg | Leu | Ala | Met | Arg | Ile | Ile | Lys | Arg | Arg | Val | Glu | Ser | |
| | | | 40 | | | | | 45 | | | | | 50 | | | |

| | | | | | | | | | | | | | | | | |
|---|---|---|---|---|---|---|---|---|---|---|---|---|---|---|---|---|
| gca | gcc | gat | gcg | gac | acc | act | aag | aac | cag | ctc | gcg | ttc | gct | ggc | gtt | 606 |
| Ala | Ala | Asp | Ala | Asp | Thr | Thr | Lys | Asn | Gln | Leu | Ala | Phe | Ala | Gly | Val | |
| | 55 | | | | | 60 | | | | | 65 | | | | | |

| | | | | | | | | | | | | | | | | |
|---|---|---|---|---|---|---|---|---|---|---|---|---|---|---|---|---|
| ggc | gtt | tat | atc | gcg | caa | att | gtg | gcg | ttt | ttc | atg | ctt | gcc | gtc | tcc | 654 |
| Gly | Val | Tyr | Ile | Ala | Gln | Ile | Val | Ala | Phe | Phe | Met | Leu | Ala | Val | Ser | |
| | 70 | | | | 75 | | | | | 80 | | | | | | |

| | | | | | | | | | | | | | | | | |
|---|---|---|---|---|---|---|---|---|---|---|---|---|---|---|---|---|
| gcg | atg | cag | gct | ttt | ggt | ttc | tct | ctc | gcg | ggc | gct | gcg | att | ccg | gca | 702 |
| Ala | Met | Gln | Ala | Phe | Gly | Phe | Ser | Leu | Ala | Gly | Ala | Ala | Ile | Pro | Ala | |
| 85 | | | | | 90 | | | | | 95 | | | | | 100 | |

| | | | | | | | | | | | | | | | | |
|---|---|---|---|---|---|---|---|---|---|---|---|---|---|---|---|---|
| acc | att | gcg | tca | gct | gcc | att | ggt | ctt | ggt | gcg | cag | tcg | att | gtt | gcg | 750 |
| Thr | Ile | Ala | Ser | Ala | Ala | Ile | Gly | Leu | Gly | Ala | Gln | Ser | Ile | Val | Ala | |
| | | | | 105 | | | | | 110 | | | | | 115 | | |

| | | | | | | | | | | | | | | | | |
|---|---|---|---|---|---|---|---|---|---|---|---|---|---|---|---|---|
| gac | ttc | ttg | gcc | gga | ttt | ttc | atc | ctg | acg | gaa | aag | caa | ttc | ggc | gtg | 798 |
| Asp | Phe | Leu | Ala | Gly | Phe | Phe | Ile | Leu | Thr | Glu | Lys | Gln | Phe | Gly | Val | |
| | | | 120 | | | | | 125 | | | | | 130 | | | |

| | | | | | | | | | | | | | | | | |
|---|---|---|---|---|---|---|---|---|---|---|---|---|---|---|---|---|
| ggt | gac | tgg | gtg | cgt | ttt | gag | ggc | aac | ggc | atc | gtt | gtt | gaa | ggc | acc | 846 |
| Gly | Asp | Trp | Val | Arg | Phe | Glu | Gly | Asn | Gly | Ile | Val | Val | Glu | Gly | Thr | |
| | | 135 | | | | | 140 | | | | | 145 | | | | |

| | | | | | | | | | | | | | | | | |
|---|---|---|---|---|---|---|---|---|---|---|---|---|---|---|---|---|
| gtc | att | gag | atc | acc | atg | cgc | gcg | acc | aaa | att | cgc | acg | att | gca | caa | 894 |
| Val | Ile | Glu | Ile | Thr | Met | Arg | Ala | Thr | Lys | Ile | Arg | Thr | Ile | Ala | Gln | |
| | 150 | | | | | 155 | | | | | 160 | | | | | |

| | | | | | | | | | | | | | | | | |
|---|---|---|---|---|---|---|---|---|---|---|---|---|---|---|---|---|
| gag | acc | gtg | atc | atc | ccc | aac | tcc | acg | gcg | aaa | gtg | tgc | atc | aac | aat | 942 |
| Glu | Thr | Val | Ile | Ile | Pro | Asn | Ser | Thr | Ala | Lys | Val | Cys | Ile | Asn | Asn | |
| 165 | | | | | 170 | | | | | 175 | | | | | 180 | |

| | | | | | | | | | | | | | | | | |
|---|---|---|---|---|---|---|---|---|---|---|---|---|---|---|---|---|
| tct | aat | aac | tgg | tcg | cgt | gcg | gtt | gtc | gtt | att | ccg | atc | ccc | atg | ttg | 990 |
| Ser | Asn | Asn | Trp | Ser | Arg | Ala | Val | Val | Val | Ile | Pro | Ile | Pro | Met | Leu | |
| | | | | 185 | | | | | 190 | | | | | 195 | | |

| | | | | | | | | | | | | | | | | |
|---|---|---|---|---|---|---|---|---|---|---|---|---|---|---|---|---|
| ggt | tct | gaa | aac | atc | aca | gat | gtc | atc | gcg | cgc | tct | gaa | gct | gcg | act | 1038 |
| Gly | Ser | Glu | Asn | Ile | Thr | Asp | Val | Ile | Ala | Arg | Ser | Glu | Ala | Ala | Thr | |
| | | | 200 | | | | | 205 | | | | | 210 | | | |

| | | | | | | | | | | | | | | | | |
|---|---|---|---|---|---|---|---|---|---|---|---|---|---|---|---|---|
| cgt | cgc | gca | ctt | ggc | cag | gag | aaa | atc | gca | ccg | gaa | atc | ctc | ggt | gaa | 1086 |
| Arg | Arg | Ala | Leu | Gly | Gln | Glu | Lys | Ile | Ala | Pro | Glu | Ile | Leu | Gly | Glu | |
| | | 215 | | | | | 220 | | | | | 225 | | | | |

| | | | | | | | | | | | | | | | | |
|---|---|---|---|---|---|---|---|---|---|---|---|---|---|---|---|---|
| ctc | gat | gtg | cac | cca | gcc | acg | gaa | gtc | aca | ccg | cca | acg | gtg | gtc | ggc | 1134 |
| Leu | Asp | Val | His | Pro | Ala | Thr | Glu | Val | Thr | Pro | Pro | Thr | Val | Val | Gly | |
| | 230 | | | | | 235 | | | | | 240 | | | | | |

| | | | | | | | | | | | | | | | | |
|---|---|---|---|---|---|---|---|---|---|---|---|---|---|---|---|---|
| atg | ccg | tgg | atg | gtc | acc | atg | cgt | ttc | ctc | gtg | caa | gtc | acc | gcc | ggc | 1182 |
| Met | Pro | Trp | Met | Val | Thr | Met | Arg | Phe | Leu | Val | Gln | Val | Thr | Ala | Gly | |

```
                  245                 250                 255                 260
aat caa tgg ctg gtc gaa cgc gcc atc cgc aca gaa atc atc aac gaa      1230
Asn Gln Trp Leu Val Glu Arg Ala Ile Arg Thr Glu Ile Ile Asn Glu
            265                 270                 275 ttc tgg gaa gaa tac ggc agc gca acc act aca tcg gga acc ctc att      1278
Phe Trp Glu Glu Tyr Gly Ser Ala Thr Thr Thr Ser Gly Thr Leu Ile
280                 285                 290 gat tcc tta cac gtt gcg cat gaa gag cca aag acc tcg ctt atc gac      1326
Asp Ser Leu His Val Ala His Glu Glu Pro Lys Thr Ser Leu Ile Asp
        295                 300                 305 gcc tcc ccc cag gct ctt aag gaa ccg aag ccg gag gct gcg gcg acg      1374
Ala Ser Pro Gln Ala Leu Lys Glu Pro Lys Pro Glu Ala Ala Ala Thr
    310                 315                 320 gtt gca tcg cta gct gca tcg tct aac gac gat gca gac aat gca gac      1422
Val Ala Ser Leu Ala Ala Ser Ser Asn Asp Asp Ala Asp Asn Ala Asp
325                 330                 335                 340 gcc tcg gcg atc aat gca ggc aat cca gag aag gaa ctt gat tcc gat      1470
Ala Ser Ala Ile Asn Ala Gly Asn Pro Glu Lys Glu Leu Asp Ser Asp
            345                 350                 355 gtg ctg gaa caa gaa ctc tcc agc gaa gaa ccg gaa gaa aca gca aaa      1518
Val Leu Glu Gln Glu Leu Ser Ser Glu Glu Pro Glu Glu Thr Ala Lys
        360                 365                 370 cca gat cac tct ctc cga ggc ttc ttc cgc act gat tac tac cca aat      1566
Pro Asp His Ser Leu Arg Gly Phe Phe Arg Thr Asp Tyr Tyr Pro Asn
    375                 380                 385 cgg tgg cag aag atc ctg tcg atc ggc gga cgt gtc cgc atg agc acg      1614
Arg Trp Gln Lys Ile Leu Ser Ile Gly Gly Arg Val Arg Met Ser Thr
390                 395                 400 tcc ctg ctg ttg ggt gcg ctc cta ttg ctg tca ctg ttt aag gtc atg      1662
Ser Leu Leu Leu Gly Ala Leu Leu Leu Ser Leu Phe Lys Val Met
405                 410                 415                 420 act gtg gaa cta agt gag aat tgg caa aac tcc agt gga tgg ctg tca      1710
Thr Val Glu Leu Ser Glu Asn Trp Gln Asn Ser Ser Gly Trp Leu Ser
            425                 430                 435 cca ggc act gcc acc tca act gcg gcg acc acc tcc gaa act tcc gcg      1758
Pro Gly Thr Ala Thr Ser Thr Ala Ala Thr Thr Ser Glu Thr Ser Ala
        440                 445                 450 cca gta agc acg cct tcg atg aca gtg ccc act acg gtg gag gag acc      1806
Pro Val Ser Thr Pro Ser Met Thr Val Pro Thr Thr Val Glu Glu Thr
    455                 460                 465 cca acg atg gaa tct agc gtc gaa acg cag cag gaa acc tca acc cct      1854
Pro Thr Met Glu Ser Ser Val Glu Thr Gln Gln Glu Thr Ser Thr Pro
470                 475                 480 gca acc gca acg ccg cag cga gcc gac acc atc gaa ccg acc gag gaa      1902
Ala Thr Ala Thr Pro Gln Arg Ala Asp Thr Ile Glu Pro Thr Glu Glu
485                 490                 495                 500 gcc acg tcg cag gag gaa acg act gcg tcg cag acg cag tct cca gca      1950
Ala Thr Ser Gln Glu Glu Thr Thr Ala Ser Gln Thr Gln Ser Pro Ala
            505                 510                 515 gtg gaa gca cca acc gcg gtc caa gag aca gtt gcg ccg acg tcc acc      1998
Val Glu Ala Pro Thr Ala Val Gln Glu Thr Val Ala Pro Thr Ser Thr
        520                 525                 530 cct taggacgctg attacagacg tgtcccattt ctttactact attggaaatt           2051
Pro atgagttcag acgcagaaaa ggcatccgtg gagctttccg aaaaatttca cccagaacgc    2111
acccatattt tgggcgccgt                                                2131

<210> SEQ ID NO 70
<211> LENGTH: 533
```

<212> TYPE: PRT
<213> ORGANISM: Corynebacterium melassecola

<400> SEQUENCE: 70

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Ala His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Ile Gly Gly Arg Val
385                 390                 395                 400
```

```
Arg Met Ser Thr Ser Leu Leu Leu Gly Ala Leu Leu Leu Ser Leu
            405                 410                 415
Phe Lys Val Met Thr Val Glu Leu Ser Glu Asn Trp Gln Asn Ser Ser
        420                 425                 430
Gly Trp Leu Ser Pro Gly Thr Ala Thr Ser Thr Ala Ala Thr Thr Ser
            435                 440                 445
Glu Thr Ser Ala Pro Val Ser Thr Pro Ser Met Thr Val Pro Thr Thr
    450                 455                 460
Val Glu Glu Thr Pro Thr Met Glu Ser Ser Val Glu Thr Gln Gln Glu
465                 470                 475                 480
Thr Ser Thr Pro Ala Thr Ala Thr Pro Gln Arg Ala Asp Thr Ile Glu
            485                 490                 495
Pro Thr Glu Glu Ala Thr Ser Gln Glu Glu Thr Ala Ser Gln Thr
            500                 505                 510
Gln Ser Pro Ala Val Glu Ala Pro Thr Ala Val Gln Glu Thr Val Ala
            515                 520                 525
Pro Thr Ser Thr Pro
    530
```

```
<210> SEQ ID NO 71
<211> LENGTH: 20
<212> TYPE: DNA
<213> ORGANISM: Artificial sequence
<220> FEATURE:
<223> OTHER INFORMATION: 5'-primer for 66-type mutation

<400> SEQUENCE: 71
gactgtggaa ctaagtgaga                                           20

<210> SEQ ID NO 72
<211> LENGTH: 20
<212> TYPE: DNA
<213> ORGANISM: Artificial sequence
<220> FEATURE:
<223> OTHER INFORMATION: 3'-primer for 66-type mutation

<400> SEQUENCE: 72
tctcacttag ttccacagtc                                           20

<210> SEQ ID NO 73
<211> LENGTH: 2592
<212> TYPE: DNA
<213> ORGANISM: Corynebacterium glutamicum
<220> FEATURE:
<221> NAME/KEY: CDS
<222> LOCATION: (548)..(2146)

<400> SEQUENCE: 73
tcgagcgatc gaacaattgc ctgtgcacct gtcatccgct caggggcggc ggatcgacca    60
cggcttgcaa ccgtggcggg agtgggctgt tgagaagctg ccacattcac gactttctgg   120
ctcctttact aaataaggat tttcacagga cccgtccaag ccaagccgat tcaactcag   180 cctaaagaca aagccctcat ttaaaattgt tccgacgcgg atgcgtgtgc acgcagtgcg   240
acagatgtct gttgcaaagt tggctacttg ggtcataacc aacaagaaag ccctcgttcc   300
aacactgtgg tgagtgttgt cgagggcgct tgacgagacg acttggaagg ccgttacggc   360
aggcgccgcg cggttactac tacaagtcga ataatggtca tggtgtgtca tgctacacac   420
atcgagtttc caattccaca acgcacgaaa attcccaccc ccaaaactcc cccacttcgg   480
ttaaggaatc aggattctca caaagttcag gcaggctccc gctactttc agcgctaatc   540
```

```
ttggctc atg att tta ggc gta ccc att caa tat ttg ctc tat tca ttg    589
        Met Ile Leu Gly Val Pro Ile Gln Tyr Leu Leu Tyr Ser Leu
         1               5                  10 tgg aat tgg att gtc gat acc ggt ttt gat gta gca att atc ctg gtc    637
Trp Asn Trp Ile Val Asp Thr Gly Phe Asp Val Ala Ile Ile Leu Val
 15              20                  25                  30 ttg gcg ttt ttg att cca cgt atc ggc cga ctg gcc atg cgt att atc    685
Leu Ala Phe Leu Ile Pro Arg Ile Gly Arg Leu Ala Met Arg Ile Ile
                 35                  40                  45 aag cag cga gtg gag tct gca gcc gat gcg gac acc act aag aac cag    733
Lys Gln Arg Val Glu Ser Ala Ala Asp Ala Asp Thr Thr Lys Asn Gln
             50                  55                  60 ctc gcg ttc gct ggc gtt ggc gtt tat atc gcg caa att gtg gcg ttt    781
Leu Ala Phe Ala Gly Val Gly Val Tyr Ile Ala Gln Ile Val Ala Phe
                 65                  70                  75 ttc atg ctt gcc gtc tcc gcg atg cag gct ttt ggt ttc tct ctc gcg    829
Phe Met Leu Ala Val Ser Ala Met Gln Ala Phe Gly Phe Ser Leu Ala
 80                  85                  90 ggc gct gcg att ccg gca acc att gcg tca gct gcc att ggt ctt ggt    877
Gly Ala Ala Ile Pro Ala Thr Ile Ala Ser Ala Ala Ile Gly Leu Gly
 95                 100                 105                 110 gcg cag tcg att gtt gcg gac ttc ttg gcc gga ttt ttc atc ctg acg    925
Ala Gln Ser Ile Val Ala Asp Phe Leu Ala Gly Phe Phe Ile Leu Thr
                115                 120                 125 gaa aag caa ttc ggc gtg ggt gac tgg gtg cgc ttt gag ggc aac ggc    973
Glu Lys Gln Phe Gly Val Gly Asp Trp Val Arg Phe Glu Gly Asn Gly
                130                 135                 140 atc gtt gtt gaa ggc acc gtc att gag atc acc atg cgc gcg acc aaa   1021
Ile Val Val Glu Gly Thr Val Ile Glu Ile Thr Met Arg Ala Thr Lys
                145                 150                 155 att cgc acg att gca caa gag acc gtg atc atc ccg aac tcc acg gcg   1069
Ile Arg Thr Ile Ala Gln Glu Thr Val Ile Ile Pro Asn Ser Thr Ala
    160                 165                 170 aaa gtg tgc atc aac aat tct aat aac tgg tcg cgt gcg gtt gtc gtt   1117
Lys Val Cys Ile Asn Asn Ser Asn Asn Trp Ser Arg Ala Val Val Val
175                 180                 185                 190 att ccg atc ccc atg ttg ggt tct gaa aac atc aca gat gtc atc gcg   1165
Ile Pro Ile Pro Met Leu Gly Ser Glu Asn Ile Thr Asp Val Ile Ala
                195                 200                 205 cgc tct gaa gct gcg act cgt cgc gca ctt ggc cag gag aaa atc gca   1213
Arg Ser Glu Ala Ala Thr Arg Arg Ala Leu Gly Gln Glu Lys Ile Ala
                210                 215                 220 ccg gaa atc ctc ggt gaa ctc gat gtg cac cca gcc acg gaa gtc aca   1261
Pro Glu Ile Leu Gly Glu Leu Asp Val His Pro Ala Thr Glu Val Thr
                225                 230                 235 ccg cca acg gtg gtc ggc atg ccg tgg atg gtc acc atg cgt ttc ctc   1309
Pro Pro Thr Val Val Gly Met Pro Trp Met Val Thr Met Arg Phe Leu
240                 245                 250 gtg caa gtc acc gcc ggc aat caa tgg ctg gtc gaa cgc gcc atc cgc   1357
Val Gln Val Thr Ala Gly Asn Gln Trp Leu Val Glu Arg Ala Ile Arg
255                 260                 265                 270 aca gaa atc atc aac gaa ttc tgg gaa gaa tac ggc agc gca acc act   1405
Thr Glu Ile Ile Asn Glu Phe Trp Glu Glu Tyr Gly Ser Ala Thr Thr
                275                 280                 285 aca tcg gga acc ctc att gat tcc tta cac gtt gag cat gaa gag cca   1453
Thr Ser Gly Thr Leu Ile Asp Ser Leu His Val Glu His Glu Glu Pro
                290                 295                 300 aag acc tcg ctt atc gac gcc tcc ccc cag gct ctt aag gaa ccg aag   1501
Lys Thr Ser Leu Ile Asp Ala Ser Pro Gln Ala Leu Lys Glu Pro Lys
    305                 310                 315
```

```
ccg gag gct gcg gcg acg gtt gca tcg cta gct gca tcg tct aac gac      1549
Pro Glu Ala Ala Ala Thr Val Ala Ser Leu Ala Ala Ser Ser Asn Asp
    320                 325                 330 gat gca gac aat gca gac gcc tcg gcg atc aat gca ggc aat cca gag      1597
Asp Ala Asp Asn Ala Asp Ala Ser Ala Ile Asn Ala Gly Asn Pro Glu
335                 340                 345                 350 aag gaa ctt gat tcc gat gtg ctg gaa caa gaa ctc tcc agc gaa gaa      1645
Lys Glu Leu Asp Ser Asp Val Leu Glu Gln Glu Leu Ser Ser Glu Glu
                355                 360                 365 ccg gaa gaa aca gca aaa cca gat cac tct ctc cga ggc ttc ttc cgc      1693
Pro Glu Glu Thr Ala Lys Pro Asp His Ser Leu Arg Gly Phe Phe Arg
            370                 375                 380 act gat tac tac cca aat cgg tgg cag aag atc ctg tcg ttt ggc gga      1741
Thr Asp Tyr Tyr Pro Asn Arg Trp Gln Lys Ile Leu Ser Phe Gly Gly
        385                 390                 395 cgt gtc cgc atg agc act tcc ctg ttg ttg ggt gcg ctg ctc ttg ctg      1789
Arg Val Arg Met Ser Thr Ser Leu Leu Leu Gly Ala Leu Leu Leu Leu
    400                 405                 410 tca cta ttt aag gtc atg act gtg gaa cca agt gag aat tgg caa aac      1837
Ser Leu Phe Lys Val Met Thr Val Glu Pro Ser Glu Asn Trp Gln Asn
415                 420                 425                 430 tcc agt gga tgg ctg tca tca agc act gcc acc tca act gcg gtg acc      1885
Ser Ser Gly Trp Leu Ser Ser Ser Thr Ala Thr Ser Thr Ala Val Thr
                435                 440                 445 acc tcc gaa act tcc gcg cca gca agc acg cct tcg atg aca gtg ccc      1933
Thr Ser Glu Thr Ser Ala Pro Ala Ser Thr Pro Ser Met Thr Val Pro
            450                 455                 460 act acg gtg gag gag acc cca acg atg gaa tct agc gtc gaa acg cag      1981
Thr Thr Val Glu Glu Thr Pro Thr Met Glu Ser Ser Val Glu Thr Gln
        465                 470                 475 cag gaa acc tca acc cct gca acc gca acg ccc cag cga gcc gac acc      2029
Gln Glu Thr Ser Thr Pro Ala Thr Ala Thr Pro Gln Arg Ala Asp Thr
    480                 485                 490 atc gaa ccg acc gag gaa gcc acg tcg cag gag gaa acg act gca tcg      2077
Ile Glu Pro Thr Glu Glu Ala Thr Ser Gln Glu Glu Thr Thr Ala Ser
495                 500                 505                 510 cag acg cag tct cca gca gtg gaa gca cca acc gcg gtc caa gaa aca      2125
Gln Thr Gln Ser Pro Ala Val Glu Ala Pro Thr Ala Val Gln Glu Thr
                515                 520                 525 gtt gcg ccg acg tcc acc cct taggacgctg attacagacg tgtctcattt         2176
Val Ala Pro Thr Ser Thr Pro
            530 ctttactact attggaaatt atgagttcag acgcagaaaa ggcatccgtg gagctttccg    2236 aaaaatttca cccagaacgc acccatattt tgggcgccgt tgttttggc ctgatctcat     2296 tattagtcat cggcgcagcc cctcagtacc tgttttggct gctcgcgctc cctgtcatct    2356 tcggttactg ggttctaaaa tcatccacga tcgttgatga acagggcatc accgcaaact    2416 acgccttcaa gggcaaaaag gttgtggcct gggaagacct cgcaggaatc ggattcaagg    2476 gtgcccgcac tttcgctcgc accacctccg atgcagaagt caccctcccc ggcgtcacct    2536 tcaactccct tccccgcctt gaagctgctt cccacggccg catccccgat gcgatc        2592

<210> SEQ ID NO 74
<211> LENGTH: 533
<212> TYPE: PRT
<213> ORGANISM: Corynebacterium glutamicum

<400> SEQUENCE: 74

Met Ile Leu Gly Val Pro Ile Gln Tyr Leu Leu Tyr Ser Leu Trp Asn
1               5                   10                  15
```

```
Trp Ile Val Asp Thr Gly Phe Asp Val Ala Ile Ile Leu Val Leu Ala
             20                  25                  30

Phe Leu Ile Pro Arg Ile Gly Arg Leu Ala Met Arg Ile Ile Lys Gln
             35                  40                  45

Arg Val Glu Ser Ala Ala Asp Ala Asp Thr Thr Lys Asn Gln Leu Ala
 50                  55                  60

Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ile Gly Leu Gly Ala Gln
                100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
            130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Gln Glu Leu Ser Ser Glu Pro Glu
            355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Ser Ser Thr Ala Thr Ser Thr Ala Val Thr Thr Ser
```

```
                    435                 440                 445
Glu Thr Ser Ala Pro Ala Ser Thr Pro Ser Met Thr Val Pro Thr Thr
            450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530
```

<210> SEQ ID NO 75
<211> LENGTH: 22
<212> TYPE: DNA
<213> ORGANISM: Artificial sequence
<220> FEATURE:
<223> OTHER INFORMATION: 5'-primer

<400> SEQUENCE: 75
caattcggcg tgggtgactg gg                                          22

<210> SEQ ID NO 76
<211> LENGTH: 25
<212> TYPE: DNA
<213> ORGANISM: Artificial sequence
<220> FEATURE:
<223> OTHER INFORMATION: 3'-primer

<400> SEQUENCE: 76
gtgcggatgg cgcgttcgac cagcc                                       25

<210> SEQ ID NO 77
<211> LENGTH: 20
<212> TYPE: DNA
<213> ORGANISM: Artificial sequence
<220> FEATURE:
<223> OTHER INFORMATION: 5'-primer for N-terminal fragment of odhA gene

<400> SEQUENCE: 77
ccaggcactc gtcctcggtt                                             20

<210> SEQ ID NO 78
<211> LENGTH: 48
<212> TYPE: DNA
<213> ORGANISM: Artificial sequence
<220> FEATURE:
<223> OTHER INFORMATION: 3'-primer for N-terminal fragment of odhA gene

<400> SEQUENCE: 78
aggctagtgc aggactataa agaccagttc tcctaaaaat aacgtgtc              48

<210> SEQ ID NO 79
<211> LENGTH: 48
<212> TYPE: DNA
<213> ORGANISM: Artificial sequence
<220> FEATURE:
<223> OTHER INFORMATION: 5'-primer for C-terminal fragment of odhA gene

<400> SEQUENCE: 79
gacacgttat ttttaggaga actggtcttt atagtcctgc actagcct              48

<210> SEQ ID NO 80
<211> LENGTH: 20
<212> TYPE: DNA
<213> ORGANISM: Artificial sequence
<220> FEATURE:
<223> OTHER INFORMATION: C'-primer for C-terminal fragment of odhA gene

<400> SEQUENCE: 80
tccatcgtgg ccaccgatcc                                              20

<210> SEQ ID NO 81
<211> LENGTH: 25
<212> TYPE: DNA
<213> ORGANISM: Artificial sequence
<220> FEATURE:
<223> OTHER INFORMATION: 5'-primer for odhA disruption

<400> SEQUENCE: 81
cgggatcccc accggcgtac tcgtg                                        25

<210> SEQ ID NO 82
<211> LENGTH: 28
<212> TYPE: DNA
<213> ORGANISM: Artificial sequence
<220> FEATURE:
<223> OTHER INFORMATION: 3'-primer for odhA disruption

<400> SEQUENCE: 82
ccacggatcc ttccaatgct attggttg                                     28

<210> SEQ ID NO 83
<211> LENGTH: 2102
<212> TYPE: DNA
<213> ORGANISM: Corynebacterium glutamicum
<220> FEATURE:
<221> NAME/KEY: CDS
<222> LOCATION: (501)..(2099)

<400> SEQUENCE: 83

```
ggcggatcga ccacggcttg caaccgtggc gggagtgggc tgttgagaag ctgccacatt    60
cacgactttc tggctccttt actaaataag gattttcaca ggacccgtcc aagccaagcc   120
gatttcaact cagcctaaag acaaagccct catttaaaat tgttccgacg cggatgcgtg   180
tgcacgcagt gcgacagatg tctgttgcaa agttggctac ttgggtcata accaacaaga   240
aagccctcgt tccaacactg tggtgagtgt tgtcgagggc gcttgacgag acgacttgga   300
aggccgttac ggcaggcgcc gcgcggttac tactacaagt cgaataatgg tcatggtgtg   360
tcatgctaca cacatcgagt ttccaattcc acaacgcacg aaaattccca ccccaaaac    420 tcccccactt cggttaagga atcaggattc tcacaaagtt caggcaggct cccgctactt   480
ttcagcgcta atcttggctc atg att tta ggc gta ccc att caa tat ttg ctc   533
                    Met Ile Leu Gly Val Pro Ile Gln Tyr Leu Leu
                     1               5                  10 tat tca ttg tgg aat tgg att gtc gat acc ggt ttt gat gta gca att    581
Tyr Ser Leu Trp Asn Trp Ile Val Asp Thr Gly Phe Asp Val Ala Ile
         15                  20                  25 atc ctg gtc ttg gcg ttt ttg att cca cgt atc ggc cga ctg gcc atg    629
Ile Leu Val Leu Ala Phe Leu Ile Pro Arg Ile Gly Arg Leu Ala Met
 30                  35                  40 cgt att atc aag cgc cga gtg gag tct gca gcc gat gcg gac acc act    677
Arg Ile Ile Lys Arg Arg Val Glu Ser Ala Ala Asp Ala Asp Thr Thr
     45                  50                  55 aag aac cag ctc gcg ttc gcc ggc gtt ggc gtt tat atc gcg caa att    725
```

```
                     -continued

Lys Asn Gln Leu Ala Phe Ala Gly Val Gly Val Tyr Ile Ala Gln Ile
 60              65                  70                  75 gtg gcg ttt ttc atg ctt gcc gtc tcc gcg atg cag gct ttt ggt ttc    773
Val Ala Phe Phe Met Leu Ala Val Ser Ala Met Gln Ala Phe Gly Phe
                 80                  85                  90 tct ctc gcg ggc gct gcg att ccg gca acc att gcg tca gct gcc att    821
Ser Leu Ala Gly Ala Ala Ile Pro Ala Thr Ile Ala Ser Ala Ala Ile
                 95                 100                 105 ggc ctt ggt gcg cag tcg att gtt gcg gac ttc ttg gcc gga ttt ttc    869
Gly Leu Gly Ala Gln Ser Ile Val Ala Asp Phe Leu Ala Gly Phe Phe
            110                 115                 120 atc ctg acg gaa aag caa ttc ggc gtg ggt gac tgg gtg cgt ttt gag    917
Ile Leu Thr Glu Lys Gln Phe Gly Val Gly Asp Trp Val Arg Phe Glu
125                 130                 135 ggc aac ggc atc gtt gtc gaa ggc acc gtc att gag atc acc atg cgc    965
Gly Asn Gly Ile Val Val Glu Gly Thr Val Ile Glu Ile Thr Met Arg
140                 145                 150                 155 gcg acc aaa att cgc acg att gca caa gag acc gtg atc atc ccc aac   1013
Ala Thr Lys Ile Arg Thr Ile Ala Gln Glu Thr Val Ile Ile Pro Asn
                160                 165                 170 tcc acg gcg aaa gtg tgc atc aac aat tct aat aac tgg tcg cgt gcg   1061
Ser Thr Ala Lys Val Cys Ile Asn Asn Ser Asn Asn Trp Ser Arg Ala
                175                 180                 185 gtt gtc gtt att ccg atc ccc atg ttg ggt tct gaa aac atc aca gat   1109
Val Val Val Ile Pro Ile Pro Met Leu Gly Ser Glu Asn Ile Thr Asp
                190                 195                 200 gtc atc gcg cgc tct gaa gct gcg act cgt cgc gca ctt ggc cag gag   1157
Val Ile Ala Arg Ser Glu Ala Ala Thr Arg Arg Ala Leu Gly Gln Glu
205                 210                 215 aaa atc gca ccg gaa atc ctc ggt gaa ctc gat gtg cac cca gcc acg   1205
Lys Ile Ala Pro Glu Ile Leu Gly Glu Leu Asp Val His Pro Ala Thr
220                 225                 230                 235 gaa gtc acg ccg cca acg gtg gtc ggc atg ccg tgg atg gtc acc atg   1253
Glu Val Thr Pro Pro Thr Val Val Gly Met Pro Trp Met Val Thr Met
                240                 245                 250 cgt ttc ctc gtg caa gtc acc gcc ggc aat caa tgg ctg gtc gaa cgc   1301
Arg Phe Leu Val Gln Val Thr Ala Gly Asn Gln Trp Leu Val Glu Arg
                255                 260                 265 gcc atc cgc aca gaa atc atc agc gaa ttc tgg gaa gaa tac ggc agc   1349
Ala Ile Arg Thr Glu Ile Ile Ser Glu Phe Trp Glu Glu Tyr Gly Ser
            270                 275                 280 gca acc act aca tcg gga acc ctc att gat tcc tta cac gtt gag cat   1397
Ala Thr Thr Thr Ser Gly Thr Leu Ile Asp Ser Leu His Val Glu His
285                 290                 295 gaa gag cca aag acc tcg ctt atc gac gcc tcc ccc cag gct ctt aag   1445
Glu Glu Pro Lys Thr Ser Leu Ile Asp Ala Ser Pro Gln Ala Leu Lys
300                 305                 310                 315 gaa ccg aag ccg gag gct gcg gcg acg gtt gca tcg cta gct gca tcc   1493
Glu Pro Lys Pro Glu Ala Ala Ala Thr Val Ala Ser Leu Ala Ala Ser
                320                 325                 330 tct aac gac gat gca gac aat gca gac gcc tcg gtg atc aat gca ggc   1541
Ser Asn Asp Asp Ala Asp Asn Ala Asp Ala Ser Val Ile Asn Ala Gly
                335                 340                 345 aat cca gag aag gaa ctt gat tcc gat gtg ctg gaa caa gaa ctc tcc   1589
Asn Pro Glu Lys Glu Leu Asp Ser Asp Val Leu Glu Gln Glu Leu Ser
                350                 355                 360 agc gaa gaa ccg gaa gaa aca gca aaa cca gat cac tct ctc cga ggc   1637
Ser Glu Glu Pro Glu Glu Thr Ala Lys Pro Asp His Ser Leu Arg Gly
365                 370                 375 ttc ttc cgc act gat tac tac cca aat cgg tgg cag aag atc ctg tcg   1685
```

-continued

| | | | | | | | | | | | | | | | |
|---|---|---|---|---|---|---|---|---|---|---|---|---|---|---|---|
| Phe | Phe | Arg | Thr | Asp | Tyr | Tyr | Pro | Asn | Arg | Trp | Gln | Lys | Ile | Leu | Ser |
| 380 | | | | | 385 | | | | | 390 | | | | | 395 |

```
ttt ggc gga cgt gtc cgc atg agc acg tcc ctg ttg ttg ggt gcg ctg     1733
Phe Gly Gly Arg Val Arg Met Ser Thr Ser Leu Leu Leu Gly Ala Leu
                400                 405                 410 ctc ttg ctg tca cta ttt aag gtc atg act gtg gaa cca agt gag aat     1781
Leu Leu Leu Ser Leu Phe Lys Val Met Thr Val Glu Pro Ser Glu Asn
                415                 420                 425 tgg caa aac tcc agt gga tgg ctg tca cca agc act gcc acc tca act     1829
Trp Gln Asn Ser Ser Gly Trp Leu Ser Pro Ser Thr Ala Thr Ser Thr
            430                 435                 440 gcg gtg acc acc tcc gaa act tcc gcg cca gta agc acg cct tcg atg     1877
Ala Val Thr Thr Ser Glu Thr Ser Ala Pro Val Ser Thr Pro Ser Met
            445                 450                 455 aca gtg ccc act acg gtg gag gag acc cca acg atg gaa tct aac gtc     1925
Thr Val Pro Thr Thr Val Glu Glu Thr Pro Thr Met Glu Ser Asn Val
460                 465                 470                 475 gaa acg cag cag gaa acc tca acc cct gca acc gca acg ccc cag cga     1973
Glu Thr Gln Gln Glu Thr Ser Thr Pro Ala Thr Ala Thr Pro Gln Arg
                480                 485                 490 gcc gac acc atc gaa ccg acc gag gaa gcc acg tcg cag gag gaa acg     2021
Ala Asp Thr Ile Glu Pro Thr Glu Glu Ala Thr Ser Gln Glu Glu Thr
                495                 500                 505 act gcg tcg cag acg cag tct cca gca gtg gaa gca cca acc gcg gtc     2069
Thr Ala Ser Gln Thr Gln Ser Pro Ala Val Glu Ala Pro Thr Ala Val
            510                 515                 520 caa gag aca gtt gcg ccg acg tcc acc cct tag                          2102
Gln Glu Thr Val Ala Pro Thr Ser Thr Pro
            525                 530
```

<210> SEQ ID NO 84
<211> LENGTH: 533
<212> TYPE: PRT
<213> ORGANISM: Corynebacterium glutamicum

<400> SEQUENCE: 84

| | | | | | | | | | | | | | | | |
|---|---|---|---|---|---|---|---|---|---|---|---|---|---|---|---|
| Met | Ile | Leu | Gly | Val | Pro | Ile | Gln | Tyr | Leu | Leu | Tyr | Ser | Leu | Trp | Asn |
| 1 | | | | 5 | | | | | 10 | | | | | 15 | |

| | | | | | | | | | | | | | | | |
|---|---|---|---|---|---|---|---|---|---|---|---|---|---|---|---|
| Trp | Ile | Val | Asp | Thr | Gly | Phe | Asp | Val | Ala | Ile | Ile | Leu | Val | Leu | Ala |
| | | | 20 | | | | | 25 | | | | | 30 | | |

| | | | | | | | | | | | | | | | |
|---|---|---|---|---|---|---|---|---|---|---|---|---|---|---|---|
| Phe | Leu | Ile | Pro | Arg | Ile | Gly | Arg | Leu | Ala | Met | Arg | Ile | Ile | Lys | Arg |
| | | | 35 | | | | | 40 | | | | | 45 | | |

| | | | | | | | | | | | | | | | |
|---|---|---|---|---|---|---|---|---|---|---|---|---|---|---|---|
| Arg | Val | Glu | Ser | Ala | Ala | Asp | Ala | Asp | Thr | Thr | Lys | Asn | Gln | Leu | Ala |
| | 50 | | | | | 55 | | | | | 60 | | | | |

| | | | | | | | | | | | | | | | |
|---|---|---|---|---|---|---|---|---|---|---|---|---|---|---|---|
| Phe | Ala | Gly | Val | Gly | Val | Tyr | Ile | Ala | Gln | Ile | Val | Ala | Phe | Phe | Met |
| 65 | | | | | 70 | | | | | 75 | | | | | 80 |

| | | | | | | | | | | | | | | | |
|---|---|---|---|---|---|---|---|---|---|---|---|---|---|---|---|
| Leu | Ala | Val | Ser | Ala | Met | Gln | Ala | Phe | Gly | Phe | Ser | Leu | Ala | Gly | Ala |
| | | | | 85 | | | | | 90 | | | | | 95 | |

| | | | | | | | | | | | | | | | |
|---|---|---|---|---|---|---|---|---|---|---|---|---|---|---|---|
| Ala | Ile | Pro | Ala | Thr | Ile | Ala | Ser | Ala | Ala | Ile | Gly | Leu | Gly | Ala | Gln |
| | | | | 100 | | | | | 105 | | | | | 110 | |

| | | | | | | | | | | | | | | | |
|---|---|---|---|---|---|---|---|---|---|---|---|---|---|---|---|
| Ser | Ile | Val | Ala | Asp | Phe | Leu | Ala | Gly | Phe | Phe | Ile | Leu | Thr | Glu | Lys |
| | | | 115 | | | | | 120 | | | | | 125 | | |

| | | | | | | | | | | | | | | | |
|---|---|---|---|---|---|---|---|---|---|---|---|---|---|---|---|
| Gln | Phe | Gly | Val | Gly | Asp | Trp | Val | Arg | Phe | Glu | Gly | Asn | Gly | Ile | Val |
| | | | 130 | | | | | 135 | | | | | 140 | | |

| | | | | | | | | | | | | | | | |
|---|---|---|---|---|---|---|---|---|---|---|---|---|---|---|---|
| Val | Glu | Gly | Thr | Val | Ile | Glu | Ile | Thr | Met | Arg | Ala | Thr | Lys | Ile | Arg |
| 145 | | | | | 150 | | | | | 155 | | | | | 160 |

| | | | | | | | | | | | | | | | |
|---|---|---|---|---|---|---|---|---|---|---|---|---|---|---|---|
| Thr | Ile | Ala | Gln | Glu | Thr | Val | Ile | Ile | Pro | Asn | Ser | Thr | Ala | Lys | Val |
| | | | | 165 | | | | | 170 | | | | | 175 | |

```
Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Ser Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
        370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Val Ser Thr Pro Ser Met Thr Val Pro Thr Thr
450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Val Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530

<210> SEQ ID NO 85
<211> LENGTH: 533
<212> TYPE: PRT
<213> ORGANISM: Corynebacterium glutamicum
<220> FEATURE:
<221> NAME/KEY: MISC_FEATURE
<222> LOCATION: (48), (275), (298), (343), (396), (438), (445), (454),
      (457), (474), (517)..(520)
```

<223> OTHER INFORMATION: Xaa = any amino acid

<400> SEQUENCE: 85

```
Met Ile Leu Gly Val Pro Ile Gln Tyr Leu Leu Tyr Ser Leu Trp Asn
 1               5                  10                  15

Trp Ile Val Asp Thr Gly Phe Asp Val Ala Ile Leu Val Leu Ala
             20                  25                  30

Phe Leu Ile Pro Arg Ile Gly Arg Leu Ala Met Arg Ile Ile Lys Xaa
         35                  40                  45

Arg Val Glu Ser Ala Ala Asp Ala Asp Thr Thr Lys Asn Gln Leu Ala
     50                  55                  60

Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
            165                 170                 175

Cys Ile Asn Asn Ser Asn Asn Trp Ser Arg Ala Val Val Ile Pro
        180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Xaa Glu Phe Trp Glu Glu Tyr Gly Ser Ala Thr Thr Thr Ser
        275                 280                 285

Gly Thr Leu Ile Asp Ser Leu His Val Xaa His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Ala
                325                 330                 335

Asp Asn Ala Asp Ala Ser Xaa Ile Asn Ala Gly Asn Pro Glu Lys Glu
            340                 345                 350

Leu Asp Ser Asp Val Leu Glu Gln Glu Leu Ser Ser Glu Pro Glu
        355                 360                 365

Glu Thr Ala Lys Pro Asp His Ser Leu Arg Gly Phe Phe Arg Thr Asp
    370                 375                 380
```

```
Tyr Tyr Pro Asn Arg Trp Gln Lys Ile Leu Ser Xaa Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Xaa Thr Ala Thr Ser Thr Ala Xaa Thr Thr Ser
                435                 440                 445

Glu Thr Ser Ala Pro Xaa Ser Thr Xaa Ser Met Thr Val Pro Thr Thr
            450                 455                 460

Val Glu Glu Thr Pro Thr Met Glu Ser Xaa Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
                500                 505                 510

Gln Ser Pro Ala Xaa Xaa Xaa Xaa Thr Ala Val Gln Glu Thr Val Ala
                515                 520                 525

Pro Thr Ser Thr Pro
    530

<210> SEQ ID NO 86
<211> LENGTH: 1550
<212> TYPE: DNA
<213> ORGANISM: Corynebacterium glutamicum
<220> FEATURE:
<221> NAME/KEY: CDS
<222> LOCATION: (585)..(1121)

<400> SEQUENCE: 86
gcattgatgt tgaggtccac gacaatgcag atgcttacat ccgcaatggt ggcgaaactg    60
tcggcatgct ggtttctgaa ggtgcagaga agattgccag cggcagcggc gctgtcatcc   120
cggacgcatc cgcagagttt tccgcacgcg tgttgtctgc cgagtaccgc accaacactc   180
ttaccggcca gcgttttatc cacgcaacag ttgatggcct cttcgctttt gatgtgtgcc   240
ttcctgatgc accagaacta cctgcccgtg acagcgtgtt gtctggcaaa gtcatgctga   300
ctgctgccgt tatccccact gaggtcaccg gctgcggtgg ctccggtggc ggctgtggct   360
caggtagctg tggctgcggc ggacactaaa attctgcaca attttttaag aggaccccag   420
ctccggggtc cttttccatt ttttacccag tacttgaaac gtgatatatg tctattctga   480
aaatcatcgc atagaatact ggtgcaatcg tttacgttcg ctattaatgt gacacgtata   540
agccgacact tttaacgaag cgcagaagga gtgagagcaa gaaa atg gga gaa caa     596
                                              Met Gly Glu Gln
                                                1 ctt ccg ttt gct aat ggt tca cgc tcc aac aaa ctg ccg ctc atc gtc     644
Leu Pro Phe Ala Asn Gly Ser Arg Ser Asn Lys Leu Pro Leu Ile Val
 5              10                  15                  20 atc ggt ttg tgc tgc ata atg ctg atc ctg tgg ctt aaa ctt ccc ggc     692
Ile Gly Leu Cys Cys Ile Met Leu Ile Leu Trp Leu Lys Leu Pro Gly
                25                  30                  35 gta ctg ctt gcc acc atc att ggg gtt gcc acg gtg agt gtg atg cgg     740
Val Leu Leu Ala Thr Ile Ile Gly Val Ala Thr Val Ser Val Met Arg
            40                  45                  50
```

| | | |
|---|---|---|
| atg cgc acc tcc acc cca gaa act gcc tcg ctg gtt act tct att cgg<br>Met Arg Thr Ser Thr Pro Glu Thr Ala Ser Leu Val Thr Ser Ile Arg<br>          55                      60                      65 | | 788 |
| ctg tct gcg gaa gat att tcc gat gtg caa cat gag tgg cag cag ttt<br>Leu Ser Ala Glu Asp Ile Ser Asp Val Gln His Glu Trp Gln Gln Phe<br>  70                        75                      80 | | 836 |
| ttg acc tcc ccc gag gcc gat gcg ctg gct gat cgc acg ctt gtc cgt<br>Leu Thr Ser Pro Glu Ala Asp Ala Leu Ala Asp Arg Thr Leu Val Arg<br>85                        90                      95                  100 | | 884 |
| ccc gca ctg gcg gat cca gat tgt ggc gat aag gct atc gag aaa ttt<br>Pro Ala Leu Ala Asp Pro Asp Cys Gly Asp Lys Ala Ile Glu Lys Phe<br>                    105                      110                      115 | | 932 |
| cat tat gaa atc agc aat gcc aat cgc ttc ttg ggc agg ttg gac gct<br>His Tyr Glu Ile Ser Asn Ala Asn Arg Phe Leu Gly Arg Leu Asp Ala<br>        120                      125                      130 | | 980 |
| cgt ctg caa caa aac ctc gtg gtc agt gag cta gaa aca ctt ctc aaa<br>Arg Leu Gln Gln Asn Leu Val Val Ser Glu Leu Glu Thr Leu Leu Lys<br>        135                      140                      145 | | 1028 |
| gta acg gac gag cgc gca cta gag ctg cgg gaa acg tgg ctg gat gcg<br>Val Thr Asp Glu Arg Ala Leu Glu Leu Arg Glu Thr Trp Leu Asp Ala<br>        150                      155                      160 | | 1076 |
| cgt aaa gcg gcc cag aaa ctt ggg ccg aac tac aat cgc gaa tct<br>Arg Lys Ala Ala Gln Lys Leu Gly Pro Asn Tyr Asn Arg Glu Ser<br>165                        170                      175 | | 1121 |
| tagatctgca cctcaccgag tgcgatgatg gcgcttgggc cggtgagtgt ggagccgtcg | | 1181 |
| tcaaatatct ggacttctac ttccccacct ggaacgcaca ctttaactgt gccttctccc | | 1241 |
| aatccagcat cagctaaagc agcacacgct gcagcaacgg ttcccgtgcc acaggagcgg | | 1301 |
| gtttcgccca ctccgcgttc ccacacgcgc atcgatactg cgtcatcttc taattctgtg | | 1361 |
| acgatttcta cgttcacacc gtggggaag aattcctgat caaacgtggg tgcgcgcagt | | 1421 |
| tccatatcgg caagagccga cgcacttaag cccggcacaa cgcacgctag gtgtgggtta | | 1481 |
| cccatatcaa cgccaaggcc agcgaatact tggccgttga tgtcgcaggt ggataatccc | | 1541 |
| gtgacgtca | | 1550 |

<210> SEQ ID NO 87
<211> LENGTH: 179
<212> TYPE: PRT
<213> ORGANISM: Corynebacterium glutamicum

<400> SEQUENCE: 87

Met Gly Glu Gln Leu Pro Phe Ala Asn Gly Ser Arg Ser Asn Lys Leu
1                  5                      10                      15

Pro Leu Ile Val Ile Gly Leu Cys Cys Ile Met Leu Ile Leu Trp Leu
                  20                      25                      30

Lys Leu Pro Gly Val Leu Leu Ala Thr Ile Ile Gly Val Ala Thr Val
                35                      40                      45

Ser Val Met Arg Met Arg Thr Ser Thr Pro Glu Thr Ala Ser Leu Val
    50                      55                      60

Thr Ser Ile Arg Leu Ser Ala Glu Asp Ile Ser Asp Val Gln His Glu
65                  70                      75                      80

Trp Gln Gln Phe Leu Thr Ser Pro Glu Ala Asp Ala Leu Ala Asp Arg
                  85                      90                      95

Thr Leu Val Arg Pro Ala Leu Ala Asp Pro Asp Cys Gly Asp Lys Ala
                100                      105                      110

```
Ile Glu Lys Phe His Tyr Glu Ile Ser Asn Ala Asn Arg Phe Leu Gly
        115                 120                 125

Arg Leu Asp Ala Arg Leu Gln Gln Asn Leu Val Val Ser Glu Leu Glu
        130                 135                 140

Thr Leu Leu Lys Val Thr Asp Glu Arg Ala Leu Glu Leu Arg Glu Thr
145                 150                 155                 160

Trp Leu Asp Ala Arg Lys Ala Ala Gln Lys Leu Gly Pro Asn Tyr Asn
                165                 170                 175

Arg Glu Ser

<210> SEQ ID NO 88
<211> LENGTH: 28
<212> TYPE: DNA
<213> ORGANISM: Artificial sequence
<220> FEATURE:
<223> OTHER INFORMATION: 5'-primer

<400> SEQUENCE: 88
ggagatctgc attgatgttg aggtccac                                         28

<210> SEQ ID NO 89
<211> LENGTH: 39
<212> TYPE: DNA
<213> ORGANISM: Artificial sequence
<220> FEATURE:
<223> OTHER INFORMATION: 3'-primer

<400> SEQUENCE: 89
cggtgaggtg cagatctatt ctcccatttt cttgctctc                             39

<210> SEQ ID NO 90
<211> LENGTH: 39
<212> TYPE: DNA
<213> ORGANISM: Artificial sequence
<220> FEATURE:
<223> OTHER INFORMATION: 5'-primer

<400> SEQUENCE: 90
gagagcaaga aaatgggaga atagatctgc acctcaccg                             39

<210> SEQ ID NO 91
<211> LENGTH: 28
<212> TYPE: DNA
<213> ORGANISM: Artificial sequence
<220> FEATURE:
<223> OTHER INFORMATION: 3'-primer

<400> SEQUENCE: 91
ggagatcttg acgtcacggg attatcca                                         28
```